United States Patent
Nakanotani et al.

(10) Patent No.: US 12,089,494 B2
(45) Date of Patent: Sep. 10, 2024

(54) ORGANIC ELECTROLUMINESCENCE ELEMENT

(71) Applicants: KYUSHU UNIVERSITY, NATIONAL UNIVERSITY CORPORATION, Fukuoka (JP); KYULUX, INC., Fukuoka (JP)

(72) Inventors: Hajime Nakanotani, Fukuoka (JP); Chihaya Adachi, Fukuoka (JP); Hiroki Noda, Fukuoka (JP); Yoshitake Suzuki, Fukuoka (JP); Naoto Notsuka, Fukuoka (JP); Hiroko Nomura, Fukuoka (JP); Ayataka Endo, Fukuoka (JP); Ping Kuen Daniel Tsang, Fukuoka (JP)

(73) Assignees: KYUSHU UNIVERSITY, NATIONAL UNIVERSITY CORPORATION, Fukuoka (JP); KYULUX, INC., Fukuoka (JP)

( * ) Notice: Subject to any disclaimer, the term of this patent is extended or adjusted under 35 U.S.C. 154(b) by 578 days.

(21) Appl. No.: 17/270,146

(22) PCT Filed: Jun. 13, 2019

(86) PCT No.: PCT/JP2019/023434
§ 371 (c)(1),
(2) Date: Feb. 22, 2021

(87) PCT Pub. No.: WO2020/039708
PCT Pub. Date: Feb. 27, 2020

(65) Prior Publication Data
US 2021/0202864 A1 Jul. 1, 2021

(30) Foreign Application Priority Data
Aug. 23, 2018 (JP) .................. 2018-156721

(51) Int. Cl.
*H10K 85/60* (2023.01)
*C07D 209/86* (2006.01)
(Continued)

(52) U.S. Cl.
CPC ....... *H10K 85/6572* (2023.02); *C07D 209/86* (2013.01); *C09K 11/06* (2013.01);
(Continued)

(58) Field of Classification Search
CPC .... H10K 85/60; H10K 85/615; H10K 85/621; H10K 85/622; H10K 85/624; H10K 85/626; H10K 85/654; H10K 85/6572
See application file for complete search history.

(56) References Cited

U.S. PATENT DOCUMENTS

2012/0241732 A1† 9/2012 Endo
2016/0071625 A1 3/2016 Kita et al.
(Continued)

FOREIGN PATENT DOCUMENTS

CN 105051014 A 11/2015
CN 105103326 A 11/2015
(Continued)

OTHER PUBLICATIONS

Machine translation of KR 2018-028183 (no date) (Year: 0000).*
(Continued)

*Primary Examiner* — Amanda C. Walke
(74) *Attorney, Agent, or Firm* — BROWDY AND NEIMARK, PLLC

(57) ABSTRACT

An organic electroluminescent device having an anode, a cathode, and a light-emitting layer between the anode and the cathode, wherein the light-emitting layer contains at least a first organic compound, a second organic compound and a third organic compound satisfying the following formula (A), the second organic compound is a delayed
(Continued)

fluorescent material, and the third organic compound is a light-emitting material, has a high light emission efficiency. Formula (A): $E_{S1}(A) > E_{S1}(B) > E_{S1}(C)$ wherein $E_{S1}(A)$, $E_{S1}(B)$ and $E_{S1}(C)$ each represent a lowest excited singlet energy level of the first organic compound, the second organic compound and the third organic compound, respectively.

21 Claims, 1 Drawing Sheet

(51) Int. Cl.
    *C09K 11/06*      (2006.01)
    *H10K 50/11*      (2023.01)
    *H10K 101/00*      (2023.01)
    *H10K 101/10*      (2023.01)
(52) U.S. Cl.
    CPC ...... *C09K 2211/1018* (2013.01); *H10K 50/11* (2023.02); *H10K 2101/10* (2023.02); *H10K 2101/90* (2023.02)

(56) References Cited

U.S. PATENT DOCUMENTS

| | | | |
|---|---|---|---|
| 2016/0172601 A1† | 6/2016 | Kawamura | |
| 2016/0190478 A1* | 6/2016 | Nakanotani | H10K 85/6572 257/40 |
| 2016/0268516 A1† | 9/2016 | Tanaka | |
| 2018/0170914 A1* | 6/2018 | Miyata | C07D 265/38 |
| 2021/0202851 A1* | 7/2021 | Nakanotani | H10K 85/6572 |

FOREIGN PATENT DOCUMENTS

| | | | |
|---|---|---|---|
| CN | 105453294 A | 3/2016 | |
| CN | 106537630 A | 3/2017 | |
| CN | 107531628 A | 1/2018 | |
| CN | 110366548 A | 10/2019 | |
| CN | 110914378 A | 3/2020 | |
| EP | 2 958 158 A1 | 12/2015 | |
| EP | 3109253 A1 * | 12/2016 | ............... C07F 5/02 |
| EP | 3 171 421 A1 | 5/2017 | |
| EP | 3 587 399 A1 | 1/2020 | |
| JP | 2005-108726 A | 4/2005 | |
| JP | 2005-108727 A | 4/2005 | |
| JP | 2006-41395 A | 2/2006 | |
| JP | 5124785 B2 | 9/2012 | |
| JP | 5669163 B1 | 12/2014 | |
| JP | 2016-115940 A1 | 6/2016 | |
| JP | 2016-516085 A | 6/2016 | |
| JP | 2017-168885 A | 9/2017 | |
| KR | 10-2016-0044522 A | 4/2016 | |
| KR | 2018028183 A * | 3/2018 | ............. C09K 11/06 |
| WO | 2014/051184 A1 | 4/2014 | |
| WO | 2014/189073 A1 | 11/2014 | |
| WO | 2014208698 A1 | 12/2014 | |
| WO | 2015/022987 A1 | 2/2015 | |
| WO | 2015098975 A1 | 7/2015 | |
| WO | 2015/129715 A1 | 9/2015 | |
| WO | 2015/133501 A1 | 9/2015 | |
| WO | 2015/137136 A1 | 9/2015 | |
| WO | 2016/138077 A1 | 1/2016 | |
| WO | 2016/181846 A1 | 11/2016 | |
| WO | 2017115835 A1 | 7/2017 | |
| WO | 2018047948 A1 | 3/2018 | |
| WO | 2018/237389 A1 | 12/2018 | |
| WO | 2019/004254 A1 | 1/2019 | |
| WO | 2019/197904 A1 | 10/2019 | |

OTHER PUBLICATIONS

Zhang et al, "Purely organic materials for extremely simple allTADF white OLEDs: a new carbazole/oxadiazole hybrid material as a dual-role non-doped light blue emitter and highly efficient orange host", Journal of Materials ChemistryC., 6, 3675-3682(2018) (Year : 2018).*
Office Action dated Jun. 7, 2022 issued in the corresponding Japanese patent application No. 2018-156721 with its English Machine Translation.
Japanese and English version of International Preliminary Report on Patentability of Chapter I, i.e., International Search Opinion which we received from the WIPO as the International Bureau of the PCT dated Feb. 23, 2021.
International Search Report and Search Opinion of PCT/JP2019/023434 dated Sep. 17, 2019 with English Translation.
Chen et al., "Energy Transfer Dynamics in Triplet-Triplet Annihilation Upconversion Using a Bichromophoric Heavy-Atom-Free Sensitizer," The Journal of Physical Chemistry, A 2018/122, 6673-6682 (2018).
Hansch, C. et al., "A Survey of Hammett Substituent Constants and Resonance and Field Parameters," Chem. Rev., 91, 165-195 (1991).
Office Action dated Aug. 8, 2023 issued in the corresponding Korean patent application No. 10-2021-7008503 with its English Machine Translation.
European search report dated Sep. 22, 2021, from corresponding European application No. 19851486.1.
Office Action dated Dec. 6, 2022 issued in the corresponding Japanese patent application No. 2018-156721 with its English Machine Translation.
Chinese Office Action dated Jan. 1, 2024, in the corresponding Chinese patent application No. 201980055087.3 with English machine translation.
Office Action dated Mar. 13, 2024 issued in the corresponding Korean patent application No. 10-2021-7008503 with its English Machine Translation.
Notice of Dispatch of Duplicates of a Written Opposition dated Apr. 16, 2024 in Japanese Patent No. 7325731.
Written Opposition dated Feb. 14, 2024.
Description of Evidence dated Feb. 14, 2024.
Kim et al., Highly efficient and color tunable thermally activated delayed fluorescent emitters using a "twin emitter" molecular design, ChemCommun., 52:339-342 (2016).
Office Action dated Jun. 13, 2024 issued in the corresponding Chinese patent application No. 201980055087.3 with its English Machine Translation.
Notice of reasons for cancellation dated Jun. 20, 2024 in Japanese Patent No. 7325731 with its English Machine Translation.
Hajime Nakanotani et al., "High Efficiency Fluorescence OLED by Utilizing a TADF Process", Journal of the Photographic Society of Japan, 2014, vol. 77, No. 4, pp. 296-300.
Press release material prepared by Public Relations Office, Kyushu University of May 27, 2014.

* cited by examiner
† cited by third party

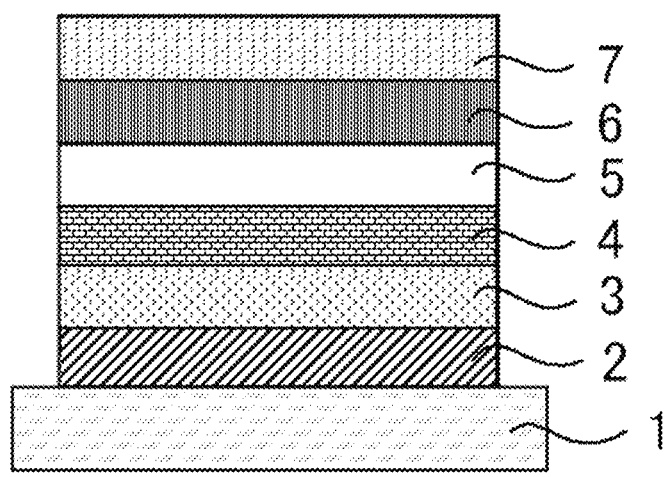

ORGANIC ELECTROLUMINESCENCE ELEMENT

TECHNICAL FIELD

The present invention relates to an organic electroluminescent device having a high light emission efficiency.

BACKGROUND ART

Studies for enhancing the light emission efficiency of organic light-emitting devices such as organic electroluminescent devices (organic EL devices) are being made actively. In particular, various kinds of efforts have been made for increasing light emission efficiency by newly developing materials for use in a light-emitting layer. Among them, there is known a study relating to an organic electroluminescent device that utilizes a host material and a guest material (light-emitting dopant) in such a manner that the excitation energy generated by the host material is transferred to the guest material for light emission.

PTLs 1 and 2 disclose an organic electroluminescent device using a host material, a light-emitting dopant and an assist dopant as materials for the light-emitting layer therein. In the organic electroluminescent device, the assist dopant is to complement carrier transfer in the light-emitting layer, and for example, for complement of electron transfer, a hole transfer material such as a phenylamine derivative is used, while for complement of hole transfer, an electron transfer material is used. In these publications, it is described that by using such an assist dopant, the probability of carrier recombination increases and the light emission efficiency of the organic electroluminescent device can be thereby increased.

PTL 3 discloses an organic electroluminescent device that uses a first dopant containing a material capable of converting a triplet excitation energy into light emission and having a first energy gap, a second dopant containing a material capable of converting a triplet excitation energy into light emission and having a second energy gap larger than the first energy gap, and a host material having a third energy gap larger than the second energy gap, as materials for the light-emitting layer therein, in which organic metal complexes having iridium as a center metal are described as examples of the first dopant and the second dopant. In this publication, it is described that, by using such two kinds of dopants and a host material as combined, the light emission efficiency of the organic electroluminescent device can be increased and the driving voltage thereof is lowered, and in addition, the emission life time thereof is thereby prolonged.

CITATION LIST

Patent Literature

PTL 1: JP 2005-108726 A
PTL 2: JP 2005-108727 A
PTL 3: JP 2006-41395 A

SUMMARY OF INVENTION

Technical Problem

However, the organic electroluminescent device of PTLs 1 and 2 could not sufficiently increase light emission efficiency owing to the following reasons.

Specifically, in an organic electroluminescent device using a host material and a light-emitting dopant, when holes and electrons are injected into the light-emitting layer, the holes and the electrons are recombined mainly in the molecule of the host material to generate excitation energy and the host material becomes in an excited singlet state and an excited triplet state. Regarding the probability of forming excitons in an excited single state (singlet excitons) and excitons in an excited triplet state (triplet excitons), statistically, the singlet excitons are 25% and the triplet excitons are 75%.

With that, in the case where the light-emitting dopant is any of perylene derivatives, oxadiazole derivatives and anthracene derivatives as exemplified in the patent publications, the energy of the singlet exciton is transferred to the light-emitting dopant so that the light-emitting dopant is thereby excited to be in an excited singlet state. The light-emitting dopant thus excited in an excited singlet state emits fluorescence when it is thereafter restored to a ground state. As opposed to this, the energy of the triplet excitons is not transferred to the light-emitting dopant, and the triplet exciton does not contribute toward light emission but is restored to a ground state as it is. Consequently, in the organic electroluminescent device of the type, even though the probability of recombination of carriers is increased by the assist dopant, the energy of the triplet excitons that account for 75% of all the excitons will run to waste, and the improvement of light efficiency in this case is therefore limited.

On the other hand, the organic electroluminescent device of PTL 3 uses a material capable of converting triplet excitation energy into light emission such as an iridium organic metal complex as the first dopant therein. An iridium organic metal complex is known to receive excited triplet energy from a host material owing to the effect of the heavy metal thereof, and also in this system, it is considered that the first dopant can receive the energy of the host material in an excited triplet state and the second dopant to convert it into light emission. However, the excited triplet state has a long lifetime therefore causing energy deactivation owing to saturation of the excited state and interaction with the exciton in an excited triplet state, and in general, therefore, phosphorescence quantum yield is not high. Consequently, it is difficult to sufficiently increase the light emission efficiency of the organic electroluminescent device of the patent publication that mainly utilizes light emission (phosphorescence) from triplet excitation energy.

Given the situation and taking these technical problems in conventional art into consideration, the present inventors have promoted assiduous studies for the purpose of providing an organic electroluminescent device having a high light emission efficiency.

Solution to Problem

As a result of further assiduous studies, the present inventors have found that, when a delayed fluorescent material is used as an assist dopant, the delayed fluorescent material in an excited triplet state can undergo reverse intersystem crossing from the excited triplet state to an excited singlet state, and therefore as a result, the triplet excitation energy can be converted into fluorescence, and an organic electroluminescent device having a high light emission efficiency can be thereby provided. Based on these findings, the present inventors have reached the following present invention as a means for solving the above-mentioned problems.

[1] An organic electroluminescent device having an anode, a cathode, and at least one organic layer that contains a light-emitting layer between the anode and the cathode, wherein the light-emitting layer contains at least a first organic compound, a second organic compound and a third organic compound satisfying the following formula (A), the second organic compound is a delayed fluorescent material, and the third organic compound is a light-emitting material:

$E_{S1}(A) > E_{S1}(B) > E_{S1}(C)$    Formula (A)

wherein $E_{S1}(A)$ represents a lowest excited singlet energy level of the first organic compound, $E_{S1}(B)$ represents a lowest excited singlet energy level of the second organic compound, $E_{S1}(C)$ represents a lowest excited singlet energy level of the third organic compound.

[2] The organic electroluminescent device according to [1], wherein the second organic compound is such that the energy difference $\Delta E_t$ between the lowest excited singlet state and the lowest excited triplet state at 77 K thereof is 0.3 eV or less.

[3] The organic electroluminescent device according to [1], wherein the second organic compound is such that the energy difference $\Delta E_t$ between the lowest excited singlet state and the lowest excited triplet state at 77 K thereof is 0.08 eV or less.

[4] The organic electroluminescent device according to any one of [1] to [3], wherein the first organic compound and the second organic compound satisfy the following formula (B):

$E_{T1}(A) > E_{T1}(B)$    Formula (B)

wherein $E_{T1}(A)$ represents a lowest excited triplet energy level at 77 K of the first organic compound, $E_{T1}(B)$ represents a lowest excited triplet energy level at 77 K of the second organic compound.

[5] The organic electroluminescent device according to any one of [1] to [4], wherein the third organic compound emits fluorescence when returning back to the ground state energy level from the lowest excited singlet energy level.

[6] The organic electroluminescent device according to any one of [1] to [5], wherein the content of the second organic compound in the light-emitting layer is smaller than the content of the first organic compound therein.

[7] The organic electroluminescent device according to any one of [1] to [6], wherein the light-emitting layer contains two or more compounds as the third organic compound.

[8] The organic electroluminescent device according to any one of [1] to [7], wherein the light-emitting layer contains one or more organic compounds in addition to the first organic compound, the second organic compound and the third organic compound.

[9] The organic electroluminescent device according to any one of [1] to [8], wherein the second organic compound is a compound represented by the following general formula (1):

(A)m-L-(D)n    General Formula (1)

wherein L represents an (m+n)-valent aromatic linking group; A represents a group having a positive Hammett's $\sigma_p$ value, or a phenyl group; D represents a group having a negative Hammett's $\sigma_p$ value (except a phenyl group); m represents an integer of 1 or more; n represents an integer of 2 or more; when m is 2 or more, plural A's may be the same as or different from each other; two of plural D's are groups containing an aromatic ring common to them but having a different structure.

The organic electroluminescent device according to any one of [1] to [8], wherein the second organic compound is a compound represented by the following general formula (12):

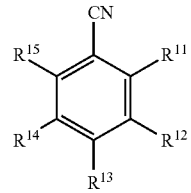

General Formula (12)

wherein at least three of $R^{11}$ to $R^{15}$ are selected from a substituted or unsubstituted diarylamino group (provided that the two aryl groups constituting the diarylamino group may bond to each other) and a halogen atom, and all the selected groups are not the same, and at least one is a substituted or unsubstituted diarylamino group (provided that the two aryl groups constituting the diarylamino group may bond to each other), and the remaining 0 to 2 each represent a hydrogen atom, a substituted or unsubstituted aryl group, or a cyano group.

The organic electroluminescent device according to any one of [1] to [8], wherein the second organic compound is a compound represented by the following general formula (14):

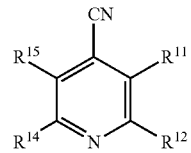

General Formula (14)

wherein at least three of $R^{11}$, $R^{12}$, $R^{14}$ and $R^{15}$ are selected from a substituted or unsubstituted diarylamino group (provided that the two aryl groups constituting the diarylamino group may bond to each other) and a halogen atom, and all the selected groups are not the same, and at least one is a substituted or unsubstituted diarylamino group (provided that the two aryl groups constituting the diarylamino group may bond to each other), and the remaining 0 to 1 represents a hydrogen atom, a substituted or unsubstituted aryl group, or a cyano group.

[12] A compound represented by the following general formula (13):

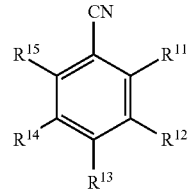

General Formula (13)

wherein at least three of $R^{11}$ to $R^{15}$ each represent a substituted or unsubstituted carbazol-9-yl group, and all these at least three substituted or unsubstituted carbazol-9-yl groups are not the same, and are not substituted with a substituted or unsubstituted diarylamino group (provided that the two aryl groups constituting the diarylamino group may bond to each other), the remaining 0 to 2 each represent a hydrogen atom, a substituted or unsubstituted aryl group, a halogen atom, or a cyano group.

A mixture at least containing a first organic compound, a second organic compound and a third organic compound satisfying the following formula (A), in which the second organic compound is a delayed fluorescent material, and the third organic compound is a light-emitting material:

$$E_{S1}(A) > E_{S1}(B) > E_{S1}(C) \qquad \text{Formula (A)}$$

wherein $E_{S1}(A)$ represents a lowest excited singlet energy level of the first organic compound, $E_{S1}(B)$ represents a lowest excited singlet energy level of the second organic compound, $E_{S1}(C)$ represents a lowest excited singlet energy level of the third organic compound.

A film at least containing a first organic compound, a second organic compound and a third organic compound satisfying the following formula (A), in which the second organic compound is a delayed fluorescent material, and the third organic compound is a light-emitting material:

$$E_{S1}(A) > E_{S1}(B) > E_{S1}(C) \qquad \text{Formula (A)}$$

wherein $E_{S1}(A)$ represents a lowest excited singlet energy level of the first organic compound, $E_{S1}(B)$ represents a lowest excited singlet energy level of the second organic compound, $E_{S1}(C)$ represents a lowest excited singlet energy level of the third organic compound.

Advantageous Effects of Invention

The organic electroluminescent device of the present invention uses three kinds of organic compounds satisfying a specific condition as combined, and is characterized by having an extremely high light emission efficiency. In particular, in the present invention where the third organic compound is a compound that emits fluorescence when returning back to a ground state energy level from the lowest excited singlet energy level, the light emission efficiency of the organic electroluminescent device can be greatly enhanced.

BRIEF DESCRIPTION OF DRAWING

FIG. 1 This is a schematic cross-sectional view showing a layer configuration example of an organic electroluminescent device.

DESCRIPTION OF EMBODIMENTS

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the numerical values described before and after "to" as the upper limit and the lower limit. The hydrogen atom that is present in the molecule of the compound used in the invention is not particularly limited in isotope species, and for example, all the hydrogen atoms in the molecule may be $^1H$, and all or a part of them may be $^2H$ (deuterium (D)).

[Layer Configuration of Organic Electroluminescent Device]

The organic electroluminescent device of the present invention is so configured as to have an anode, a cathode, and an organic layer formed between the anode and the cathode. The organic layer contains at least a light-emitting layer, and the organic electroluminescent device of the present invention is characterized by the configuration of the light-emitting layer. The configuration is described in detail hereinunder.

The organic layer may be composed of a light-emitting layer alone, or may have any other one or more organic layers than the light-emitting layer. Such other organic layers include a hole transport layer, a hole injection layer, an electron blocking layer, a hole blocking layer, an electron injection layer, an electron transport layer, and an exciton blocking layer. The hole transport layer may be a hole injection transport layer having a hole injection function, and the electron transport layer may be an electron injection transport layer having an electron injection function. A specific configuration example of an organic electroluminescent device is shown in FIG. 1. In FIG. 1, 1 is a substrate, 2 is an anode, 3 is a hole injection layer, 4 is a hole transport layer, 5 is a light-emitting layer, 6 is an electron transport layer, and 7 is a cathode.

In the following, the constituent members and the layers of the organic electroluminescent device are described.

[Light-Emitting Layer]

The light-emitting layer is a layer in which holes and electrons injected from an anode and a cathode are recombined to give excitons for light emission.

In organic electroluminescent device of the present invention, the light-emitting layer contains at least a first organic compound, a second organic compound and a third organic compound satisfying the following formula (A), the second organic compound is a delayed fluorescent material, and the third organic compound is a light-emitting material.

$$E_{S1}(A) > E_{S1}(B) > E_{S1}(C) \qquad \text{Formula (A)}$$

wherein $E_{S1}(A)$ represents a lowest excited singlet energy level of the first organic compound, $E_{S1}(B)$ represents a lowest excited singlet energy level of the second organic compound, $E_{S1}(C)$ represents a lowest excited singlet energy level of the third organic compound.

The "delayed fluorescent material" in the present invention is an organic compound which, after having transited to an excited triplet state, can undergo reverse intersystem crossing to an excited singlet state, and which can emit fluorescence when returning back to the ground state from the excited singlet state. The lifetime of the light to occur through the reverse intersystem crossing from the excited triplet state to the excited single state is longer than that of ordinary fluorescence (instantaneous fluorescence) or phosphorescence, and therefore the light can be observed as a fluorescence delayed from them. Consequently, such fluorescence is referred to as "delayed fluorescence".

In the light-emitting layer, the lowest excited singlet energy $E_{S1}(A)$, $E_{S1}(B)$ and $E_{S1}(C)$ of the first organic compound to the third organic compound satisfy the above-mentioned formula (A), and the second organic compound is a delayed fluorescent material, and therefore the excitation energy to be generated by recombination of the holes and the electrons injected into the light-emitting layer can be efficiently converted into fluorescence and can provide a high light emission efficiency. This is considered to be because of the following reasons.

Specifically, in the light-emitting layer, when excitation energy is generated by recombination of holes and electrons, the organic compounds contained in the light-emitting layer transit from the ground state to an excited singlet state and an excited triplet state. The probability of formation of the organic compound in an excited singlet state (singlet exciton) and the organic compound in an excited triplet state (triplet exciton) is statistically such that the singlet exciton accounts for 25% and the triplet exciton accounts for 75%. With that, the energy of the first organic compound and the second organic compound in an excited singlet state of the excitons transfers to the third organic compound, and the third organic compound in a ground state transits to an excited singlet state. The third organic compound that has been in an excited singlet state thereafter emits fluorescence when returning back to the ground state.

At that time, in the organic electroluminescent device of the present invention, the second organic compound is a delayed fluorescent material, and therefore the second organic compound in an excited triplet state undergoes reverse intersystem crossing to an excited singlet state, and the singlet excitation energy by the reverse intersystem crossing also transfers to the third organic compound. Consequently, the second organic compound in an excited triplet state having a large abundance ratio can indirectly contribute toward light emission, and the light-emitting layer of the type can exponentially increase the light emission efficiency of the organic electroluminescent device as compared with the configuration where the light-emitting layer does not contain a second organic compound.

In the organic electroluminescent device of the present invention, although light emission occurs mainly from the third organic compound, a part of light emission may be light emission partly from the first organic compound and the second organic compound. The light emission includes both fluorescence emission and delayed fluorescence emission.

In the organic electroluminescent device of the present invention, the type and the combination of the first organic compound, the second organic compound and the third organic compound are not specifically limited so far as the above formula (A) is satisfied, the second organic compound is a delayed fluorescent material, and the third organic compound is a light-emitting material. Preferably, the organic electroluminescent device of the present invention further satisfies the following formula (B) for realizing a further higher light emission efficiency.

$$E_{T1}(A) > E_{T1}(B) \quad \quad \text{Formula (B)}$$

wherein $E_{T1}(A)$ represents a lowest excited triplet energy level at 77 K of the first organic compound, $E_{T1}(B)$ represents a lowest excited triplet energy level at 77 K of the second organic compound. The relationship between the lowest excited triplet energy level $E_{T1}(B)$ at 77 K of the second organic compound and the lowest excited triplet energy level $E_{T1}(C)$ at 77 K of the third organic compound is not specifically limited, but for example, can be so selected as to satisfy $E_{T1}(B) > E_{T1}(C)$.

In the following, the present invention will be described more specifically with reference to preferred examples thereof, but the scope of the present invention should not be limitatively interpreted by the description based on the following specific examples.

First, the first compound, the second compound and the third compound are described in that order, and the other materials and elements are described thereafter.

[First Organic Compound]

The first organic compound is an organic compound having a larger lowest excited singlet energy than the second organic compound and the third organic compound, and has a function as a host material to take a role in carrier transport and also a function to trap the energy of the third organic compound in the compound. Accordingly, the third organic compound can efficiently convert the energy generated by recombination of holes and electrons in the molecule and the energy having received from the first organic compound and the second organic compound into light emission, and an organic electroluminescent device having a high light emission efficiency can be thereby realized.

The first organic compound is preferably an organic compound having a hole transport ability and an electron transport ability, capable of preventing the wavelength of light emission from being prolonged, and having a high glass transition temperature. Preferred compounds usable as the first organic compound are listed below. In the structural formulae of the exemplified compounds, R represents a hydrogen atom or a substituent, and n represents an integer of 3 to 5.

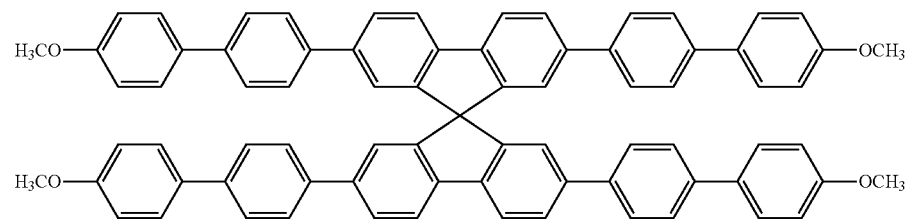

-continued
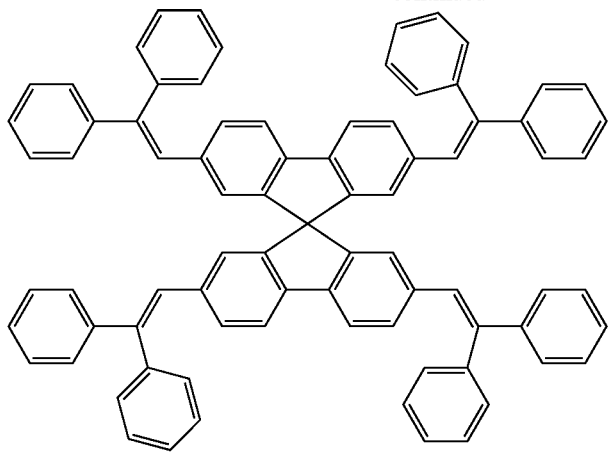
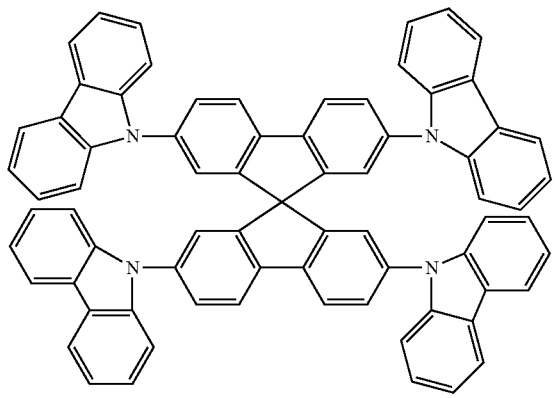
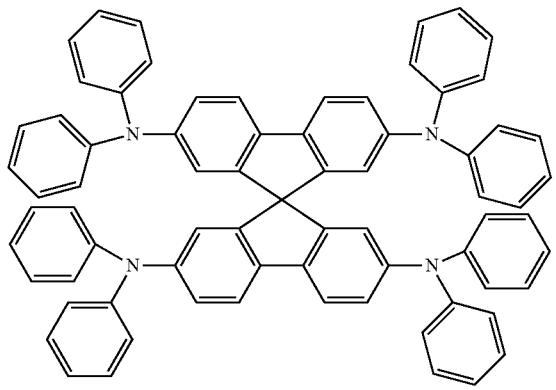
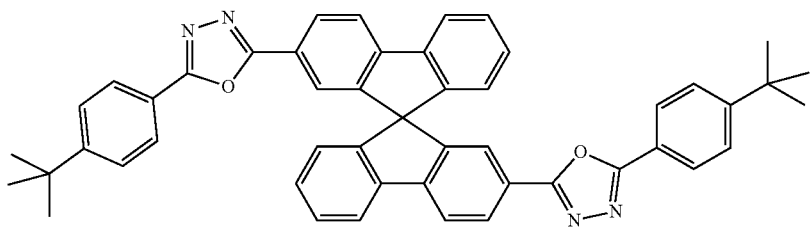

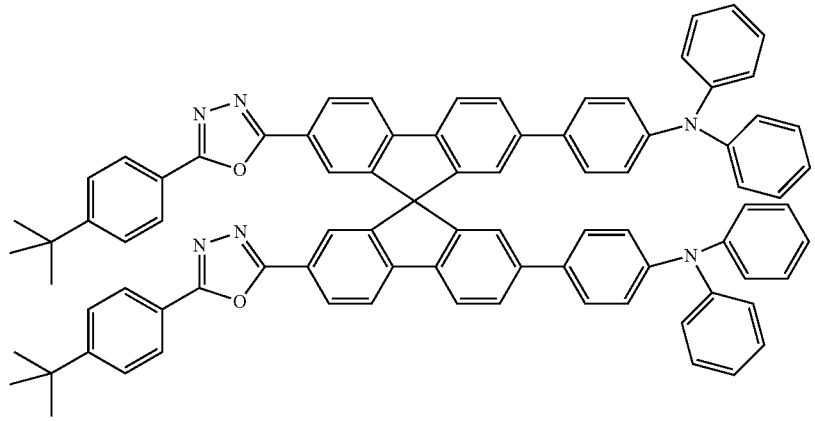
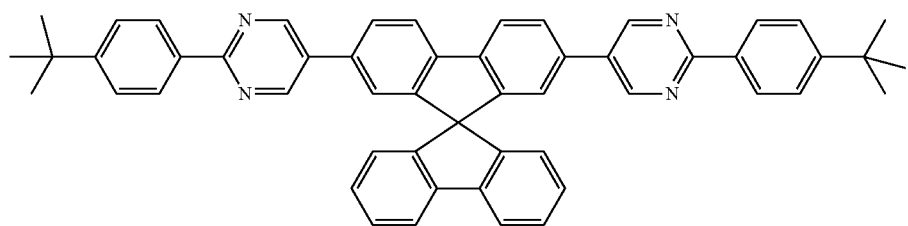
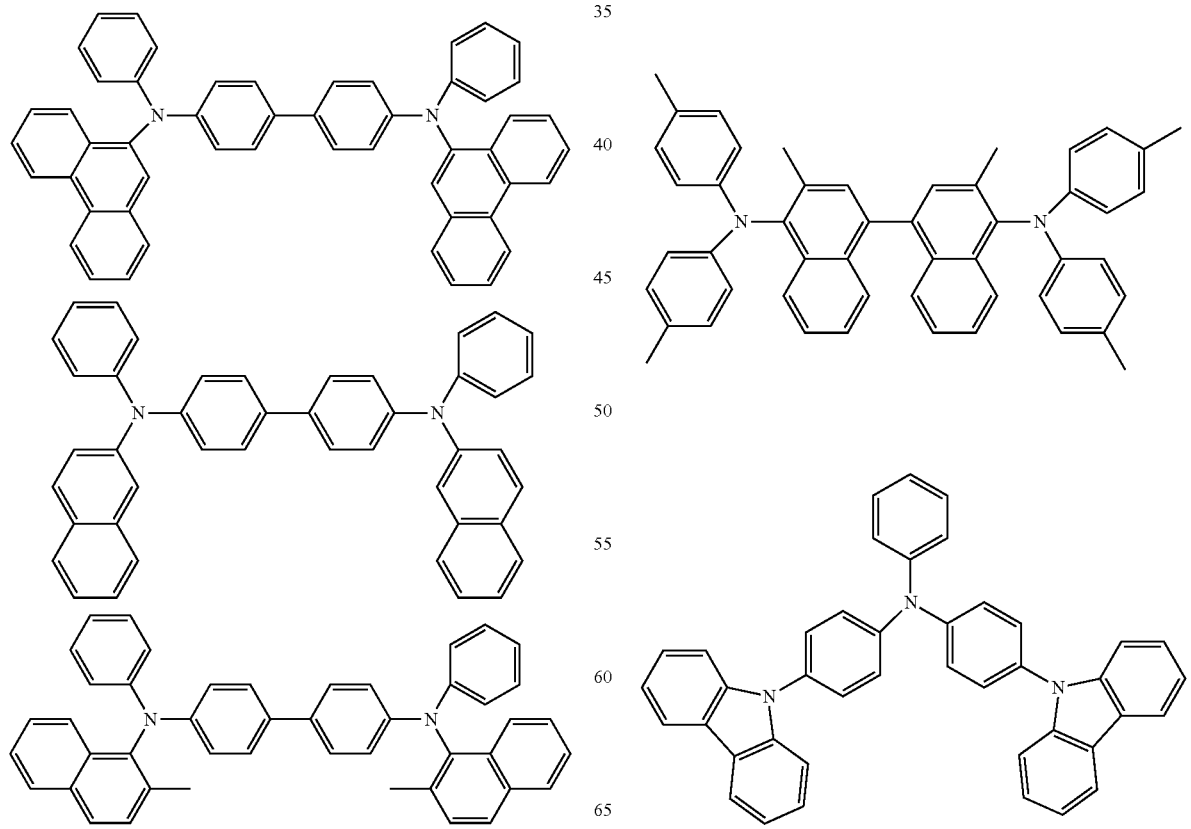

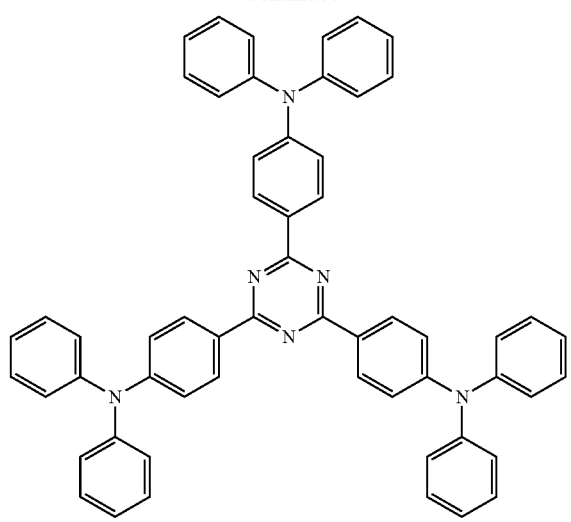
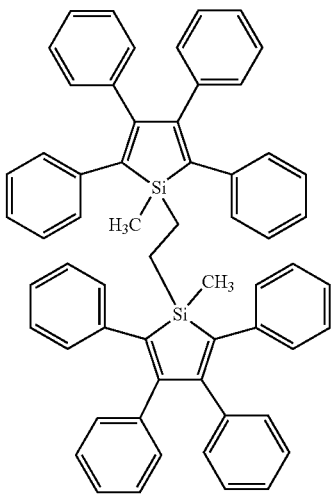
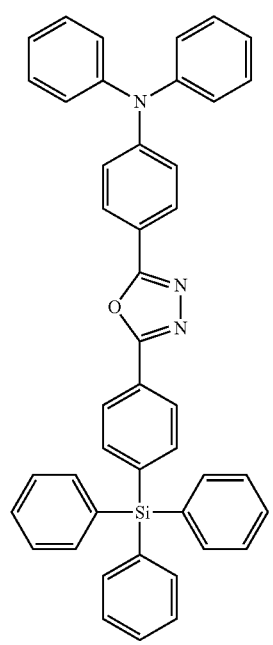
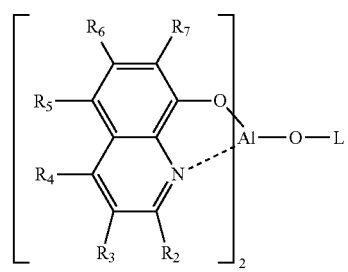
$R_2$—$R_7$ = H or substituent
L = ligand
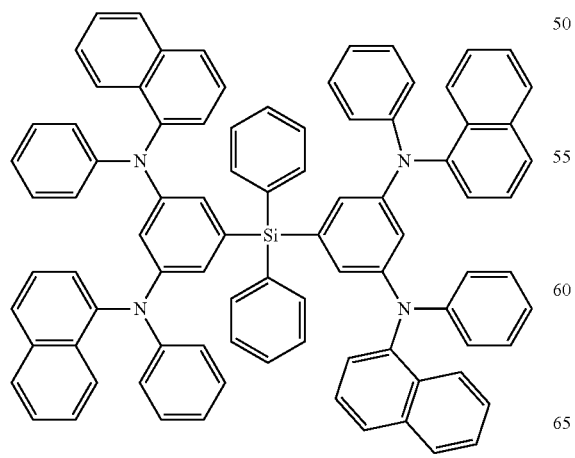
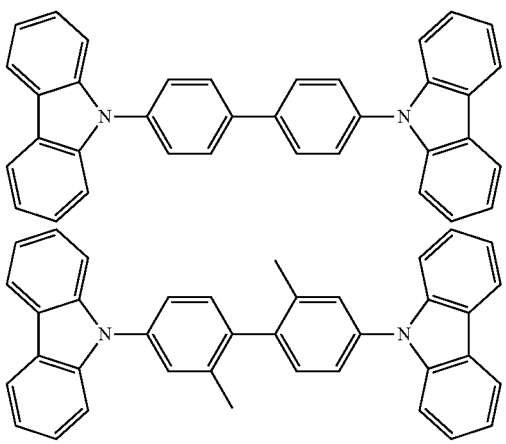

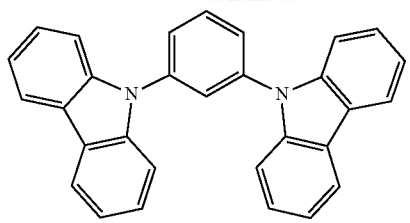
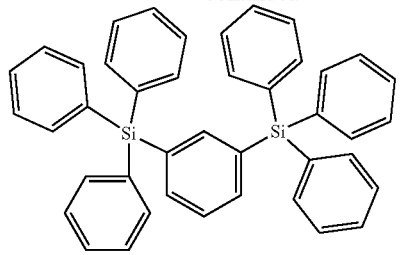
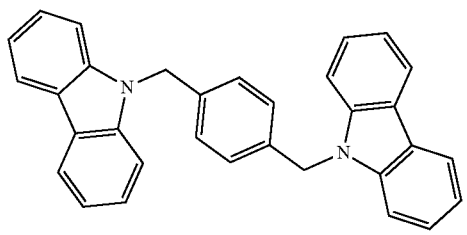
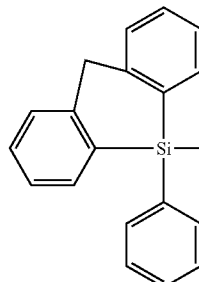
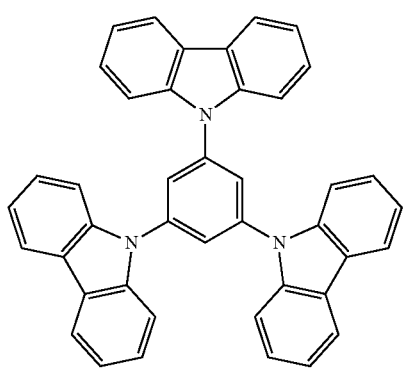
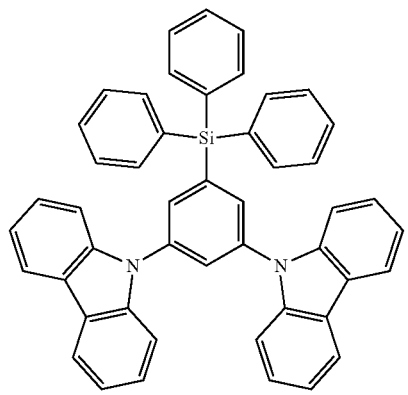
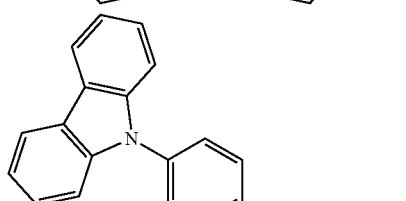
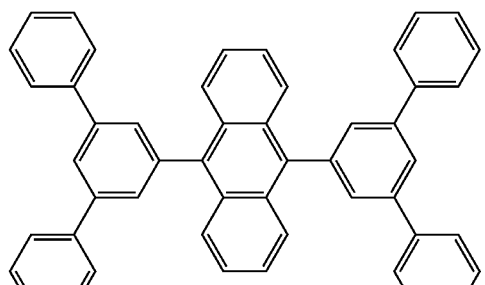
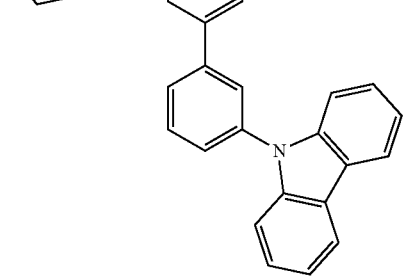
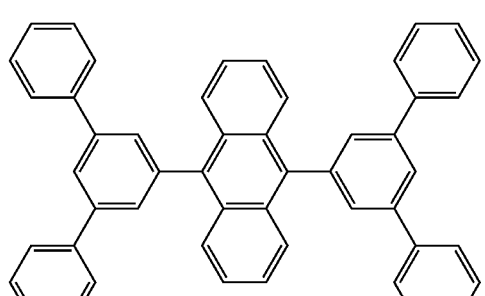
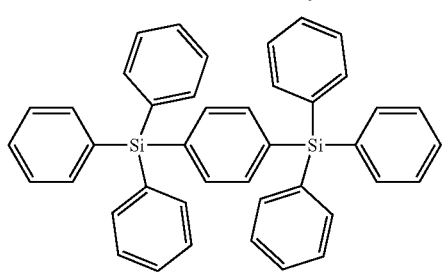
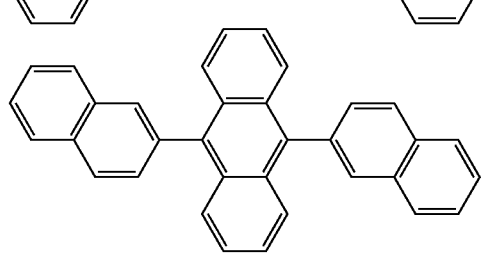

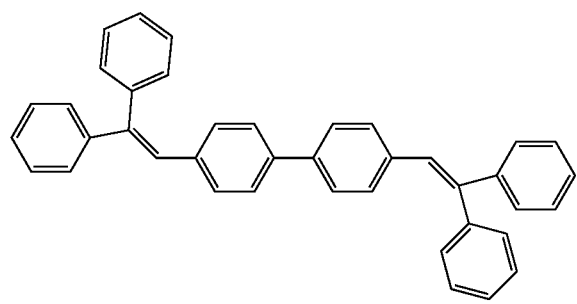
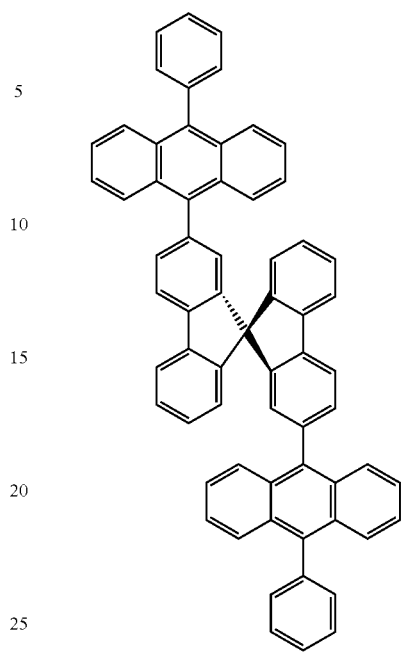
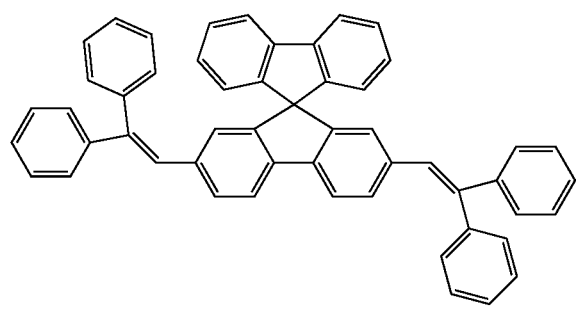
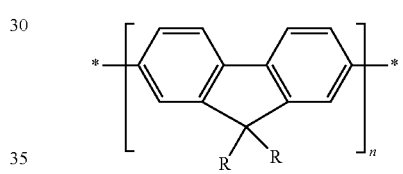
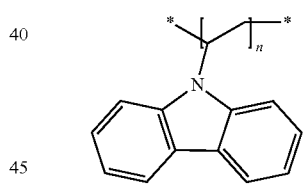
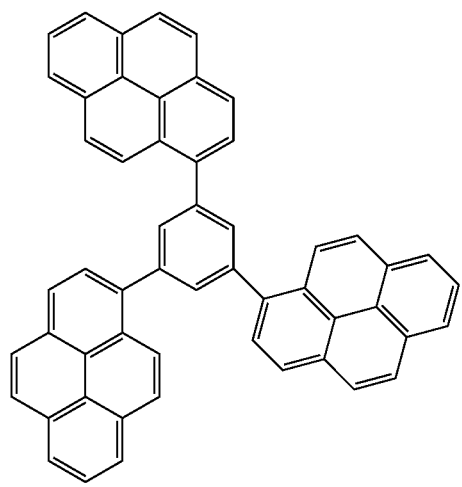
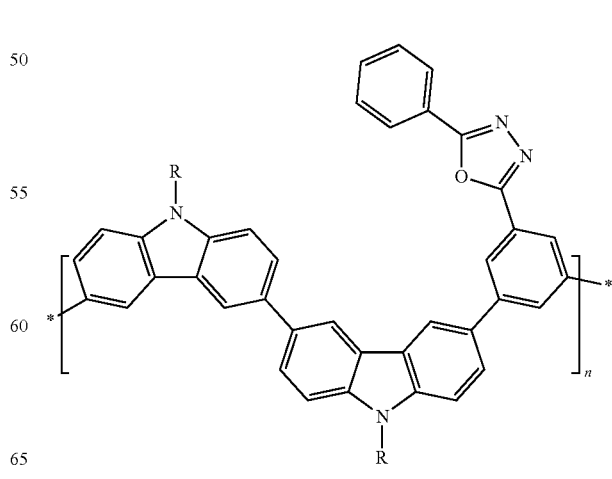

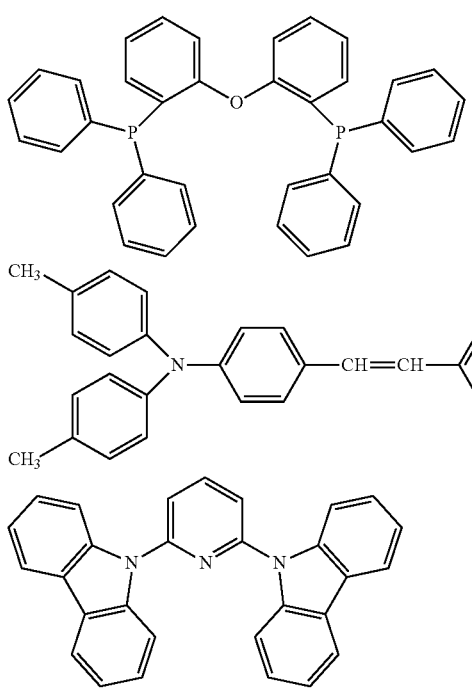
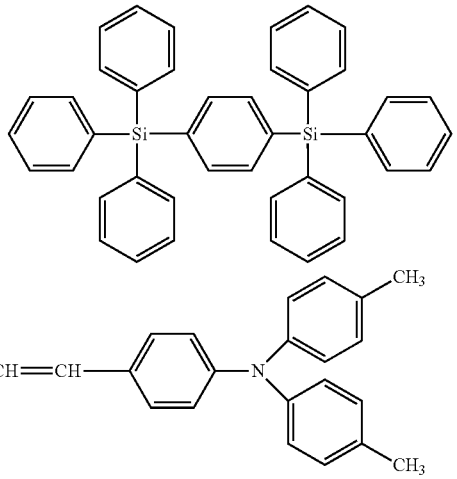

[Second Organic Compound]

In the present invention, a delayed fluorescent material capable of emitting delayed fluorescence is used as the second organic compound. In particular, a thermal activation type delayed fluorescent material that undergoes reverse intersystem crossing from an excited triplet state to an excited singlet state through absorption of thermal energy is preferably used. A thermal activation type delayed fluorescent material can absorb heat generated by a device to relatively readily undergo reverse intersystem crossing from an excited triplet state to an excited singlet state, and can make the excited triplet energy efficiently contribute toward light emission.

The delayed fluorescent material for use in the present invention is preferably such that the difference $\Delta E_{st}$ between the energy level $E_{s1}$ in a lowest excited singlet state and the energy level $E_{T1}$ in a lowest excited triplet state at 77 K is 0.3 eV or less, more preferably 0.2 eV or less, even more preferably 0.1 eV or less, further more preferably 0.08 eV or less. The delayed fluorescent material such that the energy difference $\Delta E_{st}$ thereof falls within the above range can relatively readily undergo reverse intersystem crossing from an excited triplet state to an excited singlet state, and can make the resultant excited triplet energy efficiently contribute toward light emission.

The delayed fluorescent material usable as the second organic compound is not specifically limited.

As the delayed fluorescent material for the second organic compound, specifically, compounds represented by the following general formula (1) are preferred.

$$(A)m\text{-}L\text{-}(D)n \qquad \text{General Formula (1)}$$

wherein L represents an (m+n)-valent aromatic linking group; A represents a group having a positive Hammett's $\sigma_p$ value, or a phenyl group; D represents a group having a negative Hammett's $\sigma_p$ value (except a phenyl group); m represents an integer of 1 or more; n represents an integer of 2 or more; when m is 2 or more, plural A's may be the same as or different from each other; two of plural D's are groups containing an aromatic ring common to them, but having a different structure.

In the general formula (1), L represents an (m+n)-valent aromatic linking group. m and n each correspond to the number of A and the number of D bonding to the aromatic linking group. The aromatic linking group represented by L is formed of an aromatic ring, and among the positions of the aromatic ring substitutable with a substituent, A is replaced with the hydrogen atom at the m positions to bond to a carbon atom, and D is replaced with the hydrogen atom at the n positions to bond to a carbon atom. Namely, the aromatic linking group represented by L is formed of an aromatic ring from which (m+n) hydrogen atoms have been removed. Among the positions of the aromatic ring substitutable with a substituent, a part or all of those positions can be substituted with A or D, but preferably, all the substitutable positions of the aromatic ring are substituted with A or D.

The aromatic ring to constitute the aromatic linking group represented by L may be an aromatic ring of a hydrocarbon (hereinafter referred to as "aromatic hydrocarbon ring"), or may also be an aromatic ring containing a hetero atom (hereinafter referred to as "aromatic hetero ring"). The group substitutable with a substituent of the aromatic hydrocarbon ring is a methine group (—CH═), and the group substitutable with a substituent of the aromatic hetero ring includes a methine group (—CH═) and an imino group (—NH—).

The aromatic hydrocarbon ring to constitute the aromatic linking group represented by L may be a single ring, or may be a condensed ring formed by condensation of 2 or more aromatic hydrocarbon rings, or may be a spiro ring formed of 2 or more aromatic hydrocarbon rings bonding via a spiro bond, or may be a linked ring formed of 2 or more aromatic hydrocarbon rings linking together. In the case where 2 or more aromatic hydrocarbon rings link together, they may link in a linear manner or in a branched manner. The carbon number of the aromatic hydrocarbon ring to constitute the aromatic linking group is preferably 6 to 22, more preferably 6 to 18, even more preferably 6 to 14, further more preferably 6 to 10. Specific examples of the aromatic hydrocarbon ring to constitute the aromatic linking group include a benzene ring, a naphthalene ring, a biphenyl ring, and a spirofluorene ring.

The aromatic hetero ring to constitute the aromatic linking group represented by L may be a single ring, or may be a condensed ring formed by condensation of one or more hetero rings and an aromatic hydrocarbon ring or an aromatic hetero ring, or may be a spiro ring formed of one hetero ring and one aromatic hydrocarbon ring or aromatic hetero ring bonding via a spiro bond, or may be a linked ring formed of one or more aromatic hetero ring and an aromatic hydrocarbon ring or an aromatic hetero ring that link together. The carbon number of the aromatic hetero ring is preferably 5 to 22, more preferably 5 to 18, even more preferably 5 to 14, further more preferably 5 to 10. The hetero atom to constitute the aromatic hetero ring is preferably a nitrogen atom. Specific examples of the aromatic hetero ring include a pyridine ring, a pyridazine ring, a pyrimidine ring, a triazole ring, and a benzotriazole ring.

More preferably, the aromatic ring to constitute the aromatic linking group represented by L is a benzene ring.

A is a group having a positive Hammett's $\sigma_p$ value, and D is a group having a negative Hammett's $\sigma_p$ value. However, exceptionally, a phenyl group is included in A and is not included in D.

Here, "Hammett's $\sigma_p$ value" is one propounded by L. P. Hammett, and is one to quantify the influence of a substituent on the reaction rate or the equilibrium of a para-substituted benzene derivative. Specifically, the value is a constant ($\sigma_p$) peculiar to the substituent in the following equation that is established between a substituent and a reaction rate constant or an equilibrium constant in a para-substituted benzene derivative:

$$\log(k/k_0) = p\sigma_p$$

or $$\log(K/K_0) = p\sigma_p$$

In the above equations, k represents a rate constant of a benzene derivative not having a substituent; $k_0$ represents a rate constant of a benzene derivative substituted with a substituent; K represents an equilibrium constant of a benzene derivative not having a substituent; $K_0$ represents an equilibrium constant of a benzene derivative substituted with a substituent; p represents a reaction constant to be determined by the kind and the condition of reaction. Regarding the description relating to the "Hammett's $\sigma_p$ value" and the numerical value of each substituent in the present invention, reference may be made to the description relating to $\sigma_p$ value in Hansch, C. et. al., Chem. Rev., 91, 165-195 (1991). A group having a negative Hammett's $\sigma_p$ value tends to exhibit electron-donating performance (donor-like performance) and a group having a positive Hammett's $\sigma_p$ value tends to exhibit electron-accepting performance (acceptor-like performance).

m A's bond to the aromatic linking group represented by L. m is an integer of 1 or more, and when m is 2 or more, plural A's may be the same as or different from each other. The upper limit of m is not specifically limited, but is preferably smaller than n.

The group having a positive Hammett's $\sigma_p$ value represented by A includes, though not specifically limited thereto, a cyano group, a group containing a carbonyl group or a sulfonyl group, or a substituted or unsubstituted heteroaryl group. The hetero atom that the heteroaryl group contains includes a nitrogen atom, an oxygen atom, a sulfur atom and a boron atom, and preferably the heteroaryl group contains at least one nitrogen atom as the ring member. Such a heteroaryl group includes a 5-membered or 6-membered ring group containing a nitrogen atom as the ring member, or a group having a condensed ring structure of a 5-membered or 6-membered ring having a nitrogen atom as the ring member with a benzene ring, and is preferably a monovalent group formed by removing one hydrogen atom from a pyridine ring, a pyrazine ring, a pyrimidine ring, a pyridazine ring or a triazine ring, or a group having a condensed ring structure formed by condensation of these aromatic hetero rings, or a group having a condensed ring structure of such an aromatic hetero ring with a benzene ring. In addition, a group having a condensed ring structure of a quinone ring or a pyrone ring with a benzene ring and formed by removing one hydrogen atom from the benzene ring thereof is also preferred as a group having a positive Hammett's $\sigma_p$ value. Here, the benzene ring to be condensed with a quinone ring or a pyrone ring can be substituted with a substituent. In the case where the benzene ring condensed with a quinone ring or a pyrone ring has a substituent and in the case where the heteroaryl group has a substituent, examples of the substituent in such cases include an alkyl group having 1 to 20 carbon atoms, an aryl group having 6 to 40 carbon atoms, a cyano group, a halogen atom, and a heteroaryl group having 5 to 40 carbon atoms. Of such substituents, those that can be substituted with a substituent can be substituted with a substituent. A includes a phenyl group. When m is 2 or more, the number of cyano groups of plural A's can be, for example, 0 to 2, and is more preferably 1 than 2.

Specific examples of the group having a positive Hammett's $\sigma_p$ value represented by A are shown below. However, in the present invention, the group having a positive Hammett's $\sigma_p$ value represented by A should not be limitatively interpreted by these exemplified groups. Among the groups exemplified below, those having a cyclic structure bond to L by replacing the hydrogen atom of any one methine group (—CH=) that constitutes the cyclic structure with L. The right and left lines of CO of the carbonyl group (—CO—) and the right and left lines of $SO_2$ of the sulfonyl group (—$SO_2$—) each represent a single bond (chemical bond). The carbonyl group (—CO—) and the sulfonyl group (—$SO_2$—) each directly bond to L via one single bond, or links to L via a linking group, and an atomic group bonds to the other single bond. The atomic group includes a substituted or unsubstituted alkyl group, aryl group and heteroaryl group. Preferably, the carbon number of the alkyl group is 1 to 20, the carbon number of the aryl group is 6 to 40, and the carbon number of the heteroaryl group is 5 to 40.

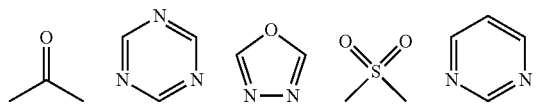

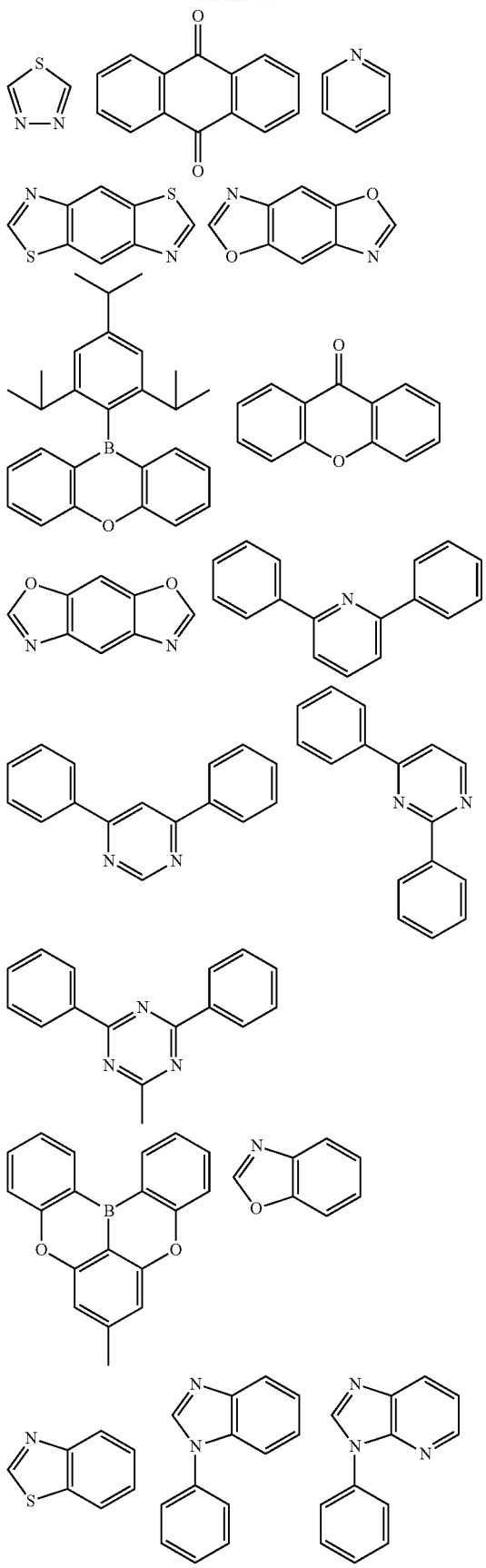

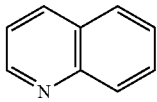

Next, D is described.

n D's bond to the aromatic linking group represented by L. n is an integer of 2 or more, and two of plural D's are groups containing an aromatic ring common to them but having a different structure. The type of the common aromatic ring is not specifically limited, and may be an aromatic hydrocarbon ring or an aromatic hetero ring. Regarding the description and the preferred range of the aromatic hydrocarbon ring and the aromatic hetero ring, reference may be made to the corresponding part in the description of the following requirements (a) and (b). Though not specifically limited thereto, a preferred aromatic ring is a benzene ring. Also though not specifically limited thereto, preferred examples of a group containing an aromatic ring include a group containing a diarylamino structure or a carbazolyl structure. Preferably, two of plural D's are both groups having a hetero atom, more preferably groups containing a nitrogen atom. Specific structures of those groups are represented by any of general formulae (2) to (9) to be mentioned below.

Preferably, two of plural D's satisfy the following requirement (a) or (b).

Requirement (a)

Two D's both have an aromatic ring that contains an atom bonding to L, and the aromatic ring is common between the two D's, but the two differ from each other in point of at least one condition of the number of the substituents on the aromatic ring, the substitution site of the aromatic ring substituted with the substituent, and the structure of the substituent on the aromatic ring.

Requirement (b)

Two D's both have a linking group bonding to L and one or more aromatic rings bonding to the linking group, and in the case where the two D's each have one aromatic ring bonding to the linking group, the linking group and the aromatic ring bonding to the linking group are common between the two D's, but the two differ from each other in point of at least one condition of the number of the substituents on the aromatic ring, the substitution site of the aromatic ring substituted with the substituent, and the structure of the substituent on the aromatic ring. In the case where the two D's each have 2 or more aromatic rings bonding to the linking group, the linking group, the number of the aromatic rings bonding to the linking group and the plural aromatic rings are common between the two D's, but at least one combination of the aromatic rings common between the two D's differs in point of at least one condition of the number of the substituents on the aromatic ring, the substitution site of the aromatic ring substituted with the substituent, and the structure of the substituent on the aromatic ring.

In the following description, one of the two D's satisfying the requirement (a) or (b) is referred to as "the one D", and the other thereof is referred to as "the other D". Two D's satisfying the requirement (a) or (b) ("the one D" and "the other D") may be composed of one combination or two or more combinations out of plural D's.

In the requirement (a), the "aromatic ring containing an atom bonding to L" that the one D has is referred to as "the one aromatic ring", and the "aromatic ring containing an atom bonding to L" that the other D has is referred to as "the other aromatic ring".

In the requirement (b) "where the two D's each have 2 or more aromatic rings bonding to the linking group, the linking group, the number of the aromatic rings bonding to the linking group and the plural aromatic rings are common between the two D's, but at least one combination of the aromatic rings common between the two D's differs in point of at least one condition of the number of the substituents on the aromatic ring, the substitution site of the aromatic ring substituted with the substituent, and the structure of the substituent on the aromatic ring" means that, with reference to an example where a benzene ring and a naphthalene ring link to L via a trivalent linking group in the one D, the two D's differ in point of at least one condition of the number of the substituents on the aromatic ring, the substitution site of the aromatic ring substituted with the substituent, and the structure of the substituent on the aromatic ring, in a combination of aromatic rings common to each other where, also in the other D, a benzene ring and a naphthalene ring link to L via a trivalent linking group like in the one D, that is, a combination of a benzene ring of the one D and a benzene ring of the other D, or a combination of a naphthalene ring of the one D and a naphthalene ring of the other D, or both these combinations. In the requirement (b), in the case where the two D's each have one aromatic ring bonding to a linking group, the "aromatic ring linking to the linking group" that the one D has is referred to as "the one aromatic ring", and the "aromatic ring linking to the linking group" that the other D has is referred to as "the other aromatic ring". In the case where two D's have two or more aromatic rings bonding to a linking group, one of the "combination of the two aromatic rings common to each other" differing in at least one substituent condition is referred to as "the one aromatic ring", and the other is referred to as "the other aromatic ring".

In the following description, "the number of the substituents on the aromatic ring", "the substitution site of the aromatic ring substituted with the substituent", and "the structure of the substituent on the aromatic ring" may be collectively referred to as "the substituent condition".

The aromatic ring in the requirements (a) and (b) may be an aromatic hydrocarbon ring or an aromatic hetero ring, and may be a single ring or a condensed ring. In the case where the aromatic ring constitutes a linked ring, the aromatic ring on the side nearest to L is the aromatic ring referred to in the requirements (a) and (b). Common aromatic rings mean that the two are completely the same between the one aromatic ring and the other aromatic ring except the number of the hydrogen atom substituted with a substituent and the substituent condition. The linking group in the requirement (b) may be divalent linking group that link L and one aromatic ring, or may be a trivalent or higher linking group that links L and two or more aromatic rings. In the case where the number of the aromatic rings bonding to the linking group is 2 or more, the aromatic rings bonding to the linking group may be the same as or different from each other.

The difference in the substituent condition in aromatic rings can be judged as follows.

First, one D and another D different from the one D are compared in point of the number of the substituents on the common aromatic rings (common aromatic rings among the aromatic rings containing an atom bonding to L, or common aromatic rings among the aromatic rings linking to L via a linking group). In the case where the number of the substituents differs, it is judged that the two D's differ in point of "the number of the substituents on the aromatic ring" among the above-mentioned substituent conditions. In the case where the number of the substituents is the same, the two are compared in point of the site (substitution site) of the aromatic ring substituted with the substituent, and when there is at least one different substitution site, it is judged that the two D's differ in point of "the substitution site of the aromatic ring substituted with the substituent" among the above-mentioned substituent conditions. When the substitution sites are all the same, the two are compared in point of the structure of the substituent on the aromatic ring. In the case where at least one substituent on the aromatic ring of the one D has a different structure from that of the substituent in the corresponding substitution site of the aromatic ring of the another D, it is judged that the two D's differ in point of "the structure of the substituent on the aromatic ring". Here, "the corresponding substitution site" of the aromatic ring of the another D is a position common to the substitution site of the aromatic ring of the one D in point of the structural formula of the aromatic ring, and specifically, when the structural formulae of the aromatic rings of the two D's are laid on each other in all the substitution sites, the overlapping positions correspond to "the corresponding substitution sites". Otherwise, the positions having a common position number of the aromatic ring given according to the IUPAC nomenclature system correspond to "the corresponding substitution sites". However, in the case where the structural formula of an aromatic ring has an axisymmetric structure, the positions that overlap in 180° rotation around the symmetrical axis as a center are also judged to be included in "the corresponding substitution sites", and in the case where at least one substituent on an aromatic ring of one D differs from both substituents at the corresponding substitution sites of the aromatic ring of another D in point of the structure, it is judged that the two D's differ in "the structure of the substituent on the aromatic ring". For example, regarding the substituent at the 3-position of a carbazole ring, a case where the substituent of the carbazole ring differs from both the substituent at the 3-position and the substituent at the 6-position of another carbazole ring corresponds to this case.

"A substituent differing in the structure" means that the substituent differs in at least one condition of, for example, the kind of the substituent, the kind of the atoms constituting the substituent and the number of each constituent atom, the presence or absence of a saturated bond or the position thereof, the chain-like structure (linear structure, branched structure, and the branching position in the branched structure), the cyclic structure (the number of ring members, aromatic or nonaromatic, presence or absence of condensed ring). In the case where two substituents on an aromatic ring bond to each other to form a cyclic structure, the two substituents can be considered to be "substituent" in the substituent conditions. For example, in the case of a naphthalene ring as an aromatic ring, the entire naphthalene ring can be considered as "an aromatic ring", or the case can be considered to be a benzene ring substituted with a substituent at the neighboring positions thereof. In the case where a naphthalene ring is considered as a benzene ring substituted with a substituent at the neighboring positions thereof, the relationship between the naphthalene ring of the type and an unsubstituted benzene ring is such that the aromatic ring is common to the two and the two differ in point of the number of the substituents. In the present invention, the case where the targeted aromatic rings are in such a relationship between two D's is also judged to satisfy the requirement (a) or (b).

Among the substituent conditions, preferably, one aromatic ring differs from another aromatic ring in point of the "number of the substituents on the aromatic ring", and more preferably, one aromatic ring is substituted with at least one substituent and another aromatic ring is unsubstituted.

Preferably, two D's satisfying the requirement (a) or (b) contain a diarylamine structure (provided that the two aryl groups constituting the diarylamine structure may bond to each other). In the present invention, the "diarylamine structure" means a structure where two aryl groups bond to a nitrogen atom, and the two aryl groups may bond to each other, and may be substituted with a substituent. Regarding the preferred range and specific examples of the substituent in the case where the aryl group has a substituent, reference may be made to the preferred range and specific examples of the substituent that $R^{11}$ to $R^{19}$ in the general formula (2) can represent. The aromatic hydrocarbon ring to constitute the aryl group of the diarylamine structure may be a single ring or a condensed ring formed by condensation of 2 or more aromatic hydrocarbon rings. The carbon number of the aromatic hydrocarbon ring to constitute the aryl group of the diarylamine structure is preferably 6 to 22, more preferably 6 to 18, even more preferably 6 to 14, further more preferably 6 to 10. Specific examples of the aryl group of the diarylamine structure include a substituted or unsubstituted phenyl group, and a substituted or unsubstituted naphthyl group. In the case where two aryl group of the diarylamine structure bond to each other, the two aryl groups may bond via a single bond, or may link via a linking group. The linking group that links the two aryl groups include an oxygen atom, a sulfur atom, and a substituted or unsubstituted alkylene group. In the case where the alkylene group has a substituent, the substituent includes a substituted or unsubstituted alkyl group, and a substituted or unsubstituted aryl group. Specific examples of the diarylamine structure where two aryl groups bond to each other include a carbazole structure, a phenoxazine structure, a phenothiazine structure and an acridine structure. More preferably, two D's satisfying the requirement (a) or (b) contain a carbazole structure.

In the group containing a diarylamine structure, the diarylamine structure may bond to L via a single bond, or may link to L via a divalent linking group. The divalent linking group is not specifically limited. The diarylamine structure may bond to L or to a divalent linking group by substitution of any hydrogen atom of the two aryl groups thereof with L or a divalent linking group, or may bond thereto by bonding of the nitrogen atom of the structure to L or a divalent linking group. Preferably, the nitrogen atom of the diarylamine structure bond to L or a divalent linking group, and more preferably, the nitrogen atom of the diarylamine structure directly bond to L (via a single bond). Specifically, the diarylamine structure is preferably a diarylamino group (provided that the two aryl groups constituting the diarylamine structure may bond to each other), and is more preferably a diarylamino group bonding to L via a single bond.

Here, regarding the relationship between the diarylamine structure and the requirement (a) or (b), first in the case where the two aryl groups of the diarylamine structure bond to each other and the one aryl group or the nitrogen atom bond to L via a single bond, the entire diarylamine structure corresponds to the aromatic ring in the requirement (a).

In the case where the two aryl groups of the diarylamine structure bond to each other and the one aryl group or the nitrogen atom links to L via a divalent linking group, the divalent linking group corresponds to the linking group in the requirement (b) and the entire diarylamine structure corresponds to the aromatic ring in the requirement (b).

In the case where the two aryl groups of the diarylamine structure do not bond to each other and the one aryl group bond to L via a single bond, the one aryl group bonding to L via a single bond corresponds to the aromatic ring in the requirement (a9.

In the case where the two aryl group of the diarylamine structure do not bond to each other and the nitrogen atom bond to L via a single bond, the nitrogen atom bonding to L via a single bond corresponds to the linking group in the requirement (b), and the two aryl groups correspond to the aromatic ring in the requirement (b).

In the case where the two aryl groups of the diarylamine structure do not bond to each other and the one aryl group links to L via a divalent linking group, the divalent linking group corresponds to the linking group in the requirement (b) and the one aryl group bonding to the divalent linking group corresponds to the aromatic ring in the requirement (b).

In the case where the two aryl groups of the diarylamine structure do not bond to each other and the nitrogen atom links to L via a divalent linking group, the divalent linking group and the nitrogen atom correspond to the linking group in the requirement (b), and the two aryl groups correspond to the aromatic ring in the requirement (b).

Preferably, the two D's ("the one D" and "the other D") satisfying the requirement (a) are groups represented by the following general formula (2).

General Formula (2)

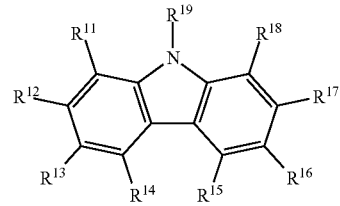

In the general formula (2), $R^{11}$ to $R^{19}$ each independently represent a hydrogen atom, a substituent or a bonding position to L, one of $R^{11}$ to $R^{19}$ is a bonding position to L. The bonding position to L is preferably $R^{19}$. The number of the substituents is not specifically limited, and among $R^{11}$ to $R^{19}$, all except the bonding position to L may be unsubstituted (hydrogen atom). In the case where two or more of $R^{11}$ to $R^{19}$ are substituents, the plural substituents may be the same as or different from each other. However, the group represented by the general formula (2) to be one D differs from the group represented by the general formula (2) to be the other D in point of at least one condition of the number of the substituents of $R^{11}$ to $R^{19}$, the position of the substituent and the structure of the substituent, so as to satisfy the requirement (a).

For example, preferably, in one D, at least one of $R^{11}$ to $R^{18}$ is a substituent, and in the other D, one of $R^{11}$ to $R^{18}$ corresponding to the substituent in the one D is a hydrogen atom, and more preferably, in one D, at least one of $R^{13}$ and $R^{16}$ is a substituent, and in the other D, one corresponding to a substituent in the one D of $R^{13}$ and $R^{16}$ is a hydrogen atom. Further preferably, in one D, both of $R^{11}$ and $R^{16}$ are substituents, and even more preferably, both of $R^{13}$ and $R^{16}$ are substituted or unsubstituted aryl groups. In the other D, even more preferably, all of $R^{11}$ to $R^{18}$ are hydrogen atoms.

In the following, specific examples of the group represented by the general formula (2) are shown. However, the groups represented by the general formula (2) usable in the present invention are not limitatively interpreted by these specific examples. In the groups shown below, the single line extending from a benzene ring and not expressed as a linking group to any other atom means a methyl group. In the following groups, the hydrogen atom bonding at 1 to 9-positions of the carbazole ring is replaced with L to bond to L. Preferably, the bonding position to L in the carbazole ring is a 9-position. As a combination of two D's satisfying the requirement (a), for example, combinations of two groups selected from the following groups can be employed here.

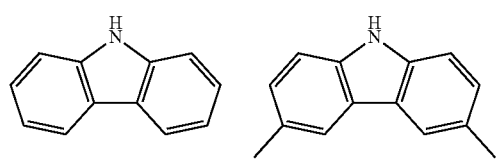

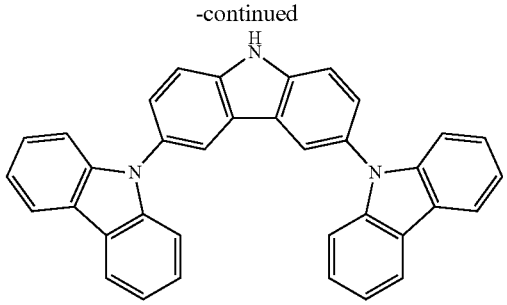

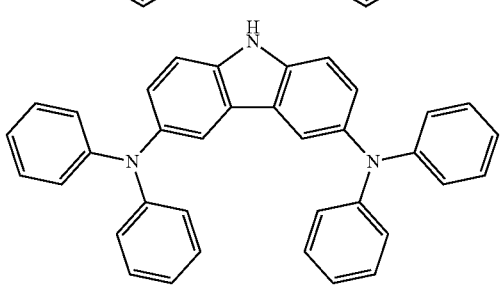

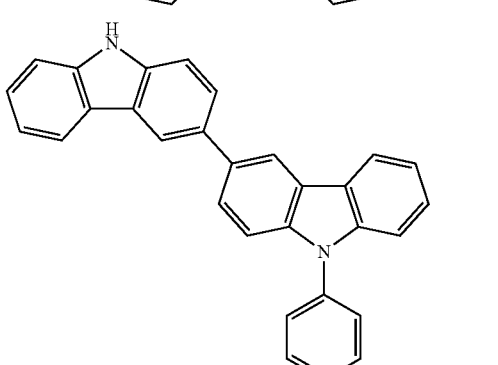

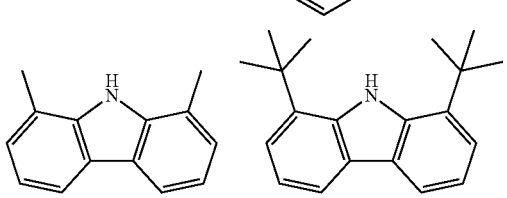

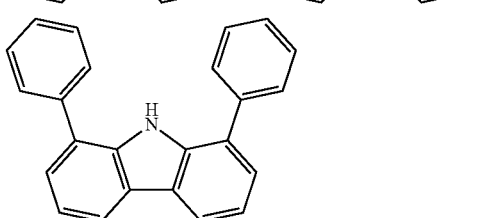

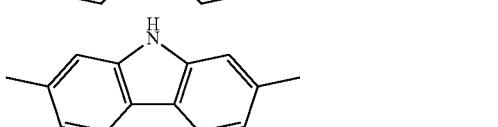

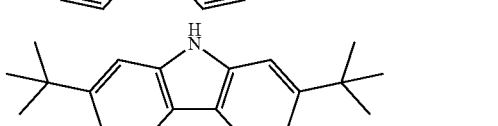

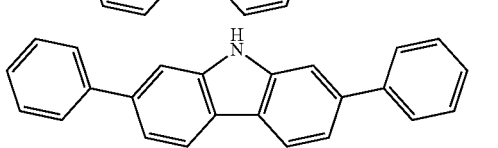

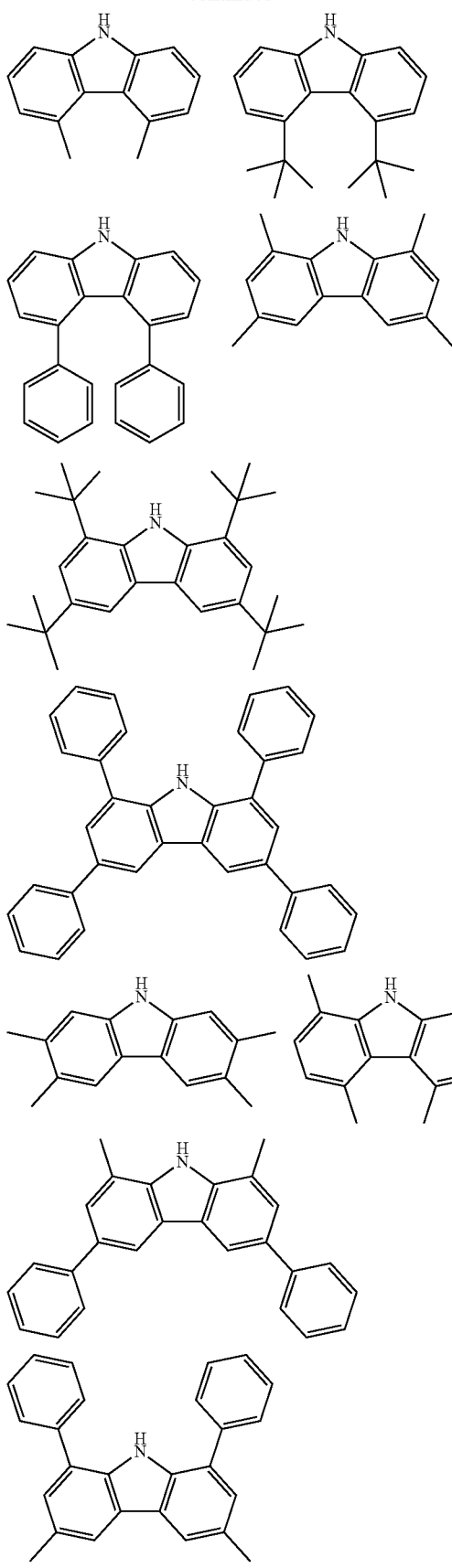
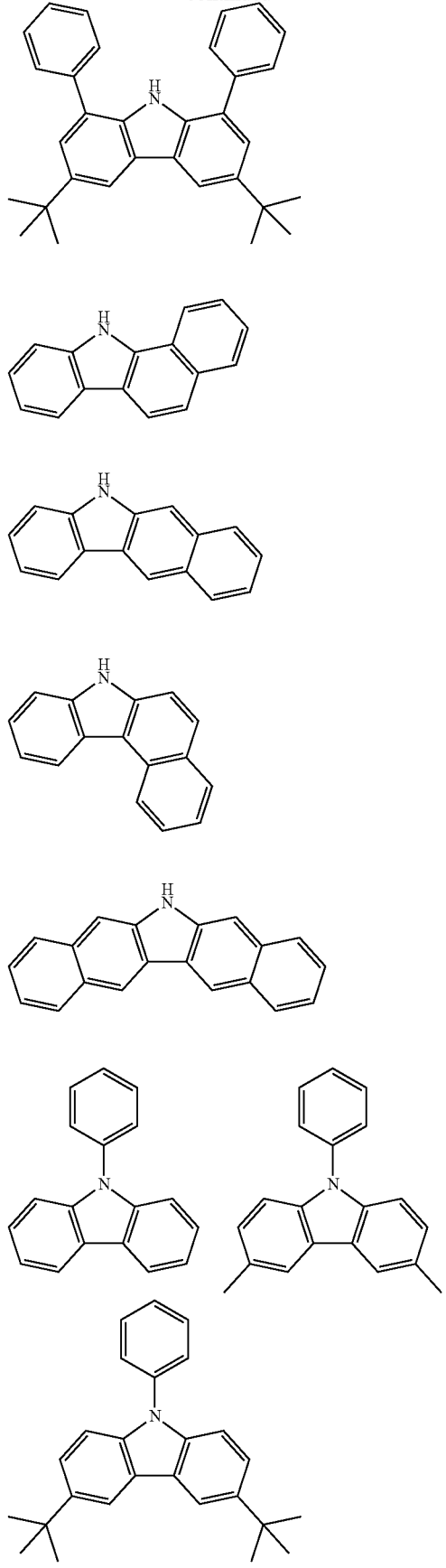

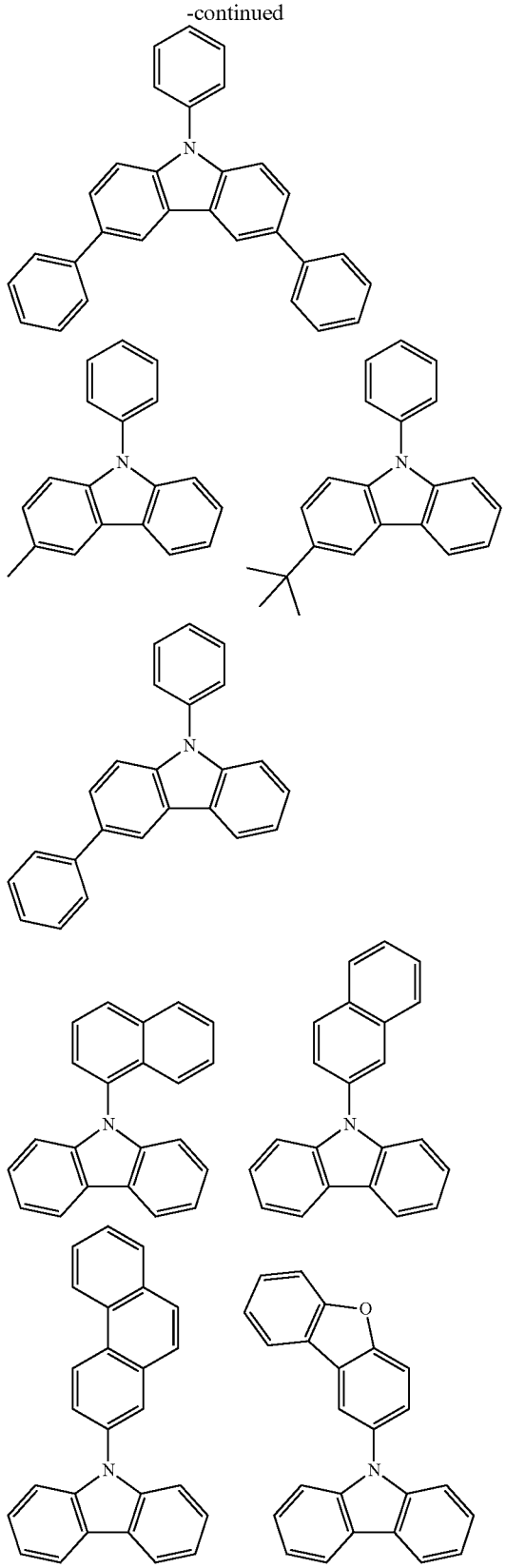

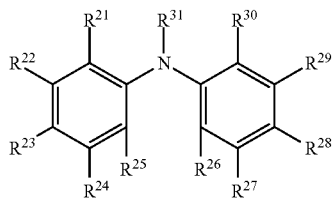

General Formula (3)

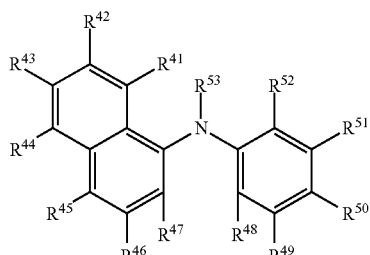

General Formula (4)

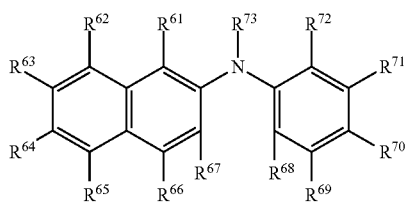

General Formula (5)

In the general formulae (3) to (5), $R^{21}$ to $R^{31}$, $R^{41}$ to $R^{53}$, and $R^{61}$ to $R^{73}$ each independently represent a hydrogen atom, a substituent, or a bonding position to L, one of $R^{21}$ to $R^{31}$, one of $R^{41}$ to $R^{53}$, and one of $R^{61}$ to $R^{73}$ each are a bonding position to L. The bonding position to L is preferably $R^{31}$, $R^{53}$, and $R^{73}$. In the case where one of $R^{21}$ to $R^{30}$, one of $R^{41}$ to $R^{32}$, and one of $R^{61}$ to $R^{72}$ are a bonding position to L, the group represented by any of the general formulae (3) to (5) is to satisfy the requirement (a). In the case where $R^{31}$, $R^{53}$, and $R^{73}$ are a bonding position to L, the group represented by any of the general formulae (3) to (5) is to satisfy the requirement (b), and the nitrogen atom corresponds to the linking group in the requirement (b), and the benzene ring and the naphthalene ring bonding to the nitrogen atom correspond to the aromatic rings in the requirement (b). The number of the substituents in the general formulae (3) to (5) is not specifically limited, and all of $R^{21}$ to $R^{31}$, $R^{41}$ to $R^{53}$, $R^{61}$ to $R^{67}$, and $R^{68}$ to $R^{72}$ excepting the bonding position to L can be unsubstituted (hydrogen atom). In the case where the general formulae (3) to (5) each have 2 or more substituents, the substituents may be the same as or different from each other. However, the group represented by any of the general formulae (3) to (5) to be one D and the group represented by any of the general formulae (3) to (5) to be the other D differ from each other in at least any group of $R^{21}$ to $R^{31}$, $R^{41}$ to $R^{53}$, and $R^{61}$ to $R^{73}$ in point of at least one condition of the number of the substituents, the position of the substituent, and the structure of the substituent, so as to satisfy the requirement (a) or the requirement (b).

Also preferably, the two D's ("the one D" and "the other D") satisfying the requirement (a) or (b) are groups represented by any of the following general formulae (3) to (5).

In the following, specific examples of the groups represented by any of the general formulae (3) to (5) are shown. However, the groups represented by any of the general formulae (3) to (5) usable in the present invention are not limitatively interpreted by these specific examples. In the groups shown below, the single line extending from a benzene ring and not expressed as a linking group to any other atom means a methyl group. The groups exemplified below bond to L by replacing the hydrogen atom of any one methine group (—CH═) constituting the cyclic structure, or the hydrogen atom bonding to the nitrogen atom with L. Preferably, the bonding position to L in these groups is the nitrogen atom. As a combination of two D's satisfying the requirement (a) or (b), for example, combinations of two groups selected from the following groups can be employed here.

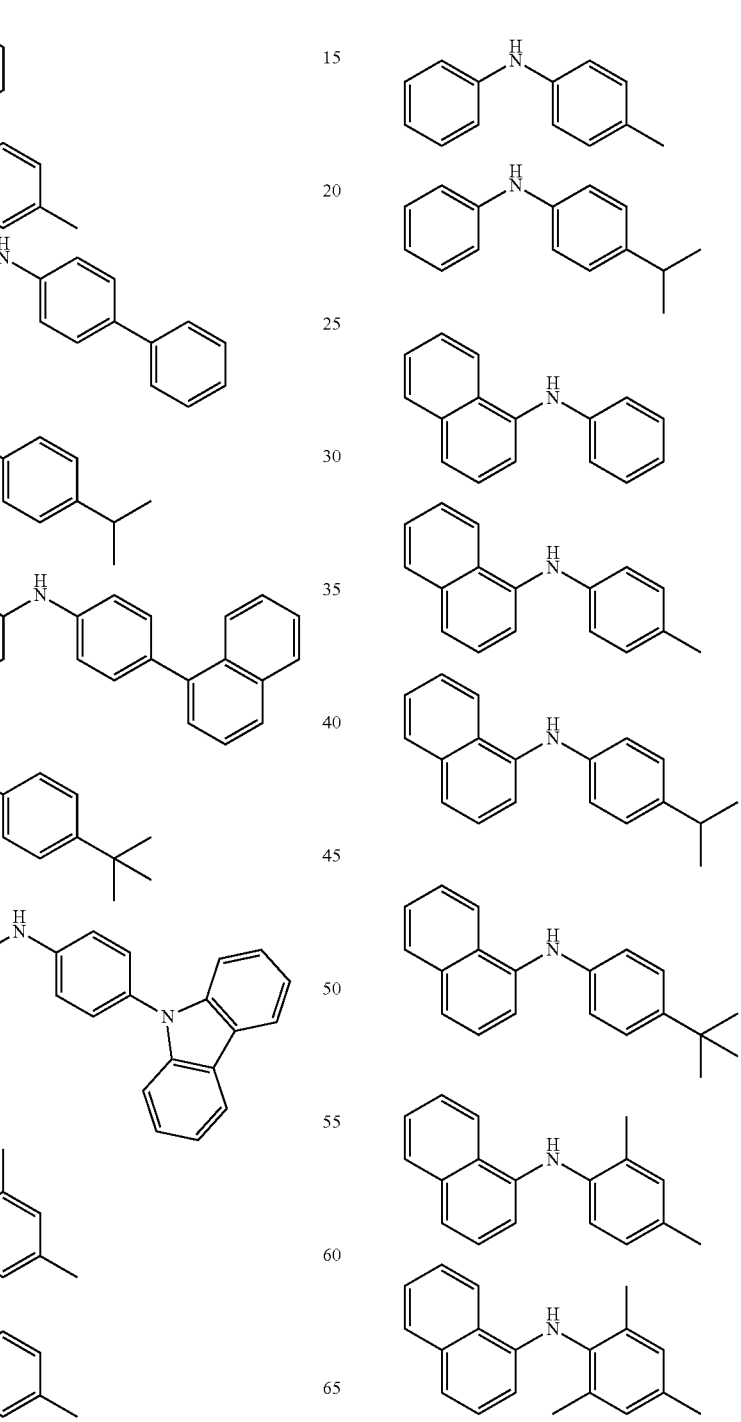

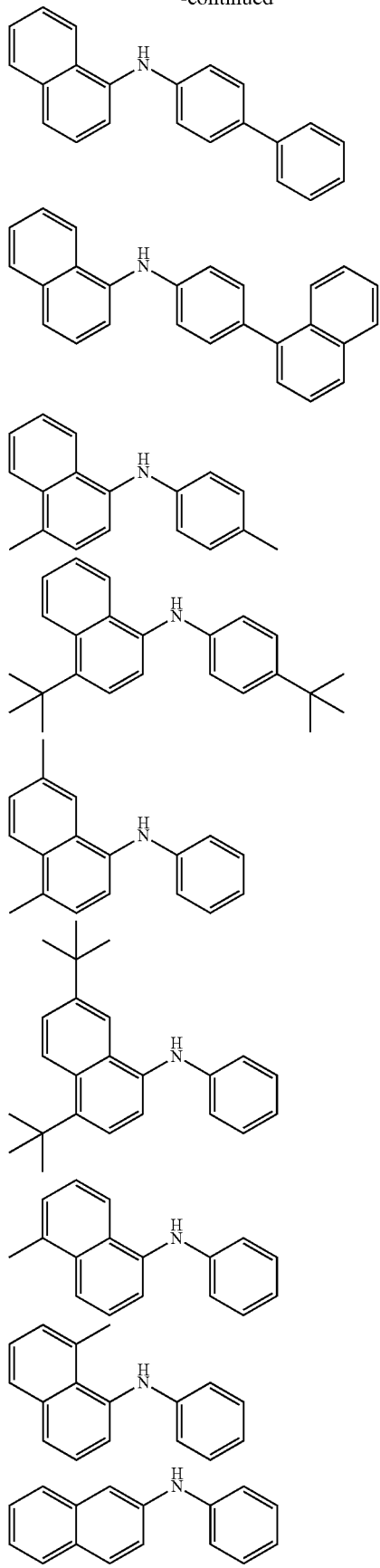
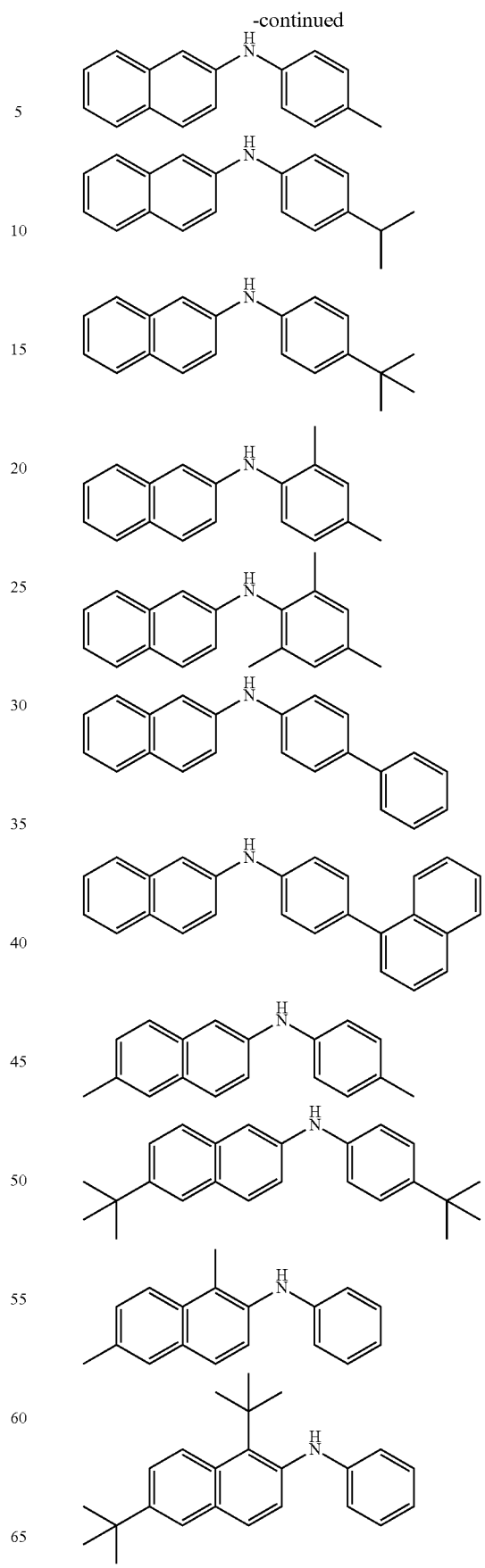

-continued

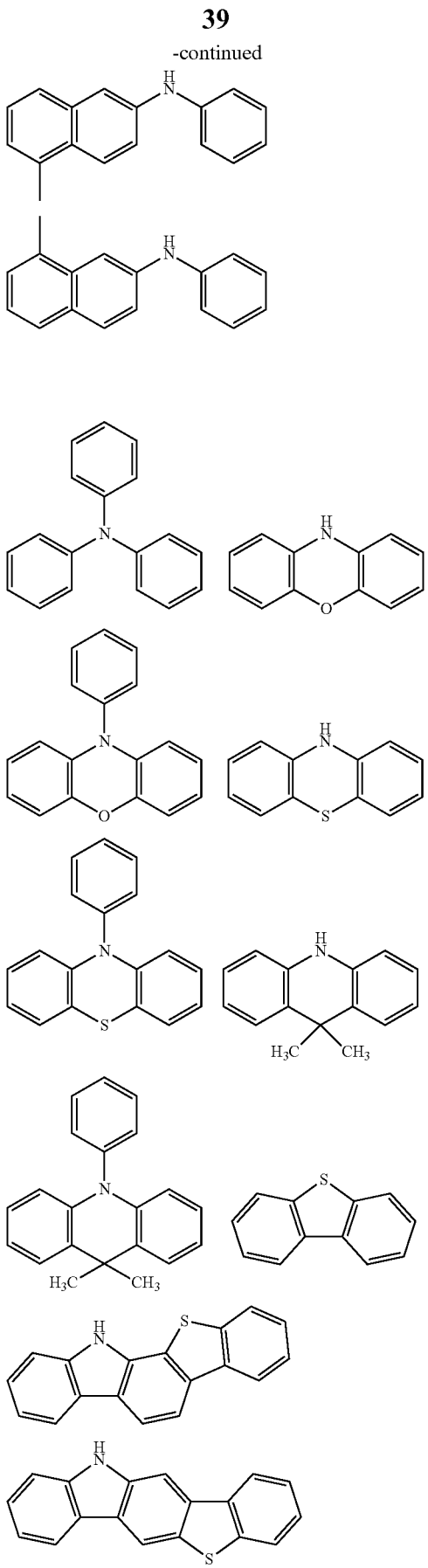

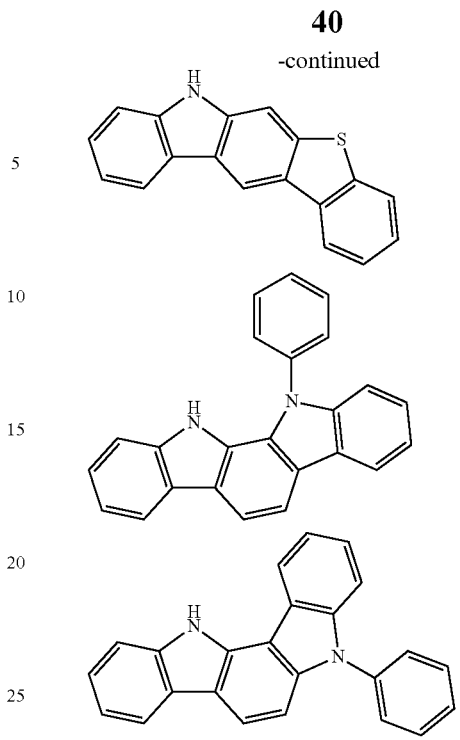

Also preferably, two D's ("one D" and "the other D") satisfying the requirement (a) or (b) each are a group represented by the following general formula (6).

General Formula (6)

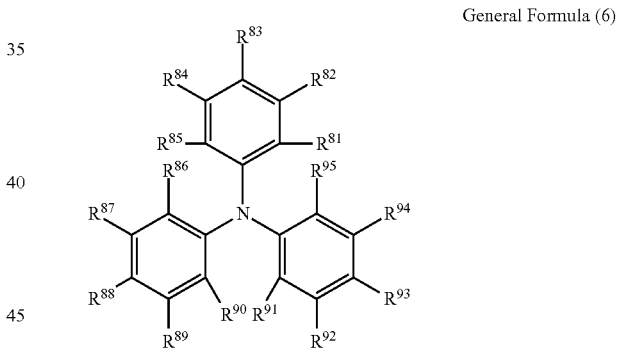

In the general formula (6), $R^{81}$ to $R^{95}$ each independently represent a hydrogen atom, a substituent or a bonding position to L, one of $R^{81}$ to $R^{95}$ is a bonding position to L. Preferably, $R^{83}$ is a bonding position to L. In the group represented by the general formula (6), the benzene ring having a bonding position to L among the three benzene rings bonding to the nitrogen atom corresponds to the aromatic ring in the requirement (a). Also, the benzene ring having a bonding position to L and the nitrogen atom can be considered to correspond to the linking group in the requirement (b) and the remaining two benzene rings can be considered to correspond to the aromatic ring in the requirement (b). The number of the substituents is not specifically limited, and among $R^{81}$ to $R^{95}$, all except the bonding position to L can be unsubstituted (hydrogen atom). In the case where two or more of $R^{81}$ to $R^{95}$ are substituents, the plural substituents may be the same or different from each other. However, at least in any group of $R^{81}$ to $R^{83}$, $R^{86}$ to $R^{90}$ and $R^{91}$ to $R^{95}$, the group represented by the general formula (6) to be one D and the group represented by the general formula (6) to be the other D differ from each other in point of at least one condition of the number of the substituents, the position of the substituent and the structure of the substituent so as to satisfy the requirement (a) or (b).

Also preferably, two D's ("one D" and "the other D") satisfying the requirement (a) each are a group represented by the following general formula (7).

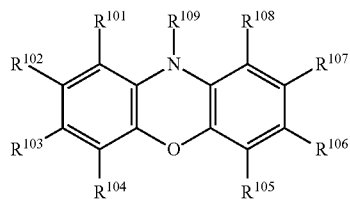

General Formula (7)

In the general formula (7), $R^{101}$ to $R^{109}$ each independently represent a hydrogen atom, a substituent or a bonding position to L, one of $R^{101}$ to $R^{109}$ is a bonding position to L. $R^{109}$ is preferably a bonding position to L. The number of the substituents is not specifically limited, and among $R^{101}$ to $R^{109}$, all except the bonding position to L can be unsubstituted (hydrogen atom). In the case where two or more of $R^{101}$ to $R^{109}$ are substituents, the plural substituents may be the same or different from each other. However, among $R^{101}$ to $R^{109}$, the group represented by the general formula (7) to be one D and the group represented by the general formula (7) to be the other D differ from each other in point of at least one condition of the number of the substituents, the position of the substituent and the structure of the substituent so as to satisfy the requirement (a).

Also preferably, two D's ("one D" and "the other D") satisfying the requirement (a) each are a group represented by the following general formula (8).

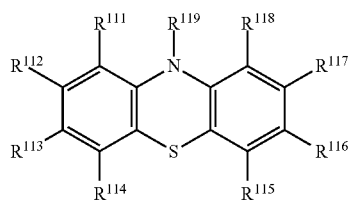

General Formula (8)

In the general formula (8), $R^{111}$ to $R^{119}$ each independently represent a hydrogen atom, a substituent or a bonding position to L, one of $R^{111}$ to $R^{119}$ is a bonding position to L. $R^{119}$ is preferably a bonding position to L. The number of the substituents is not specifically limited, and among $R^{111}$ to $R^{119}$, all except the bonding position to L can be unsubstituted (hydrogen atom). In the case where two or more of $R^{111}$ to $R^{119}$ are substituents, the plural substituents may be the same or different from each other. However, among $R^{111}$ to $R^{119}$, the group represented by the general formula (8) to be one D and the group represented by the general formula (8) to be the other D differ from each other in point of at least one condition of the number of the substituents, the position of the substituent and the structure of the substituent so as to satisfy the requirement (a).

Also preferably, two D's ("one D" and "the other D") satisfying the requirement (a) each are a group represented by the following general formula (9).

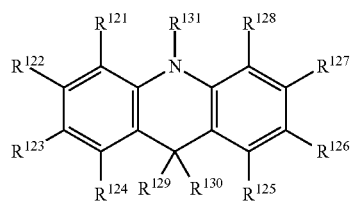

General Formula (9)

In the general formula (9), $R^{121}$ to $R^{131}$ each independently represent a hydrogen atom, a substituent or a bonding position to L, one of $R^{121}$ to $R^{131}$ is a bonding position to L. $R^{131}$ is preferably a bonding position to L. The number of the substituents is not specifically limited, and among $R^{121}$ to $R^{131}$, all except the bonding position to L can be unsubstituted (hydrogen atom). In the case where two or more of $R^{121}$ to $R^{131}$ are substituents, the plural substituents may be the same or different from each other. However, among $R^{121}$ to $R^{131}$, the group represented by the general formula (9) to be one D and the group represented by the general formula (9) to be the other D differ from each other in point of at least one condition of the number of the substituents, the position of the substituent and the structure of the substituent so as to satisfy the requirement (a).

Examples of the substituents that $R^{11}$ to $R^{19}$ in the general formula (2), $R^{21}$ to $R^{31}$ in the general formula (3), $R^{41}$ to $R^{53}$ in the general formula (4), $R^{61}$ to $R^{73}$ in the general formula (5), $R^{81}$ to $R^{95}$ in the general formula (6), $R^{101}$ to $R^{109}$ in the general formula (7), $R^{111}$ to $R^{119}$ in the general formula (8), and $R^{121}$ to $R^{131}$ in the general formula (9) can represent include a hydroxy group, a halogen atom, a cyano group, an alkyl group having 1 to 20 carbon atoms, an alkoxy group having 1 to 20 carbon atoms, an alkylthio group having 1 to 20 carbon atoms, an alkyl-substituted amino group having 1 to 20 carbon atoms, an acyl group having 2 to 20 carbon atoms, an aryl group having 6 to 40 carbon atoms, a heteroaryl group having 3 to 40 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an amide group, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, a trialkylsilylalkynyl group having 5 to 20 carbon atoms, and a nitro group. Among these specific examples, those that can be further substituted with a substituent can be substituted with, for example, a substituent of these specific examples. More preferred substituents are a substituted or unsubstituted alkyl group having 1 to 20 carbon atoms, an alkoxy group having 1 to 20 carbon atoms, a substituted or unsubstituted aryl group having 6 to 40 carbon atoms, a substituted or unsubstituted diarylamino group having 1 to 20 carbon atoms, and a substituted or unsubstituted carbazolyl group.

Among D's, the other groups than those satisfying the requirement (a) or (b) may be any ones having a negative Hammett's $\sigma_p$ value, and, with no other specific limitations, preferably contain a diarylamine structure (provided that the two aryl groups constituting the diarylamine structure may bond to each other), more preferably contains a diarylamino group (provided that the two aryl groups constituting the diarylamino group may bond to each other), and are even more preferably any of the groups represented by the general formulae (2) to (9). Regarding the description, the preferred ranges and the specific examples of these structures and groups, reference may be made to the description, the preferred ranges and the specific examples of the diarylamine structure, the diarylamino group and the groups represented by the general formulae (2) to (9) for the two D's satisfying the requirement (a) or (b). However, regarding these references, the description relating to the requirement (a) or (b) is not included in the matters to be referred to.

Preferably, the compound represented by the general formula (1) is a compound represented by the following general formula (10).

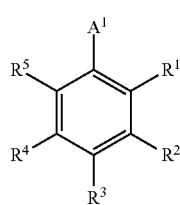

General Formula (10)

In the general formula (10), A1 represents a group having a positive Hammett's $\sigma_p$ value. $R^1$ to $R^5$ each represent a hydrogen atom, a group having a positive Hammett's $\sigma_p$ value, or a group having a negative Hammett's $\sigma_p$ value, and at least two of $R^1$ to $R^5$ each are a group having a negative Hammett's $\sigma_p$ value (except a phenyl group). When one or more of $R^1$ to $R^5$ each are a group having a positive Hammett's $\sigma_p$ value, the group having a positive Hammett's $\sigma_p$ value represented by A1 and the group having a positive Hammett's $\sigma_p$ value of $R^1$ to $R^5$ may be the same as or different from each other.

Two groups having a negative Hammett's $\sigma_p$ value of $R^1$ to $R^5$ preferably satisfy the following requirement (a) or the requirement (b).

Requirement (a)

The two groups having a negative Hammett's $\sigma_p$ value both have an aromatic ring that contains an atom bonding to L, and the aromatic ring is common between the two groups having a negative Hammett's $\sigma_p$ value, but the two differ from each other in point of at least one condition of the number of the substituents on the aromatic ring, the substitution site of the aromatic ring substituted with the substituent, and the structure of the substituent on the aromatic ring.

Requirement (b)

The two groups having a negative Hammett's $\sigma_p$ value both have a linking group bonding to L and one or more aromatic rings bonding to the linking group, and in the case where the two groups having a negative Hammett's $\sigma_p$ value each have one aromatic ring bonding to the linking group, the linking group and the aromatic ring bonding to the linking group are common between the two groups having a negative Hammett's $\sigma_p$ value, but the two differ from each other in point of at least one condition of the number of the substituents on the aromatic ring, the substitution site of the aromatic ring substituted with the substituent, and the structure of the substituent on the aromatic ring. In the case where the two groups having a negative Hammett's $\sigma_p$ value each have 2 or more aromatic rings bonding to the linking group, the linking group, the number of the aromatic rings bonding to the linking group and the plural aromatic rings are common between the two groups having a negative Hammett's $\sigma_p$ value, but at least one combination of the aromatic rings common between the two groups having a negative Hammett's $\sigma_p$ value differs in point of at least one condition of the number of the substituents on the aromatic ring, the substitution site of the aromatic ring substituted with the substituent, and the structure of the substituent on the aromatic ring.

Regarding the description, the preferred ranges and the specific examples of the group having a positive Hammett's $\sigma_p$ value represented by A1 and $R^1$ to $R^5$, the group having a negative Hammett's $\sigma_p$ value represented by $R^1$ to $R^5$, and the two groups having a negative Hammett's $\sigma_p$ value of $R^1$ to $R^5$, and regarding the description of the requirements (a) and (b), reference may be made to the description, the preferred ranges and the specific examples of the group having a positive Hammett's $\sigma_p$ value represented by A in the general formula (1), the group having a negative Hammett's $\sigma_p$ value represented by D, and two of the plural D's, as well as to the description relating to the requirements (a) and (b) given hereinabove.

Preferably, the number of the groups having a positive Hammett's $\sigma_p$ value of $R^1$ to $R^5$ is 0 to 3, more preferably 0 to 2, even more preferably 0 or 1, and most preferably 0. Preferably, the number of the groups having a negative Hammett's $\sigma_p$ value of $R^1$ to $R^5$ is 2 to 5, more preferably 3 to 5, even more preferably 4 or 5, and most preferably 5. Among $R^1$ to $R^5$, the number of a combination of two groups satisfying the requirement (a) or the requirement (b) may be 1 or 2. Preferably, the combination of the two groups satisfying the requirement (a) or the requirement (b) is a combination of those in a point-symmetric position relative to the benzene ring in the general formula (10). Specifically, it is preferable that one or both of a combination of $R^1$ and $R^4$ and a combination of $R^2$ and $R^5$ satisfy the requirement (a) or the requirement (b).

The compound represented by the general formula (1) is also preferably a compound represented by the following general formula (11).

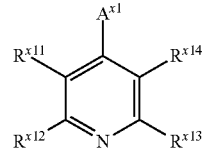

General Formula (11)

In the general formula (11), $A^{X1}$ represents a group having a positive Hammett's $\sigma_p$ value. $R^{X11}$ to $R^{X14}$ each represent a hydrogen atom, a group having a positive Hammett's $\sigma_p$ value, or a group having a negative Hammett's $\sigma_p$ value, and at least two of $R^{X11}$ to $R^{X14}$ each are a group having a negative Hammett's $\sigma_p$ value (except a phenyl group). When one or more of $R^{X11}$ to $R^{X14}$ each are a group having a positive Hammett's $\sigma_p$ value, the group having a positive Hammett's $\sigma_p$ value represented by $A^{X1}$ and the group having a positive Hammett's $\sigma_p$ value of $R^{X11}$ to $R^{X14}$ may be the same as or different from each other.

Two groups having a negative Hammett's $\sigma_p$ value of $R^{X11}$ to $R^{X14}$ preferably satisfy the above-mentioned requirement (a) or requirement (b).

Regarding the description, the preferred ranges and the specific examples of the group having a positive Hammett's $\sigma_p$ value represented by $A^{X1}$ and $R^{X11}$ to $R^{X14}$, the group having a negative Hammett's $\sigma_p$ value represented by $R^{X11}$ to $R^{X14}$, and the two groups having a negative Hammett's $\sigma_p$ value of $R^{X11}$ to $R^{X14}$, and regarding the description of the requirements (a) and (b), reference may be made to the description, the preferred ranges and the specific examples of the group having a positive Hammett's $\sigma_p$ value represented by A in the general formula (1), the group having a negative Hammett's $\sigma_p$ value represented by D, and two of the plural D's, as well as to the description relating to the requirements (a) and (b) given hereinabove.

Preferably, the number of the groups having a positive Hammett's $\sigma_p$ value of $R^{X11}$ to $R^{X14}$ is 0 to 2, more preferably 0 or 1, and most preferably 0. Preferably, the number of the groups having a negative Hammett's $\sigma_p$ value of $R^{X11}$ to $R^{X14}$ is 2 to 4, more preferably 3 or 4, even more preferably 4. Among $R^{X11}$ to $R^{X14}$, the number of a combination of two groups satisfying the requirement (a) or the requirement (b) may be 1 or 2.

Also preferably, the second organic compound is a compound represented by the following general formula (12). An organic electroluminescent device produced using the compound represented by the general formula (12) as a second organic compound can have an enhanced light emission efficiency and a prolonged lifetime.

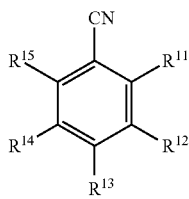

General Formula (12)

In the general formula (12), at least three of $R^{11}$ to $R^{15}$ are selected from a substituted or unsubstituted diarylamino group (provided that the two aryl groups constituting the diarylamino group may bond to each other) and a halogen atom, and all the selected groups are not the same, and at least one is a substituted or unsubstituted diarylamino group (provided that the two aryl groups constituting the diarylamino group may bond to each other), and the remaining 0 to 2 each represent a hydrogen atom, a substituted or unsubstituted aryl group, or a cyano group.

For example, the compound can include a case where at least three of $R^{11}$ to $R^{15}$ each are a substituted or unsubstituted amino group and some of $R^{11}$ to $R^{15}$ each are a halogen atom. In that case, all the substituted or unsubstituted diarylamino group existing in the molecule are not the same. The compound can also include a case where at least two of $R^{11}$ to $R^{15}$ each are a substituted or unsubstituted diarylamino group and at least one of $R^{11}$ to $R^{15}$ is a halogen atom. In that case, all the substituted or unsubstituted diarylamino group existing in the molecule can be the same or can be different. In still another case of the compound, at least one of $R^{11}$ to $R^{15}$ is a substituted or unsubstituted diarylamino group and at least two of $R^{11}$ to $R^{15}$ each are a halogen atom. In that case, all the halogen atoms existing in the molecule can be the same or can be different.

Regarding the description and the preferred range of the diarylamino group that $R^{11}$ to $R^{15}$ can represent, reference may be made to the description and the preferred range of the diarylamine structure that the two D's satisfying the above-mentioned requirement (a) or (b) can represent. Regarding the specific structure, reference may be made to the description relating to the above-mentioned general formulae (2) to (5) an (7) to (9). Here, $R^{19}$ in the general formula (2), $R^{31}$ in the general formula (3), R in the general formula (4), $R^{73}$ in the general formula (5), $R^{109}$ in the general formula (7), $R^{119}$ in the general formula (8), and $R^{131}$ in the general formula (9) each are a bonding position. In particular, the diarylamino group that $R^{11}$ to $R^{15}$ can represent is preferably a group represented by the general formula (2) (where $R^{19}$ is a bonding position).

The substituent with which the two aryl groups to constitute the diarylamino group for $R^{11}$ to $R^{15}$ can be substituted is preferably a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group, a substituted or unsubstituted alkyl group, a substituted or unsubstituted alkoxy group, or a substituted or unsubstituted aryloxy group. These groups can be further substituted with any of these substituents.

Specific examples of the substituted diarylamino group that $R^{11}$ to $R^{15}$ can represent include a 3-methylcarbazol-9-yl group, a 3,6-dimethylcarbazol-9-yl group, a 3-ethylcarbazol-9-yl group, a 3,6-diethylcarbazol-9-yl group, a 3-t-butylcarbazol-9-yl group, a 3,6-di-t-butylcarbazol-9-yl group, a 3-phenylcarbazol-9-yl group, a 3,6-diphenylcarbazol-9-yl group, a 3-(carbazol-9-yl)carbazol-9-yl group, and a 3,6-bis(carbazol-9-yl)carbazol-9-yl group.

When $R^{11}$ to $R^{15}$ each are a substituted or unsubstituted carbazol-9-yl group, preferably the substituted or unsubstituted carbazol-9-yl group is not substituted with a substituted or unsubstituted diarylamino group in point of the light emission efficiency and the lifetime of organic electroluminescent devices. The substituent for the carbazol-9-yl group is preferably a substituted or unsubstituted aryl group, a substituted or unsubstituted heteroaryl group, a substituted or unsubstituted diarylamino group, a substituted or unsubstituted diheteroarylamino group, a substituted or unsubstituted arylheteroarylamino group, a substituted or unsubstituted alkyl group, a substituted or unsubstituted alkoxy group, or a substituted or unsubstituted aryloxy group.

In the case where the compound has two or more substituted or unsubstituted diarylamino groups in the molecule and where the groups differ, the number of the kinds of the substituted or unsubstituted diarylamino groups existing in the molecule is preferably 2 or 3, more preferably 2. For example, in the case where three of $R^{11}$ to $R^{15}$ each are a substituted or unsubstituted diarylamino group, preferably, two of these are the same and one differs. Examples thereof include a case where $R^{11}$ and $R^{15}$ are the same and $R^{12}$ differs, a case where $R^{11}$ and $R^{14}$ are the same and $R^{12}$ differs, a case where $R^{12}$ and $R^{14}$ are the same and $R^5$ differs, and a case where $R^{12}$ and $R^{14}$ are the same and $R^{11}$ differs. For example, in the case where four of $R^{11}$ to $R^{15}$ each are a substituted or unsubstituted diarylamino group, preferably, three of them are the same and one differs or two of them are the same and the other two are the same. Examples thereof include a case where $R^{11}$ and $R^{15}$ are the same and $R^{12}$ and $R^{14}$ are the same, a case where $R^{11}$ and $R^{12}$ are the same and $R^{14}$ and $R^{15}$ are the same, a case where $R^{11}$ and $R^{14}$ are the same and $R^{12}$ and $R^5$ are the same, a case where $R^{12}$ and $R^{14}$ and $R^{15}$ are the same and $R^{11}$ alone differs, and a case where $R^{11}$ and $R^{14}$ and $R^{15}$ are the same and $R^{12}$ alone differs. In the case where all of $R^{11}$ to $R^{15}$ each are a substituted or unsubstituted diarylamino group, preferably, four of them are the same and one differs, or three are the same and two differ. Examples thereof include $R^{11}$ and $R^{13}$ and $R^{15}$ are the same and $R^{12}$ and $R^{14}$ are the same, a case where $R^{11}$ and $R^{12}$ and $R^{11}$ are the same and $R^{14}$ and $R^{15}$ are the same, a case where $R^{12}$ and $R^{11}$ and $R^{14}$ are the same and $R^{11}$ and $R^{15}$ are the same, and a case where $R^{11}$ and $R^{12}$ and $R^{14}$ are the same and $R^{11}$ and $R^{15}$ are the same.

In the case where the compound has two or more different kinds of substituted or unsubstituted diarylamino groups in the molecule, the difference may be a difference whether or not the diarylamino group has a substituent, or may be a difference in the point of the kind of the substituent bonding to the diarylamino group, or may be a difference in the point of the bonding site of the substituent bonding to the diarylamino group. Preferred is a difference whether or not the diarylamino group has a substituent, or a difference in the point of the kind of the substituent bonding to the diarylamino group. One example of the difference in the point of the kind of the substituent bonding to the diarylamino group is an embodiment having a carbazol-9-yl group substituted with an alkyl group and a carbazol-9-yl group substituted with an aryl group in the molecule. One example of the difference in the point of the bonding site of the substituent bonding to the diarylamino group is an embodiment having a carbazol-9-yl group substituted with an alkyl group at the 3-position and the 6-position and a carbazol-9-yl group substituted with an alkyl group at the 3-position alone in the molecule.

The halogen atom that $R^{11}$ to $R^{15}$ can represent may be any of a fluorine atom, a chlorine atom, a bromine atom and an iodine atom, but is preferably a fluorine atom.

The remaining 0 to 2 of $R^{11}$ to $R^{15}$ each represent a hydrogen atom, a substituted or unsubstituted aryl group or a cyano group. Preferred is a substituted or unsubstituted aryl group, or a cyano group. In the case where the compound has such remaining $R^{11}$ to $R^{15}$ (that is, when the number of the remaining groups is 1 or 2), the remaining group may be any of $R^{11}$ to $R^{15}$, but preferably includes at least one of $R^{12}$, $R^{13}$ and $R^{14}$, more preferably one or two of $R^{12}$, $R^{13}$ and $R^{14}$, even more preferably the remaining group at least includes $R^{13}$. Regarding the description and the preferred range of the aryl group that the remaining one of $R^{11}$ to $R^{15}$ can represent, reference may be made to the description and the preferred range of the aryl group of the diarylamine structure that the two D's satisfying the above-mentioned requirement (a) or (b) can represent. The aryl group that the remaining $R^{11}$ to $R^{15}$ can represent may be substituted, and the substituent is preferably an alkyl group or an aryl group. The aryl group that the remaining $R^{11}$ to $R^{15}$ can represent includes, for example, a phenyl group substituted with an alkyl group or an aryl group at the 4-position, or a phenyl group substituted with an alkyl group or an aryl group at the 3-position and the 5-position.

A preferred compound group of the compounds represented by the general formula (12) is a group of compounds of the formula where at least three of $R^{11}$ to $R^{15}$ each are a substituted or unsubstituted diarylamino group, and none of $R^{11}$ to $R^{15}$ is a halogen atom.

A preferred compound group of the compounds represented by the general formula (12) is a group of compounds of the formula where at least three of $R^{11}$ to $R^{15}$ each are a substituted or unsubstituted carbazol-9-yl group. Among these, a more preferred compound group is a group of the compounds where all the carbazol-9-yl groups existing in the molecule are not substituted with a substituted or unsubstituted diarylamino group (provided that the two aryl groups constituting the diarylamino group may bond to each other, and, for example, a carbazol-9-yl group is included). The compounds of the type are preferred in point of the light emission efficiency and the lifetime, as compared with compounds having a carbazol-9-yl group substituted with a substituted or unsubstituted diarylamino group. A group of the compounds of the type includes compounds represented by the following general formula (13).

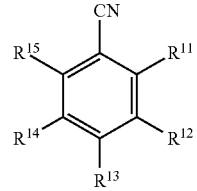

General Formula (13)

In the general formula (13), at least three of $R^{11}$ to $R^{15}$ each represent a substituted or unsubstituted carbazol-9-yl group, and all these at least three substituted or unsubstituted carbazol-9-yl groups are not the same, and are not substituted with a substituted or unsubstituted diarylamino group (provided that the two aryl groups constituting the diarylamino group may bond to each other), the remaining 0 to 2 each represent a hydrogen atom, a substituted or unsubstituted aryl group, a halogen atom, or a cyano group.

Among the compounds represented by the general formula (13), for example, a group of compounds in which the remaining 0 to 2 each are a substituted or unsubstituted aryl group or a cyano group can be selected, and further, a group of compounds in which the remaining 0 to 2 each are a substituted or unsubstituted aryl group can also be selected.

Among the compound represented by the general formula (13), for example, a group of compounds in which $R^{13}$ is a hydrogen atom, a substituted or unsubstituted aryl group, a halogen atom or a cyano group, or a group of compounds in which $R^{13}$ is a hydrogen atom, a substituted or unsubstituted aryl group or a cyano group, or a group of compounds in which $R^{13}$ is a substituted or unsubstituted aryl group, or a cyano group, or a group of compounds in which $R^{13}$ is a substituted or unsubstituted aryl group can also be selected.

Among the compounds represented by the general formula (13), a group of compounds in which at least three of $R^{11}$ to $R^{15}$ each represent a substituted carbazol-9-yl group, and at least any one substituent of those groups (one substituent of the carbazol-9-yl groups) differs can also be selected.

Among the compounds represented by the general formula (13), a group of compounds in which at least one of $R^{11}$ to $R^{15}$ is a substituted carbazol-9-yl group, and at least one of $R^{11}$ to $R^{15}$ is an unsubstituted carbazol-9-yl group can also be selected.

Among the compounds represented by the general formula (13), a group of compounds in which $R^{11}$ and $R^{15}$ are the same, a group of compounds in which $R^{12}$ and $R^{14}$ are the same, a group of compounds in which $R^{11}$ and $R^{12}$ and $R^{15}$ are the same, and a group of compounds in which $R^{11}$ and $R^{12}$ and $R^{14}$ are the same can also be selected.

Also preferably, the second organic compound is a compound represented by the following general formula (14).

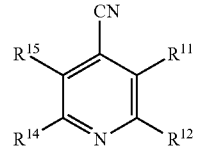

General Formula (14)

In the general formula (14), at least three of $R^{11}$, $R^{12}$, $R^{14}$ and $R^{15}$ are selected from a substituted or unsubstituted diarylamino group (provided that the two aryl groups constituting the diarylamino group may bond to each other) and a halogen atom, and all the selected groups are not the same, and at least one is a substituted or unsubstituted diarylamino group (provided that the two aryl groups constituting the diarylamino group may bond to each other), and the remaining 0 to 1 represents a hydrogen atom, a substituted or unsubstituted aryl group, or a cyano group.

Regarding the description and the preferred ranges of $R^{11}$, $R^{12}$, $R^{14}$ and $R^{15}$ in the general formula (14), reference may be made to the corresponding description of the general formula (12).

A group of specific compounds usable as a delayed fluorescent material for the second organic compound includes, for example, a group of compounds represented by the following general formula.

General Formula (15)

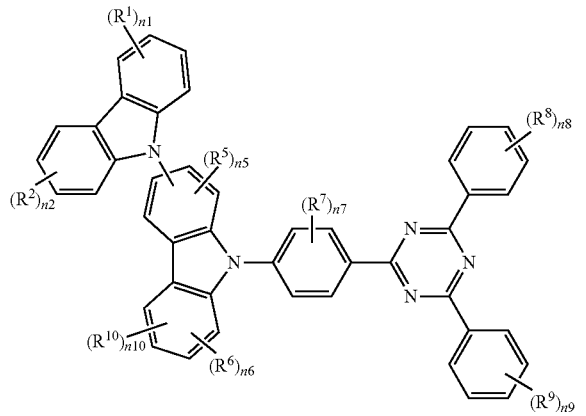

In the general formula (15), $R^1$ and $R^2$ each independently represent a substituted or unsubstituted carbazolyl group, a substituted or unsubstituted aryl group, a substituted or unsubstituted heteroaryl group, a substituted or unsubstituted alkyl group, or a substituted or unsubstituted cycloalkyl group, $R^5$ and $R^6$ each independently represent a substituted or unsubstituted alkyl group, $R^7$, $R^8$ and $R^9$ each independently represent a substituted or unsubstituted aryl group, a substituted or unsubstituted alkyl group, or a substituted or unsubstituted carbazolyl group, $R^{10}$ represents a carbazolyl group, and the carbazolyl group may be substituted with a substituted or unsubstituted carbazolyl group, a substituted or unsubstituted aryl group, a substituted or unsubstituted heteroaryl group, a substituted or unsubstituted alkyl group, or a substituted or unsubstituted cycloalkyl group, n1, n2, n6 and n7 each independently represent an integer of any of 0 to 4, n5 represents an integer of any of 0 to 3, n8 and n9 each independently represent an integer of any of 0 to 5. n10 represents 0 or 1, and when n1, n2 and n5 to n9 each are an integer of 2 or more, plural $R^1$'s, $R^2$'s and $R^5$'s to $R^9$'s corresponding to n1, n2 and n5 to n9, respectively, each may be the same as or different from each other.

Regarding the detailed description and the preferred range of the general formula (15), and regarding specific examples of the compound, reference may be made to the relating description in WO2014/051184 that is referred to herein as a part of the present description.

Specific examples of a group of other compounds usable as a delayed fluorescent material for the second organic compound include, for example, a group of compounds represented by the following general formula.

D-A-D  General Formula (16)

In the general formula (16), A represents a divalent group having a structure represented by any of the following general formulae (2-a) to (5-a) (provided that the hydrogen atom in the structure of the general formulae (2-a) to (5-a) may be substituted with a substituent).

General Formula (2-a)

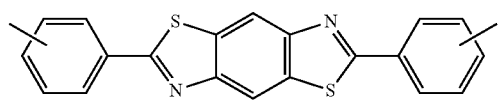

General Formula (3-a)

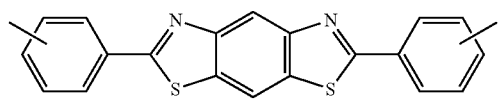

General Formula (4-a)

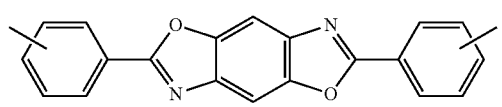

General Formula (5-a)

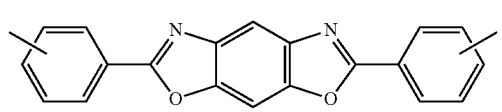

In the general formula (16), two D's each independently represent a group having a structure selected from the following group (provided that the hydrogen atom in the structure may be substituted with a substituent).

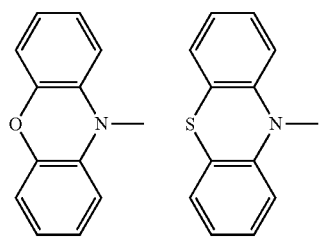

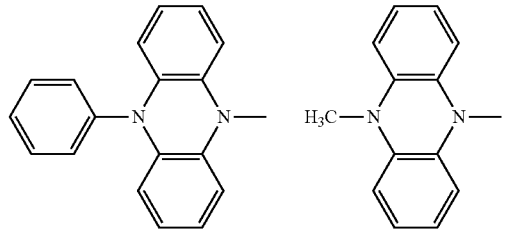

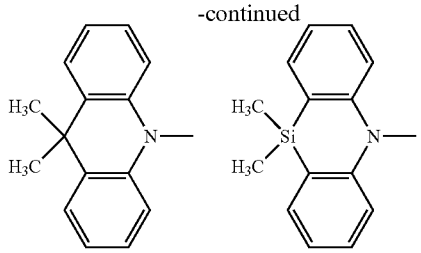

Regarding the detailed description and the preferred range of the general formula (16), and regarding specific examples of the compound, reference may be made to the relating description in WO2014/126200 that is referred to herein as a part of the present description.

Specific examples of a group of other compounds usable as a delayed fluorescent material for the second organic compound include, for example, a group of compounds represented by the following general formula.

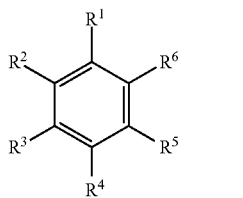

General Formula (17)

In the general formula (17), $R^1$, $R^3$ and $R^5$ each represent a cyano group, or $R^1$, $R^2$, $R^4$ and $R^5$ each represent a cyano group, and the remaining $R^1$ to $R^6$ each independently represent a group represented by any of the following general formula (2-b) to (8-b).

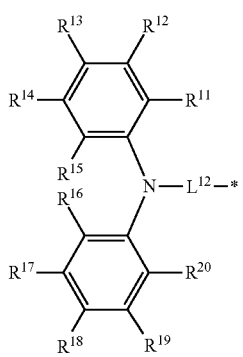

General Formula (2-b)

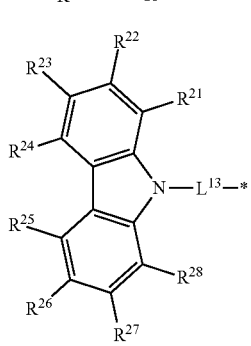

General Formula (3-b)

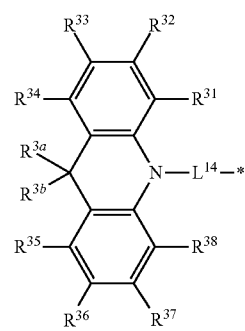

General Formula (4-b)

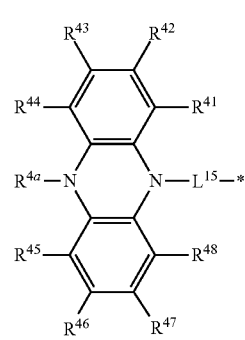

General Formula (5-b)

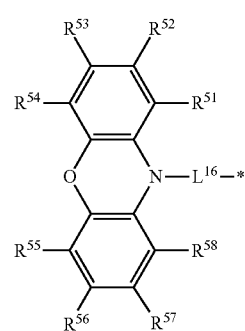

General Formula (6-b)

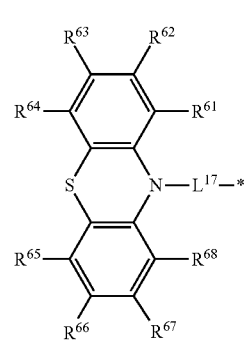

General Formula (7-b)

-continued

General Formula (8-b)

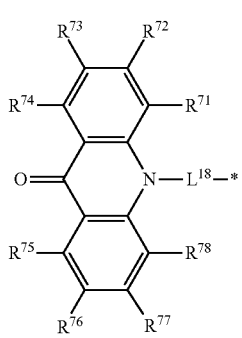

In the general formulae (2-b) to (8-b), $L^{12}$ to $L^{18}$ each represent a single bond, or a substituted or unsubstituted arylene group, * represents a bonding position to the benzene ring in the general formula (1). $R^{11}$ to $R^{20}$, $R^{21}$ to $R^{28}$, $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each independently represent a hydrogen atom or a substituent. $R^{11}$ and $R^{12}$, $R^{12}$ and $R^{13}$, $R^{13}$ and $R^{14}$, $R^{14}$ and $R^{15}$, $R^{16}$ and $R^{17}$, $R^{17}$ and $R^{18}$, $R^{18}$ and $R^{19}$, $R^{19}$ and $R^{20}$, $R^{21}$ and $R^{22}$, $R^{22}$ and $R^{23}$, $R^{23}$ and $R^{24}$, $R^{24}$ and $R^{25}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may bond to each other to form a cyclic structure.

Regarding the detailed description, the preferred range and specific examples of the compound of the general formula (17), reference may be made to the relating description in WO2015/129715 that is referred to herein as a part of the present description.

Specific examples of a group of other compounds usable as a delayed fluorescent material for the second organic compound include, for example, a group of compounds represented by the following general formula.

General Formula (18)

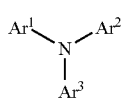

In the general formula (18), $Ar^1$ to $Ar^3$ each independently represent a substituted or unsubstituted aryl group, and at least one of $Ar^1$ to $Ar^3$ is independently a carbazolyl group substituted with a group containing an electron-attracting group at the N-position.

Regarding the detailed description and the preferred range of the general formula (18) and specific examples of the compound thereof, reference may be made to the relating description in WO2015/133501 that is referred to herein as a part of the present description.

Specific examples of a group of other compounds usable as a delayed fluorescent material for the second organic compound include, for example, a group of compounds represented by the following general formula.

General Formula (19)

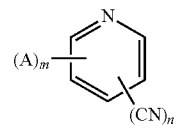

In the general formula (19), m and n each independently represent an integer of 1 to 3, m+n is 2 to 4; A represents an electron-donating substituted heteroaryl group, and at least one substituent on the aromatic hetero ring is an electron-attracting group; and when m is 2 or more, plural A's may be the same or different.

Regarding the detailed description and the preferred range of the general formula (19) and specific examples of the compound thereof, reference may be made to the relating description in WO2015/137136 that is referred to herein as a part of the present description.

Specific examples of a group of other compounds usable as a delayed fluorescent material for the second organic compound include, for example, a group of compounds represented by the following general formula.

General Formula (20)

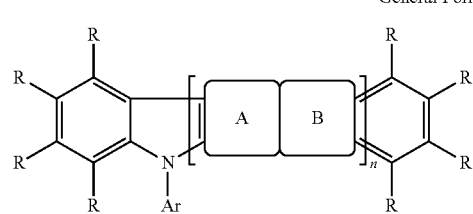

In the general formula (20), the ring A represents an aromatic ring represented by the following formula (1a) that is condensed with the neighboring ring at an arbitrary position, the ring B represents a hetero ring represented by the following formula (1b) that is condensed with the neighboring ring at an arbitrary position. Ar in the formulae (20) and (1b) independently represents an aromatic hydrocarbon group or an aromatic heterocyclic group. R in the formulae (20) and (1a) independently represents a hydrogen atom or a monovalent substituent, and the neighboring substituents may integrally form a ring. n represents an integer of 1 or more and 4 or less.

(1a)

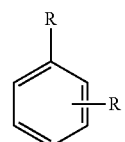

(1b)

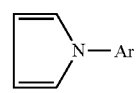

Regarding the detailed description and the preferred range of the general formula (20) and specific examples of the compound thereof, reference may be made to the relating description in JP 5124785 that is referred to herein as a part of the present description.

Specific examples of a group of other compounds usable as a delayed fluorescent material for the second organic compound include, for example, a group of compounds represented by the following general formula.

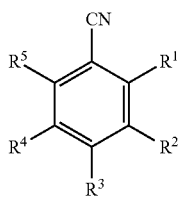

General formula (21)

In the general formula (21), $R^1$ to $R^5$ each independently represent a hydrogen atom or a substituent, one of $R^1$ to $R^5$ is a cyano group, one to three of $R^1$ to $R^5$ each are an aryl group Ar optionally substituted with an alkyl group or an aryl group (in which the benzene ring to constitute the aryl group Ar may be condensed with a ring that may optionally contain an oxygen atom or a sulfur atom in addition to carbon atoms as a ring skeleton-constituting atom, but is not condensed with a ring containing any other hetero atom than an oxygen atom and a sulfur atom as a ring skeleton-constituting atom), and when two or more of $R^1$ to $R^5$ are Ar's, these Ar's may be the same as or different from each other, one to three of $R^1$ to $R^5$ each are a donor group D (but excepting one that corresponds to Ar), and when two or more of $R^1$ to $R^5$ are D's, these D's may be the same as or different from each other.

In the general formula (21), preferably, $R^1$ to $R^5$ each are independently a cyano group, Ar or D; D preferably contains a substituted amino group; and D is preferably a group represented by the following general formula (2c).

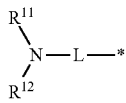

General Formula (2c)

In the general formula (2c), $R^{11}$ and $R^{12}$ each independently represent a substituted or unsubstituted alkyl group, a substituted or unsubstituted alkenyl group, a substituted or unsubstituted aryl group, or a substituted or unsubstituted heteroaryl group. L represents a single bond, a substituted or unsubstituted arylene group, or a substituted or unsubstituted heteroarylene group. * indicates a bonding position to the carbon atom (C) constituting a ring skeleton of the benzene ring in the general formula (21). $R^{11}$ and $R^{12}$ may bond to each other to form a cyclic structure.

D is preferably a group represented by the following general formula (3c).

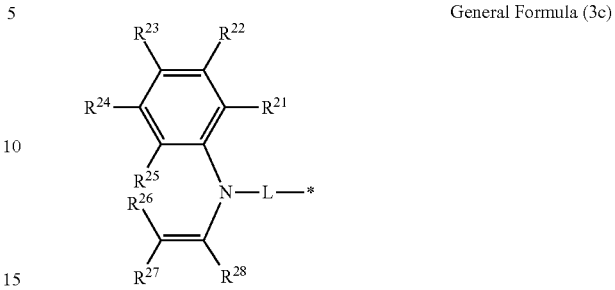

General Formula (3c)

In the general formula (3c), $R^{21}$ to $R^{28}$ each independently represent a hydrogen atom or a substituent. L represents a single bond, a substituted or unsubstituted arylene group, or a substituted or unsubstituted heteroarylene group. $R^{21}$ and $R^{22}$, $R^{22}$ and $R^{23}$, $R^{23}$ and $R^{24}$, $R^{24}$ and $R^{23}$, $R^{26}$ and $R^{27}$, and $R^{27}$ and $R^{28}$ each may bond to each other to form a linking group necessary for forming a cyclic structure. $R^{21}$ and $R^{26}$ may bond to each other to form a single bond or a linking group.

D is preferably a group represented by the following general formula (4c).

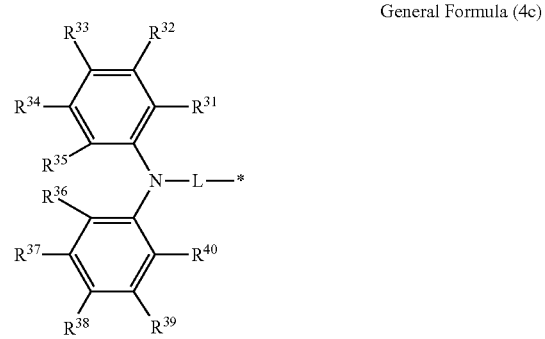

General Formula (4c)

In the general formula (4c), $R^{31}$ to $R^{40}$ each independently represent a hydrogen atom or a substituent. L represents a single bond, a substituted or unsubstituted arylene group, or a substituted or unsubstituted heteroarylene group. $R^{31}$ and $R^{32}$, $R^{32}$ and $R^{33}$, $R^{33}$ and $R^{34}$, $R^{34}$ and $R^{35}$, $R^{36}$ and $R^{37}$, $R^{37}$ and $R^{38}$, $R^{38}$ and $R^{39}$, and $R^{39}$ and $R^{40}$ each may bond to each other to form a linking group necessary for forming a cyclic structure. $R^{35}$ and $R^{36}$ may bond to each other to form a single bond or a linking group. * indicates a bonding position to the carbon atom (C) constituting the ring skeleton of the benzene ring in the general formula (21).

L is preferably a single bond. Also preferably, $R^3$ is a cyano group and L is a substituted or unsubstituted phenylene group. D is preferably a group represented by any of the following general formulae (5c) to (8c).

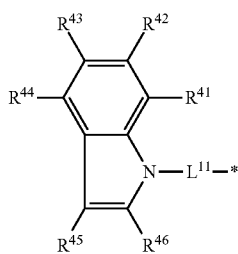
General Formula (5c)

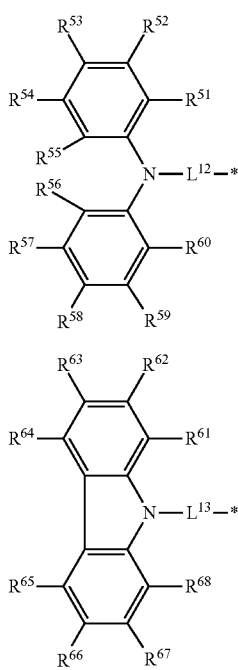
General Formula (6c)

General Formula (7c)

General Formula (8c)

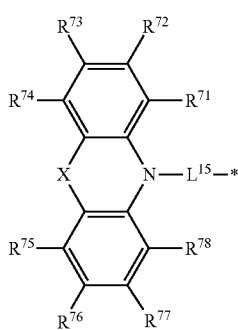

In the general formulae (5c) to (8c), $R^{41}$ to $R^{46}$, $R^{51}$ to $R^{60}$, $R^{61}$ to $R^{68}$, and $R^{71}$ to $R^{78}$ each independently represent a hydrogen atom or a substituent. $L^{11}$ to $L^{14}$ each independently represent a single bond, a substituted or unsubstituted arylene group, or a substituted or unsubstituted heteroarylene group. In the general formula (8c), X represents an oxygen atom, a sulfur atom, a substituted or unsubstituted nitrogen atom, a substituted or unsubstituted carbon atom, a substituted or unsubstituted silicon atom or a carbonyl group, which is divalent and which has a linking chain length of one atom, or represents a substituted or unsubstituted ethylene group, a substituted or unsubstituted vinylene group, a substituted or unsubstituted o-arylene group or a substituted or unsubstituted o-heteroarylene group, which is divalent and which has a bonding chain length of two atoms.

Regarding the detailed description and the preferred range of the general formula (21) and specific examples of the compound thereof, reference may be made to the relating description in PCT/JP2018/024302 and a laid-open publication thereof that are referred to herein as a part of the present description.

Specific examples of a group of other compounds usable as a delayed fluorescent material for the second organic compound include, for example, a group of compounds represented by the following general formula.

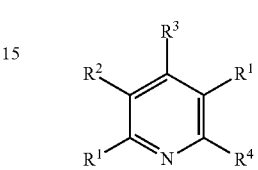
General Formula (22)

In the general formula (22), $R^1$ to $R^5$ each independently represent a hydrogen atom or a substituent, 0 to 3 of $R^1$ to $R^5$ each are an aryl group Ar optionally substituted with an alkyl group or an aryl group (in which the benzene ring to constitute the aryl group Ar may be condensed with a ring that may optionally contain an oxygen atom or a sulfur atom in addition to carbon atoms as a ring skeleton-constituting atom, but is not condensed with a ring containing any other hetero atom than an oxygen atom and a sulfur atom as a ring skeleton-constituting atom), and when two or more of $R^1$ to $R^5$ are Ar's, these Ar's may be the same as or different from each other, 1 to 4 of $R^1$ to $R^5$ each are an acceptor group A (but excepting one that corresponds to Ar), and when two or more of $R^1$ to $R^5$ are A's, these A's may be the same as or different from each other, 1 to 4 of $R^1$ to $R^5$ each are a donor group D (but excepting one that corresponds to Ar), and when two or more of $R^1$ to $R^5$ are D's, these D's may be the same as or different from each other.

Preferably, 1 to 3 of $R^1$ to $R^5$ in the general formula (22) each are an aryl group Ar optionally substituted with an alkyl group or an aryl group; $R^3$ is preferably an acceptor group A; $R^1$ and $R^5$ each are preferably a donor group D; the donor group D is preferably a substituted or unsubstituted diarylamino group (in which the two aryl groups constituting the diarylamino group may bond to each other); preferably, the donor group D is a substituted or unsubstituted diarylamino group and the two aryl groups constituting the diarylamino group bond to each other; preferably, the acceptor group A is a substituted or unsubstituted heteroaryl group; preferably, the acceptor group A is a heteroaryl group containing a nitrogen atom as a ring skeleton constituting atom; and preferably the acceptor group A is an aryl-substituted heteroaryl group.

Regarding the detailed description and the preferred range of the general formula (22) and specific examples of the compound thereof, reference may be made to the relating description in Japanese Patent Application No. 2017-168885 and a laid-open publication thereof that are referred to herein as a part of the present description.

Specific examples of compounds usable as the second organic compound are shown below. In the specific examples, the compounds 1 to 7 are specifically described in the following Tables and the structural formulae thereof are also shown below. The compound 8 and after that are specifically described only in the following Tables. However, the compounds represented by the general formula (1)

usable in the present invention should not be limitatively interpreted by these specific examples.
Compound 1
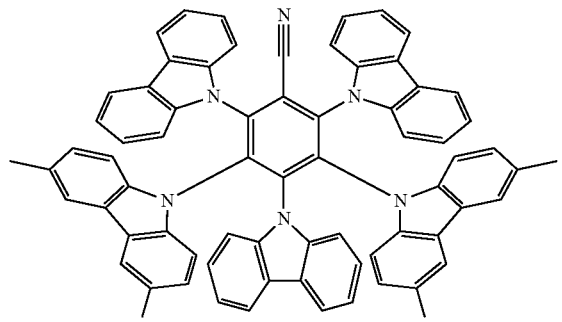
Compound 2
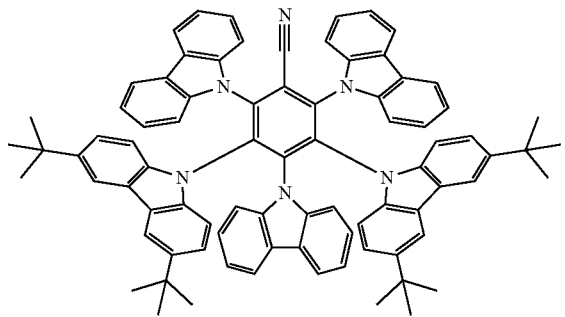
Compound 3
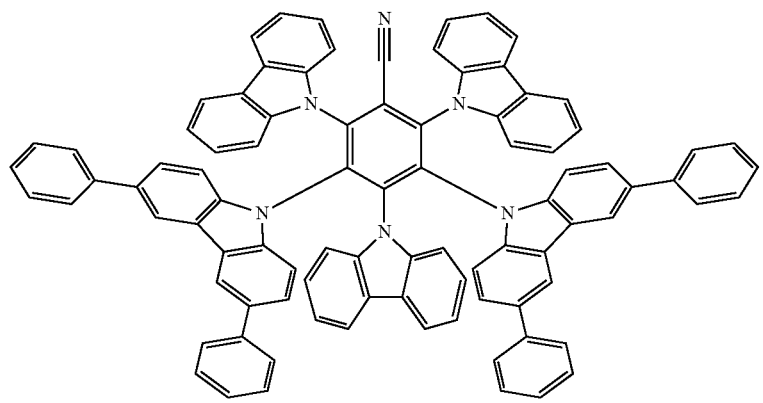
Compound 4
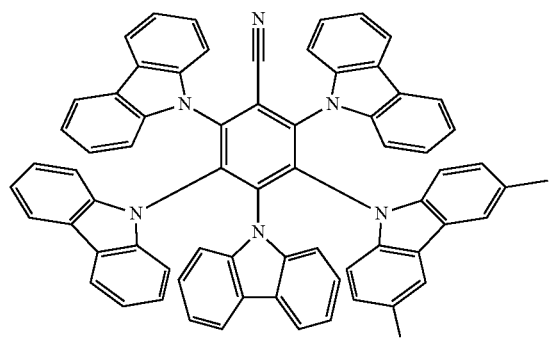
Compound 5
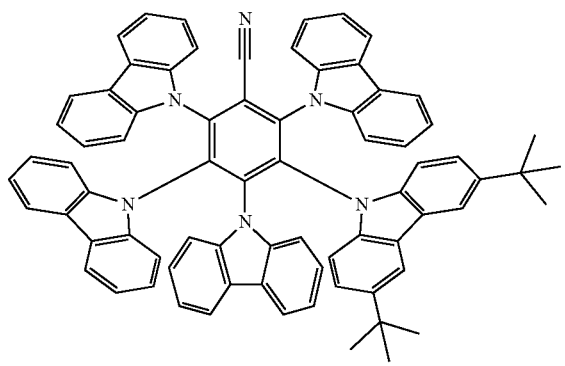

Compound 6

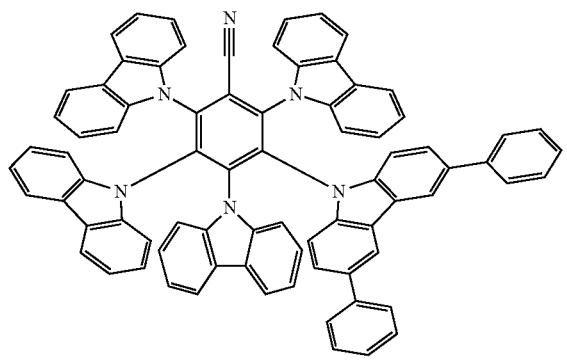

Compound 7

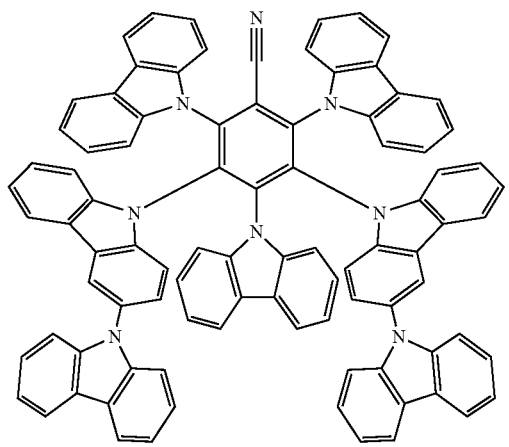

In the following Tables, specific examples of compounds represented by the following general formula (10) or general formula (11) are shown. The general formula (2a) and the general formula (2b) representing the substituents in the general formula (10) and the general formula (11) are also shown below.

General Formula (10)

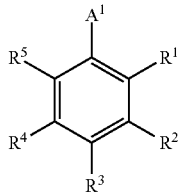

General Formula (11)

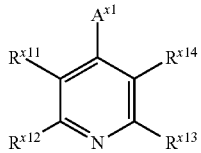

General Formula (2a)

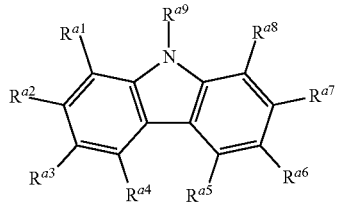

General Formula (2b)

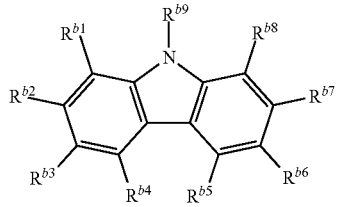

TABLE 1

| Compound No. | A¹ | General formula (10) | | | | | General formula (2a) | | | | | |
|---|---|---|---|---|---|---|---|---|---|---|---|---|
| | | R¹ | R² | R³ | R⁴ | R⁵ | R^{a1} | R^{a2} | R^{a3} | R^{a4} | R^{a5} | R^{a6} |
| 1 | CN | General formula (2a) | General formula (2b) | General formula (2a) | General formula (2a) | General formula (2b) | H | H | H | H | H | H |
| 2 | CN | General formula (2a) | General formula (2b) | General formula (2a) | General formula (2a) | General formula (2b) | H | H | H | H | H | H |
| 3 | CN | General formula (2a) | General formula (2b) | General formula (2a) | General formula (2a) | General formula (2b) | H | H | H | H | H | H |
| 4 | CN | General formula (2a) | General formula (2b) | General formula (2a) | General formula (2a) | General formula (2b) | H | H | H | H | H | H |
| 5 | CN | General formula (2a) | General formula (2b) | General formula (2a) | General formula (2a) | General formula (2b) | H | H | H | H | H | H |
| 6 | CN | General formula (2a) | General formula (2b) | General formula (2a) | General formula (2a) | General formula (2b) | H | H | H | H | H | H |
| 7 | CN | General formula (2a) | General formula (2b) | General formula (2a) | General formula (2a) | General formula (2b) | H | H | H | H | H | H |
| 8 | CN | General formula (2a) | General formula (2b) | General formula (2a) | General formula (2a) | General formula (2b) | H | H | H | H | H | H |
| 9 | CN | General formula (2a) | General formula (2b) | General formula (2a) | General formula (2a) | General formula (2b) | H | H | H | H | H | H |
| 10 | CN | General formula (2a) | General formula (2b) | General formula (2a) | General formula (2a) | General formula (2b) | H | H | H | H | H | H |
| 11 | CN | General formula (2a) | General formula (2b) | General formula (2a) | General formula (2a) | General formula (2b) | H | H | H | H | H | H |
| 12 | CN | General formula (2a) | General formula (2b) | General formula (2a) | General formula (2a) | General formula (2b) | H | H | H | H | H | H |
| 13 | CN | General formula (2a) | General formula (2b) | General formula (2a) | General formula (2a) | General formula (2b) | H | H | H | H | H | H |
| 14 | CN | General formula (2a) | General formula (2b) | General formula (2a) | General formula (2a) | General formula (2b) | H | H | H | H | H | H |
| 15 | CN | General formula (2a) | General formula (2b) | General formula (2a) | General formula (2a) | General formula (2b) | H | H | H | H | H | H |
| 16 | CN | General formula (2a) | General formula (2b) | General formula (2a) | General formula (2a) | General formula (2b) | H | H | H | H | H | H |
| 17 | CN | General formula (2a) | General formula (2b) | General formula (2a) | General formula (2a) | General formula (2b) | H | H | CH₃ | H | H | CH₃ |
| 18 | CN | General formula (2a) | General formula (2b) | General formula (2a) | General formula (2a) | General formula (2b) | H | H | CH₃ | H | H | CH₃ |
| 19 | CN | General formula (2a) | General formula (2b) | General formula (2a) | General formula (2a) | General formula (2b) | H | H | CH₃ | H | H | CH₃ |
| 20 | CN | General formula (2a) | General formula (2b) | General formula (2a) | General formula (2a) | General formula (2b) | H | H | tert-C₄H₉ | H | H | tert-C₄H₉ |
| 21 | CN | General formula (2a) | General formula (2b) | General formula (2a) | General formula (2a) | General formula (2b) | H | H | Phenyl | H | H | Phenyl |
| 22 | CN | General formula (2a) | General formula (2b) | General formula (2a) | General formula (2a) | General formula (2b) | H | H | H | H | H | H |
| 23 | CN | General formula (2a) | General formula (2b) | General formula (2a) | General formula (2a) | General formula (2b) | H | H | Phenyl | H | H | Phenyl |
| 24 | CN | General formula (2a) | General formula (2b) | General formula (2a) | General formula (2a) | General formula (2b) | H | H | H | H | H | H |
| 25 | CN | General formula (2a) | General formula (2b) | General formula (2a) | General formula (2a) | General formula (2b) | H | H | H | H | H | H |
| 26 | CN | General formula (2a) | General formula (2b) | General formula (2a) | General formula (2a) | General formula (2b) | H | H | H | H | H | H |
| 27 | CN | General formula (2a) | General formula (2b) | General formula (2a) | General formula (2a) | General formula (2b) | H | H | H | H | H | H |
| 28 | CN | General formula (2a) | General formula (2b) | General formula (2a) | General formula (2a) | General formula (2b) | H | H | H | H | H | H |
| 29 | CN | General formula (2a) | General formula (2b) | General formula (2a) | General formula (2a) | General formula (2b) | H | H | H | H | H | H |
| 30 | CN | General formula (2a) | General formula (2b) | General formula (2a) | General formula (2a) | General formula (2b) | H | H | H | H | H | H |
| 31 | CN | General formula (2a) | General formula (2b) | General formula (2a) | General formula (2a) | General formula (2b) | H | H | H | H | H | H |
| 32 | CN | General formula (2a) | General formula (2b) | General formula (2a) | General formula (2a) | General formula (2b) | H | H | H | H | H | H |
| 33 | CN | General formula (2a) | General formula (2b) | General formula (2a) | General formula (2a) | General formula (2b) | H | H | H | H | H | H |
| 34 | CN | General formula (2a) | General formula (2b) | Phenyl | General formula (2a) | General formula (2b) | H | H | H | H | H | H |
| 35 | CN | General formula (2a) | General formula (2b) | Phenyl | General formula (2a) | General formula (2b) | H | H | H | H | H | H |
| 36 | CN | General formula (2a) | General formula (2b) | Phenyl | General formula (2a) | General formula (2b) | H | H | H | H | H | H |
| 37 | CN | General formula (2a) | General formula (2b) | Phenyl | General formula (2a) | General formula (2b) | H | H | H | H | H | H |
| 38 | CN | General formula (2a) | General formula (2b) | Phenyl | General formula (2a) | General formula (2b) | H | H | H | H | H | H |
| 39 | CN | General formula (2a) | General formula (2b) | Phenyl | General formula (2a) | General formula (2b) | H | H | H | H | H | H |
| 40 | CN | General formula (2a) | General formula (2b) | Phenyl | General formula (2a) | General formula (2b) | H | H | H | H | H | H |
| 41 | CN | General formula (2a) | General formula (2b) | Phenyl | General formula (2a) | General formula (2b) | H | H | H | H | H | H |
| 42 | CN | General formula (2a) | General formula (2b) | Phenyl | General formula (2a) | General formula (2b) | H | H | H | H | H | H |
| 43 | CN | General formula (2a) | General formula (2b) | Phenyl | General formula (2a) | General formula (2b) | H | H | H | H | H | H |
| 44 | CN | General formula (2a) | General formula (2b) | Phenyl | General formula (2a) | General formula (2b) | H | H | H | H | H | H |
| 45 | CN | General formula (2a) | General formula (2b) | Phenyl | General formula (2a) | General formula (2b) | H | H | CH₃ | H | H | CH₃ |
| 46 | CN | General formula (2a) | General formula (2b) | Phenyl | General formula (2a) | General formula (2b) | H | H | CH₃ | H | H | CH₃ |
| 47 | CN | General formula (2a) | General formula (2b) | Phenyl | General formula (2a) | General formula (2b) | H | H | CH₃ | H | H | CH₃ |

TABLE 1-continued

| | | | | | | | |
|---|---|---|---|---|---|---|---|
| 48 | CN | General formula (2a) | Phenyl | General formula (2b) | H | H | Phenyl |
| 49 | CN | General formula (2a) | Phenyl | General formula (2b) | H | H | Phenyl |
| 50 | CN | General formula (2a) | Phenyl | General formula (2b) | H | H | H |
| 51 | CN | General formula (2a) | Phenyl | General formula (2b) | H | H | H |
| 52 | CN | General formula (2a) | Phenyl | General formula (2b) | H | H | H |
| 53 | CN | General formula (2a) | H | General formula (2b) | H | H | H |
| 54 | CN | General formula (2a) | H | General formula (2b) | H | H | H |
| 55 | CN | General formula (2a) | H | General formula (2b) | H | H | H |
| 56 | CN | General formula (2a) | H | General formula (2b) | H | H | H |
| 57 | CN | General formula (2a) | H | General formula (2b) | H | H | H |
| 58 | CN | General formula (2a) | H | General formula (2b) | H | H | H |
| 59 | CN | General formula (2a) | General formula (2a) | General formula (2b) | H | H | H |
| 60 | CN | General formula (2a) | General formula (2a) | General formula (2b) | H | H | H |
| 61 | CN | General formula (2a) | General formula (2a) | General formula (2b) | H | H | $CH_3$ |
| 62 | CN | General formula (2a) | General formula (2a) | General formula (2b) | H | H | H |
| 63 | CN | General formula (2a) | General formula (2a) | General formula (2b) | H | H | H |
| 64 | CN | General formula (2a) | General formula (2a) | General formula (2b) | H | H | $CH_3$ |
| 65 | CN | General formula (2a) | General formula (2a) | General formula (2b) | H | H | H |
| 66 | CN | General formula (2a) | General formula (2a) | General formula (2b) | H | H | $CH_3$ |
| 67 | CN | General formula (2a) | General formula (2a) | General formula (2b) | H | H | H |
| 68 | CN | General formula (2a) | General formula (2a) | General formula (2b) | H | H | $CH_3$ |
| 69 | CN | General formula (2a) | General formula (2a) | General formula (2b) | H | H | $CH_3$ |
| 70 | CN | General formula (2a) | General formula (2a) | General formula (2b) | H | H | $CH_3$ |
| 71 | CN | General formula (2a) | General formula (2a) | General formula (2b) | H | H | tert-$C_4H_9$ |
| 72 | CN | General formula (2a) | General formula (2a) | General formula (2b) | H | H | tert-$C_4H_9$ |
| 73 | CN | General formula (2a) | General formula (2a) | General formula (2b) | H | H | Phenyl |
| 74 | CN | General formula (2a) | General formula (2a) | General formula (2b) | H | H | H |
| 75 | CN | General formula (2a) | General formula (2a) | General formula (2b) | H | H | H |
| 76 | CN | General formula (2a) | CN | General formula (2b) | H | H | H |
| 77 | CN | General formula (2a) | CN | General formula (2b) | H | H | H |
| 78 | CN | General formula (2a) | CN | General formula (2b) | H | H | H |
| 79 | CN | General formula (2a) | CN | General formula (2b) | H | H | $CH_3$ |
| 80 | CN | General formula (2a) | CN | General formula (2b) | H | H | H |
| 81 | CN | General formula (2a) | CN | General formula (2b) | H | H | H |
| 82 | CN | General formula (2a) | CN | General formula (2b) | H | H | $CH_3$ |
| 83 | CN | General formula (2a) | CN | General formula (2b) | H | H | $CH_3$ |
| 84 | CN | General formula (2a) | CN | General formula (2b) | H | H | $CH_3$ |
| 85 | CN | General formula (2a) | CN | General formula (2b) | H | H | tert-$C_4H_9$ |
| 86 | CN | General formula (2a) | CN | General formula (2b) | H | H | tert-$C_4H_9$ |
| 87 | CN | General formula (2a) | CN | General formula (2b) | H | H | Phenyl |
| 88 | CN | General formula (2a) | CN | General formula (2b) | H | H | Phenyl |
| 89 | CN | General formula (2a) | CN | General formula (2b) | H | H | H |
| 90 | CN | General formula (2a) | CN | General formula (2b) | H | H | H |
| 91 | CN | General formula (2a) | CN | General formula (2b) | H | H | $CH_3$ |
| 92 | CN | General formula (2a) | CN | General formula (2b) | H | H | H |
| 93 | CN | General formula (2a) | CN | H | H | H | $CH_3$ |
| 94 | CN | General formula (2a) | CN | H | H | H | $CH_3$ |
| 95 | CN | General formula (2a) | CN | H | H | H | H |
| 96 | CN | General formula (2a) | CN | H | H | H | $CH_3$ |
| 97 | CN | General formula (2a) | CN | H | H | H | tert-$C_4H_9$ |
| 98 | CN | General formula (2a) | CN | General formula (2b) | H | H | tert-$C_4H_9$ |
| 99 | CN | General formula (2a) | CN | General formula (2b) | H | H | Phenyl |
| 100 | CN | General formula (2a) | CN | General formula (2b) | H | H | H |

TABLE 1-continued

| No. | | | | | | | | | | | | |
|---|---|---|---|---|---|---|---|---|---|---|---|---|
| 101 | CN | General formula (2a) | Phenyl | CN | General formula (2b) | General formula (2b) | General formula (2a) | H | H | H | H | H |
| 102 | CN | General formula (2a) | Phenyl | CN | General formula (2b) | General formula (2b) | General formula (2a) | H | H | H | H | H |
| 103 | CN | General formula (2a) | Phenyl | CN | General formula (2a) | General formula (2b) | General formula (2b) | H | H | CH₃ | CH₃ | CH₃ |
| 104 | CN | General formula (2a) | Phenyl | CN | General formula (2b) | General formula (2b) | General formula (2a) | H | H | H | H | H |
| 105 | CN | General formula (2a) | Phenyl | CN | General formula (2b) | General formula (2b) | General formula (2a) | H | H | H | H | H |
| 106 | CN | General formula (2a) | Phenyl | CN | General formula (2b) | General formula (2b) | General formula (2a) | H | H | H | H | H |
| 107 | CN | General formula (2a) | Phenyl | CN | General formula (2b) | General formula (2a) | General formula (2a) | H | H | CH₃ | CH₃ | CH₃ |
| 108 | CN | General formula (2a) | Phenyl | CN | General formula (2b) | General formula (2a) | General formula (2a) | H | H | CH₃ | CH₃ | CH₃ |
| 109 | CN | General formula (2a) | Phenyl | CN | General formula (2b) | General formula (2a) | General formula (2a) | H | H | H | H | H |
| 110 | CN | General formula (2a) | Phenyl | CN | General formula (2b) | General formula (2b) | General formula (2a) | H | H | H | H | H |
| 111 | CN | General formula (2a) | Phenyl | CN | General formula (2b) | General formula (2b) | General formula (2a) | H | H | H | H | H |
| 112 | CN | General formula (2a) | Phenyl | CN | General formula (2b) | General formula (2b) | General formula (2a) | H | H | CH₃ | CH₃ | CH₃ |
| 113 | CN | General formula (2a) | Phenyl | General formula (2b) | General formula (2b) | General formula (2b) | General formula (2a) | H | H | H | H | H |
| 114 | CN | General formula (2a) | Phenyl | CN | General formula (2b) | General formula (2b) | General formula (2a) | H | H | CH₃ | CH₃ | CH₃ |
| 115 | CN | General formula (2a) | Phenyl | General formula (2b) | General formula (2b) | General formula (2b) | General formula (2a) | H | H | H | H | H |
| 116 | CN | General formula (2a) | Phenyl | General formula (2b) | General formula (2b) | General formula (2b) | General formula (2a) | H | H | H | H | H |
| 117 | CN | General formula (2a) | Phenyl | General formula (2b) | General formula (2b) | General formula (2b) | General formula (2a) | H | H | CH₃ | CH₃ | CH₃ |
| 118 | CN | General formula (2a) | Phenyl | CN | General formula (2b) | General formula (2b) | General formula (2a) | H | H | H | H | H |
| 119 | CN | General formula (2a) | Phenyl | CN | General formula (2b) | General formula (2b) | General formula (2a) | H | H | H | H | H |
| 120 | CN | General formula (2a) | Phenyl | CN | General formula (2b) | General formula (2b) | General formula (2a) | H | H | H | H | H |
| 121 | CN | General formula (2a) | Phenyl | CN | General formula (2b) | General formula (2b) | General formula (2a) | H | H | CH₃ | CH₃ | CH₃ |
| 122 | CN | General formula (2a) | Phenyl | CN | General formula (2b) | General formula (2b) | General formula (2a) | H | H | H | H | H |
| 123 | CN | General formula (2a) | Phenyl | CN | General formula (2b) | General formula (2b) | General formula (2a) | H | H | H | H | H |
| 124 | CN | General formula (2a) | Phenyl | CN | General formula (2b) | General formula (2b) | General formula (2a) | H | H | H | H | H |
| 125 | CN | Phenyl | General formula (2a) | General formula (2b) | General formula (2b) | Phenyl | Phenyl | H | H | CH₃ | CH₃ | CH₃ |
| 126 | CN | Phenyl | General formula (2a) | General formula (2b) | General formula (2b) | Phenyl | Phenyl | H | H | CH₃ | CH₃ | CH₃ |
| 127 | CN | Phenyl | General formula (2a) | General formula (2b) | General formula (2b) | Phenyl | Phenyl | H | H | CH₃ | CH₃ | CH₃ |
| 128 | CN | Phenyl 1 | General formula (2a) | General formula (2b) | General formula (2b) | Phenyl | Phenyl | H | H | tert-C₄H₉ | tert-C₄H₉ | tert-C₄H₉ |
| 129 | CN | Phenyl | General formula (2a) | General formula (2b) | General formula (2b) | Phenyl | Phenyl | H | H | tert-C₄H₉ | tert-C₄H₉ | tert-C₄H₉ |
| 130 | CN | Phenyl | General formula (2a) | General formula (2b) | General formula (2b) | Phenyl | Phenyl | H | H | tert-C₄H₉ | tert-C₄H₉ | tert-C₄H₉ |
| 131 | CN | Phenyl | General formula (2a) | General formula (2b) | General formula (2b) | Phenyl | Phenyl | H | H | Phenyl | Phenyl | Phenyl |
| 132 | CN | Phenyl | General formula (2a) | General formula (2b) | General formula (2b) | Phenyl | Phenyl | H | H | Phenyl | Phenyl | Phenyl |
| 133 | CN | General formula (2a) | Phenyl | General formula (2b) | General formula (2b) | General formula (2a) | General formula (2a) | H | H | H | H | H |
| 134 | CN | Phenyl | Phenyl | General formula (2b) | General formula (2b) | Phenyl | Phenyl | H | H | H | H | CH₃ |
| 135 | CN | Phenyl | Phenyl | General formula (2b) | General formula (2b) | Phenyl | Phenyl | H | H | CH₃ | CH₃ | CH₃ |
| 136 | CN | Phenyl | Phenyl | General formula (2b) | General formula (2b) | Phenyl | Phenyl | H | H | CH₃ | CH₃ | CH₃ |
| 137 | CN | Phenyl | Phenyl | General formula (2b) | General formula (2b) | Phenyl | Phenyl | H | H | H | H | H |
| 138 | CN | Phenyl | Phenyl | General formula (2b) | General formula (2b) | Phenyl | Phenyl | H | H | tert-C₄H₉ | tert-C₄H₉ | tert-C₄H₉ |
| 139 | CN | Phenyl | Phenyl | General formula (2b) | General formula (2b) | Phenyl | Phenyl | H | H | tert-C₄H₉ | tert-C₄H₉ | tert-C₄H₉ |
| 140 | CN | Phenyl | Phenyl | General formula (2b) | General formula (2b) | Phenyl | Phenyl | H | H | tert-C₄H₉ | tert-C₄H₉ | tert-C₄H₉ |
| 141 | CN | Phenyl | Phenyl | General formula (2b) | General formula (2b) | Phenyl | Phenyl | H | H | Phenyl | Phenyl | Phenyl |
| 142 | CN | Phenyl | Phenyl | General formula (2b) | General formula (2b) | Phenyl | Phenyl | H | H | Phenyl | Phenyl | Phenyl |
| 143 | CN | Phenyl | Phenyl | General formula (2b) | General formula (2b) | Phenyl | Phenyl | H | H | Phenyl | Phenyl | Phenyl |
| 144 | CN | Phenyl | Phenyl | General formula (2b) | General formula (2b) | Phenyl | Phenyl | H | H | Phenyl | Phenyl | Phenyl |
| 145 | CN | General formula (2a) | General formula (2b) | General formula (2b) | General formula (2b) | General formula (2a) | General formula (2a) | H | H | H | H | H |
| 146 | CN | General formula (2a) | General formula (2b) | General formula (2b) | General formula (2b) | General formula (2a) | General formula (2a) | H | H | CH₃ | CH₃ | CH₃ |
| 147 | CN | General formula (2a) | General formula (2b) | General formula (2b) | General formula (2b) | General formula (2a) | General formula (2a) | H | H | tert-C₄H₉ | tert-C₄H₉ | tert-C₄H₉ |
| 148 | CN | General formula (2a) | General formula (2b) | General formula (2b) | General formula (2b) | General formula (2a) | General formula (2a) | H | H | Phenyl | Phenyl | Phenyl |
| 149 | CN | General formula (2a) | Phenyl | General formula (2b) | General formula (2a) | General formula (2a) | General formula (2a) | H | H | Phenyl | Phenyl | Phenyl |
| 150 | CN | General formula (2a) | H | m, m-DPP*² | General formula (2b) | General formula (2a) | General formula (2a) | H | H | H | H | H |
| 151 | CN | General formula (2a) | Phenyl | General formula (2b) | General formula (2b) | General formula (2a) | General formula (2a) | H | H | H | H | H |
| 152 | CN | General formula (2a) | Phenyl | General formula (2b) | General formula (2a) | General formula (2a) | General formula (2a) | H | H | H | H | H |

TABLE 1-continued

| Compound No. | General formula (2a) | | | General formula (2b) | | | | | | | | |
|---|---|---|---|---|---|---|---|---|---|---|---|---|
| | R$^{a7}$ | R$^{a8}$ | R$^{a9}$ | R$^{b1}$ | R$^{b2}$ | R$^{b3}$ | R$^{b4}$ | R$^{b5}$ | R$^{b6}$ | R$^{b7}$ | R$^{b8}$ | R$^{b9}$ |
| 1 | H | H | *1 | H | H | CH$_3$ | H | H | CH$_3$ | H | H | *1 |
| 2 | H | H | *1 | H | H | tert-C$_4$H$_9$ | H | H | tert-C$_4$H$_9$ | H | H | *1 |
| 3 | H | H | *1 | H | H | Phenyl | H | H | Phenyl | H | H | *1 |
| 4 | H | H | *1 | H | H | CH$_3$ | H | H | CH$_3$ | H | H | *1 |
| 5 | H | H | *1 | H | H | tert-C$_4$H$_9$ | H | H | tert-C$_4$H$_9$ | H | H | *1 |
| 6 | H | H | *1 | H | H | Phenyl | H | H | Phenyl | H | H | *1 |
| 7 | H | H | *1 | H | H | 9-Carbazolyl | H | H | 9-Carbazolyl | H | H | *1 |
| 8 | H | H | *1 | H | H | iso-Butyl | H | H | iso-Butyl | H | H | *1 |
| 9 | H | H | *1 | H | H | 2-Ethylhexyl | H | H | 2-Ethylhexyl | H | H | *1 |
| 10 | H | H | *1 | H | H | Trimethylsilyl | H | H | Trimethylsilyl | H | H | *1 |
| 11 | H | H | *1 | H | H | CH$_3$ | H | H | H | H | H | *1 |
| 12 | H | H | *1 | H | H | Phenyl | H | H | H | H | H | *1 |
| 13 | H | H | *1 | H | H | CH$_3$ | H | H | tert-C$_4$H$_9$ | H | H | *1 |
| 14 | H | H | *1 | H | H | CH$_3$ | H | H | Phenyl | H | H | *1 |
| 15 | H | H | *1 | H | H | Diphenylamino | H | H | Diphenylamino | H | H | *1 |
| 16 | H | H | *1 | H | H | Diphenylamino | H | H | H | H | H | *1 |
| 17 | H | H | *1 | H | H | H | H | H | H | H | H | *1 |
| 18 | H | H | *1 | H | H | tert-C$_4$H$_9$ | H | H | tert-C$_4$H$_9$ | H | H | *1 |
| 19 | H | H | *1 | H | H | Phenyl | H | H | Phenyl | H | H | *1 |
| 20 | H | H | *1 | H | H | CH$_3$ | H | H | CH$_3$ | H | H | *1 |
| 21 | H | H | *1 | H | H | CH$_3$ | H | H | CH$_3$ | H | H | *1 |
| 22 | H | H | *1 | H | H | Phenyl | H | H | H | H | H | *1 |
| 23 | H | H | *1 | H | H | H | H | H | H | H | H | *1 |
| 24 | H | H | *1 | CH$_3$ | CH$_3$ | H | H | H | H | H | H | *1 |
| 25 | H | H | *1 | tert-C$_4$H$_9$ | tert-C$_4$H$_9$ | H | H | H | H | H | H | *1 |
| 26 | H | H | *1 | H | H | H | H | H | H | H | H | *1 |
| 27 | H | H | *1 | Phenyl | Phenyl | H | H | H | H | H | H | *1 |
| 28 | H | H | *1 | H | H | H | CH$_3$ | CH$_3$ | H | H | H | *1 |
| 29 | H | H | *1 | H | H | H | Phenyl | Phenyl | H | H | H | *1 |
| 30 | H | H | *1 | CH$_3$ | H | CH$_3$ | H | CH$_3$ | H | H | CH$_3$ | *1 |
| 31 | H | H | *1 | H | H | CH$_3$ | CH$_3$ | H | H | H | H | *1 |
| 32 | H | H | *1 | CH$_3$ | CH$_3$ | H | H | H | CH$_3$ | H | CH$_3$ | *1 |
| 33 | H | H | *1 | H | H | tert-C$_4$H$_9$ | H | H | tert-C$_4$H$_9$ | H | H | *1 |
| 34 | H | H | *1 | H | H | Phenyl | H | H | Phenyl | H | H | *1 |
| 35 | H | H | *1 | H | H | CH$_3$ | H | H | CH$_3$ | H | H | *1 |
| 36 | H | H | *1 | H | H | CH$_3$ | H | H | CH$_3$ | H | H | *1 |
| 37 | H | H | *1 | H | H | tert-C$_4$H$_9$ | H | H | tert-C$_4$H$_9$ | H | H | *1 |
| 38 | H | H | *1 | H | H | Phenyl | H | H | Phenyl | H | H | *1 |
| 39 | H | H | *1 | H | H | 2-Phenylphenyl | H | H | 2-Phenylphenyl | H | H | *1 |
| 40 | H | H | *1 | H | H | 3-Phenylphenyl | H | H | 3-Phenylphenyl | H | H | *1 |
| 41 | H | H | *1 | H | H | 4-Phenylphenyl | H | H | 4-Phenylphenyl | H | H | *1 |
| 42 | H | H | *1 | H | H | 2-Phenylphenyl | H | H | Phenyl | H | H | *1 |
| 43 | H | H | *1 | H | H | 3-Phenylphenyl | H | H | Phenyl | H | H | *1 |
| 44 | H | H | *1 | H | H | 4-Phenylphenyl | H | H | Phenyl | H | H | *1 |
| 45 | H | H | *1 | H | H | H | H | H | H | H | H | *1 |
| 46 | H | H | *1 | H | H | tert-C$_4$H$_9$ | H | H | tert-C$_4$H$_9$ | H | H | *1 |
| 47 | H | H | *1 | H | H | Phenyl | H | H | Phenyl | H | H | *1 |
| 48 | H | H | *1 | H | H | H | H | H | H | H | H | *1 |
| 49 | H | H | *1 | H | H | CH$_3$ | H | H | CH$_3$ | H | H | *1 |

TABLE 1-continued

| No | | | | | | | | | | |
|---|---|---|---|---|---|---|---|---|---|---|
| 50 | H | H | H | 2-Phenylphenyl | H | H | Phenyl | H | H | *1 |
| 51 | H | H | H | 3-Phenylphenyl | H | H | Phenyl | H | H | *1 |
| 52 | H | H | H | 4-Phenylphenyl | H | H | Phenyl | H | H | *1 |
| 53 | H | H | H | CH₃ | H | H | CH₃ | H | H | *1 |
| 54 | H | H | H | tert-C₄H₉ | H | H | tert-C₄H₉ | H | H | *1 |
| 55 | H | H | H | Phenyl | H | H | Phenyl | H | H | *1 |
| 56 | H | H | H | 2-Phenylphenyl | H | H | Phenyl | H | H | *1 |
| 57 | H | H | H | 3-Phenylphenyl | H | H | Phenyl | H | H | *1 |
| 58 | H | H | H | 4-Phenylphenyl | H | H | Phenyl | H | H | *1 |
| 59 | H | H | H | CH₃ | H | H | CH₃ | H | H | *1 |
| 60 | H | H | H | tert-C₄H₉ | H | H | tert-C₄H₉ | H | H | *1 |
| 61 | H | H | H | Phenyl | H | H | Phenyl | H | H | *1 |
| 62 | H | H | H | Phenyl | H | H | Phenyl | H | H | *1 |
| 63 | H | H | H | CH₃ | H | H | CH₃ | H | H | *1 |
| 64 | H | H | H | tert-C₄H₉ | H | H | tert-C₄H₉ | H | H | *1 |
| 65 | H | H | H | Phenyl | H | H | Phenyl | H | H | *1 |
| 66 | H | H | H | Phenyl | H | H | Phenyl | H | H | *1 |
| 67 | H | H | H | CH₃ | H | H | CH₃ | H | H | *1 |
| 68 | H | H | H | tert-C₄H₉ | H | H | tert-C₄H₉ | H | H | *1 |
| 69 | H | H | H | Phenyl | H | H | Phenyl | H | H | *1 |
| 70 | H | H | H | H | H | H | H | H | H | *1 |
| 71 | H | H | H | tert-C₄H₉ | H | H | tert-C₄H₉ | H | H | *1 |
| 72 | H | H | H | Phenyl | H | H | Phenyl | H | H | *1 |
| 73 | H | H | H | H | H | H | H | H | H | *1 |
| 74 | H | H | H | CH₃ | H | H | CH₃ | H | H | *1 |
| 75 | H | H | H | H | H | H | H | H | H | *1 |
| 76 | H | H | H | CH₃ | H | H | CH₃ | H | H | *1 |
| 77 | H | H | H | tert-C₄H₉ | H | H | tert-C₄H₉ | H | H | *1 |
| 78 | H | H | H | Phenyl | H | H | Phenyl | H | H | *1 |
| 79 | H | H | H | CH₃ | H | H | CH₃ | H | H | *1 |
| 80 | H | H | H | tert-C₄H₉ | H | H | tert-C₄H₉ | H | H | *1 |
| 81 | H | H | H | Phenyl | H | H | Phenyl | H | H | *1 |
| 82 | H | H | H | H | H | H | H | H | H | *1 |
| 83 | H | H | H | tert-C₄H₉ | H | H | tert-C₄H₉ | H | H | *1 |
| 84 | H | H | H | Phenyl | H | H | Phenyl | H | H | *1 |
| 85 | H | H | H | H | H | H | H | H | H | *1 |
| 86 | H | H | H | CH₃ | H | H | CH₃ | H | H | *1 |
| 87 | H | H | H | H | H | H | H | H | H | *1 |
| 88 | H | H | H | CH₃ | H | H | CH₃ | H | H | *1 |
| 89 | H | H | H | CH₃ | H | H | CH₃ | H | H | *1 |
| 90 | H | H | H | tert-C₄H₉ | H | H | tert-C₄H₉ | H | H | *1 |
| 91 | H | H | H | Phenyl | H | H | Phenyl | H | H | *1 |
| 92 | H | H | H | CH₃ | H | H | CH₃ | H | H | *1 |
| 93 | H | H | H | tert-C₄H₉ | H | H | tert-C₄H₉ | H | H | *1 |
| 94 | H | H | H | Phenyl | H | H | Phenyl | H | H | *1 |
| 95 | H | H | H | H | H | H | H | H | H | *1 |
| 96 | H | H | H | tert-C₄H₉ | H | H | tert-C₄H₉ | H | H | *1 |
| 97 | H | H | H | Phenyl | H | H | Phenyl | H | H | *1 |
| 98 | H | H | H | H | H | H | H | H | H | *1 |
| 99 | H | H | H | CH₃ | H | H | CH₃ | H | H | *1 |
| 100 | H | H | H | tert-C₄H₉ | H | H | tert-C₄H₉ | H | H | *1 |
| 101 | H | H | H | Phenyl | H | H | Phenyl | H | H | *1 |
| 102 | H | H | H | Phenyl | H | H | Phenyl | H | H | *1 |

TABLE 1-continued

| | | | | | | | | |
|---|---|---|---|---|---|---|---|---|
| 103 | H | H | *1 | H | Phenyl | H | H | Phenyl | *1 |
| 104 | H | H | *1 | H | CH₃ | H | H | CH₃ | *1 |
| 105 | H | H | *1 | H | tert-C₄H₉ | H | H | tert-C₄H₉ | *1 |
| 106 | H | H | *1 | H | Phenyl | H | H | Phenyl | *1 |
| 107 | H | H | *1 | H | tert-C₄H₉ | H | H | tert-C₄H₉ | *1 |
| 108 | H | H | *1 | H | Phenyl | H | H | Phenyl | *1 |
| 109 | H | H | *1 | H | CH₃ | H | H | CH₃ | *1 |
| 110 | H | H | *1 | H | tert-C₄H₉ | H | H | tert-C₄H₉ | *1 |
| 111 | H | H | *1 | H | Phenyl | H | H | Phenyl | *1 |
| 112 | H | H | *1 | H | Phenyl | H | H | Phenyl | *1 |
| 113 | H | H | *1 | H | CH₃ | H | H | CH₃ | *1 |
| 114 | H | H | *1 | H | tert-C₄H₉ | H | H | tert-C₄H₉ | *1 |
| 115 | H | H | *1 | H | Phenyl | H | H | Phenyl | *1 |
| 116 | H | H | *1 | H | Phenyl | H | H | Phenyl | *1 |
| 117 | H | H | *1 | H | CH₃ | H | H | CH₃ | *1 |
| 118 | H | H | *1 | H | tert-C₄H₉ | H | H | tert-C₄H₉ | *1 |
| 119 | H | H | *1 | H | Phenyl | H | H | Phenyl | *1 |
| 120 | H | H | *1 | H | Phenyl | H | H | Phenyl | *1 |
| 121 | H | H | *1 | H | CH₃ | H | H | CH₃ | *1 |
| 122 | H | H | *1 | H | tert-C₄H₉ | H | H | tert-C₄H₉ | *1 |
| 123 | H | H | *1 | H | Phenyl | H | H | Phenyl | *1 |
| 124 | H | H | *1 | H | Phenyl | H | H | Phenyl | *1 |
| 125 | H | H | *1 | H | Phenyl | H | H | Phenyl | *1 |
| 126 | H | H | *1 | H | CH₃ | H | H | CH₃ | *1 |
| 127 | H | H | *1 | H | tert-C₄H₉ | H | H | tert-C₄H₉ | *1 |
| 128 | H | H | *1 | H | Phenyl | H | H | Phenyl | *1 |
| 129 | H | H | *1 | H | H | H | H | H | *1 |
| 130 | H | H | *1 | H | CH₃ | H | H | CH₃ | *1 |
| 131 | H | H | *1 | H | Phenyl | H | H | Phenyl | *1 |
| 132 | H | H | *1 | H | H | H | H | H | *1 |
| 133 | H | H | *1 | H | CH₃ | H | H | CH₃ | *1 |
| 134 | H | H | *1 | H | CH₃ | H | H | CH₃ | *1 |
| 135 | H | H | *1 | H | tert-C₄H₉ | H | H | tert-C₄H₉ | *1 |
| 136 | H | H | *1 | H | Phenyl | H | H | Phenyl | *1 |
| 137 | H | H | *1 | H | H | H | H | H | *1 |
| 138 | H | H | *1 | H | tert-C₄H₉ | H | H | tert-C₄H₉ | *1 |
| 139 | H | H | *1 | H | Phenyl | H | H | Phenyl | *1 |
| 140 | H | H | *1 | H | H | H | H | H | *1 |
| 141 | H | H | *1 | H | CH₃ | H | H | CH₃ | *1 |
| 142 | H | H | *1 | H | Phenyl | H | H | Phenyl | *1 |
| 143 | H | H | *1 | H | H | H | H | H | *1 |
| 144 | H | H | *1 | H | CH₃ | H | H | CH₃ | *1 |
| 145 | H | H | *1 | H | tert-C₄H₉ | H | H | tert-C₄H₉ | *1 |
| 146 | H | H | *1 | H | CH₃ | H | H | CH₃ | *1 |
| 147 | H | H | *1 | H | H | H | H | H | *1 |
| 148 | H | H | *1 | H | H | H | H | H | *1 |
| 149 | H | H | *1 | H | H | H | H | H | *1 |
| 150 | H | H | *1 | H | CH₃ | H | H | CH₃ | *1 |
| 151 | H | H | *1 | H | Phenyl | H | H | Phenyl | *1 |
| 152 | H | H | *1 | H | Phenyl | H | H | Phenyl | *1 |

In the Tables, the general formula (2a) and the general formula (2b) are synonymous with the general formula (2). *1: This links to the benzene corresponding to D in the general formula (1).
*2: "m,m-DPP" is m,m-diphenylphenyl.

TABLE 2

| Compound No. | $A^1$ | $R^1$ | $R^2$ | $R^3$ | $R^4$ | $R^5$ | $R^{a1}$ | $R^{a2}$ | $R^{a3}$ | $R^{a4}$ | $R^{a5}$ | $R^{a6}$ | $R^{a7}$ | $R^{a8}$ | $R^{a9}$ |
|---|---|---|---|---|---|---|---|---|---|---|---|---|---|---|---|
| | | General formula (10) | | | | | | | General formula (2a) | | | | | | |
| 153 | CN | General formula (2a) | D1 | CN | General formula (2a) | D1 | H | H | CH$_3$ | H | H | CH$_3$ | H | H | *1 |
| 154 | CN | General formula (2a) | D2 | CN | General formula (2a) | D2 | H | H | CH$_3$ | H | H | CH$_3$ | H | H | *1 |
| 155 | CN | General formula (2a) | D3 | CN | General formula (2a) | D3 | H | H | CH$_3$ | H | H | CH$_3$ | H | H | *1 |
| 156 | CN | General formula (2a) | D4 | CN | General formula (2a) | D4 | H | H | CH$_3$ | H | H | CH$_3$ | H | H | *1 |
| 157 | CN | General formula (2a) | D5 | CN | General formula (2a) | D5 | H | H | CH$_3$ | H | H | CH$_3$ | H | H | *1 |
| 158 | CN | General formula (2a) | D6 | CN | General formula (2a) | D6 | H | H | CH$_3$ | H | H | CH$_3$ | H | H | *1 |
| 159 | CN | General formula (2a) | D7 | CN | General formula (2a) | D7 | H | H | CH$_3$ | H | H | CH$_3$ | H | H | *1 |
| 160 | CN | General formula (2a) | D8 | CN | General formula (2a) | D8 | H | H | CH$_3$ | H | H | CH$_3$ | H | H | *1 |
| 161 | CN | General formula (2a) | D9 | CN | General formula (2a) | D9 | H | H | CH$_3$ | H | H | CH$_3$ | H | H | *1 |
| 162 | CN | General formula (2a) | D10 | CN | General formula (2a) | D10 | H | H | CH$_3$ | H | H | CH$_3$ | H | H | *1 |
| 163 | CN | General formula (2a) | D11 | CN | General formula (2a) | D11 | H | H | CH$_3$ | H | H | CH$_3$ | H | H | *1 |
| 164 | CN | General formula (2a) | D12 | CN | General formula (2a) | D12 | H | H | CH$_3$ | H | H | CH$_3$ | H | H | *1 |
| 165 | CN | General formula (2a) | D13 | CN | General formula (2a) | D13 | H | H | CH$_3$ | H | H | CH$_3$ | H | H | *1 |
| 166 | CN | General formula (2a) | D14 | CN | General formula (2a) | D14 | H | H | CH$_3$ | H | H | CH$_3$ | H | H | *1 |
| 167 | CN | General formula (2a) | D15 | CN | General formula (2a) | D15 | H | H | CH$_3$ | H | H | CH$_3$ | H | H | *1 |
| 168 | CN | General formula (2a) | D16 | CN | General formula (2a) | D16 | H | H | CH$_3$ | H | H | CH$_3$ | H | H | *1 |
| 169 | CN | General formula (2a) | D17 | CN | General formula (2a) | D17 | H | H | CH$_3$ | H | H | CH$_3$ | H | H | *1 |
| 170 | CN | General formula (2a) | D18 | CN | General formula (2a) | D18 | H | H | CH$_3$ | H | H | CH$_3$ | H | H | *1 |
| 171 | CN | General formula (2a) | D19 | CN | General formula (2a) | D19 | H | H | CH$_3$ | H | H | CH$_3$ | H | H | *1 |
| 172 | CN | General formula (2a) | D20 | CN | General formula (2a) | D20 | H | H | CH$_3$ | H | H | CH$_3$ | H | H | *1 |
| 173 | CN | General formula (2a) | D21 | CN | General formula (2a) | D21 | H | H | CH$_3$ | H | H | CH$_3$ | H | H | *1 |
| 174 | CN | General formula (2a) | D22 | CN | General formula (2a) | D22 | H | H | CH$_3$ | H | H | CH$_3$ | H | H | *1 |
| 175 | CN | General formula (2a) | D23 | CN | General formula (2a) | D23 | H | H | CH$_3$ | H | H | CH$_3$ | H | H | *1 |
| 176 | CN | General formula (2a) | D24 | CN | General formula (2a) | D24 | H | H | CH$_3$ | H | H | CH$_3$ | H | H | *1 |
| 177 | CN | General formula (2a) | D25 | CN | General formula (2a) | D25 | H | H | CH$_3$ | H | H | CH$_3$ | H | H | *1 |
| 178 | CN | General formula (2a) | D26 | CN | General formula (2a) | D26 | H | H | CH$_3$ | H | H | CH$_3$ | H | H | *1 |
| 179 | CN | General formula (2a) | D27 | CN | General formula (2a) | D27 | H | H | CH$_3$ | H | H | CH$_3$ | H | H | *1 |
| 180 | CN | General formula (2a) | D28 | CN | General formula (2a) | D28 | H | H | CH$_3$ | H | H | CH$_3$ | H | H | *1 |
| 181 | CN | General formula (2a) | D29 | CN | General formula (2a) | D29 | H | H | CH$_3$ | H | H | CH$_3$ | H | H | *1 |
| 182 | CN | General formula (2a) | D30 | CN | General formula (2a) | D30 | H | H | CH$_3$ | H | H | CH$_3$ | H | H | *1 |
| 183 | CN | General formula (2a) | D31 | CN | General formula (2a) | D31 | H | H | CH$_3$ | H | H | CH$_3$ | H | H | *1 |
| 184 | CN | General formula (2a) | D32 | CN | General formula (2a) | D32 | H | H | CH$_3$ | H | H | CH$_3$ | H | H | *1 |
| 185 | CN | General formula (2a) | D33 | CN | General formula (2a) | D33 | H | H | CH$_3$ | H | H | CH$_3$ | H | H | *1 |
| 186 | CN | General formula (2a) | D34 | CN | General formula (2a) | D34 | H | H | CH$_3$ | H | H | CH$_3$ | H | H | *1 |
| 187 | CN | General formula (2a) | D35 | CN | General formula (2a) | D35 | H | H | CH$_3$ | H | H | CH$_3$ | H | H | *1 |
| 188 | CN | General formula (2a) | D36 | CN | General formula (2a) | D36 | H | H | CH$_3$ | H | H | CH$_3$ | H | H | *1 |
| 189 | CN | General formula (2a) | D37 | CN | General formula (2a) | D37 | H | H | CH$_3$ | H | H | CH$_3$ | H | H | *1 |
| 190 | CN | General formula (2a) | D38 | CN | General formula (2a) | D38 | H | H | CH$_3$ | H | H | CH$_3$ | H | H | *1 |
| 191 | CN | General formula (2a) | D39 | CN | General formula (2a) | D39 | H | H | CH$_3$ | H | H | CH$_3$ | H | H | *1 |
| 192 | CN | General formula (2a) | D40 | CN | General formula (2a) | D40 | H | H | CH$_3$ | H | H | CH$_3$ | H | H | *1 |
| 193 | CN | General formula (2a) | D41 | CN | General formula (2a) | D41 | H | H | CH$_3$ | H | H | CH$_3$ | H | H | *1 |
| 194 | CN | General formula (2a) | D42 | CN | General formula (2a) | D42 | H | H | CH$_3$ | H | H | CH$_3$ | H | H | *1 |
| 195 | CN | General formula (2a) | D43 | CN | General formula (2a) | D43 | H | H | CH$_3$ | H | H | CH$_3$ | H | H | *1 |
| 196 | CN | General formula (2a) | D44 | CN | General formula (2a) | D44 | H | H | CH$_3$ | H | H | CH$_3$ | H | H | *1 |
| 197 | CN | General formula (2a) | D45 | CN | General formula (2a) | D45 | H | H | CH$_3$ | H | H | CH$_3$ | H | H | *1 |
| 198 | CN | General formula (2a) | D46 | CN | General formula (2a) | D46 | H | H | CH$_3$ | H | H | CH$_3$ | H | H | *1 |
| 199 | CN | General formula (2a) | D47 | CN | General formula (2a) | D47 | H | H | CH$_3$ | H | H | CH$_3$ | H | H | *1 |

TABLE 2-continued

| Compound No. | A¹ | R¹ | R² | R³ | R⁴ | R⁵ | R^{a1} | R^{a2} | R^{a3} | R^{a4} | R^{a5} | R^{a6} | R^{a7} | R^{a8} | R^{a9} |
|---|---|---|---|---|---|---|---|---|---|---|---|---|---|---|---|
| 200 | CN | General formula (2a) | D48 | CN | General formula (2a) | D48 | H | H | CH₃ | H | H | CH₃ | H | H | *1 |
| 201 | CN | General formula (2a) | D49 | CN | General formula (2a) | D49 | H | H | CH₃ | H | H | CH₃ | H | H | *1 |
| 202 | CN | General formula (2a) | D50 | CN | General formula (2a) | D50 | H | H | CH₃ | H | H | CH₃ | H | H | *1 |
| 203 | CN | General formula (2a) | D51 | CN | General formula (2a) | D51 | H | H | CH₃ | H | H | CH₃ | H | H | *1 |
| 204 | CN | General formula (2a) | D52 | CN | General formula (2a) | D52 | H | H | CH₃ | H | H | CH₃ | H | H | *1 |
| 205 | CN | General formula (2a) | D53 | CN | General formula (2a) | D53 | H | H | CH₃ | H | H | CH₃ | H | H | *1 |
| 206 | CN | General formula (2a) | D54 | CN | General formula (2a) | D54 | H | H | CH₃ | H | H | CH₃ | H | H | *1 |
| 207 | CN | General formula (2a) | D55 | CN | General formula (2a) | D55 | H | H | CH₃ | H | H | CH₃ | H | H | *1 |
| 208 | CN | General formula (2a) | D56 | CN | General formula (2a) | D56 | H | H | CH₃ | H | H | CH₃ | H | H | *1 |
| 209 | CN | General formula (2a) | D57 | CN | General formula (2a) | D57 | H | H | CH₃ | H | H | CH₃ | H | H | *1 |
| 210 | CN | General formula (2a) | D58 | CN | General formula (2a) | D58 | H | H | CH₃ | H | H | CH₃ | H | H | *1 |
| 211 | CN | General formula (2a) | D59 | CN | General formula (2a) | D59 | H | H | CH₃ | H | H | CH₃ | H | H | *1 |
| 212 | CN | General formula (2a) | D60 | CN | General formula (2a) | D60 | H | H | CH₃ | H | H | CH₃ | H | H | *1 |
| 213 | CN | General formula (2a) | D24 | Phenyl | General formula (2a) | General formula (2a) | H | H | H | H | H | H | H | H | *1 |
| 214 | CN | General formula (2a) | D24 | Phenyl | General formula (2a) | General formula (2a) | H | H | CH₃ | H | H | CH₃ | H | H | *1 |
| 215 | CN | General formula (2a) | D24 | Phenyl | General formula (2a) | General formula (2a) | H | H | tert-C₄H₉ | H | H | tert-C₄H₉ | H | H | *1 |
| 216 | CN | General formula (2a) | D24 | Phenyl | General formula (2a) | General formula (2a) | H | H | Phenyl | H | H | Phenyl | H | H | *1 |
| 217 | CN | General formula (2a) | Phenyl | D11 | Phenyl | General formula (2a) | H | H | CH₃ | H | H | CH₃ | H | H | *1 |
| 218 | CN | General formula (2a) | Phenyl | D11 | Phenyl | General formula (2a) | H | H | tert-C₄H₉ | H | H | tert-C₄H₉ | H | H | *1 |
| 219 | CN | General formula (2a) | Phenyl | D11 | Phenyl | General formula (2a) | H | H | Phenyl | H | H | Phenyl | H | H | *1 |
| 220 | CN | CN | D24 | General formula (2a) | General formula (2a) | D24 | H | H | H | H | H | H | H | H | *1 |
| 221 | CN | CN | D24 | General formula (2a) | General formula (2a) | D24 | H | H | CH₃ | H | H | CH₃ | H | H | *1 |
| 222 | CN | CN | D24 | General formula (2a) | General formula (2a) | D24 | H | H | tert-C₄H₉ | H | H | tert-C₄H₉ | H | H | *1 |
| 223 | CN | General formula (2a) | CN | General formula (2a) | General formula (2a) | D24 | H | H | tert-C₄H₉ | H | H | tert-C₄H₉ | H | H | *1 |
| 224 | CN | CN | General formula (2a) | D24 | General formula (2a) | D24 | H | H | tert-C₄H₉ | H | H | tert-C₄H₉ | H | H | *1 |
| 225 | CN | General formula (2a) | CN | General formula (2a) | General formula (2a) | D24 | H | H | tert-C₄H₉ | H | H | tert-C₄H₉ | H | H | *1 |
| 226 | CN | D24 | General formula (2a) | CN | D24 | General formula (2a) | H | H | H | H | H | H | H | H | *1 |
| 227 | CN | D24 | General formula (2a) | CN | D24 | General formula (2a) | H | H | CH₃ | H | H | CH₃ | H | H | *1 |
| 228 | CN | D24 | General formula (2a) | CN | D24 | General formula (2a) | H | H | tert-C₄H₉ | H | H | tert-C₄H₉ | H | H | *1 |
| 229 | CN | D24 | General formula (2a) | CN | D24 | General formula (2a) | H | H | tert-C₄H₉ | H | H | tert-C₄H₉ | H | H | *1 |
| 230 | CN | D24 | General formula (2a) | CN | D24 | General formula (2a) | H | H | Phenyl | H | H | Phenyl | H | H | *1 |

TABLE 3

| Compound No | $A^{x1}$ | General formula (11) | | | | General formula (2a) | | | | | |
|---|---|---|---|---|---|---|---|---|---|---|---|
| | | $R^{x11}$ | $R^{x12}$ | $R^{x13}$ | $R^{x14}$ | $R^{a1}$ | $R^{a2}$ | $R^{a3}$ | $R^{a4}$ | $R^{a5}$ | $R^{a6}$ |
| 231 | CN | General formula (2a) | General formula (2a) | General formula (2a) | General formula (2b) | H | H | H | H | H | H |
| 232 | CN | General formula (2a) | General formula (2a) | General formula (2a) | General formula (2b) | H | H | H | H | H | H |
| 233 | CN | General formula (2a) | General formula (2a) | General formula (2a) | General formula (2b) | H | H | H | H | H | H |
| 234 | CN | General formula (2a) | General formula (2a) | General formula (2a) | General formula (2b) | H | H | H | H | H | H |
| 235 | CN | General formula (2a) | General formula (2a) | General formula (2a) | General formula (2b) | H | H | H | H | H | H |
| 236 | CN | General formula (2a) | General formula (2a) | General formula (2a) | General formula (2b) | H | H | H | H | H | H |
| 237 | CN | General formula (2a) | General formula (2a) | General formula (2a) | General formula (2b) | H | H | H | H | H | H |
| 238 | CN | General formula (2a) | General formula (2a) | General formula (2a) | General formula (2b) | H | H | H | H | H | H |
| 239 | CN | General formula (2a) | General formula (2a) | General formula (2a) | General formula (2b) | H | H | H | H | H | H |
| 240 | CN | General formula (2a) | General formula (2a) | General formula (2b) | General formula (2b) | H | H | H | H | H | H |
| 241 | CN | General formula (2a) | General formula (2a) | General formula (2b) | General formula (2b) | H | H | H | H | H | H |
| 242 | CN | General formula (2a) | General formula (2a) | General formula (2b) | General formula (2b) | H | H | H | H | H | H |
| 243 | CN | General formula (2a) | General formula (2a) | General formula (2b) | General formula (2b) | H | H | H | H | H | H |
| 244 | CN | General formula (2a) | General formula (2a) | General formula (2b) | General formula (2b) | H | H | H | H | H | H |
| 245 | CN | General formula (2a) | General formula (2a) | General formula (2b) | General formula (2b) | H | H | H | H | H | H |
| 246 | CN | General formula (2a) | General formula (2a) | General formula (2b) | General formula (2b) | H | H | H | H | H | H |
| 247 | CN | General formula (2a) | General formula (2a) | General formula (2b) | General formula (2b) | H | H | H | H | H | H |
| 248 | CN | General formula (2a) | General formula (2a) | General formula (2b) | General formula (2b) | H | H | H | H | H | H |
| 249 | CN | General formula (2a) | General formula (2a) | General formula (2b) | General formula (2b) | H | H | H | H | H | H |
| 250 | CN | General formula (2a) | General formula (2a) | General formula (2b) | General formula (2b) | H | H | H | H | H | H |
| 251 | CN | General formula (2a) | General formula (2a) | General formula (2b) | General formula (2a) | H | H | H | H | H | H |
| 252 | CN | General formula (2a) | General formula (2a) | General formula (2b) | General formula (2a) | H | H | H | H | H | H |
| 253 | CN | General formula (2a) | General formula (2a) | General formula (2b) | General formula (2a) | H | H | H | H | H | H |
| 254 | CN | General formula (2a) | General formula (2a) | General formula (2b) | General formula (2a) | H | H | H | H | H | H |
| 255 | CN | General formula (2a) | General formula (2a) | General formula (2b) | General formula (2a) | H | H | H | H | H | H |
| 256 | CN | General formula (2a) | General formula (2a) | General formula (2b) | General formula (2a) | H | H | H | H | H | H |
| 257 | CN | General formula (2a) | General formula (2a) | General formula (2b) | General formula (2a) | H | H | H | H | H | H |
| 258 | CN | General formula (2a) | General formula (2a) | General formula (2b) | General formula (2a) | H | H | H | H | H | H |
| 259 | CN | General formula (2a) | General formula (2a) | General formula (2b) | General formula (2a) | H | H | H | H | H | H |
| 260 | CN | General formula (2a) | General formula (2a) | General formula (2b) | General formula (2a) | H | H | H | H | H | H |
| 261 | CN | General formula (2a) | General formula (2a) | General formula (2a) | General formula (2a) | H | H | H | H | H | H |
| 262 | CN | General formula (2a) | General formula (2a) | General formula (2a) | General formula (2a) | H | H | H | H | H | H |
| 263 | CN | General formula (2a) | General formula (2a) | General formula (2a) | General formula (2a) | H | H | H | H | H | H |
| 264 | CN | General formula (2a) | General formula (2a) | General formula (2a) | General formula (2a) | H | H | H | H | H | H |
| 265 | CN | General formula (2a) | General formula (2a) | General formula (2a) | General formula (2a) | H | H | H | H | H | H |
| 266 | CN | General formula (2a) | General formula (2a) | General formula (2a) | General formula (2a) | H | H | H | H | H | H |
| 267 | CN | General formula (2a) | General formula (2a) | General formula (2a) | General formula (2a) | H | H | H | H | H | H |
| 268 | CN | General formula (2a) | General formula (2a) | General formula (2a) | General formula (2a) | H | H | H | H | H | H |
| 269 | CN | General formula (2a) | General formula (2a) | General formula (2a) | General formula (2a) | H | H | H | H | H | H |
| 270 | CN | General formula (2a) | General formula (2a) | General formula (2a) | General formula (2a) | H | H | H | H | H | H |
| 271 | CN | General formula (2a) | General formula (2a) | General formula (2a) | General formula (2a) | H | H | H | H | H | H |
| 272 | CN | General formula (2a) | General formula (2a) | General formula (2a) | General formula (2a) | H | H | H | H | H | H |
| 273 | CN | General formula (2a) | General formula (2a) | General formula (2a) | General formula (2a) | H | H | $CH_3$ | H | H | $CH_3$ |
| 274 | CN | General formula (2a) | General formula (2a) | General formula (2a) | General formula (2a) | H | H | tert-$C_4H_9$ | H | H | tert-$C_4H_9$ |
| 275 | CN | General formula (2a) | General formula (2a) | General formula (2a) | General formula (2a) | H | H | Phenyl | H | H | Phenyl |
| 276 | CN | General formula (2a) | General formula (2a) | General formula (2a) | General formula (2a) | H | H | $CH_3$ | H | H | H |
| 277 | CN | General formula (2a) | General formula (2a) | General formula (2a) | General formula (2a) | H | H | tert-$C_4H_9$ | H | H | H |

TABLE 3-continued

| Compound | 278 | CN | General formula (2a) | | General formula (2a) | General formula (2b) | General formula (2b) | | | | | | H | Phenyl | | |
|---|---|---|---|---|---|---|---|---|---|---|---|---|---|---|---|---|
| | | | General formula (2a) | | | | | General formula (2b) | | | | | | | | |
| No | $R^{a7}$ | $R^{a8}$ | $R^{a9}$ | | | $R^{b1}$ | $R^{b2}$ | $R^{b3}$ | $R^{b4}$ | $R^{b5}$ | $R^{b6}$ | $R^{b7}$ | $R^{b8}$ | $R^{b9}$ | | |
| 231 | H | H | *1 | | | H | H | $CH_3$ | H | H | $CH_3$ | H | H | *1 | | |
| 232 | H | H | *1 | | | H | H | tert-$C_4H_9$ | H | H | tert-$C_4H_9$ | H | H | *1 | | |
| 233 | H | H | *1 | | | H | H | Phenyl | H | H | Phenyl | H | H | *1 | | |
| 234 | H | H | *1 | | | H | H | $CH_3$ | H | H | H | H | H | *1 | | |
| 235 | H | H | *1 | | | H | H | tert-$C_4H_9$ | H | H | H | H | H | *1 | | |
| 236 | H | H | *1 | | | H | H | Phenyl | H | H | H | H | H | *1 | | |
| 237 | H | H | *1 | | | H | H | 9-Carbazolyl | H | H | 9-Carbazolyl | H | H | *1 | | |
| 238 | H | H | *1 | | | H | H | iso-Butyl | H | H | iso-Butyl | H | H | *1 | | |
| 239 | H | H | *1 | | | H | H | 2-Ethylhexyl | H | H | 2-Ethylhexyl | H | H | *1 | | |
| 240 | H | H | *1 | | | H | H | Trimehylsilyl | H | H | Trimehylsilyl | H | H | *1 | | |
| 241 | H | H | *1 | | | H | H | Dipheylamino | H | H | Dipheylamino | H | H | *1 | | |
| 242 | H | H | *1 | | | H | H | Dipheylamino | H | H | H | H | H | *1 | | |
| 243 | H | H | *1 | | | H | H | $CH_3$ | H | H | $CH_3$ | H | H | *1 | | |
| 244 | H | H | *1 | | | H | H | tert-$C_4H_9$ | H | H | tert-$C_4H_9$ | H | H | *1 | | |
| 245 | H | H | *1 | | | H | H | Phenyl | H | H | Phenyl | H | H | *1 | | |
| 246 | H | H | *1 | | | H | H | $CH_3$ | H | H | H | H | H | *1 | | |
| 247 | H | H | *1 | | | H | H | tert-$C_4H_9$ | H | H | H | H | H | *1 | | |
| 248 | H | H | *1 | | | H | H | Phenyl | H | H | H | H | H | *1 | | |
| 249 | H | H | *1 | | | H | H | 9-Carbazolyl | H | H | 9-Carbazolyl | H | H | *1 | | |
| 250 | H | H | *1 | | | H | H | iso-Butyl | H | H | iso-Butyl | H | H | *1 | | |
| 251 | H | H | *1 | | | H | H | 2-Ethylhexyl | H | H | 2-Ethylhexyl | H | H | *1 | | |
| 252 | H | H | *1 | | | H | H | Trimehylsilyl | H | H | Trimehylsilyl | H | H | *1 | | |
| 253 | H | H | *1 | | | H | H | Dipheylamino | H | H | Dipheylamino | H | H | *1 | | |
| 254 | H | H | *1 | | | H | H | Dipheylamino | H | H | H | H | H | *1 | | |
| 255 | H | H | *1 | | | H | H | $CH_3$ | H | H | $CH_3$ | H | H | *1 | | |
| 256 | H | H | *1 | | | H | H | tert-$C_4H_9$ | H | H | tert-$C_4H_9$ | H | H | *1 | | |
| 257 | H | H | *1 | | | H | H | Phenyl | H | H | Phenyl | H | H | *1 | | |
| 258 | H | H | *1 | | | H | H | $CH_3$ | H | H | H | H | H | *1 | | |
| 259 | H | H | *1 | | | H | H | tert-$C_4H_9$ | H | H | H | H | H | *1 | | |
| 260 | H | H | *1 | | | H | H | Phenyl | H | H | H | H | H | *1 | | |
| 261 | H | H | *1 | | | H | H | 9-Carbazolyl | H | H | 9-Carbazolyl | H | H | *1 | | |
| 262 | H | H | *1 | | | H | H | iso-Butyl | H | H | iso-Butyl | H | H | *1 | | |
| 263 | H | H | *1 | | | H | H | 2-Ethylhexyl | H | H | 2-Ethylhexyl | H | H | *1 | | |
| 264 | H | H | *1 | | | H | H | Trimehylsilyl | H | H | Trimehylsilyl | H | H | *1 | | |
| 265 | H | H | *1 | | | H | H | Dipheylamino | H | H | Dipheylamino | H | H | *1 | | |
| 266 | H | H | *1 | | | H | H | Dipheylamino | H | H | H | H | H | *1 | | |
| 267 | H | H | *1 | | | H | H | $CH_3$ | H | H | $CH_3$ | H | H | *1 | | |
| 268 | H | H | *1 | | | H | H | tert-$C_4H_9$ | H | H | tert-$C_4H_9$ | H | H | *1 | | |
| 269 | H | H | *1 | | | H | H | Phenyl | H | H | Phenyl | H | H | *1 | | |
| 270 | H | H | *1 | | | H | H | $CH_3$ | H | H | H | H | H | *1 | | |
| 271 | H | H | *1 | | | H | H | tert-$C_4H_9$ | H | H | H | H | H | *1 | | |
| 272 | H | H | *1 | | | H | H | Phenyl | H | H | H | H | H | *1 | | |
| 273 | H | H | *1 | | | H | H | H | H | H | H | H | H | *1 | | |
| 274 | H | H | *1 | | | H | H | H | H | H | H | H | H | *1 | | |
| 275 | H | H | *1 | | | H | H | H | H | H | H | H | H | *1 | | |
| 276 | H | H | *1 | | | H | H | H | H | H | H | H | H | *1 | | |
| 277 | H | H | *1 | | | H | H | H | H | H | H | H | H | *1 | | |

TABLE 3-continued

| 278 | H | H | *1 | H | H | H | H | H | H | H | *1 |

TABLE 4

| Compound No. | A¹ | General formula (10) | | | | | General formula (2a) | | | | | |
|---|---|---|---|---|---|---|---|---|---|---|---|---|
| | | R¹ | R² | R³ | R⁴ | R⁵ | Rᵃ¹ | Rᵃ² | Rᵃ³ | Rᵃ⁴ | Rᵃ⁵ | Rᵃ⁶ |
| 279 | A1 | General formula (2a) | General formula (2a) | General formula (2b) | General formula (2a) | General formula (2b) | H | H | H | H | H | H |
| 280 | A1 | General formula (2a) | General formula (2a) | General formula (2b) | General formula (2a) | General formula (2b) | H | H | H | H | H | H |
| 281 | A1 | General formula (2a) | General formula (2a) | General formula (2b) | General formula (2a) | General formula (2b) | H | H | H | H | H | H |
| 282 | A1 | General formula (2a) | General formula (2a) | General formula (2b) | General formula (2a) | General formula (2b) | H | H | H | H | H | H |
| 283 | A1 | General formula (2a) | General formula (2a) | General formula (2b) | General formula (2a) | General formula (2b) | H | H | H | H | H | H |
| 284 | A1 | General formula (2a) | General formula (2a) | General formula (2b) | General formula (2a) | General formula (2b) | H | H | H | H | H | H |
| 285 | A1 | General formula (2a) | General formula (2a) | General formula (2b) | General formula (2a) | General formula (2b) | H | H | H | H | H | H |
| 286 | A2 | General formula (2a) | General formula (2a) | General formula (2b) | General formula (2a) | General formula (2b) | H | H | H | H | H | H |
| 287 | A2 | General formula (2a) | General formula (2a) | General formula (2b) | General formula (2a) | General formula (2b) | H | H | H | H | H | H |
| 288 | A2 | General formula (2a) | General formula (2a) | General formula (2b) | General formula (2a) | General formula (2b) | H | H | H | H | H | H |
| 289 | A2 | General formula (2a) | General formula (2a) | General formula (2b) | General formula (2a) | General formula (2b) | H | H | H | H | H | H |
| 290 | A2 | General formula (2a) | General formula (2a) | General formula (2b) | General formula (2a) | General formula (2b) | H | H | H | H | H | H |
| 291 | A2 | General formula (2a) | General formula (2a) | General formula (2b) | General formula (2a) | General formula (2b) | H | H | H | H | H | H |
| 292 | A3 | General formula (2a) | General formula (2a) | General formula (2b) | General formula (2a) | General formula (2b) | H | H | H | H | H | H |
| 293 | A3 | General formula (2a) | General formula (2a) | General formula (2b) | General formula (2a) | General formula (2b) | H | H | H | H | H | H |
| 294 | A3 | General formula (2a) | General formula (2a) | General formula (2b) | General formula (2a) | General formula (2b) | H | H | H | H | H | H |
| 295 | A3 | General formula (2a) | General formula (2a) | General formula (2b) | General formula (2a) | General formula (2b) | H | H | H | H | H | H |
| 296 | A3 | General formula (2a) | General formula (2a) | General formula (2b) | General formula (2a) | General formula (2b) | H | H | H | H | H | H |
| 297 | A3 | General formula (2a) | General formula (2a) | General formula (2b) | General formula (2a) | General formula (2b) | H | H | H | H | H | H |
| 298 | A4 | General formula (2a) | General formula (2a) | General formula (2b) | General formula (2a) | General formula (2b) | H | H | H | H | H | H |
| 299 | A4 | General formula (2a) | General formula (2a) | General formula (2b) | General formula (2a) | General formula (2b) | H | H | H | H | H | H |
| 300 | A4 | General formula (2a) | General formula (2a) | General formula (2b) | General formula (2a) | General formula (2b) | H | H | H | H | H | H |
| 301 | A4 | General formula (2a) | General formula (2a) | General formula (2b) | General formula (2a) | General formula (2b) | H | H | H | H | H | H |
| 302 | A4 | General formula (2a) | General formula (2a) | General formula (2b) | General formula (2a) | General formula (2b) | H | H | H | H | H | H |
| 303 | A4 | General formula (2a) | General formula (2a) | General formula (2b) | General formula (2a) | General formula (2b) | H | H | H | H | H | H |
| 304 | A5 | General formula (2a) | General formula (2a) | General formula (2b) | General formula (2a) | General formula (2b) | H | H | H | H | H | H |
| 305 | A5 | General formula (2a) | General formula (2a) | General formula (2b) | General formula (2a) | General formula (2b) | H | H | H | H | H | H |
| 306 | A5 | General formula (2a) | General formula (2a) | General formula (2b) | General formula (2a) | General formula (2b) | H | H | H | H | H | H |
| 307 | A5 | General formula (2a) | General formula (2a) | General formula (2b) | General formula (2a) | General formula (2b) | H | H | H | H | H | H |
| 308 | A5 | General formula (2a) | General formula (2a) | General formula (2b) | General formula (2a) | General formula (2b) | H | H | H | H | H | H |
| 309 | A5 | General formula (2a) | General formula (2a) | General formula (2b) | General formula (2a) | General formula (2b) | H | H | H | H | H | H |
| 310 | A6 | General formula (2a) | General formula (2a) | General formula (2b) | General formula (2a) | General formula (2b) | H | H | H | H | H | H |
| 311 | A6 | General formula (2a) | General formula (2a) | General formula (2b) | General formula (2a) | General formula (2b) | H | H | H | H | H | H |
| 312 | A6 | General formula (2a) | General formula (2a) | General formula (2b) | General formula (2a) | General formula (2b) | H | H | H | H | H | H |
| 313 | A6 | General formula (2a) | General formula (2a) | General formula (2b) | General formula (2a) | General formula (2b) | H | H | H | H | H | H |
| 314 | A6 | General formula (2a) | General formula (2a) | General formula (2b) | General formula (2a) | General formula (2b) | H | H | H | H | H | H |
| 315 | A6 | General formula (2a) | General formula (2a) | General formula (2b) | General formula (2a) | General formula (2b) | H | H | H | H | H | H |
| 316 | A7 | General formula (2a) | General formula (2a) | General formula (2b) | General formula (2a) | General formula (2b) | H | H | H | H | H | H |
| 317 | A7 | General formula (2a) | General formula (2a) | General formula (2b) | General formula (2a) | General formula (2b) | H | H | H | H | H | H |
| 318 | A7 | General formula (2a) | General formula (2a) | General formula (2b) | General formula (2a) | General formula (2b) | H | H | H | H | H | H |
| 319 | A7 | General formula (2a) | General formula (2a) | General formula (2b) | General formula (2a) | General formula (2b) | H | H | H | H | H | H |
| 320 | A7 | General formula (2a) | General formula (2a) | General formula (2b) | General formula (2a) | General formula (2b) | H | H | H | H | H | H |
| 321 | A7 | General formula (2a) | General formula (2a) | General formula (2b) | General formula (2a) | General formula (2b) | H | H | H | H | H | H |
| 322 | A7 | General formula (2a) | General formula (2a) | General formula (2b) | General formula (2a) | General formula (2b) | H | H | H | H | H | H |
| 323 | A7 | General formula (2a) | General formula (2a) | General formula (2b) | General formula (2a) | General formula (2b) | H | H | H | H | H | H |
| 324 | A7 | General formula (2a) | General formula (2a) | General formula (2b) | General formula (2a) | General formula (2b) | H | H | H | H | H | H |
| 325 | A7 | General formula (2a) | General formula (2a) | General formula (2b) | General formula (2a) | General formula (2b) | H | H | H | H | H | H |

TABLE 4-continued

| No. | R^{a7} | R^{a8} | R^{a9} | | |
|---|---|---|---|---|---|
| | | | General formula (2a) | | |
| 326 | A7 | H | General formula (2a) | General formula (2b) |
| 327 | A7 | H | General formula (2a) | General formula (2b) |
| 328 | A7 | H | H | General formula (2b) |
| 329 | A8 | H | General formula (2a) | General formula (2b) |
| 330 | A8 | H | General formula (2a) | General formula (2b) |
| 331 | A8 | H | General formula (2a) | General formula (2b) |
| 332 | A8 | H | General formula (2a) | General formula (2b) |
| 333 | A8 | H | General formula (2a) | General formula (2b) |
| 334 | A9 | H | General formula (2a) | General formula (2b) |
| 335 | A9 | H | General formula (2a) | General formula (2b) |
| 336 | A9 | H | General formula (2a) | General formula (2b) |
| 337 | A9 | H | General formula (2a) | General formula (2b) |
| 338 | A9 | H | General formula (2a) | General formula (2b) |
| 339 | A9 | H | General formula (2a) | General formula (2b) |
| 340 | A9 | H | General formula (2a) | General formula (2b) |
| 341 | A9 | H | General formula (2a) | General formula (2b) |
| 342 | A10 | H | General formula (2a) | General formula (2b) |
| 343 | A10 | H | General formula (2a) | General formula (2b) |
| 344 | A10 | H | General formula (2a) | General formula (2b) |
| 345 | A10 | H | General formula (2a) | General formula (2b) |
| 346 | A10 | H | General formula (2a) | General formula (2b) |
| 347 | A10 | H | General formula (2a) | General formula (2b) |
| 348 | A10 | H | General formula (2a) | General formula (2b) |
| 349 | A10 | H | General formula (2a) | General formula (2b) |
| 350 | A11 | H | General formula (2a) | General formula (2b) |
| 351 | A11 | H | General formula (2a) | General formula (2b) |
| 352 | A11 | H | General formula (2a) | General formula (2b) |
| 353 | A11 | H | General formula (2a) | General formula (2b) |
| 354 | A11 | H | General formula (2a) | General formula (2b) |
| 355 | A11 | H | General formula (2a) | General formula (2b) |
| 356 | A11 | H | General formula (2a) | General formula (2b) |
| 357 | A12 | H | General formula (2a) | General formula (2b) |
| 358 | A12 | H | General formula (2a) | General formula (2b) |
| 359 | A12 | H | General formula (2a) | General formula (2b) |
| 360 | A12 | H | General formula (2a) | General formula (2b) |
| 361 | A12 | H | General formula (2a) | General formula (2b) |
| 362 | A12 | H | General formula (2a) | General formula (2b) |
| 363 | A13 | H | General formula (2a) | General formula (2b) |
| 364 | A13 | H | General formula (2a) | General formula (2b) |
| 365 | A13 | H | General formula (2a) | General formula (2b) |
| 366 | A13 | H | General formula (2a) | General formula (2b) |
| 367 | A13 | H | General formula (2a) | General formula (2b) |
| 368 | A13 | H | General formula (2a) | General formula (2b) |
| 369 | A13 | H | General formula (2a) | General formula (2b) |
| 370 | A13 | H | General formula (2a) | General formula (2b) |

| Compound No. | General formula (2a) | | | General formula (2b) | | | | | |
|---|---|---|---|---|---|---|---|---|---|
| | R^{a9} | | | R^{b1} | R^{b2} | R^{b3} | R^{b4} | R^{b5} | R^{b6} | R^{b7} | R^{b8} | R^{b9} |
| 279 | *1 | | | H | H | CH$_3$ | H | H | CH$_3$ | H | H | *1 |
| 280 | *1 | | | H | H | tert-C$_4$H$_9$ | H | H | tert-C$_4$H$_9$ | H | H | *1 |
| 281 | *1 | | | H | H | Phenyl | H | H | Phenyl | H | H | *1 |

TABLE 4-continued

| | | | | | | | | | |
|---|---|---|---|---|---|---|---|---|---|
| 282 | H | H | H | CH₃ | H | H | CH₃ | H | *1 |
| 283 | H | H | H | tert-C₄H₉ | H | H | tert-C₄H₉ | H | *1 |
| 284 | H | H | H | Phenyl | H | H | Phenyl | H | *1 |
| 285 | H | H | H | 9-Carbazolyl | H | H | 9-Carbazolyl | H | *1 |
| 286 | H | H | H | CH₃ | H | H | CH₃ | H | *1 |
| 287 | H | H | H | tert-C₄H₉ | H | H | tert-C₄H₉ | H | *1 |
| 288 | H | H | H | Phenyl | H | H | Phenyl | H | *1 |
| 289 | H | H | H | CH₃ | H | H | CH₃ | H | *1 |
| 290 | H | H | H | tert-C₄H₉ | H | H | tert-C₄H₉ | H | *1 |
| 291 | H | H | H | Phenyl | H | H | Phenyl | H | *1 |
| 292 | H | H | H | 9-Carbazolyl | H | H | 9-Carbazolyl | H | *1 |
| 293 | H | H | H | CH₃ | H | H | CH₃ | H | *1 |
| 294 | H | H | H | tert-C₄H₉ | H | H | tert-C₄H₉ | H | *1 |
| 295 | H | H | H | Phenyl | H | H | Phenyl | H | *1 |
| 296 | H | H | H | CH₃ | H | H | CH₃ | H | *1 |
| 297 | H | H | H | tert-C₄H₉ | H | H | tert-C₄H₉ | H | *1 |
| 298 | H | H | H | Phenyl | H | H | Phenyl | H | *1 |
| 299 | H | H | H | 9-Carbazolyl | H | H | 9-Carbazolyl | H | *1 |
| 300 | H | H | H | CH₃ | H | H | CH₃ | H | *1 |
| 301 | H | H | H | tert-C₄H₉ | H | H | tert-C₄H₉ | H | *1 |
| 302 | H | H | H | Phenyl | H | H | Phenyl | H | *1 |
| 303 | H | H | H | CH₃ | H | H | CH₃ | H | *1 |
| 304 | H | H | H | tert-C₄H₉ | H | H | tert-C₄H₉ | H | *1 |
| 305 | H | H | H | Phenyl | H | H | Phenyl | H | *1 |
| 306 | H | H | H | 9-Carbazolyl | H | H | 9-Carbazolyl | H | *1 |
| 307 | H | H | H | CH₃ | H | H | CH₃ | H | *1 |
| 308 | H | H | H | tert-C₄H₉ | H | H | tert-C₄H₉ | H | *1 |
| 309 | H | H | H | Phenyl | H | H | Phenyl | H | *1 |
| 310 | H | H | H | CH₃ | H | H | CH₃ | H | *1 |
| 311 | H | H | H | tert-C₄H₉ | H | H | tert-C₄H₉ | H | *1 |
| 312 | H | H | H | Phenyl | H | H | Phenyl | H | *1 |
| 313 | H | H | H | 9-Carbazolyl | H | H | 9-Carbazolyl | H | *1 |
| 314 | H | H | H | CH₃ | H | H | CH₃ | H | *1 |
| 315 | H | H | H | tert-C₄H₉ | H | H | tert-C₄H₉ | H | *1 |
| 316 | H | H | H | Phenyl | H | H | Phenyl | H | *1 |
| 317 | H | H | H | CH₃ | H | H | CH₃ | H | *1 |
| 318 | H | H | H | tert-C₄H₉ | H | H | tert-C₄H₉ | H | *1 |
| 319 | H | H | H | Phenyl | H | H | Phenyl | H | *1 |
| 320 | H | H | H | 9-Carbazolyl | H | H | 9-Carbazolyl | H | *1 |
| 321 | H | H | H | CH₃ | H | H | CH₃ | H | *1 |
| 322 | H | H | H | tert-C₄H₉ | H | H | tert-C₄H₉ | H | *1 |
| 323 | H | H | H | Phenyl | H | H | Phenyl | H | *1 |
| 324 | H | H | H | CH₃ | H | H | CH₃ | H | *1 |
| 325 | H | H | H | tert-C₄H₉ | H | H | tert-C₄H₉ | H | *1 |
| 326 | H | H | H | Phenyl | H | H | Phenyl | H | *1 |
| 327 | H | H | H | 9-Carbazolyl | H | H | 9-Carbazolyl | H | *1 |
| 328 | H | H | H | CH₃ | H | H | CH₃ | H | *1 |
| 329 | H | H | H | tert-C₄H₉ | H | H | tert-C₄H₉ | H | *1 |
| 330 | H | H | H | Phenyl | H | H | Phenyl | H | *1 |
| 331 | H | H | H | CH₃ | H | H | CH₃ | H | *1 |
| 332 | H | H | H | tert-C₄H₉ | H | H | tert-C₄H₉ | H | *1 |
| 333 | H | H | H | CH₃ | H | H | CH₃ | H | *1 |
| 334 | H | H | H | tert-C₄H₉ | H | H | tert-C₄H₉ | H | *1 |

TABLE 4-continued

| No. | | | | | | | | | | |
|---|---|---|---|---|---|---|---|---|---|---|
| 335 | H | H | H | 9-Carbazolyl | H | H | 9-Carbazolyl | H | H | *1 |
| 336 | H | H | H | CH$_3$ | H | H | CH$_3$ | H | H | *1 |
| 337 | H | H | H | tert-C$_4$H$_9$ | H | H | tert-C$_4$H$_9$ | H | H | *1 |
| 338 | H | H | H | Phenyl | H | H | Phenyl | H | H | *1 |
| 339 | H | H | H | CH$_3$ | H | H | CH$_3$ | H | H | *1 |
| 340 | H | H | H | tert-C$_4$H$_9$ | H | H | tert-C$_4$H$_9$ | H | H | *1 |
| 341 | H | H | H | Phenyl | H | H | Phenyl | H | H | *1 |
| 342 | H | H | H | 9-Carbazolyl | H | H | 9-Carbazolyl | H | H | *1 |
| 343 | H | H | H | CH$_3$ | H | H | CH$_3$ | H | H | *1 |
| 344 | H | H | H | tert-C$_4$H$_9$ | H | H | tert-C$_4$H$_9$ | H | H | *1 |
| 345 | H | H | H | Phenyl | H | H | Phenyl | H | H | *1 |
| 346 | H | H | H | CH$_3$ | H | H | CH$_3$ | H | H | *1 |
| 347 | H | H | H | tert-C$_4$H$_9$ | H | H | tert-C$_4$H$_9$ | H | H | *1 |
| 348 | H | H | H | Phenyl | H | H | Phenyl | H | H | *1 |
| 349 | H | H | H | 9-Carbazolyl | H | H | 9-Carbazolyl | H | H | *1 |
| 350 | H | H | H | CH$_3$ | H | H | CH$_3$ | H | H | *1 |
| 351 | H | H | H | tert-C$_4$H$_9$ | H | H | tert-C$_4$H$_9$ | H | H | *1 |
| 352 | H | H | H | Phenyl | H | H | Phenyl | H | H | *1 |
| 353 | H | H | H | CH$_3$ | H | H | CH$_3$ | H | H | *1 |
| 354 | H | H | H | tert-C$_4$H$_9$ | H | H | tert-C$_4$H$_9$ | H | H | *1 |
| 355 | H | H | H | Phenyl | H | H | Phenyl | H | H | *1 |
| 356 | H | H | H | 9-Carbazolyl | H | H | 9-Carbazolyl | H | H | *1 |
| 357 | H | H | H | CH$_3$ | H | H | CH$_3$ | H | H | *1 |
| 358 | H | H | H | tert-C$_4$H$_9$ | H | H | tert-C$_4$H$_9$ | H | H | *1 |
| 359 | H | H | H | Phenyl | H | H | Phenyl | H | H | *1 |
| 360 | H | H | H | CH$_3$ | H | H | CH$_3$ | H | H | *1 |
| 361 | H | H | H | tert-C$_4$H$_9$ | H | H | tert-C$_4$H$_9$ | H | H | *1 |
| 362 | H | H | H | Phenyl | H | H | Phenyl | H | H | *1 |
| 363 | H | H | H | 9-Carbazolyl | H | H | 9-Carbazolyl | H | H | *1 |
| 364 | H | H | H | CH$_3$ | H | H | CH$_3$ | H | H | *1 |
| 365 | H | H | H | tert-C$_4$H$_9$ | H | H | tert-C$_4$H$_9$ | H | H | *1 |
| 366 | H | H | H | Phenyl | H | H | Phenyl | H | H | *1 |
| 367 | H | H | H | CH$_3$ | H | H | CH$_3$ | H | H | *1 |
| 368 | H | H | H | tert-C$_4$H$_9$ | H | H | tert-C$_4$H$_9$ | H | H | *1 |
| 369 | H | H | H | Phenyl | H | H | Phenyl | H | H | *1 |
| 370 | H | H | H | 9-Carbazolyl | H | H | 9-Carbazolyl | H | H | *1 |

TABLE 5

| Compound No. | $A^1$ | $R^1$ | $R^2$ | $R^3$ | $R^4$ | $R^5$ | General formula (10) $R^{a1}$ | $R^{a2}$ | $R^{a3}$ | General formula (2a) $R^{a4}$ | $R^{a5}$ | $R^{a6}$ |
|---|---|---|---|---|---|---|---|---|---|---|---|---|
| 371 | A5 | General formula (2a) | A5 | General formula (2a) | General formula (2b) | General formula (2b) | H | H | H | H | H | H |
| 372 | A5 | General formula (2a) | A5 | General formula (2a) | General formula (2b) | General formula (2b) | H | H | H | H | H | H |
| 373 | A5 | General formula (2a) | A5 | General formula (2a) | General formula (2b) | General formula (2b) | H | H | H | H | H | $CH_3$ |
| 374 | A5 | General formula (2a) | A5 | General formula (2a) | General formula (2b) | General formula (2b) | H | H | $CH_3$ | H | H | $CH_3$ |
| 375 | A5 | General formula (2a) | A5 | General formula (2a) | General formula (2b) | General formula (2b) | H | H | H | H | H | H |
| 376 | A5 | General formula (2a) | A5 | General formula (2a) | General formula (2b) | General formula (2b) | H | H | H | H | H | H |
| 377 | A5 | General formula (2a) | A5 | General formula (2a) | General formula (2b) | General formula (2b) | H | H | $CH_3$ | H | H | $CH_3$ |
| 378 | A5 | General formula (2a) | A5 | General formula (2a) | General formula (2b) | General formula (2b) | H | H | $CH_3$ | H | H | $CH_3$ |
| 379 | A5 | General formula (2a) | A5 | General formula (2a) | General formula (2b) | General formula (2b) | H | H | Phenyl | H | H | Phenyl |
| 380 | A5 | General formula (2a) | A5 | General formula (2a) | General formula (2b) | General formula (2b) | H | H | H | H | H | H |
| 381 | A5 | General formula (2a) | A5 | General formula (2a) | General formula (2b) | General formula (2b) | H | H | H | H | H | H |
| 382 | A5 | General formula (2a) | A5 | General formula (2a) | General formula (2b) | General formula (2b) | H | H | H | H | H | H |
| 383 | A5 | General formula (2a) | A5 | General formula (2a) | General formula (2b) | General formula (2b) | H | H | H | H | H | $CH_3$ |
| 384 | A5 | General formula (2a) | A5 | General formula (2a) | General formula (2b) | General formula (2a) | H | H | $CH_3$ | H | H | H |
| 385 | A5 | General formula (2a) | A5 | General formula (2a) | General formula (2b) | General formula (2a) | H | H | H | H | H | H |
| 386 | A5 | General formula (2a) | A5 | General formula (2a) | H | General formula (2b) | H | H | H | H | H | H |
| 387 | A5 | General formula (2a) | A5 | General formula (2a) | H | General formula (2b) | H | H | H | H | H | H |
| 388 | A5 | General formula (2a) | A5 | General formula (2a) | H | General formula (2b) | H | H | $CH_3$ | H | H | $CH_3$ |
| 389 | A5 | General formula (2a) | A5 | General formula (2a) | H | General formula (2b) | H | H | tert-$C_4H_9$ | H | H | tert-$C_4H_9$ |
| 390 | A5 | General formula (2a) | A6 | General formula (2a) | H | General formula (2b) | H | H | Phenyl | H | H | Phenyl |
| 391 | A6 | General formula (2a) | A6 | General formula (2a) | General formula (2b) | General formula (2b) | H | H | H | H | H | H |
| 392 | A6 | General formula (2a) | A6 | General formula (2a) | General formula (2b) | General formula (2b) | H | H | H | H | H | H |
| 393 | A6 | General formula (2a) | A6 | General formula (2a) | General formula (2b) | General formula (2b) | H | H | H | H | H | $CH_3$ |
| 394 | A6 | General formula (2a) | A6 | General formula (2a) | General formula (2b) | General formula (2b) | H | H | $CH_3$ | H | H | $CH_3$ |
| 395 | A6 | General formula (2a) | A6 | General formula (2a) | General formula (2b) | General formula (2b) | H | H | $CH_3$ | H | H | $CH_3$ |
| 396 | A6 | General formula (2a) | A6 | General formula (2a) | General formula (2b) | General formula (2b) | H | H | Phenyl | H | H | Phenyl |
| 397 | A6 | General formula (2a) | A6 | General formula (2a) | General formula (2b) | General formula (2b) | H | H | H | H | H | H |
| 398 | A6 | General formula (2a) | A6 | General formula (2a) | General formula (2b) | General formula (2b) | H | H | H | H | H | H |
| 399 | A6 | General formula (2a) | A6 | General formula (2a) | General formula (2b) | General formula (2b) | H | H | $CH_3$ | H | H | $CH_3$ |
| 400 | A6 | General formula (2a) | A6 | General formula (2a) | General formula (2b) | General formula (2b) | H | H | $CH_3$ | H | H | $CH_3$ |
| 401 | A6 | General formula (2a) | A6 | General formula (2a) | General formula (2b) | General formula (2b) | H | H | Phenyl | H | H | Phenyl |
| 402 | A6 | General formula (2a) | A6 | General formula (2a) | General formula (2b) | General formula (2b) | H | H | H | H | H | H |
| 403 | A6 | General formula (2a) | A6 | General formula (2a) | General formula (2b) | General formula (2b) | H | H | H | H | H | H |
| 404 | A6 | General formula (2a) | A6 | General formula (2a) | General formula (2b) | General formula (2b) | H | H | $CH_3$ | H | H | $CH_3$ |
| 405 | A6 | General formula (2a) | A6 | General formula (2a) | H | General formula (2b) | H | H | H | H | H | H |
| 406 | A6 | General formula (2a) | A6 | General formula (2a) | H | General formula (2b) | H | H | H | H | H | H |
| 407 | A6 | General formula (2a) | A6 | General formula (2a) | H | General formula (2b) | H | H | $CH_3$ | H | H | $CH_3$ |
| 408 | A6 | General formula (2a) | A6 | General formula (2a) | H | General formula (2b) | H | H | $CH_3$ | H | H | $CH_3$ |
| 409 | A6 | General formula (2a) | A6 | General formula (2a) | H | General formula (2b) | H | H | Phenyl | H | H | Phenyl |
| 410 | A6 | General formula (2a) | A6 | General formula (2a) | General formula (2b) | General formula (2a) | H | H | H | H | H | H |
| 411 | A7 | General formula (2a) | A7 | General formula (2a) | General formula (2b) | General formula (2b) | H | H | H | H | H | H |
| 412 | A7 | General formula (2a) | A7 | General formula (2a) | General formula (2b) | General formula (2b) | H | H | H | H | H | $CH_3$ |
| 413 | A7 | General formula (2a) | A7 | General formula (2a) | General formula (2b) | General formula (2b) | H | H | $CH_3$ | H | H | $CH_3$ |
| 414 | A7 | General formula (2a) | A7 | General formula (2a) | General formula (2b) | General formula (2b) | H | H | tert-$C_4H_9$ | H | H | tert-$C_4H_9$ |
| 415 | A7 | General formula (2a) | A7 | General formula (2a) | General formula (2b) | General formula (2b) | H | H | H | H | H | H |
| 416 | A7 | General formula (2a) | A7 | General formula (2a) | General formula (2b) | General formula (2b) | H | H | H | H | H | $CH_3$ |

TABLE 5-continued

| # | | | | | | | | | | |
|---|---|---|---|---|---|---|---|---|---|---|
| 417 | A7 | General formula (2a) | General formula (2b) | General formula (2a) | General formula (2b) | H | H | H | H | H |
| 418 | A7 | General formula (2a) | General formula (2b) | General formula (2a) | General formula (2b) | H | H | CH₃ | H | CH₃ |
| 419 | A7 | General formula (2a) | General formula (2b) | General formula (2a) | General formula (2b) | H | H | CH₃ | H | CH₃ |
| 420 | A7 | General formula (2a) | General formula (2b) | General formula (2a) | General formula (2b) | H | H | Phenyl | H | Phenyl |
| 421 | A7 | General formula (2a) | General formula (2b) | General formula (2a) | General formula (2b) | H | H | H | H | H |
| 422 | A7 | General formula (2a) | General formula (2b) | General formula (2a) | General formula (2b) | H | H | H | H | H |
| 423 | A7 | General formula (2a) | General formula (2b) | General formula (2a) | General formula (2b) | H | H | CH₃ | H | CH₃ |
| 424 | A7 | General formula (2a) | General formula (2b) | General formula (2a) | General formula (2b) | H | H | H | H | H |
| 425 | A7 | General formula (2a) | H | General formula (2a) | H | H | H | H | H | H |
| 426 | A7 | General formula (2a) | H | General formula (2a) | H | H | H | H | H | H |
| 427 | A7 | General formula (2a) | H | General formula (2a) | H | H | H | CH₃ | H | CH₃ |
| 428 | A7 | General formula (2a) | H | General formula (2a) | H | H | H | tert-C₄H₉ | H | tert-C₄H₉ |
| 429 | A7 | General formula (2a) | H | General formula (2a) | H | H | H | Phenyl | H | Phenyl |
| 430 | A7 | General formula (2a) | General formula (2b) | General formula (2a) | General formula (2b) | H | H | H | H | H |
| 431 | A5 | General formula (2a) | General formula (2b) | General formula (2a) | General formula (2b) | H | H | H | H | H |
| 432 | A5 | General formula (2a) | General formula (2b) | General formula (2a) | General formula (2b) | H | H | CH₃ | H | CH₃ |
| 433 | A5 | General formula (2a) | General formula (2b) | General formula (2a) | General formula (2b) | H | H | H | H | H |
| 434 | A5 | General formula (2a) | General formula (2b) | General formula (2a) | General formula (2b) | H | H | H | H | H |
| 435 | A5 | General formula (2a) | General formula (2b) | General formula (2a) | General formula (2b) | H | H | CH₃ | H | CH₃ |
| 436 | A5 | General formula (2a) | General formula (2b) | General formula (2a) | General formula (2b) | H | H | H | H | H |
| 437 | A5 | General formula (2a) | General formula (2b) | General formula (2a) | General formula (2b) | H | H | H | H | H |
| 438 | A5 | General formula (2a) | General formula (2b) | General formula (2a) | General formula (2b) | H | H | CH₃ | H | CH₃ |
| 439 | A5 | General formula (2a) | General formula (2b) | General formula (2a) | General formula (2b) | H | H | H | H | H |
| 440 | A5 | General formula (2a) | General formula (2b) | General formula (2a) | General formula (2b) | H | H | H | H | H |
| 441 | A5 | General formula (2a) | General formula (2b) | General formula (2a) | General formula (2b) | H | H | CH₃ | H | CH₃ |
| 442 | A5 | General formula (2a) | General formula (2b) | General formula (2a) | General formula (2b) | H | H | H | H | H |
| 443 | A.5 | General formula (2a) | General formula (2b) | A5 | General formula (2b) | H | H | H | H | H |
| 444 | A5 | General formula (2a) | General formula (2b) | A5 | General formula (2b) | H | H | CH₃ | H | CH₃ |
| 445 | A5 | General formula (2a) | General formula (2b) | A5 | General formula (2b) | H | H | H | H | H |
| 446 | A5 | General formula (2a) | General formula (2b) | A5 | General formula (2b) | H | H | H | H | H |
| 447 | A5 | General formula (2a) | General formula (2b) | A5 | General formula (2b) | H | H | CH₃ | H | CH₃ |
| 448 | A5 | General formula (2a) | General formula (2b) | A5 | General formula (2b) | H | H | H | H | H |
| 449 | A5 | General formula (2a) | General formula (2b) | A5 | General formula (2b) | H | H | H | H | H |
| 450 | A5 | General formula (2a) | General formula (2b) | A5 | General formula (2b) | H | H | CH₃ | H | CH₃ |
| 451 | A5 | General formula (2a) | General formula (2b) | A5 | General formula (2b) | H | H | H | H | H |
| 452 | A5 | General formula (2a) | General formula (2b) | A5 | General formula (2b) | H | H | H | H | H |
| 453 | A5 | General formula (2a) | General formula (2b) | A5 | General formula (2b) | H | H | CH₃ | H | CH₃ |
| 454 | A5 | General formula (2a) | General formula (2b) | A5 | General formula (2b) | H | H | H | H | H |
| 455 | A6 | General formula (2a) | General formula (2b) | A6 | General formula (2b) | H | H | H | H | H |
| 456 | A6 | General formula (2a) | General formula (2b) | A6 | General formula (2b) | H | H | CH₃ | H | CH₃ |
| 457 | A6 | General formula (2a) | General formula (2b) | A6 | General formula (2b) | H | H | H | H | H |
| 458 | A6 | General formula (2a) | General formula (2b) | A6 | General formula (2b) | H | H | H | H | H |
| 459 | A6 | General formula (2a) | General formula (2b) | A6 | General formula (2b) | H | H | CH₃ | H | CH₃ |
| 460 | A6 | General formula (2a) | General formula (2b) | A6 | General formula (2b) | H | H | H | H | H |
| 461 | A6 | General formula (2a) | General formula (2b) | A6 | General formula (2b) | H | H | H | H | H |
| 462 | A6 | General formula (2a) | General formula (2b) | A6 | General formula (2b) | H | H | CH₃ | H | CH₃ |
| 463 | A6 | General formula (2a) | General formula (2b) | A6 | General formula (2b) | H | H | H | H | H |
| 464 | A6 | General formula (2a) | General formula (2b) | A6 | General formula (2b) | H | H | H | H | H |
| 465 | A6 | General formula (2a) | General formula (2b) | A6 | General formula (2b) | H | H | CH₃ | H | CH₃ |
| 466 | A6 | General formula (2a) | General formula (2b) | A6 | General formula (2b) | H | H | H | H | H |
| 467 | A6 | General formula (2a) | General formula (2b) | A6 | General formula (2b) | H | H | H | H | H |
| 468 | A6 | General formula (2a) | General formula (2b) | A6 | General formula (2b) | H | H | H | H | H |
| 469 | A6 | General formula (2a) | General formula (2b) | A6 | General formula (2b) | H | H | H | H | H |

TABLE 5-continued

| Compound No. | R$^{a7}$ | R$^{a8}$ | General formula (2a) R$^{a9}$ | | |
|---|---|---|---|---|---|
| 470 | A6 | General formula (2b) | A6 | | |
| 471 | A6 | General formula (2b) | A6 | | |
| 472 | A6 | General formula (2b) | A6 | | |
| 473 | A6 | General formula (2b) | A6 | | |
| 474 | A6 | General formula (2b) | A6 | | |
| 475 | A6 | General formula (2b) | A6 | | |
| 476 | A6 | General formula (2b) | A6 | | |
| 477 | A6 | General formula (2b) | A6 | | |
| 478 | A6 | General formula (2b) | A6 | | |
| 479 | A7 | General formula (2b) | General formula (2a) | | |
| 480 | A7 | General formula (2b) | A7 | | |
| 481 | A7 | General formula (2b) | A7 | | |
| 482 | A7 | General formula (2b) | A7 | | |
| 483 | A7 | General formula (2b) | A7 | | |
| 484 | A7 | General formula (2b) | A7 | | |
| 485 | A7 | General formula (2b) | A7 | | |
| 486 | A7 | General formula (2b) | A7 | | |
| 487 | A7 | General formula (2b) | A7 | | |
| 488 | A7 | General formula (2b) | A7 | | |
| 489 | A7 | General formula (2b) | A7 | | |
| 490 | A7 | General formula (2b) | A7 | | |
| 491 | A7 | H | *1 | General formula (2a) | |
| 492 | A7 | H | *1 | General formula (2b) | |
| 493 | A7 | H | *1 | General formula (2b) | |
| 494 | A7 | H | *1 | General formula (2b) | |
| 495 | A7 | H | *1 | General formula (2b) | |
| 496 | A7 | H | *1 | General formula (2b) | |
| 497 | A7 | H | *1 | General formula (2b) | |
| 498 | A7 | H | *1 | General formula (2b) | |
| 499 | A7 | H | *1 | General formula (2b) | |
| 500 | A7 | H | *1 | General formula (2b) | |
| 501 | A7 | H | *1 | General formula (2b) | |
| 502 | A7 | H | *1 | General formula (2b) | |

| Compound No. | R$^{b1}$ | R$^{b2}$ | R$^{b3}$ | General formula (2b) R$^{b4}$ | R$^{b5}$ | R$^{b6}$ | R$^{b7}$ | R$^{b8}$ | R$^{b9}$ |
|---|---|---|---|---|---|---|---|---|---|
| 371 | H | H | CH$_3$ | H | H | CH$_3$ | H | H | *1 |
| 372 | H | H | tert-C$_4$H$_9$ | H | H | tert-C$_4$H$_9$ | H | H | *1 |
| 373 | H | H | Phenyl | H | H | Phenyl | H | H | *1 |
| 374 | H | H | Phenyl | H | H | Phenyl | H | H | *1 |
| 375 | H | H | CH$_3$ | H | H | CH$_3$ | H | H | *1 |
| 376 | H | H | tert-C$_4$H$_9$ | H | H | tert-C$_4$H$_9$ | H | H | *1 |
| 377 | H | H | Phenyl | H | H | Phenyl | H | H | *1 |
| 378 | H | H | H | H | H | H | H | H | *1 |
| 379 | H | H | Phenyl | H | H | Phenyl | H | H | *1 |
| 380 | H | H | H | H | H | H | H | H | *1 |
| 381 | H | H | CH$_3$ | H | H | CH$_3$ | H | H | *1 |
| 382 | H | H | tert-C$_4$H$_9$ | H | H | tert-C$_4$H$_9$ | H | H | *1 |
| 383 | H | H | Phenyl | H | H | Phenyl | H | H | *1 |
| 384 | H | H | Phenyl | H | H | Phenyl | H | H | *1 |

TABLE 5-continued

| | | | | | | | | | | | | |
|---|---|---|---|---|---|---|---|---|---|---|---|---|
| 385 | H | H | *1 | H | CH₃ | H | H | CH₃ | H | *1 | H | H |
| 386 | H | H | *1 | H | tert-C₄H₉ | H | H | tert-C₄H₉ | H | *1 | H | H |
| 387 | H | H | *1 | H | Phenyl | H | H | Phenyl | H | *1 | H | H |
| 388 | H | H | *1 | H | H | H | H | H | H | *1 | H | H |
| 389 | H | H | *1 | H | H | H | H | H | H | *1 | H | H |
| 390 | H | H | *1 | H | H | H | H | H | H | *1 | H | H |
| 391 | H | H | *1 | H | CH₃ | H | H | CH₃ | H | *1 | H | H |
| 392 | H | H | *1 | H | tert-C₄H₉ | H | H | tert-C₄H₉ | H | *1 | H | H |
| 393 | H | H | *1 | H | Phenyl | H | H | Phenyl | H | *1 | H | H |
| 394 | H | H | *1 | H | Phenyl | H | H | Phenyl | H | *1 | H | H |
| 395 | H | H | *1 | H | CH₃ | H | H | CH₃ | H | *1 | H | H |
| 396 | H | H | *1 | H | tert-C₄H₉ | H | H | tert-C₄H₉ | H | *1 | H | H |
| 397 | H | H | *1 | H | H | H | H | H | H | *1 | H | H |
| 398 | H | H | *1 | H | Phenyl | H | H | Phenyl | H | *1 | H | H |
| 399 | H | H | *1 | H | H | H | H | H | H | *1 | H | H |
| 400 | H | H | *1 | H | H | H | H | H | H | *1 | H | H |
| 401 | H | H | *1 | H | CH₃ | H | H | CH₃ | H | *1 | H | H |
| 402 | H | H | *1 | H | tert-C₄H₉ | H | H | tert-C₄H₉ | H | *1 | H | H |
| 403 | H | H | *1 | H | Phenyl | H | H | Phenyl | H | *1 | H | H |
| 404 | H | H | *1 | H | Phenyl | H | H | Phenyl | H | *1 | H | H |
| 405 | H | H | *1 | H | CH₃ | H | H | CH₃ | H | *1 | H | H |
| 406 | H | H | *1 | H | tert-C₄H₉ | H | H | tert-C₄H₉ | H | *1 | H | H |
| 407 | H | H | *1 | H | Phenyl | H | H | Phenyl | H | *1 | H | H |
| 408 | H | H | *1 | H | H | H | H | H | H | *1 | H | H |
| 409 | H | H | *1 | H | H | H | H | H | H | *1 | H | H |
| 410 | H | H | *1 | H | H | H | H | H | H | *1 | H | H |
| 411 | H | H | *1 | H | CH₃ | H | H | CH₃ | H | *1 | H | H |
| 412 | H | H | *1 | H | tert-C₄H₉ | H | H | tert-C₄H₉ | H | *1 | H | H |
| 413 | H | H | *1 | H | Phenyl | H | H | Phenyl | H | *1 | H | H |
| 414 | H | H | *1 | H | Phenyl | H | H | Phenyl | H | *1 | H | H |
| 415 | H | H | *1 | H | CH₃ | H | H | CH₃ | H | *1 | H | H |
| 416 | H | H | *1 | H | tert-C₄H₉ | H | H | tert-C₄H₉ | H | *1 | H | H |
| 417 | H | H | *1 | H | Phenyl | H | H | Phenyl | H | *1 | H | H |
| 418 | H | H | *1 | H | H | H | H | H | H | *1 | H | H |
| 419 | H | H | *1 | H | Phenyl | H | H | Phenyl | H | *1 | H | H |
| 420 | H | H | *1 | H | H | H | H | H | H | *1 | H | H |
| 421 | H | H | *1 | H | CH₃ | H | H | CH₃ | H | *1 | H | H |
| 422 | H | H | *1 | H | tert-C₄H₉ | H | H | tert-C₄H₉ | H | *1 | H | H |
| 423 | H | H | *1 | H | Phenyl | H | H | Phenyl | H | *1 | H | H |
| 424 | H | H | *1 | H | Phenyl | H | H | Phenyl | H | *1 | H | H |
| 425 | H | H | *1 | H | CH₃ | H | H | CH₃ | H | *1 | H | H |
| 426 | H | H | *1 | H | tert-C₄H₉ | H | H | tert-C₄H₉ | H | *1 | H | H |
| 427 | H | H | *1 | H | Phenyl | H | H | Phenyl | H | *1 | H | H |
| 428 | H | H | *1 | H | H | H | H | H | H | *1 | H | H |
| 429 | H | H | *1 | H | Phenyl | H | H | Phenyl | H | *1 | H | H |
| 430 | H | H | *1 | H | H | H | H | H | H | *1 | H | H |
| 431 | H | H | *1 | H | CH₃ | H | H | CH₃ | H | *1 | H | H |
| 432 | H | H | *1 | H | tert-C₄H₉ | H | H | tert-C₄H₉ | H | *1 | H | H |
| 433 | H | H | *1 | H | Phenyl | H | H | Phenyl | H | *1 | H | H |
| 434 | H | H | *1 | H | Phenyl | H | H | Phenyl | H | *1 | H | H |
| 435 | H | H | *1 | H | CH₃ | H | H | CH₃ | H | *1 | H | H |
| 436 | H | H | *1 | H | tert-C₄H₉ | H | H | tert-C₄H₉ | H | *1 | H | H |
| 437 | H | H | *1 | H | Phenyl | H | H | Phenyl | H | *1 | H | H |

TABLE 5-continued

| | | | | | | | | | | |
|---|---|---|---|---|---|---|---|---|---|---|
| 438 | H | H | H | Phenyl | H | H | Phenyl | H | H | *1 |
| 439 | H | H | H | CH$_3$ | H | H | CH$_3$ | H | H | *1 |
| 440 | H | H | H | tert-C$_4$H$_9$ | H | H | tert-C$_4$H$_9$ | H | H | *1 |
| 441 | H | H | H | Phenyl | H | H | Phenyl | H | H | *1 |
| 442 | H | H | H | Phenyl | H | H | Phenyl | H | H | *1 |
| 443 | H | H | H | CH$_3$ | H | H | CH$_3$ | H | H | *1 |
| 444 | H | H | H | tert-C$_4$H$_9$ | H | H | tert-C$_4$H$_9$ | H | H | *1 |
| 445 | H | H | H | Phenyl | H | H | Phenyl | H | H | *1 |
| 446 | H | H | H | Phenyl | H | H | Phenyl | H | H | *1 |
| 447 | H | H | H | CH$_3$ | H | H | CH$_3$ | H | H | *1 |
| 448 | H | H | H | tert-C$_4$H$_9$ | H | H | tert-C$_4$H$_9$ | H | H | *1 |
| 449 | H | H | H | Phenyl | H | H | Phenyl | H | H | *1 |
| 450 | H | H | H | Phenyl | H | H | Phenyl | H | H | *1 |
| 451 | H | H | H | CH$_3$ | H | H | CH$_3$ | H | H | *1 |
| 452 | H | H | H | tert-C$_4$H$_9$ | H | H | tert-C$_4$H$_9$ | H | H | *1 |
| 453 | H | H | H | Phenyl | H | H | Phenyl | H | H | *1 |
| 454 | H | H | H | Phenyl | H | H | Phenyl | H | H | *1 |
| 455 | H | H | H | CH$_3$ | H | H | CH$_3$ | H | H | *1 |
| 456 | H | H | H | tert-C$_4$H$_9$ | H | H | tert-C$_4$H$_9$ | H | H | *1 |
| 457 | H | H | H | Phenyl | H | H | Phenyl | H | H | *1 |
| 458 | H | H | H | Phenyl | H | H | Phenyl | H | H | *1 |
| 459 | H | H | H | CH$_3$ | H | H | CH$_3$ | H | H | *1 |
| 460 | H | H | H | tert-C$_4$H$_9$ | H | H | tert-C$_4$H$_9$ | H | H | *1 |
| 461 | H | H | H | Phenyl | H | H | Phenyl | H | H | *1 |
| 462 | H | H | H | Phenyl | H | H | Phenyl | H | H | *1 |
| 463 | H | H | H | CH$_3$ | H | H | CH$_3$ | H | H | *1 |
| 464 | H | H | H | tert-C$_4$H$_9$ | H | H | tert-C$_4$H$_9$ | H | H | *1 |
| 465 | H | H | H | Phenyl | H | H | Phenyl | H | H | *1 |
| 466 | H | H | H | Phenyl | H | H | Phenyl | H | H | *1 |
| 467 | H | H | H | CH$_3$ | H | H | CH$_3$ | H | H | *1 |
| 468 | H | H | H | tert-C$_4$H$_9$ | H | H | tert-C$_4$H$_9$ | H | H | *1 |
| 469 | H | H | H | Phenyl | H | H | Phenyl | H | H | *1 |
| 470 | H | H | H | Phenyl | H | H | Phenyl | H | H | *1 |
| 471 | H | H | H | CH$_3$ | H | H | CH$_3$ | H | H | *1 |
| 472 | H | H | H | tert-C$_4$H$_9$ | H | H | tert-C$_4$H$_9$ | H | H | *1 |
| 473 | H | H | H | Phenyl | H | H | Phenyl | H | H | *1 |
| 474 | H | H | H | Phenyl | H | H | Phenyl | H | H | *1 |
| 475 | H | H | H | CH$_3$ | H | H | CH$_3$ | H | H | *1 |
| 476 | H | H | H | tert-C$_4$H$_9$ | H | H | tert-C$_4$H$_9$ | H | H | *1 |
| 477 | H | H | H | Phenyl | H | H | Phenyl | H | H | *1 |
| 478 | H | H | H | Phenyl | H | H | Phenyl | H | H | *1 |
| 479 | H | H | H | CH$_3$ | H | H | CH$_3$ | H | H | *1 |
| 480 | H | H | H | tert-C$_4$H$_9$ | H | H | tert-C$_4$H$_9$ | H | H | *1 |
| 481 | H | H | H | Phenyl | H | H | Phenyl | H | H | *1 |
| 482 | H | H | H | Phenyl | H | H | Phenyl | H | H | *1 |
| 483 | H | H | H | CH$_3$ | H | H | CH$_3$ | H | H | *1 |
| 484 | H | H | H | tert-C$_4$H$_9$ | H | H | tert-C$_4$H$_9$ | H | H | *1 |
| 485 | H | H | H | Phenyl | H | H | Phenyl | H | H | *1 |
| 486 | H | H | H | Phenyl | H | H | Phenyl | H | H | *1 |
| 487 | H | H | H | CH$_3$ | H | H | CH$_3$ | H | H | *1 |
| 488 | H | H | H | tert-C$_4$H$_9$ | H | H | tert-C$_4$H$_9$ | H | H | *1 |
| 489 | H | H | H | Phenyl | H | H | Phenyl | H | H | *1 |
| 490 | H | H | H | Phenyl | H | H | Phenyl | H | H | *1 |

TABLE 5-continued

| | | | | | | | | |
|---|---|---|---|---|---|---|---|---|
| 491 | H H H H H | *1 | H | H | CH₃ | H | H | *1 |
| 492 | H H H H H | *1 | H | H | tert-C₄H₉ | H | H | *1 |
| 493 | H H H H H | *1 | H | H | Phenyl | H | H | *1 |
| 494 | H H H H H | *1 | H | H | Phenyl | H | H | *1 |
| 495 | H H H H H | *1 | H | H | CH₃ | H | H | *1 |
| 496 | H H H H H | *1 | H | H | tert-C₄H₉ | H | H | *1 |
| 497 | H H H H H | *1 | H | H | Phenyl | H | H | *1 |
| 498 | H H H H H | *1 | H | H | Phenyl | H | H | *1 |
| 499 | H H H H H | *1 | H | H | CH₃ | H | H | *1 |
| 500 | H H H H H | *1 | H | H | tert-C₄H₉ | H | H | *1 |
| 501 | H H H H | *1 | H | H | Phenyl | H | H | *1 |
| 502 | H H H H | *1 | H | H | Phenyl | H | H | *1 |

TABLE 6

| Compound No. | General formula (10) | | | | | | General formula (2a) | | | | | |
|---|---|---|---|---|---|---|---|---|---|---|---|---|
| | $A^1$ | $R^1$ | $R^2$ | $R^3$ | $R^4$ | $R^5$ | $R^{a1}$ | $R^{a2}$ | $R^{a3}$ | $R^{a4}$ | $R^{a5}$ | $R^{a6}$ |
| 503 | CN | General formula (2a) | General formula (2b) | A5 | General formula (2b) | General formula (2b) | H | H | H | H | H | H |
| 504 | CN | General formula (2a) | General formula (2b) | A5 | General formula (2b) | General formula (2b) | H | H | H | H | H | H |
| 505 | CN | General formula (2a) | General formula (2b) | A6 | General formula (2b) | General formula (2b) | H | H | H | H | H | H |
| 506 | CN | General formula (2a) | General formula (2b) | A6 | General formula (2b) | General formula (2b) | H | H | H | H | H | H |
| 507 | CN | General formula (2a) | General formula (2b) | A7 | General formula (2b) | General formula (2b) | H | H | H | H | H | H |
| 508 | CN | General formula (2a) | General formula (2b) | A7 | General formula (2b) | General formula (2b) | H | H | H | H | H | H |
| 509 | CN | General formula (2a) | General formula (2b) | A9 | General formula (2b) | General formula (2b) | H | H | H | H | H | H |
| 510 | CN | General formula (2a) | General formula (2b) | A9 | General formula (2b) | General formula (2b) | H | H | H | H | H | H |
| 511 | CN | General formula (2a) | General formula (2b) | A10 | General formula (2b) | General formula (2b) | H | H | H | H | H | H |
| 512 | CN | General formula (2a) | General formula (2b) | A10 | General formula (2b) | General formula (2b) | H | H | H | H | H | H |
| 513 | A5 | General formula (2a) | General formula (2b) | A5 | General formula (2b) | General formula (2b) | H | H | H | H | H | H |
| 514 | A5 | General formula (2a) | General formula (2b) | A7 | General formula (2b) | General formula (2b) | H | H | $CH_3$ | H | H | $CH_3$ |
| 515 | A5 | General formula (2a) | General formula (2b) | A9 | General formula (2b) | General formula (2b) | H | H | $CH_3$ | H | H | $CH_3$ |
| 516 | A5 | General formula (2a) | General formula (2b) | A10 | General formula (2b) | General formula (2b) | H | H | H | H | H | H |
| 517 | A5 | General formula (2a) | General formula (2b) | A10 | General formula (2b) | General formula (2b) | H | H | H | H | H | H |
| 518 | A7 | General formula (2a) | General formula (2b) | A7 | General formula (2b) | General formula (2b) | H | H | H | H | H | H |
| 519 | A7 | General formula (2a) | General formula (2b) | H | General formula (2b) | General formula (2b) | H | H | $CH_3$ | H | H | $CH_3$ |
| 520 | A7 | General formula (2a) | General formula (2b) | H | General formula (2b) | General formula (2b) | H | H | $CH_3$ | H | H | $CH_3$ |
| 521 | A7 | General formula (2a) | General formula (2b) | H | General formula (2b) | General formula (2b) | H | H | $CH_3$ | H | H | $CH_3$ |
| 522 | A7 | General formula (2a) | General formula (2b) | H | General formula (2b) | General formula (2b) | H | H | $CH_3$ | H | H | $CH_3$ |
| 523 | A7 | General formula (2a) | General formula (2b) | H | General formula (2b) | General formula (2b) | H | H | tert-$C_4H_9$ | H | H | tert-$C_4H_9$ |
| 524 | A7 | General formula (2a) | General formula (2b) | H | General formula (2b) | General formula (2b) | H | H | tert-$C_4H_9$ | H | H | tert-$C_4H_9$ |
| 525 | A7 | General formula (2a) | General formula (2b) | H | General formula (2b) | General formula (2b) | H | H | Phenyl | H | H | Phenyl |
| 526 | A7 | General formula (2a) | General formula (2b) | H | General formula (2b) | General formula (2b) | H | H | H | H | H | H |
| 527 | A7 | General formula (2a) | General formula (2b) | A7 | General formula (2b) | General formula (2b) | H | H | H | H | H | H |
| 528 | A7 | General formula (2a) | General formula (2b) | A9 | General formula (2b) | General formula (2b) | H | H | tert-$C_4H_9$ | H | H | tert-$C_4H_9$ |
| 529 | A7 | General formula (2a) | General formula (2b) | A9 | General formula (2b) | General formula (2b) | H | H | H | H | H | H |
| 530 | A7 | General formula (2a) | General formula (2b) | A10 | General formula (2b) | General formula (2b) | H | H | $CH_3$ | H | H | $CH_3$ |
| 531 | A7 | General formula (2a) | General formula (2b) | A10 | General formula (2b) | General formula (2b) | H | H | H | H | H | H |
| 532 | A7 | General formula (2a) | General formula (2b) | H | General formula (2b) | General formula (2b) | H | H | $CH_3$ | H | H | $CH_3$ |
| 533 | A7 | General formula (2a) | General formula (2b) | H | General formula (2b) | General formula (2b) | H | H | $CH_3$ | H | H | $CH_3$ |
| 534 | A7 | General formula (2a) | General formula (2b) | H | General formula (2b) | General formula (2b) | H | H | $CH_3$ | H | H | $CH_3$ |
| 535 | A9 | General formula (2a) | General formula (2b) | H | General formula (2b) | General formula (2b) | H | H | tert-$C_4H_9$ | H | H | tert-$C_4H_9$ |
| 536 | A9 | General formula (2a) | General formula (2b) | H | General formula (2b) | General formula (2b) | H | H | tert-$C_4H_9$ | H | H | tert-$C_4H_9$ |
| 537 | A9 | General formula (2a) | General formula (2b) | H | General formula (2b) | General formula (2b) | H | H | tert-$C_4H_9$ | H | H | tert-$C_4H_9$ |
| 538 | A9 | General formula (2a) | General formula (2b) | H | General formula (2b) | General formula (2b) | H | H | Phenyl | H | H | Phenyl |
| 539 | A9 | General formula (2a) | General formula (2b) | H | General formula (2b) | General formula (2b) | H | H | Phenyl | H | H | Phenyl |
| 540 | A9 | General formula (2a) | General formula (2b) | H | General formula (2b) | General formula (2b) | H | H | H | H | H | H |
| 541 | A9 | General formula (2a) | General formula (2b) | H | General formula (2b) | General formula (2b) | H | H | H | H | H | H |
| 542 | A9 | General formula (2a) | General formula (2b) | A7 | General formula (2b) | General formula (2b) | H | H | H | H | H | H |
| 543 | A9 | General formula (2a) | General formula (2b) | A9 | General formula (2b) | General formula (2b) | H | H | H | H | H | H |
| 544 | A9 | General formula (2a) | General formula (2b) | A9 | General formula (2b) | General formula (2b) | H | H | H | H | H | H |
| 545 | A9 | General formula (2a) | General formula (2b) | A9 | General formula (2b) | General formula (2b) | H | H | H | H | H | H |
| 546 | A9 | General formula (2a) | General formula (2b) | A9 | General formula (2b) | General formula (2b) | H | H | H | H | H | H |
| 547 | A9 | General formula (2a) | General formula (2b) | A9 | General formula (2b) | General formula (2b) | H | H | $CH_3$ | H | H | $CH_3$ |
| 548 | A9 | General formula (2a) | General formula (2b) | A9 | General formula (2b) | General formula (2b) | H | H | H | H | H | H |
| 549 | A9 | General formula (2a) | General formula (2b) | A9 | General formula (2b) | General formula (2b) | H | H | H | H | H | H |

TABLE 6-continued

| No. | R$^{a7}$ | R$^{a8}$ | R$^{a9}$ | | R$^{b1}$ | R$^{b2}$ | R$^{b3}$ | | R$^{b4}$ | R$^{b5}$ | R$^{b6}$ | R$^{b7}$ | R$^{b8}$ | R$^{b9}$ |
|---|---|---|---|---|---|---|---|---|---|---|---|---|---|---|
| 550 | A9 | H | General formula (2a) | General formula (2b) | | | | | | | | | | |
| 551 | A9 | H | General formula (2a) | General formula (2b) | | | | | | | | | | |
| 552 | A9 | H | General formula (2a) | General formula (2b) | | | | | | | | | | |
| 553 | A9 | H | General formula (2a) | General formula (2b) | | | | | | | | | | |
| 554 | A9 | H | General formula (2a) | General formula (2b) | | | | | | | | | | |
| 555 | A9 | H | General formula (2a) | General formula (2b) | | | | | | | | | | |
| 556 | A9 | H | General formula (2a) | General formula (2b) | | | | | | | | | | |
| 557 | A9 | H | General formula (2a) | General formula (2b) | | | | | | | | | | |
| 558 | A9 | H | General formula (2a) | General formula (2b) | | | | | | | | | | |
| 559 | A9 | H | General formula (2a) | General formula (2b) | | | | | | | | | | |
| 560 | A9 | H | General formula (2a) | General formula (2b) | | | | | | | | | | |
| 561 | A9 | H | General formula (2a) | General formula (2b) | | | | | | | | | | |
| 562 | A10 | H | General formula (2a) | General formula (2b) | | | | | | | | | | |
| 563 | A10 | H | General formula (2a) | General formula (2b) | | | | | | | | | | |
| 564 | A10 | H | General formula (2a) | H | | | | | | | | | | |
| 565 | A10 | H | General formula (2a) | A10 | | | | | | | | | | |
| 566 | A10 | H | General formula (2a) | A10 | | | | | | | | | | |
| 567 | A10 | H | General formula (2a) | A10 | | | | | | | | | | |
| 568 | A10 | H | General formula (2a) | A10 | | | | | | | | | | |

| Compound No. | R$^{a7}$ | R$^{a8}$ | R$^{a9}$ | R$^{b1}$ | R$^{b2}$ | R$^{b3}$ | | R$^{b4}$ | R$^{b5}$ | R$^{b6}$ | R$^{b7}$ | R$^{b8}$ | R$^{b9}$ |
|---|---|---|---|---|---|---|---|---|---|---|---|---|---|
| | | General formula (2a) | | | | | General formula (2b) | | | | | | |
| 503 | H | H | *1 | H | H | CH$_3$ | | H | H | CH$_3$ | H | H | *1 |
| 504 | H | H | *1 | H | H | CH$_3$ | | H | H | CH$_3$ | H | H | *1 |
| 505 | H | H | *1 | H | H | CH$_3$ | | H | H | CH$_3$ | H | H | *1 |
| 506 | H | H | *1 | H | H | CH$_3$ | | H | H | CH$_3$ | H | H | *1 |
| 507 | H | H | *1 | H | H | CH$_3$ | | H | H | CH$_3$ | H | H | *1 |
| 508 | H | H | *1 | H | H | CH$_3$ | | H | H | CH$_3$ | H | H | *1 |
| 509 | H | H | *1 | H | H | CH$_3$ | | H | H | CH$_3$ | H | H | *1 |
| 510 | H | H | *1 | H | H | CH$_3$ | | H | H | CH$_3$ | H | H | *1 |
| 511 | H | H | *1 | H | H | CH$_3$ | | H | H | CH$_3$ | H | H | *1 |
| 512 | H | H | *1 | H | H | CH$_3$ | | H | H | CH$_3$ | H | H | *1 |
| 513 | H | H | *1 | H | H | CH$_3$ | | H | H | CH$_3$ | H | H | *1 |
| 514 | H | H | *1 | H | H | CH$_3$ | | H | H | CH$_3$ | H | H | *1 |
| 515 | H | H | *1 | H | H | H | | H | H | H | H | H | *1 |
| 516 | H | H | *1 | H | H | CH$_3$ | | H | H | CH$_3$ | H | H | *1 |
| 517 | H | H | *1 | H | H | CH$_3$ | | H | H | CH$_3$ | H | H | *1 |
| 518 | H | H | *1 | H | H | tert-C$_4$H$_9$ | | H | H | tert-C$_4$H$_9$ | H | H | *1 |
| 519 | H | H | *1 | H | H | Phenyl | | H | H | Phenyl | H | H | *1 |
| 520 | H | H | *1 | H | H | H | | H | H | H | H | H | *1 |
| 521 | H | H | *1 | H | H | tert-C$_4$H$_9$ | | H | H | tert-C$_4$H$_9$ | H | H | *1 |
| 522 | H | H | *1 | H | H | H | | H | H | H | H | H | *1 |
| 523 | H | H | *1 | H | H | CH$_3$ | | H | H | CH$_3$ | H | H | *1 |
| 524 | H | H | *1 | H | H | H | | H | H | H | H | H | *1 |
| 525 | H | H | *1 | H | H | CH$_3$ | | H | H | CH$_3$ | H | H | *1 |
| 526 | H | H | *1 | H | H | CH$_3$ | | H | H | CH$_3$ | H | H | *1 |
| 527 | H | H | *1 | H | H | tert-C$_4$H$_9$ | | H | H | tert-C$_4$H$_9$ | H | H | *1 |
| 528 | H | H | *1 | H | H | CH$_3$ | | H | H | CH$_3$ | H | H | *1 |
| 529 | H | H | *1 | H | H | CH$_3$ | | H | H | CH$_3$ | H | H | *1 |
| 530 | H | H | *1 | H | H | CH$_3$ | | H | H | CH$_3$ | H | H | *1 |
| 531 | H | H | *1 | H | H | H | | H | H | H | H | H | *1 |

TABLE 6-continued

| | | | | | | | | | | |
|---|---|---|---|---|---|---|---|---|---|---|
| 532 | H | *1 | H | CH$_3$ | H | H | CH$_3$ | H | H | *1 |
| 533 | H | *1 | H | CH$_3$ | H | H | CH$_3$ | H | H | *1 |
| 534 | H | *1 | H | H | H | H | H | H | H | *1 |
| 535 | H | *1 | H | H | H | H | H | H | H | *1 |
| 536 | H | *1 | H | tert-C$_4$H$_9$ | H | H | tert-C$_4$H$_9$ | H | H | *1 |
| 537 | H | *1 | H | H | H | H | H | H | H | *1 |
| 538 | H | *1 | H | CH$_3$ | H | H | CH$_3$ | H | H | *1 |
| 539 | H | *1 | H | H | H | H | H | H | H | *1 |
| 540 | H | *1 | H | CH$_3$ | H | H | CH$_3$ | H | H | *1 |
| 541 | H | *1 | H | CH$_3$ | H | H | CH$_3$ | H | H | *1 |
| 542 | H | *1 | H | tert-C$_4$H$_9$ | H | H | tert-C$_4$H$_9$ | H | H | *1 |
| 543 | H | *1 | H | Phenyl | H | H | Phenyl | H | H | *1 |
| 544 | H | *1 | H | CH$_3$ | H | H | CH$_3$ | H | H | *1 |
| 545 | H | *1 | H | tert-C$_4$H$_9$ | H | H | tert-C$_4$H$_9$ | H | H | *1 |
| 546 | H | *1 | H | Phenyl | H | H | Phenyl | H | H | *1 |
| 547 | H | *1 | H | tert-C$_4$H$_9$ | H | H | tert-C$_4$H$_9$ | H | H | *1 |
| 548 | H | *1 | H | CH$_3$ | H | H | CH$_3$ | H | H | *1 |
| 549 | H | *1 | H | tert-C$_4$H$_9$ | H | H | tert-C$_4$H$_9$ | H | H | *1 |
| 550 | H | *1 | H | Phenyl | H | H | Phenyl | H | H | *1 |
| 551 | H | *1 | H | tert-C$_4$H$_9$ | H | H | tert-C$_4$H$_9$ | H | H | *1 |
| 552 | H | *1 | H | CH$_3$ | H | H | CH$_3$ | H | H | *1 |
| 553 | H | *1 | H | tert-C$_4$H$_9$ | H | H | tert-C$_4$H$_9$ | H | H | *1 |
| 554 | H | *1 | H | Phenyl | H | H | Phenyl | H | H | *1 |
| 555 | H | *1 | H | tert-C$_4$H$_9$ | H | H | tert-C$_4$H$_9$ | H | H | *1 |
| 556 | H | *1 | H | H | H | H | H | H | H | *1 |
| 557 | H | *1 | H | CH$_3$ | H | H | CH$_3$ | H | H | *1 |
| 558 | H | *1 | H | CH$_3$ | H | H | CH$_3$ | H | H | *1 |
| 559 | H | *1 | H | tert-C$_4$H$_9$ | H | H | tert-C$_4$H$_9$ | H | H | *1 |
| 560 | H | *1 | H | Phenyl | H | H | Phenyl | H | H | *1 |
| 561 | H | *1 | H | H | H | H | H | H | H | *1 |
| 562 | H | *1 | H | CH$_3$ | H | H | CH$_3$ | H | H | *1 |
| 563 | H | *1 | H | H | H | H | H | H | H | *1 |
| 564 | H | *1 | H | CH$_3$ | H | H | CH$_3$ | H | H | *1 |
| 565 | H | *1 | H | tert-C$_4$H$_9$ | H | H | tert-C$_4$H$_9$ | H | H | *1 |
| 566 | H | *1 | H | CH$_3$ | H | H | CH$_3$ | H | H | *1 |
| 567 | H | *1 | H | CH$_3$ | H | H | CH$_3$ | H | H | *1 |
| 568 | H | *1 | H | tert-C$_4$H$_9$ | H | H | tert-C$_4$H$_9$ | H | H | *1 |

TABLE 7

| Compound No. | General formula (10) | | | | | | General formula (2a) | | | | | | | | | |
|---|---|---|---|---|---|---|---|---|---|---|---|---|---|---|---|---|
| | $A^1$ | $R^1$ | $R^2$ | $R^3$ | $R^4$ | $R^5$ | $R^{a1}$ | $R^{a2}$ | $R^{a3}$ | $R^{a4}$ | $R^{a5}$ | $R^{a6}$ | $R^{a7}$ | $R^{a8}$ | $R^{a9}$ |
| 569 | A5 | General formula (2a) | D11 | H | D11 | General formula (2a) | H | H | tert-$C_4H_9$ | H | H | tert-$C_4H_9$ | H | H | *1 |
| 570 | A5 | D11 | General formula (2a) | H | General formula (2a) | D11 | H | H | $CH_3$ | H | H | $CH_3$ | H | H | *1 |
| 571 | A5 | D24 | General formula (2a) | H | General formula (2a) | D24 | H | H | H | H | H | H | H | H | *1 |
| 572 | A5 | D24 | General formula (2a) | H | General formula (2a) | D24 | H | H | $CH_3$ | H | H | $CH_3$ | H | H | *1 |
| 573 | A5 | D11 | General formula (2a) | General formula (2a) | D11 | General formula (2a) | H | H | H | H | H | H | H | H | *1 |
| 574 | A5 | D24 | General formula (2a) | General formula (2a) | General formula (2a) | D24 | H | H | H | H | H | H | H | H | *1 |
| 575 | A5 | D11 | General formula (2a) | A5 | D11 | General formula (2a) | H | H | H | H | H | H | H | H | *1 |
| 576 | A5 | D11 | General formula (2a) | A5 | D11 | General formula (2a) | H | H | $CH_3$ | H | H | $CH_3$ | H | H | *1 |
| 577 | A5 | D11 | General formula (2a) | A7 | D11 | General formula (2a) | H | H | $CH_3$ | H | H | $CH_3$ | H | H | *1 |
| 578 | A5 | D11 | General formula (2a) | A9 | D11 | General formula (2a) | H | H | H | H | H | H | H | H | *1 |
| 579 | A5 | D11 | General formula (2a) | A9 | D11 | General formula (2a) | H | H | $CH_3$ | H | H | $CH_3$ | H | H | *1 |
| 580 | A5 | D24 | General formula (2a) | A9 | D24 | General formula (2a) | H | H | $CH_3$ | H | H | $CH_3$ | H | H | *1 |
| 581 | A5 | General formula (2a) | D11 | A10 | D11 | General formula (2a) | H | H | H | H | H | H | H | H | *1 |
| 582 | A5 | General formula (2a) | D11 | A10 | D11 | General formula (2a) | H | H | $CH_3$ | H | H | $CH_3$ | H | H | *1 |
| 583 | A5 | D24 | General formula (2a) | A10 | General formula (2a) | D24 | H | H | H | H | H | H | H | H | *1 |
| 584 | A7 | D11 | General formula (2a) | H | D11 | General formula (2a) | H | H | H | H | H | H | H | H | *1 |
| 585 | A7 | D11 | General formula (2a) | H | D11 | General formula (2a) | H | H | $CH_3$ | H | H | $CH_3$ | H | H | *1 |
| 586 | A7 | D24 | General formula (2a) | H | D24 | General formula (2a) | H | H | $CH_3$ | H | H | $CH_3$ | H | H | *1 |
| 587 | A7 | D11 | General formula (2a) | H | General formula (2a) | D11 | H | H | tert-$C_4H_9$ | H | H | tert-$C_4H_9$ | H | H | *1 |
| 588 | A7 | D24 | General formula (2a) | H | General formula (2a) | D24 | H | H | H | H | H | H | H | H | *1 |
| 589 | A7 | D11 | General formula (2a) | General formula (2a) | D11 | General formula (2a) | H | H | $CH_3$ | H | H | $CH_3$ | H | H | *1 |
| 590 | A7 | D11 | General formula (2a) | General formula (2a) | D11 | General formula (2a) | H | H | H | H | H | H | H | H | *1 |
| 591 | A7 | D11 | General formula (2a) | General formula (2a) | D11 | General formula (2a) | H | H | $CH_3$ | H | H | $CH_3$ | H | H | *1 |
| 592 | A7 | D11 | General formula (2a) | A7 | D11 | General formula (2a) | H | H | H | H | H | H | H | H | *1 |
| 593 | A7 | D11 | General formula (2a) | A9 | D11 | General formula (2a) | H | H | H | H | H | H | H | H | *1 |
| 594 | A7 | D11 | General formula (2a) | A9 | General formula (2a) | D11 | H | H | $CH_3$ | H | H | $CH_3$ | H | H | *1 |
| 595 | A7 | D24 | General formula (2a) | A9 | D24 | General formula (2a) | H | H | H | H | H | H | H | H | *1 |
| 596 | A7 | D24 | General formula (2a) | A9 | General formula (2a) | D24 | H | H | $CH_3$ | H | H | $CH_3$ | H | H | *1 |
| 597 | A7 | D11 | General formula (2a) | A9 | General formula (2a) | D11 | H | H | H | H | H | H | H | H | *1 |
| 598 | A7 | D11 | General formula (2a) | A10 | General formula (2a) | D11 | H | H | $CH_3$ | H | H | $CH_3$ | H | H | *1 |
| 599 | A7 | D24 | General formula (2a) | A10 | General formula (2a) | D24 | H | H | H | H | H | H | H | H | *1 |
| 600 | A7 | General formula (2a) | D11 | A10 | D11 | General formula (2a) | H | H | H | H | H | H | H | H | *1 |
| 601 | A7 | General formula (2a) | D11 | A10 | D11 | General formula (2a) | H | H | $CH_3$ | H | H | $CH_3$ | H | H | *1 |
| 602 | A7 | D11 | General formula (2a) | A10 | General formula (2a) | D11 | H | H | $CH_3$ | H | H | $CH_3$ | H | H | *1 |
| 603 | A7 | D11 | General formula (2a) | A10 | D11 | General formula (2a) | H | H | H | H | H | H | H | H | *1 |
| 604 | A7 | D24 | General formula (2a) | A10 | D24 | General formula (2a) | H | H | H | H | H | H | H | H | *1 |
| 605 | A7 | D24 | General formula (2a) | A10 | D24 | General formula (2a) | H | H | H | H | H | H | H | H | *1 |
| 606 | A7 | General formula (2a) | D11 | A10 | D11 | General formula (2a) | H | H | $CH_3$ | H | H | $CH_3$ | H | H | *1 |
| 607 | A7 | General formula (2a) | D11 | H | D11 | General formula (2a) | H | H | $CH_3$ | H | H | $CH_3$ | H | H | *1 |
| 608 | A7 | General formula (2a) | D11 | H | General formula (2a) | D11 | H | H | Phenyl | H | H | Phenyl | H | H | *1 |
| 609 | A7 | D11 | General formula (2a) | H | D11 | General formula (2a) | H | H | H | H | H | H | H | H | *1 |
| 610 | A7 | D11 | General formula (2a) | A9 | General formula (2a) | D11 | H | H | tert-$C_4H_9$ | H | H | tert-$C_4H_9$ | H | H | *1 |
| 611 | A9 | General formula (2a) | D24 | A9 | D24 | General formula (2a) | H | H | H | H | H | H | H | H | *1 |
| 612 | A9 | General formula (2a) | D24 | A10 | D24 | General formula (2a) | H | H | $CH_3$ | H | H | $CH_3$ | H | H | *1 |
| 613 | A9 | D24 | D24 | A10 | D24 | General formula (2a) | H | H | H | H | H | H | H | H | *1 |
| 614 | A9 | General formula (2a) | D24 | A10 | D24 | General formula (2a) | H | H | $CH_3$ | H | H | $CH_3$ | H | H | *1 |
| 615 | A10 | D11 | General formula (2a) | A10 | General formula (2a) | D11 | H | H | $CH_3$ | H | H | $CH_3$ | H | H | *1 |

TABLE 7-continued

| | | General formula (10) | | | | General formula (2a) | | | | | | | |
|---|---|---|---|---|---|---|---|---|---|---|---|---|---|
| Compound No. | $A^1$ | $R^1$ | $R^2$ | $R^3$ | $R^4$ | $R^5$ | $R^{a1}$ | $R^{a2}$ | $R^{a3}$ | $R^{a4}$ | $R^{a5}$ | $R^{a6}$ | $R^{a7}$ | $R^{a8}$ | $R^{a9}$ |

TABLE 8

| Compound No. | General formula (10) | | | | |
|---|---|---|---|---|---|
| | A¹ | R¹ | R² | R³ | R⁴ | R⁵ |
| 616 | CN | D11 | CN | D24 | D11 | D24 |
| 617 | CN | D11 | D24 | A7 | D11 | D24 |
| 618 | A5 | D11 | D24 | A9 | D11 | D24 |
| 619 | A5 | D24 | D11 | A9 | D11 | D24 |
| 620 | A5 | D11 | D24 | A10 | D11 | D24 |
| 621 | A7 | D11 | D24 | H | D11 | D24 |
| 622 | A7 | D24 | D11 | H | D11 | D24 |
| 623 | A7 | D11 | D24 | A9 | D11 | D24 |
| 624 | A7 | D11 | D24 | A9 | D24 | D11 |

TABLE 8-continued

| Compound No. | General formula (10) | | | | |
|---|---|---|---|---|---|
| | A¹ | R¹ | R² | R³ | R⁴ | R⁵ |
| 625 | A7 | D11 | D24 | A10 | D24 | D11 |
| 626 | A7 | D11 | D24 | A10 | D11 | D24 |
| 627 | A7 | D24 | D11 | D11 | D11 | D24 |

In the following, specific examples of compounds that are not included in the general formula (1) but are employable as the second organic compound in the present invention are shown below.

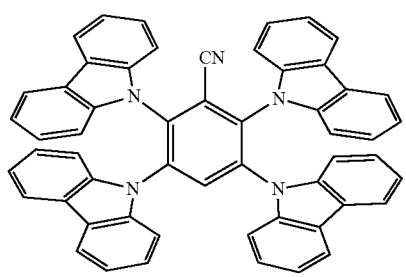

Compound 628

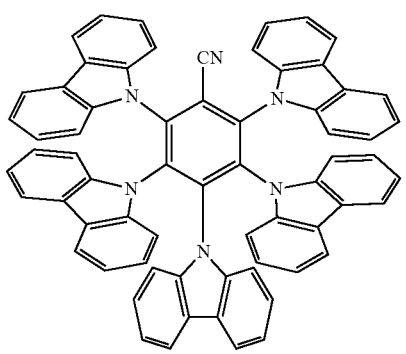

Compound 629

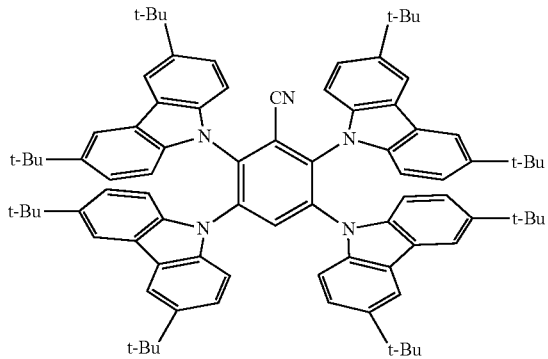

Compound 630

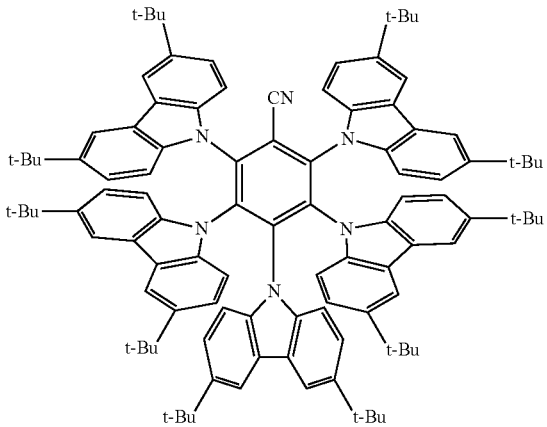

Compound 631

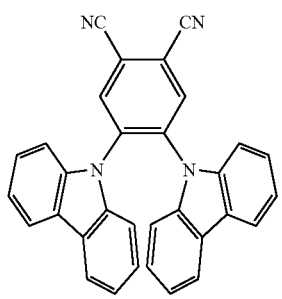

Compound 632

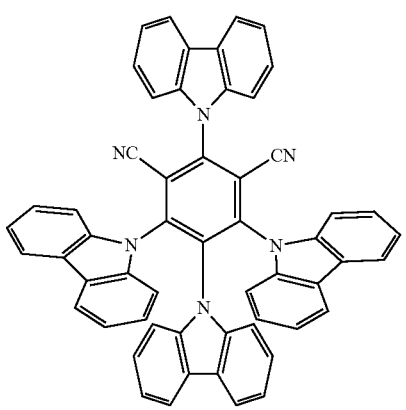

Compound 633

-continued
Compound 634
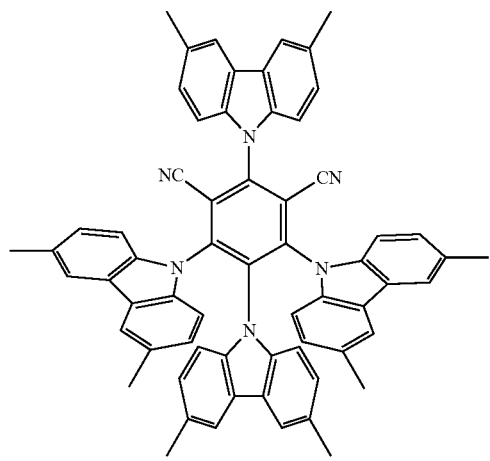
Compound 635
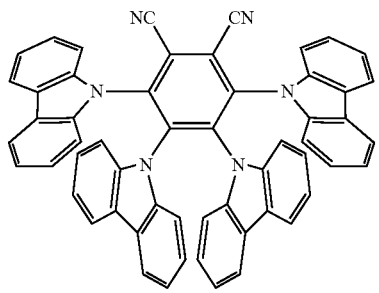
Compound 636
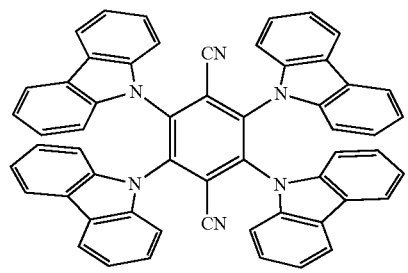
Compound 637
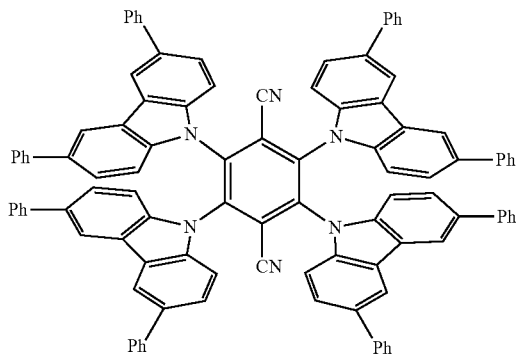
Compound 638
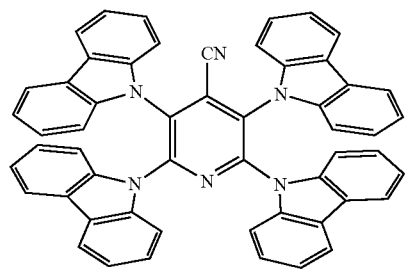
Compound 639
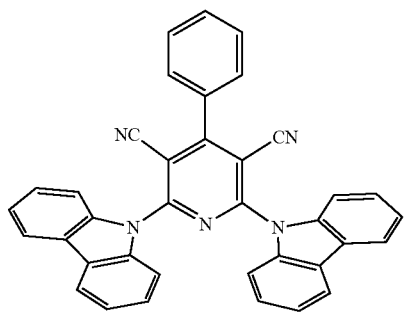
Compound 640
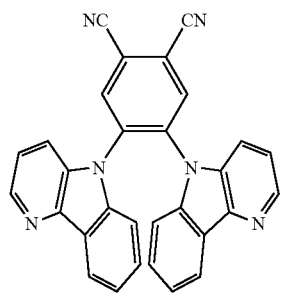
Compound 641
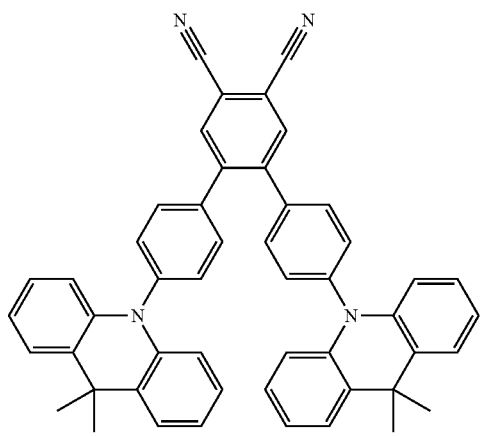

-continued
Compound 642
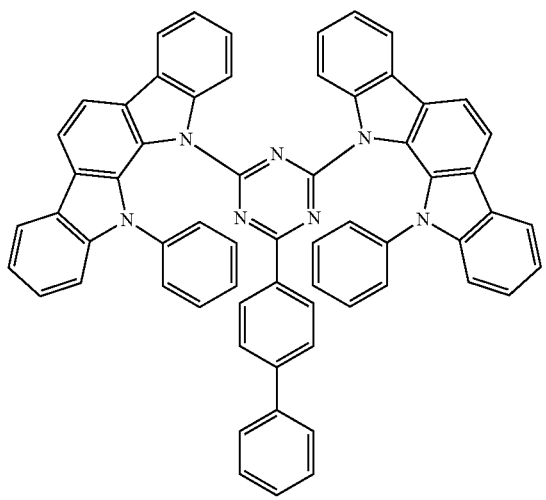
Compound 643
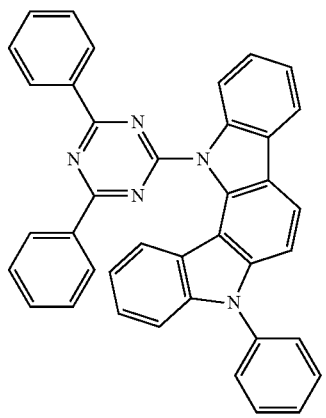
Compound 644
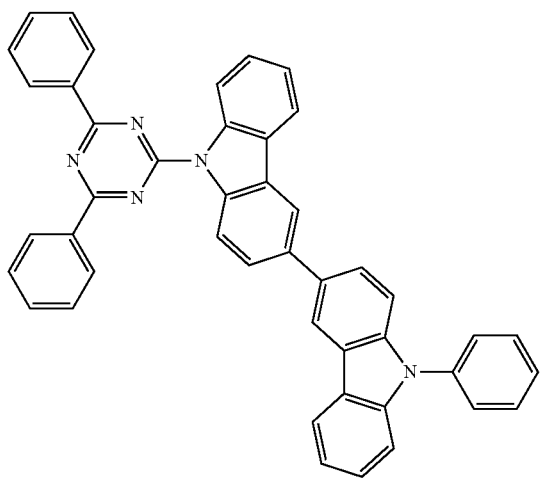
Compound 645
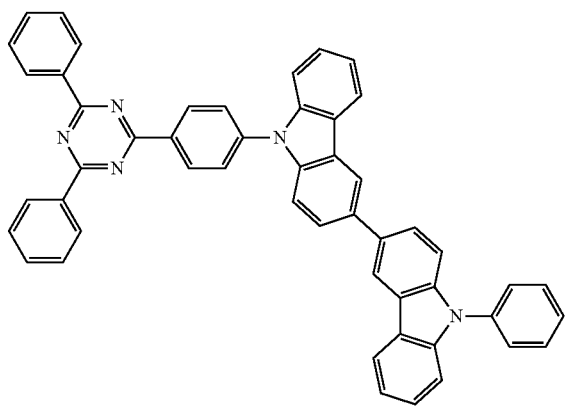
Compound 646
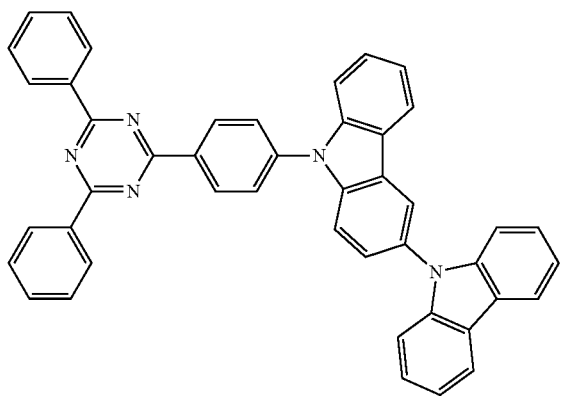
Compound 647
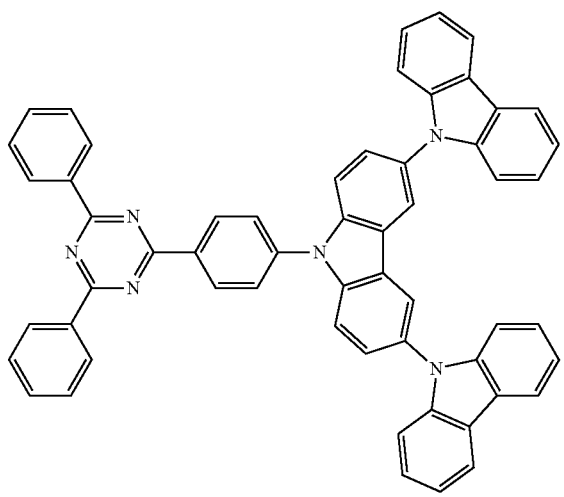

Compound 648
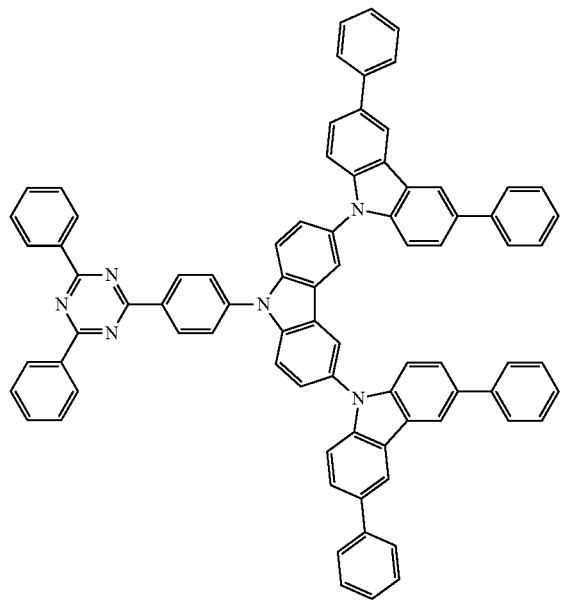
Compound 649
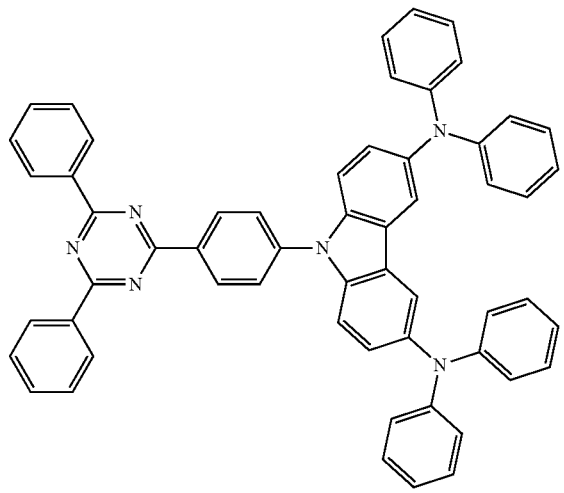
Compound 650
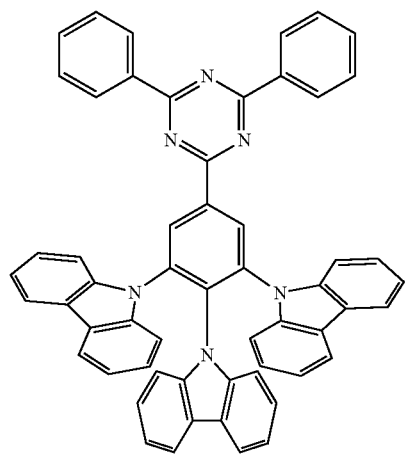
Compound 651
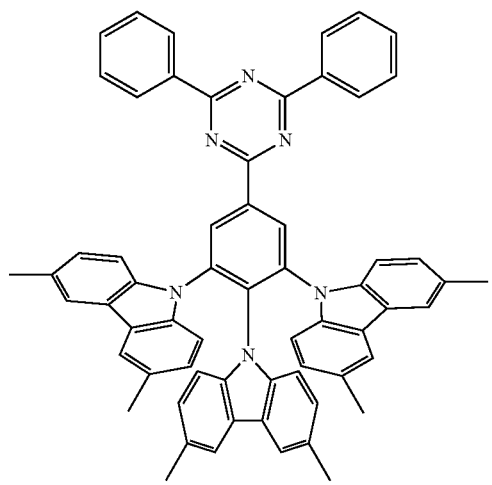
Compound 652
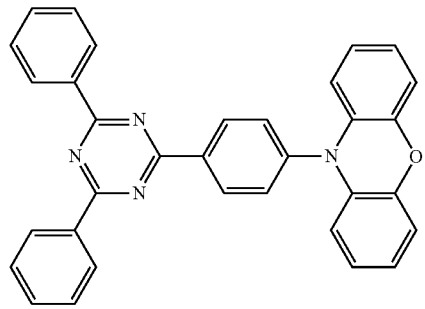
Compound 653
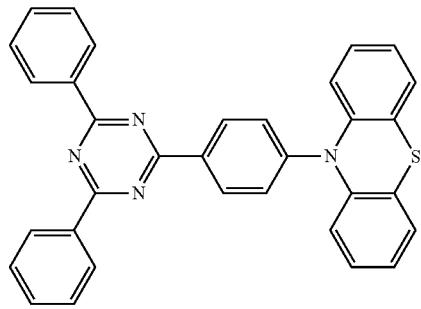

-continued
Compound 654
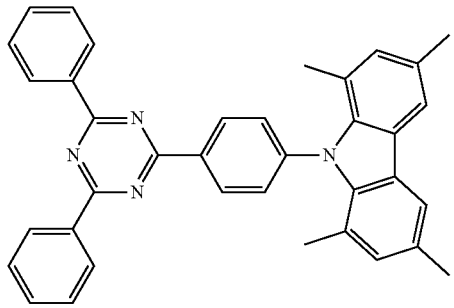
Compound 655
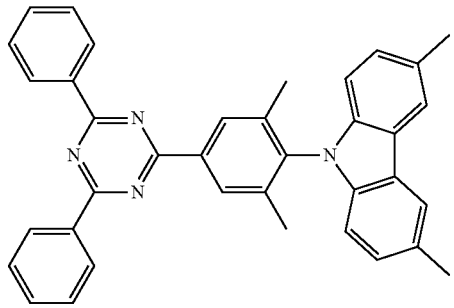
Compound 656
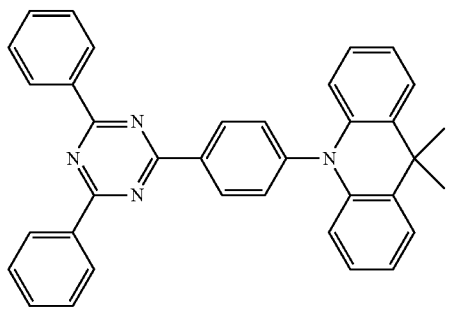
Compound 657
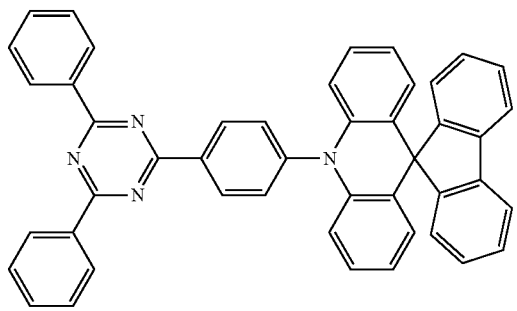
Compound 658
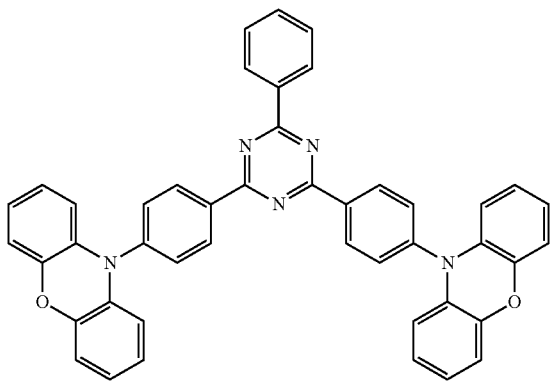
Compound 659
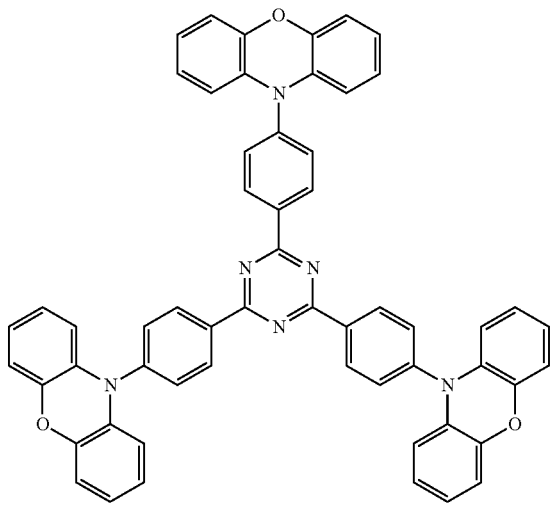

Compound 660
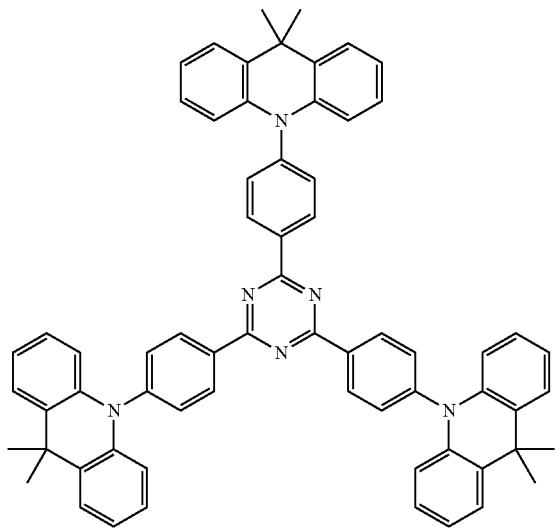
Compound 661
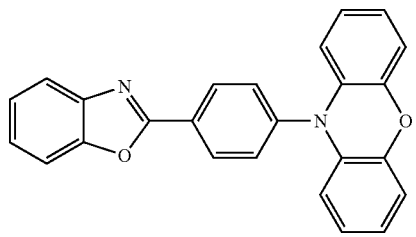
Compound 662
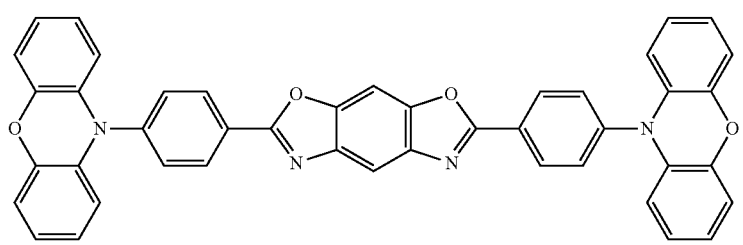
Compound 663
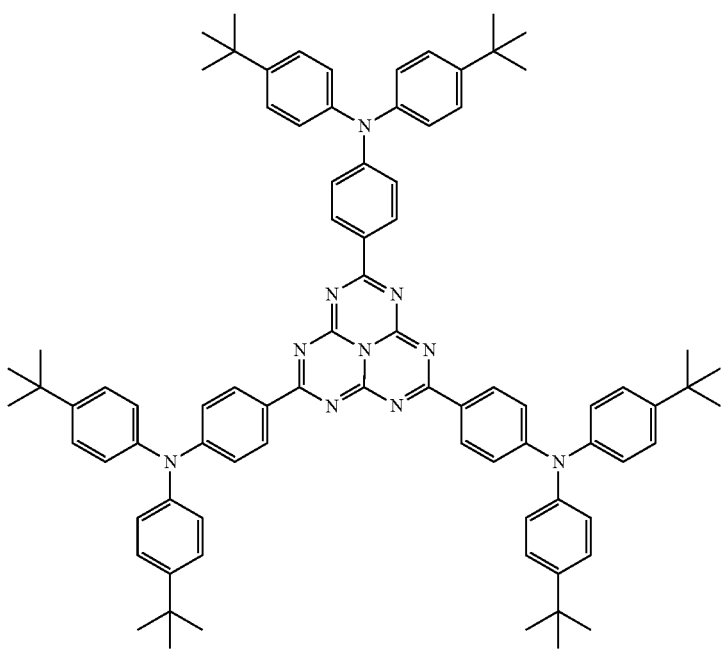

Compound 664
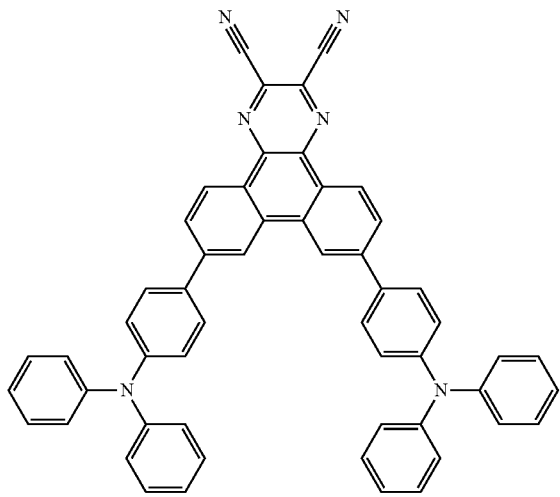
Compound 665
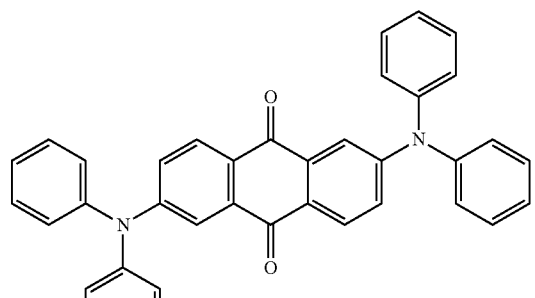
Compound 666
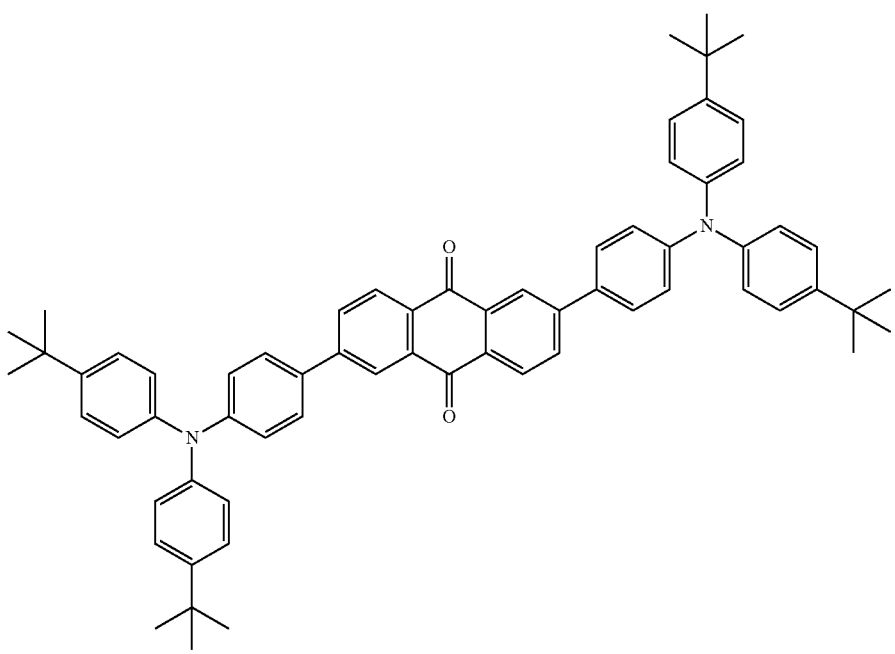
Compound 667
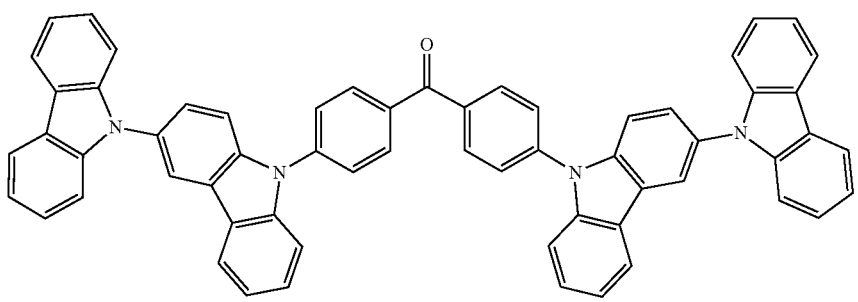

-continued
Compound 668
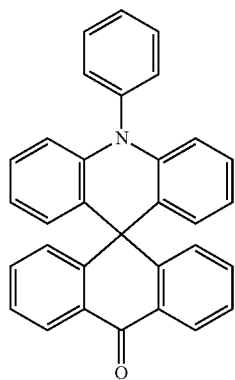
Compound 669
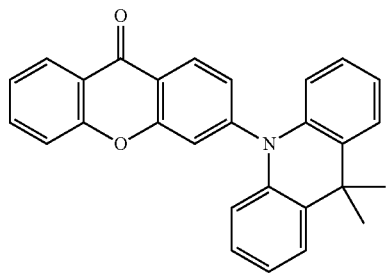
Compound 670
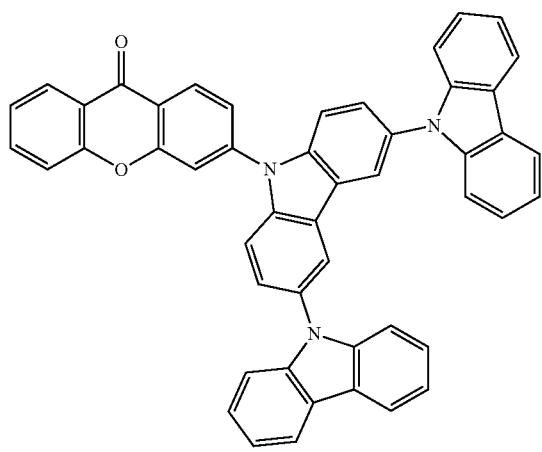
Compound 671
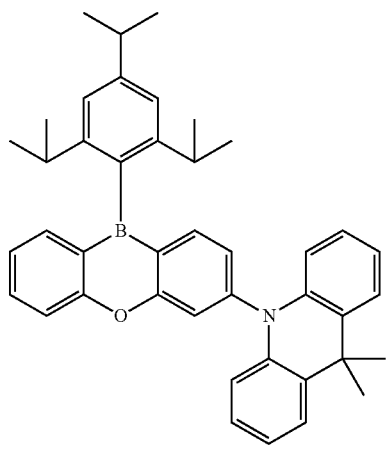
Compound 672
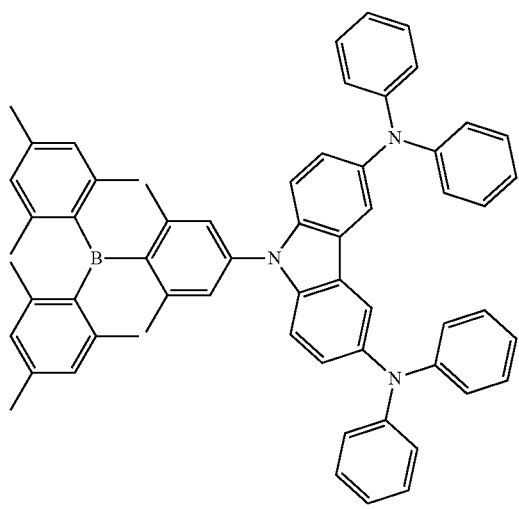
Compound 673
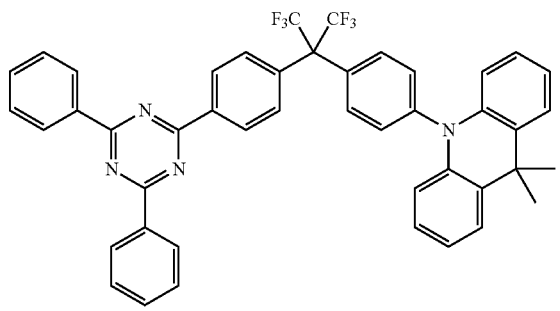

Compound 674
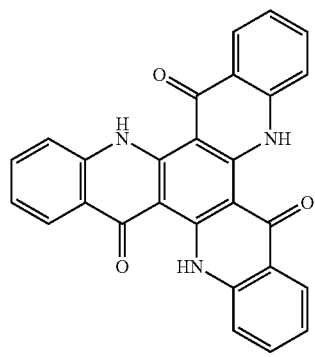
Compound 675
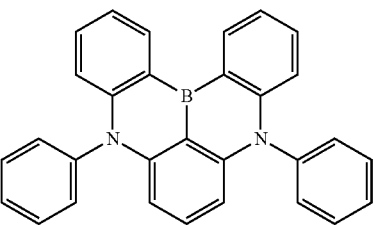
Compound 676
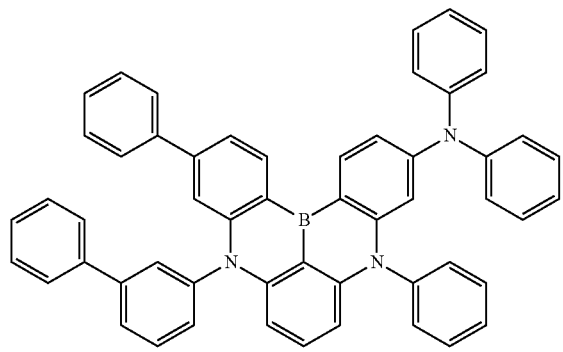
Compound 677
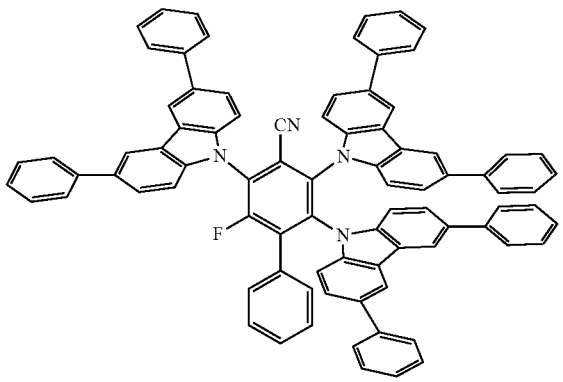
Compound 678
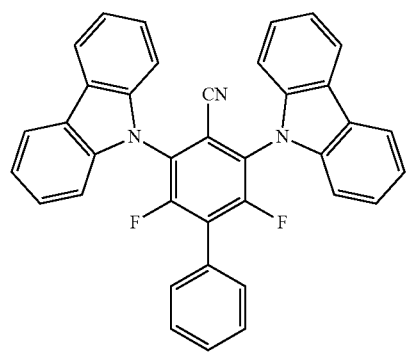
Structures of D1 to D60 and A1 to A13 in the above Tables 1 to 8 are shown below.
D1
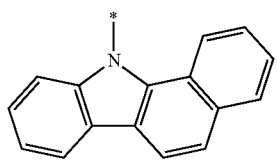
D2
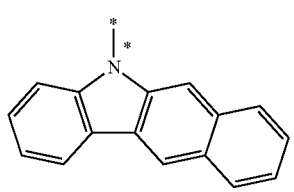
D3
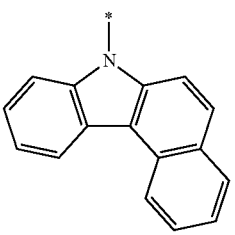

-continued
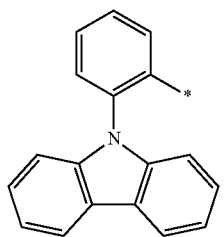
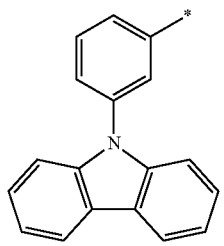
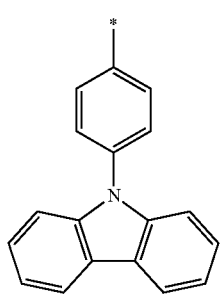
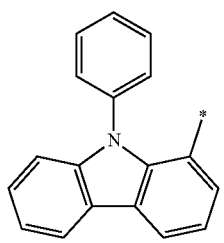
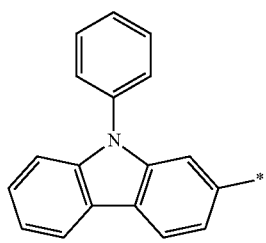
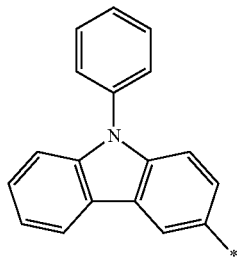
-continued
D4
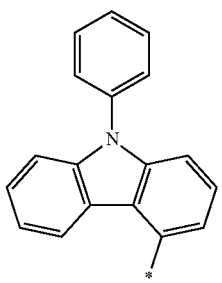
D10
D5
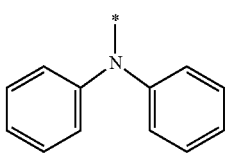
D11
D6
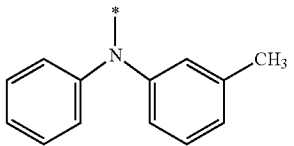
D12
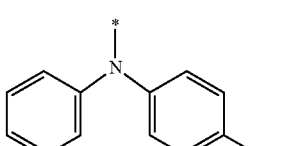
D13
D7
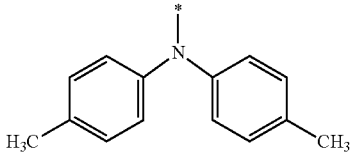
D14
D8
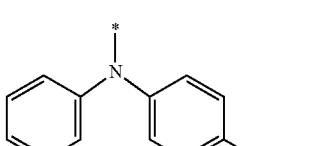
D15
D9
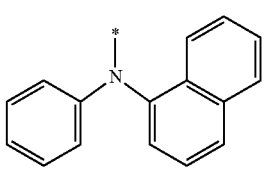
D16
D17

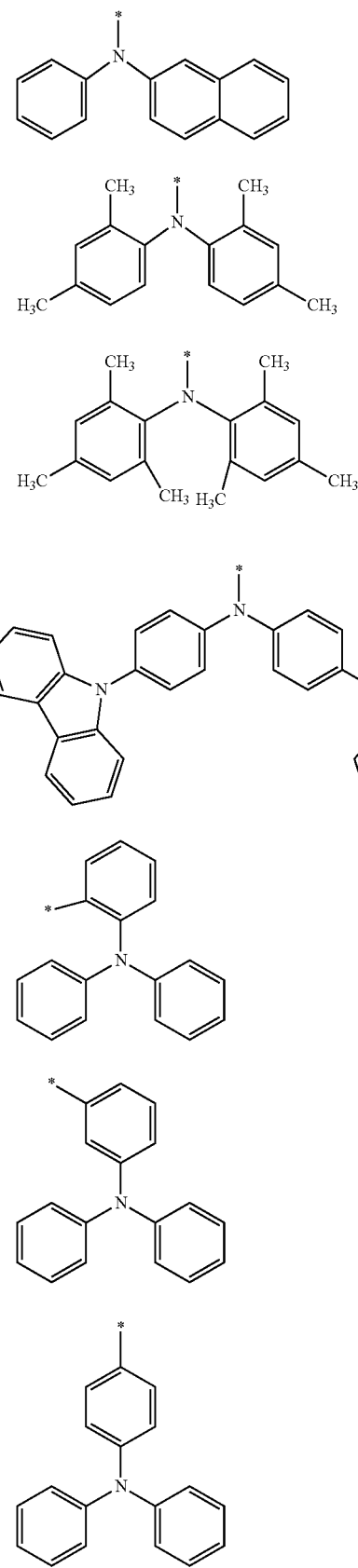
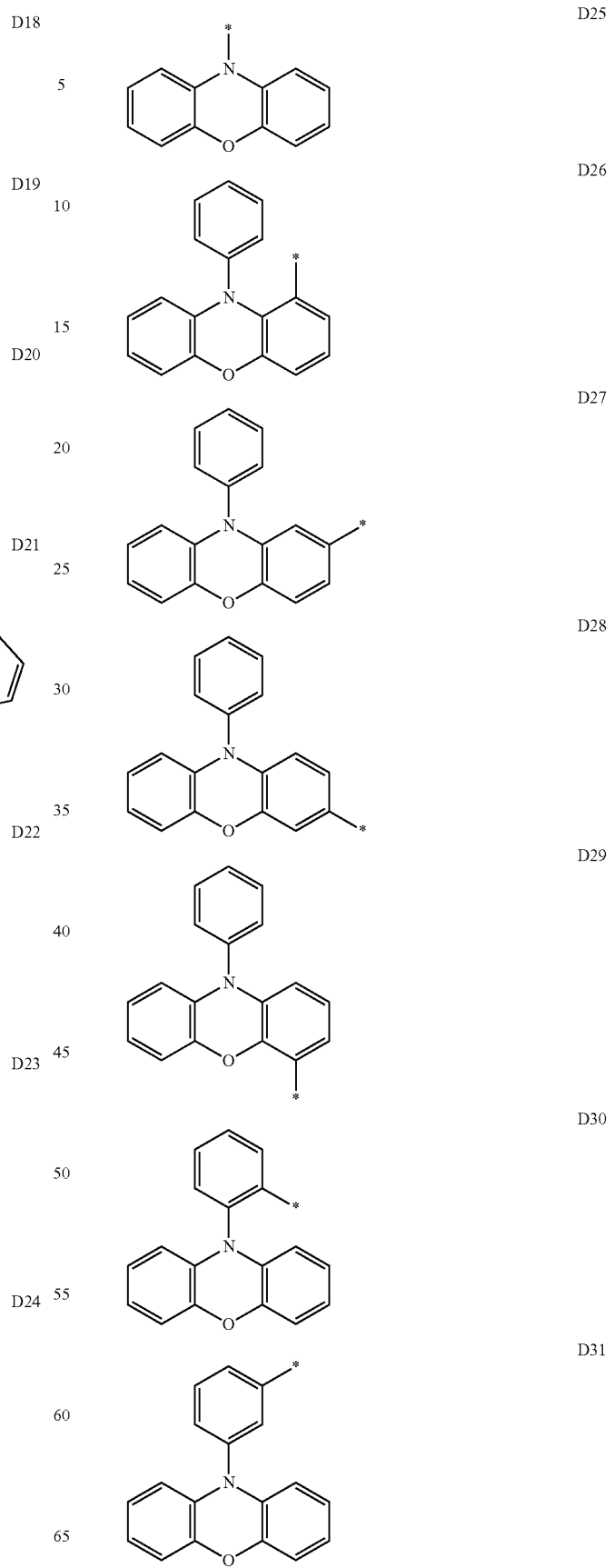

D32 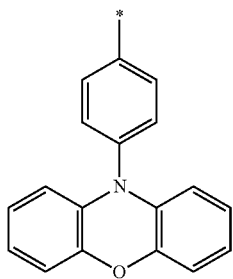
D33 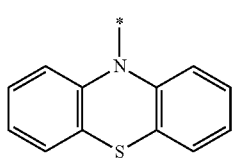
D34 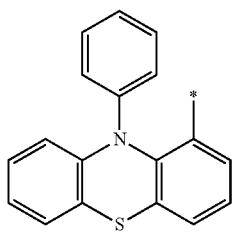
D35 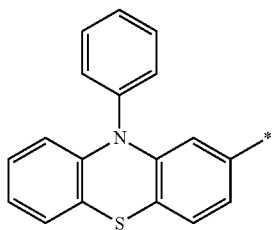
D36 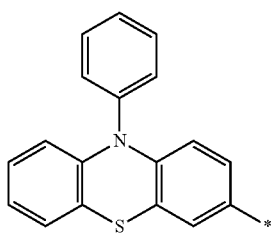
D37 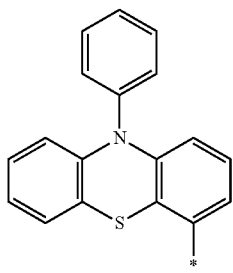
D38 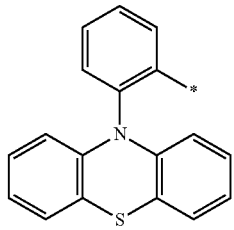
D39 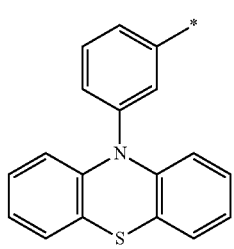
D40 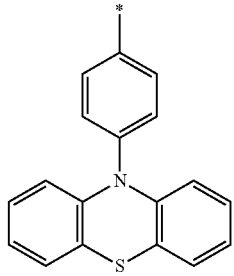
D41 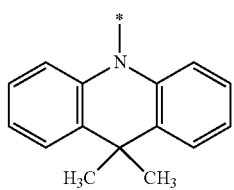
D42 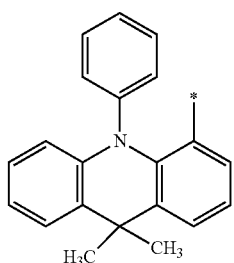
D43 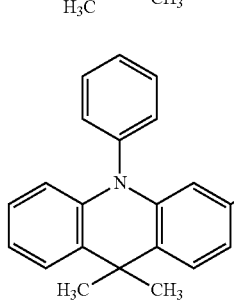

D44 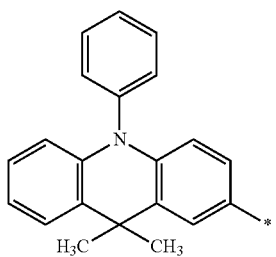
D45 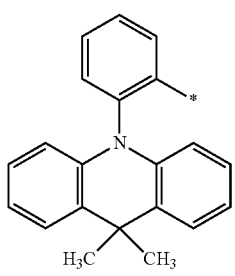
D46 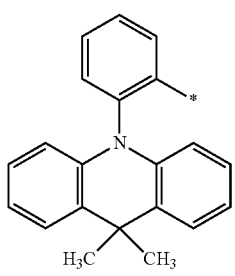
D47 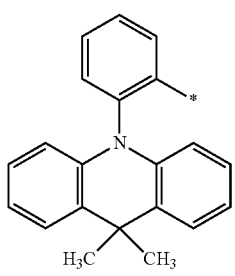
D48 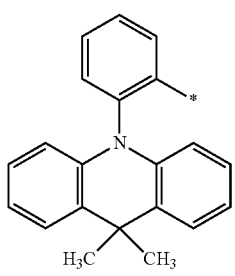
D49 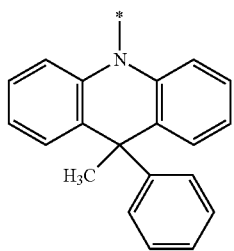
D50 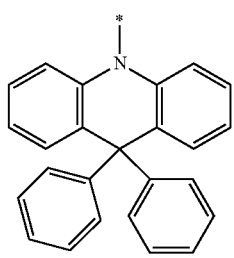
D51 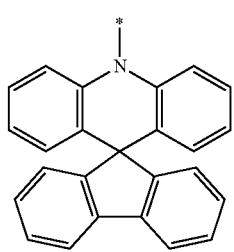
D52 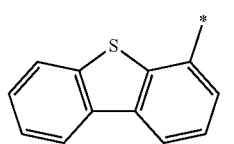
D53 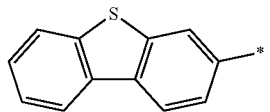
D54 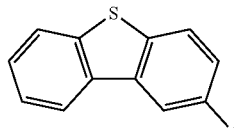
D55 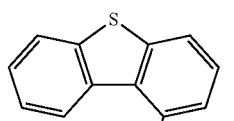
D56 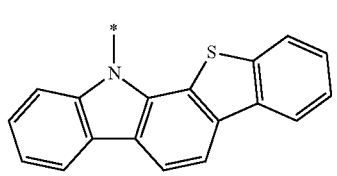

-continued
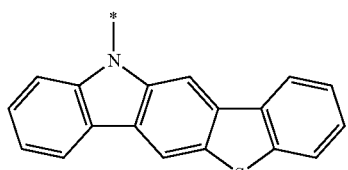  D57
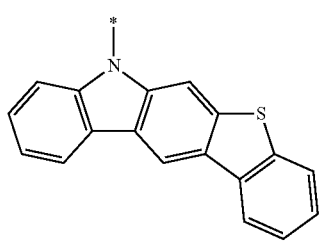  D58
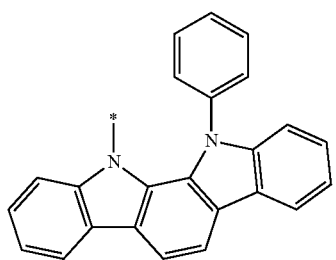  D59
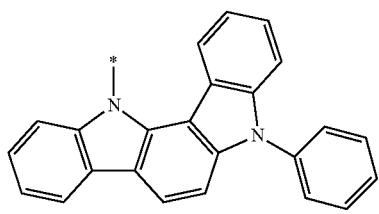  D60
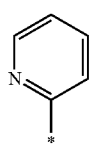  A1
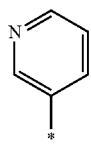  A2
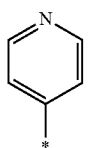  A3
-continued
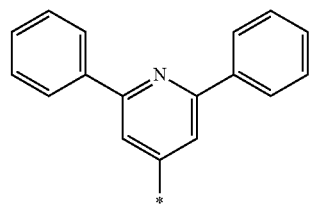  A4
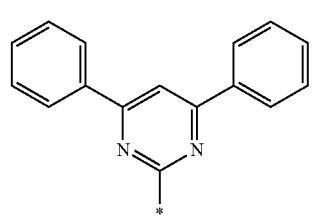  A5
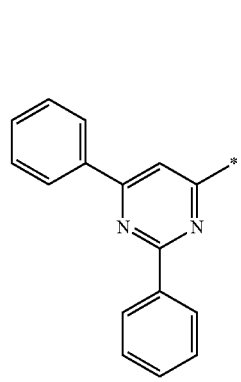  A6
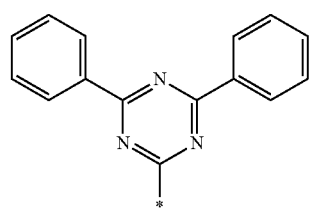  A7
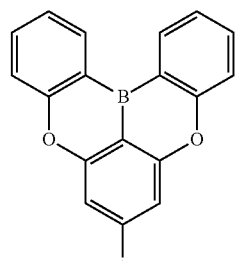  A8
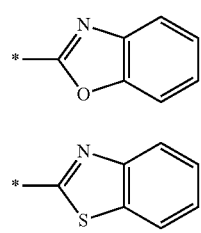  A9
A10

-continued

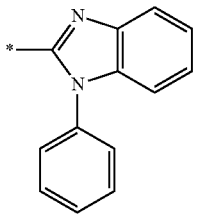 A11

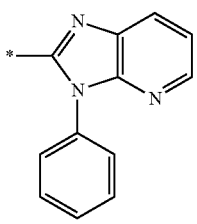 A12

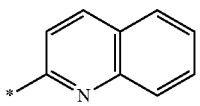 A13

[Third Organic Compound]

The third organic compound is a light-emitting material having a smaller lowest excited singlet energy than the first organic compound and the second organic compound. The third organic compound receives energy from the first organic compound and the second organic compound that are in an excited singlet state and from the second organic compound that has become in an excited singlet state through reverse intersystem crossing from an excited triplet state, and transits to a singlet excited state, and thereafter when returning back to a ground state, it emits fluorescence. The light-emitting material to be used as the third organic compound is not specifically limited so far as it can receive energy from the first organic compound and the second organic compound to emit light, and the light emission from the material may be fluorescence or delayed fluorescence or may also be phosphorescence. In particular, the light-emitting material to be used as the third organic compound is preferably one capable of emitting fluorescence when returning back from a lowest excited singlet energy level to a ground state energy level. Two or more different types of third organic compounds can be used so far as they satisfy the relationship of the formula (A). For example, by combining two or more kinds of third organic compounds that differ in the emission color, it is possible to emit light of a desired color.

The third organic compound usable herein include an anthracene derivative, a tetracene derivative, a naphthacene derivative, a pyrene derivative, a perylene derivative, a chrysene derivative, a rubrene derivative, a coumarin derivative, a pyran derivative, a stilbene derivative, a fluorene derivative, an anthryl derivative, a terphenyl derivative, a terphenylene derivative, a fluoranthene derivative, an amine derivative, a quinacridone derivative, an oxadiazole derivative, a malononitrile derivative, a carbazole derivative, a julolidine derivative, a thiazole derivative, and a derivative having a metal (Al, Zn). The skeleton of these derivatives may have a substituent, or may not have a substituent. In the derivatives, plural skeletons can be combined.

Preferred examples of compounds usable as the third organic compound are shown below.

anthracene
tetracene
5,6,11,12-tetraphenyltetracene
2,8-di-tert-butyl-5,11-bis(4-(tert-butyl)phenyl)-6,12-diphenyltetracene perylene
2,5,8,11-tetra-tert-butylperylene
1,3,6,8-tetraphenylpyrene
benzo[e]pyrene
5,12-dihydroquinolino[2,3-b]acridine-7,14-dione
5,12-dimethyl-5,12-dihydroquinolino[2,3-b]acridine-7,14-dione
5,12-di-tert-butyl-5,12-dihydroquinolino[2,3-b]acridine-7,14-dione
5,12-di-tert-butyl-1,3,8,10-tetramethyl-5,12-dihydroquinolino[2,3-b]acridine-7,14-dione
3-(benzo[d]thiazol-2-yl)-7-(diethylamino)-2H-chromen-2-one
3-(1H-benzo[d]imidazol-2-yl)-7-(diethylamino)-2H-chromen-2-one
7-(diethylamino)-3-(1-methyl-1H-benzo[d]imidazol-2-yl)-2H-chromen-2-one
10-(benzo[d]thiazol-2-yl)-2,3,6,7-tetrahydro-1H,5H,11H-pyrano[2,3-f]pyrido[3,2,1-ij]quinolin-11-one
10-(benzo[d]thiazol-2-yl)-1,1,7,7-tetramethyl-2,3,6,7-tetrahydro-1H,5H,11H-pyrano[2,3-f]pyrido[3,2,1-ij]quinolin-11-one
7-(dimethylamino)-4-(trifluoromethyl)-2H-chromen-2-one
7-(diethylamino)-4-(trifluoromethyl)-2H-chromen-2-one
1,1,7,7-tetramethyl-9-(trifluoromethyl)-2,3,6,7-tetrahydro-1H,5H,11H-pyrano[2,3-f]pyrido[3,2,1-ij]quinolin-11-one
(E)-2-(2-(4-(dimethylamino)styryl)-6-methyl-4H-pyran-4-ylidene)malononitrile
(E)-2-(2-methyl-6-(2-(2,3,6,7-tetrahydro-1H,5H-pyrido[3,2,1-ij]quinolin-9-yl)vinyl)-4H-pyran-4-ylidene)malononitrile
(E)-2-(2-methyl-6-(2-(1,1,7,7-tetramethyl-2,3,6,7-tetrahydro-1H,5H-pyrido[3,2,1-ij]quinolin-9-yl)vinyl)-4H-pyran-4-ylidene)malononitrile
(E)-2-(2-(tert-butyl)-6-(2-(1,1,7,7-tetramethyl-2,3,6,7-tetrahydro-1H,5H-pyrido[3,2,1-ij]quinolin-9-yl)vinyl)-4H-pyran-4-ylidene)malononitrile
(E)-2-(2-(tert-butyl)-6-(2-(2,6,6-trimethyl-1,2,5,6-tetrahydro-4H-pyrrolo[3,2,1-ij]quinolin-8-yl)vinyl)-4H-pyran-4-ylidene)malononitrile
(E)-2-(2-(4-(dimethylamino)styryl)-1-ethylquinolin-4(1H)-ylidene)malononitrile
(E)-2-(2-(2-(7-(4-(bis(4-methoxyphenyl)amino)phenyl)-2,3-dihydrothieno[3,4-b][1,4]dioxin-5-yl)vinyl)-1-ethylquinolin-4(1H)-ylidene)malononitrile
4,4'-((1E,1'E)-1,4-phenylenebis(ethene-2,1-diyl))bis(N,N-diphenylaniline) 4,4'-((1E,1'E)-1,4-phenylenebis(ethene-2,1-diyl))bis(N,N-di-p-tolylaniline)
1,4-bis((E)-4-(9H-carbazol-9-yl)styryl)benzene
4,4'-((1E,1'E)-[1,1'-biphenyl]-4,4'-diylbis(ethene-2,1-diyl))bis(N,N-diphenylaniline)
4,4'-((1E,1'E)-[1,1'-biphenyl]-4,4'-diylbis(ethene-2,1-diyl))bis(N,N-di-p-tolylaniline)
4,4'-((1E,1'E)-9,9'-spirobi[fluorene]-2,7-diylbis(ethene-2,1-diyl))bis(N,N-diphenylaniline)
4,4'-bis((E)-4-(9H-carbazol-9-yl)styryl)-1,1'-biphenyl
4,4'-((1E,1'E)-naphthalene-2,6-diylbis(ethene-2,1-diyl))bis(N,N-diphenylaniline) 4,4'-((1E,1'E)-naphthalene-2,6-diylbis(ethene-2,1-diyl))bis(N,N-bis(4-hexylphenyl)aniline)
1,4-bis((E)-2-(9-ethyl-9H-carbazol-3-yl)vinyl)benzene
4,4'-bis((E)-2-(9-ethyl-9H-carbazol-3-yl)vinyl)-1,1'-biphenyl
1,1,4,4-tetraphenylbuta-1,3-diene
(E)-N,N-diphenyl-4-styrylaniline
(E)-N,N-diphenyl-4-(4-(pyren-1-yl)styryl)aniline
(E)-9,9-diethyl-N,N-diphenyl-7-(4-(9-phenyl-9H-fluoren-9-yl)styryl)-9H-fluoren-2-amine
tris(quinolin-8-yloxy)aluminum
bis(2-(benzo[d]oxazol-2-yl)phenoxy)zinc bis(2-(benzo[d]thiazol-2-yl)phenoxy)zinc
bis(quinolin-8-yloxy)zinc
N4,N4,N4''',N4'''-tetraphenyl-[1,1':4',1'':4'',1'''-quaterphenyl]-4,4'''-diamine
9,9,9',9',9'',9''-hexamethyl-N7,N7''-diphenyl-N7,N7''-di-m-tolyl-9H,9'H,9''H-[2,2':7',2''-terfluorene]-7,7''-diamine
9,9,9',9',9'',9''-hexamethyl-N7,N7''-di(naphthalen-2-yl)-N7,N7''-diphenyl-9H,9'H,9''H-[2 ,2':7',2''-terfluorene]-7,7''-diamine
N9,N10-diphenyl-N9,N10-di-p-tolylanthracene-9,10-diamine
N9,N10-diphenyl-N9,N10-di-m-tolylanthracene-9,10-diamine
N9,N10-di(naphthalen-2-yl)-N9,N10-diphenylanthracene-9,10-diamine
N9,N9,N10,N10-tetra-p-tolylanthracene-9,10-diamine
N10,N10,N10',N10'-tetraphenyl-[9,9'-bianthracene]-10,10'-diamine
N10,N10,N10',N10'-tetra-p-tolyl-[9,9'-bianthracene]-10,10'-diamine
N10,N10'-bis(4-isopropylphenyl)-N10,N10'-di-p-tolyl-[9,9'-bianthracene]-10,10'-diamine
N10,N10'-di(naphthalen-1-yl)-N10,N10'-diphenyl-[9,9'-bianthracene]-10,10'-diamine
N,N-diphenyldibenzo[g,p]chrysen-2-amine
N5,N5,N9,N9-tetraphenylspiro[benzo[c]fluorene-7,9'-fluorene]-5,9-diamine
N5,N9-diphenyl-N5,N9-di-m-tolylspiro[benzo[c]fluorene-7,9'-fluorene]-5,9-diamine
2,6-bis(diphenylamino)anthracene-9,10-dione
9,9'-diphenyl-9H,9'H-3,3'-bicarbazole
3-(10-(naphthalen-1-yl)anthracen-9-yl)-9-phenyl-9H-carbazole
cyclopenta-1,3-diene-1,2,3,4-tetrayltetrabenzene
cyclopenta-1,3-diene-1,2,3,4,5-pentaylpentabenzene
15,15-difluoro-3,11-dimesityl-15H-1414,1514-[1,3,5,2]triazaborinino[1,6-a:3,4-a']diquinoline
10,10'-bis(3,5-bis(trifluoromethyl)phenyl)-9,9'-bianthracene
9,10-bis(4-(benzo[d]thiazol-2-yl)phenyl)anthracene

D1

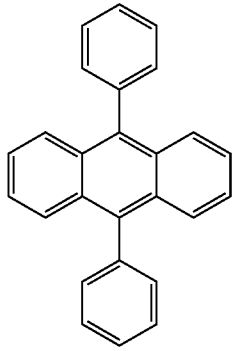

D2

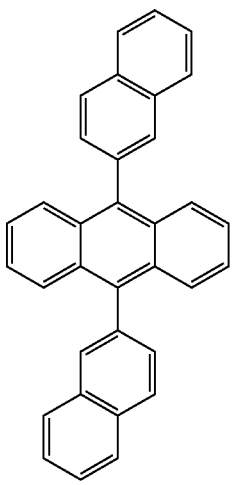

D3

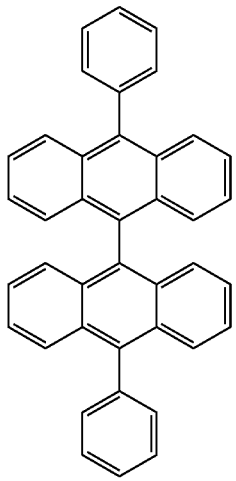

D4

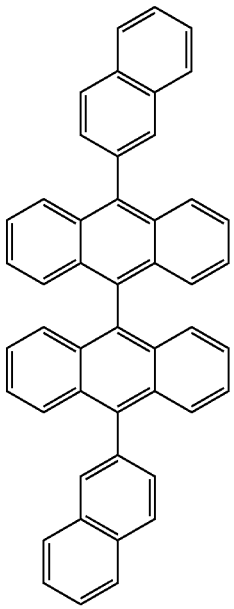

-continued
D5
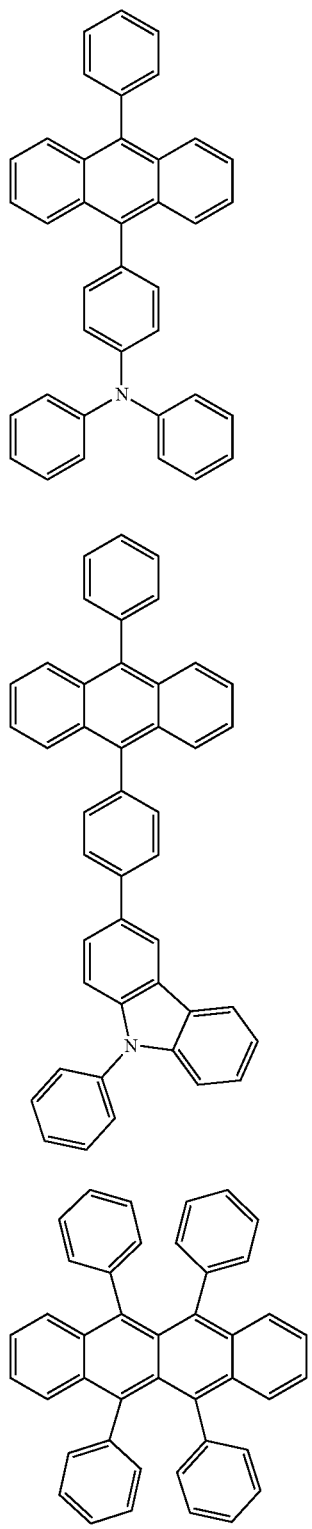
D6
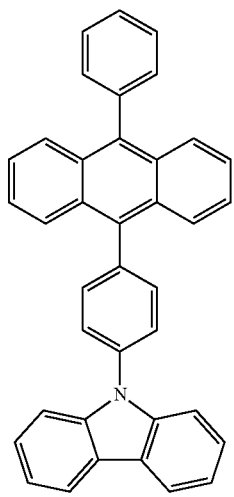
D7
D8
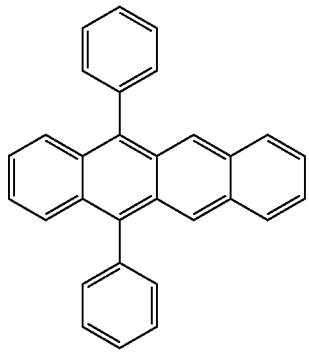
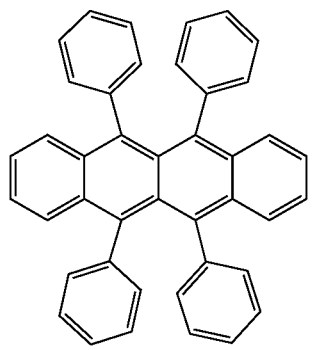
D9
D10
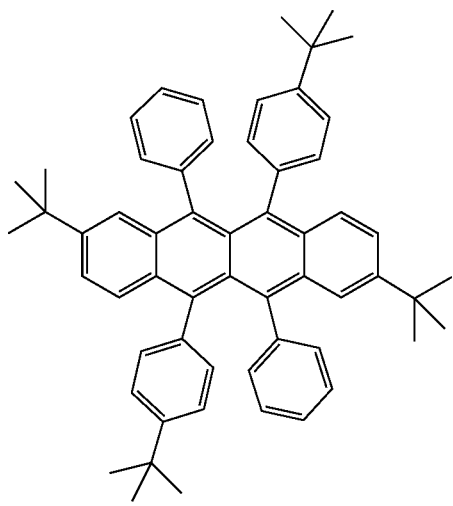

-continued
D11
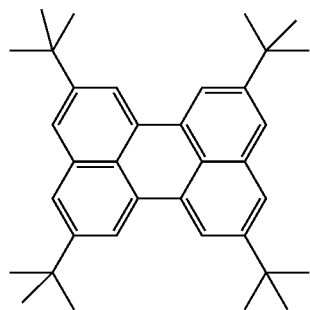
D12
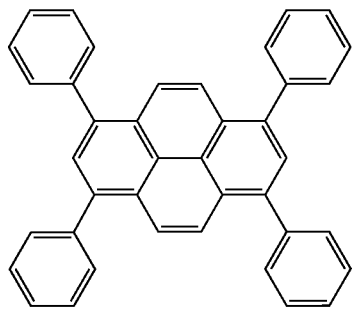
D13
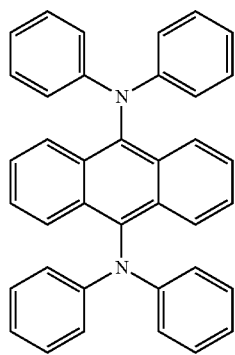
D14
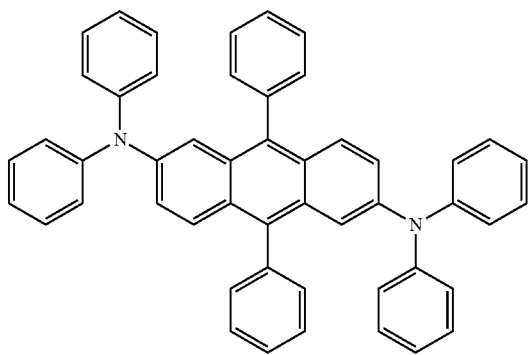
D15
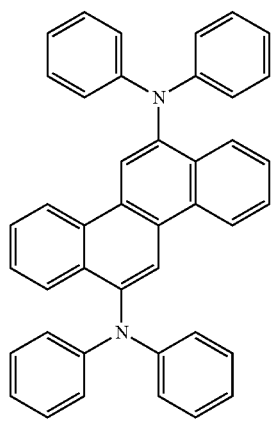
D16
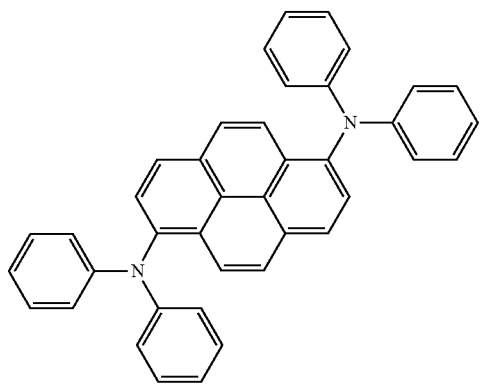
D17
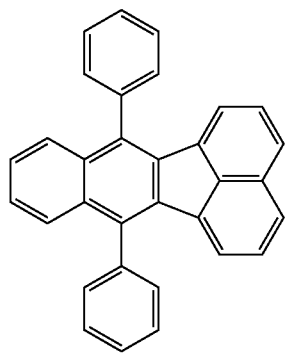
D18
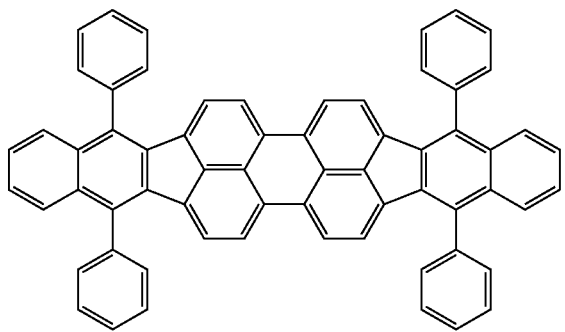

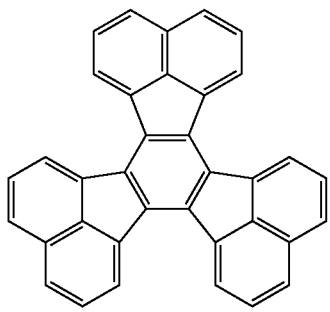
D19
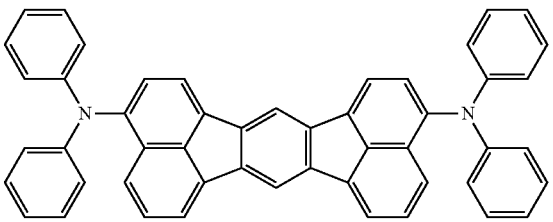
D20
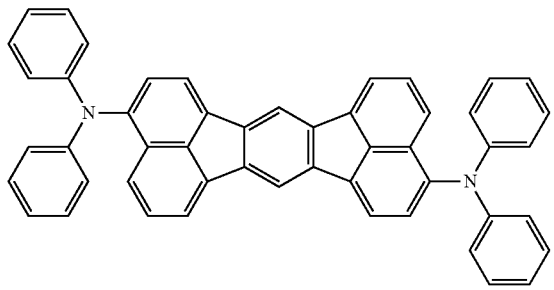
D21
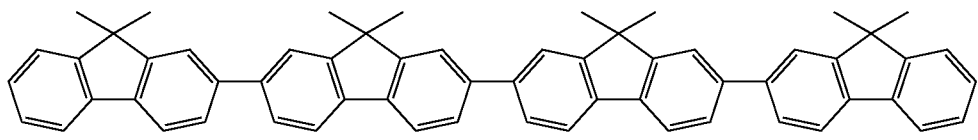
D22
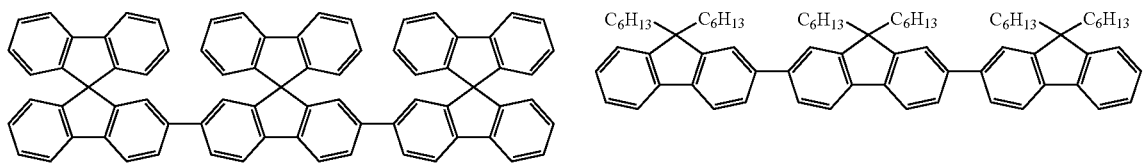
D23
D24
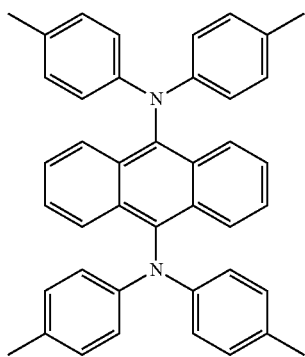
D25
Light-emitting materials described in the following patent publications can be used as the third organic compound in the present invention.
JP2018-078242, JP2016-208021, JP2016-183331, WO2016/133058, WO2016/136425, JP2018-507909, WO2016/131521, JP2018-503619, WO2016/102048, JP2017-053941, WO2016/006674, JP2016-088927, JP2017-529316, WO2016/017919, WO2015/182547, JP2017-514878, WO2015/146912, JP2015-173263, JP2017-513855, WO2015/158411, JP2015-173263, JP2016-108297, JP2016-540381, WO2015/071473, WO2015/050057, WO2015/033559, JP2015-203027, JP2015-204357, JP2015-199670, JP2015-177138, WO2014/141725, JP2015-174901, JP2015-176694, JP2015-176693, WO2014/132917, WO2014/129048, JP2015-109370, JP2015-088563, WO2014/057874, JP2014-214148, JP2014-177442, JP2014-165346, JP2013-189426, WO2013/114941, JP2013-144675, JP2014-073986, JP2015-233024, JP2015-233023, JP2015-216135, JP2014-017373, JP2014-003247, JP2014-001349, JP2013-173726, JP2013-234221, WO2012/144176, JP2012-219098, JP2013-207139, JP2012-212662, WO2012/115218, JP2013-171736, JP2013-171735, JP2012-188416, JP2013-107845, WO2012/046839, JP2012-176928, JP2012-067077, JP2013-014525, JP2012-254948, JP2012-238445, JP2011-238922, JP2012-224569, JP2012-227244, JP2011-241383, WO2012/096506, WO2012/085982, WO2011/077691, WO2011/077690, WO2011/077689, WO2011/074254, WO2011/074253, WO2011/068083, JP2011-109098, JP2011-105718, JP2013-510890, WO2011/060877, JP2012-046478, JP2013-510889, WO2011/060859, JP2012-087187, JP2011-079822, JP2012-044010, JP2012-036096, JP2013-500585, WO2011/011501, JP2013-500281, WO2011/012212, JP2012-531383, WO2011/000455, JP2012-530695, WO2010/147318, JP2011-006405, WO2010/137285, JP2012-528208, WO2010/136110, JP2011-222831, JP2011-195515, JP2011-168550, JP2012-518275, WO2010/093457, JP2011-151108, JP2011-132419, JP2012-515734, WO2010/083873, JP2012-515733, WO2010/083872, JP2010-168363, JP2012-512912, WO2010/071871, JP2010-163430, JP2012-509317, WO2010/058946, JP2010-209059, JP2011-063550, WO2010/032453, WO2010/032447, JP2011-060878, JP2012-501354, WO2010/027181, JP2010-083868, WO2010/018842, JP2011-037743, WO2010/013676, JP2011-530802, WO2010/015306, JP2011-011994, WO2009/154207, WO2009/142230, JP2011-519971, WO2009/139580, JP2009-299049, WO2009/133917, JP2009-280576, JP2009-280571, JP2010-241874, JP2010-232533, JP2009-298770, WO2009/116628, JP2009-292806, WO2009/102054, WO2009/102026, JP2009-209133, JP2009-218568, JP2009-173642, JP2010-143879, JP2011-506564, WO2009/080716, JP2009-167175, WO2009/066600, JP2010-111635, JP2010-090085, JP2009-076450, JP2010-537383, WO2009/025810, JP2010-030973, JP2009-152529, JP2009-152528, WO2009/008357, WO2009/008311, JP2009-010364, WO2008/143229, JP2008-308685, JP2008-308673, WO2008/136522, JP2009-196970, JP2008-266309, JP2008-258603, WO2008/111554, WO2008/111553, JP2009-203203, WO2008/105472, WO2008/105471, JP2008-244465, WO2008/108177, JP2009-188136, JP2008-214339, JP2009-161468, JP2009-161465, JP2008-179614, JP2010-511696, WO2008/069586, WO2008/062773, JP2008-169197, JP2008-133264, JP2008-133263, WO2008/047744, JP2008-106063, JP2008-106055, JP2008-106054, JP2008-110965, JP2008-106044, JP2008-095080, JP2008-081497, JP2009-049094, JP2009-040731, JP2009-040730, JP2009-545156, WO2008/013399, JP2009-029725, JP2010-241687, JP2009-013066, JP2008-290999, JP2008-214332, JP2008-280312, JP2008-273861, JP2008-081490, JP2009-534376, WO2007/123339, JP2009-535813, WO2007/130259, JP2008-263112, WO2007/116828, JP2009-502778, WO2007/105917, JP2009-529035, WO2007/102683, JP2008-214271, JP2009-531341, WO2007/110129, WO2007/099983, JP2008-208065, JP2008-208039, WO2007/105448, JP2007-314510, JP2007-308477, JP2009-524653, WO2007/086695, JP2007-221113, JP2008-162911, JP2008-156316, JP2008-159779, JP2009-518342, WO2007/065678, JP2009-518328, WO2007/065550, JP2007-162009, WO2007/052759, JP2008-115093, JP2007-145834, JP2007-176928, JP2007-119457, JP2007-091721, JP2008-050308, JP2007-091715, JP2009-512179, WO2007/039344, JP2009-504730, WO2007/021117, JP2007-056006, JP2008-521243, WO2007/004799, JP2007-329176, JP2006-332668, JP2007-297302, JP2007-291012, JP2008-539189, WO2006/114364, JP2007-277113, JP2007-269736, JP2007-039431, JP2007-230887, WO2006/085434, JP2007-045809, JP2007-055996, WO2006/070712, WO2006/070711, JP2007-112729, JP2007-051208, JP2007-036127, JP2007-015961, JP2007-015933, JP2008-505449, WO2006/028546, WO2005/121057, JP2006-008663, WO2005/115950, JP2006-310351, JP2006-306732, JP2006-282533, WO2005/091686, JP2006-248900, JP2006-245172, JP2006-245021, JP2007-524745, WO2005/080527, JP2006-210747, JP2006-199629, JP2006-199628, JP2006-199595, JP2006-176448, WO2005/061656, WO2005/054162, WO2005/042621, JP2006-100756, JP2007-512685, WO2005/048370, JP2007-511067, WO2005/042668, WO2005/121203, WO2005/100437, JP2007-510294, WO2005/042667, JP2005-126431, JP2007-507449, WO2005/033051, JP2007-505074, WO2005/026088, JP2005-097283, JP2005-320277, JP2005-289842, JP2005-235633, JP2004-210786, JP2005-126399, JP2005-108746, JP2005-068366, WO2004/018587, JP2005-538999, WO2004/013080, JP2005-053806, JP2005-041804, JP2004-063465, WO2004/018588, JP2005-015420, JP2004-356033, JP2003-338377, JP2004-244400, JP2004-256469, JP2004-256468, JP2004-265623, JP2004-231563, JP2004-224766, JP2004-115441, JP2004-075580, JP2003-059668, JP2004-067528, JP2004-059535, JP2004-043646, JP2003-104916, JP2003-051388, JP2003-055652, JP2002-359081, JP2003-261560, JP2003-249372, JP2003-249371, JP2003-206289, JP2003-197375, JP2003-187980, JP2003-187979, JP2003-168563, JP2003-168562, JP2003-123978, JP2002-179630, JP2003-012612, JP2002-343569, JP2002-332420, JP2002-334784, JP2002-319490, JP2002-317175, JP2002-313575, JP2002-313573, WO2001/072673, JP2002-280182, JP2001-307885, JP2002-234892, JP2002-080822, JP2002-047282, JP2002-237386, JP2002-226484, JP2002-170682, JP2002-164176, JP2002-164175, WO2001/021729, JP2002-012861, JP2002-003833, JP2001-338763, JP2001-329257, JP2001-294585, JP2001-284050, JP2001-081090, JP2001-217077, JP2001-072683, JP2001-196179, JP2001-131434, JP2001-076876, JP2001-076875, JP2001-052869, JP2000-344691, JP2000-311786, JPH11-312588, JP2000-260569, JPH11-242995, JP2000-133457, JP2000-034234, JP2000-026325, JP2000-026324, JPH11-012205, JPH10-330295, JPH11-273864, JPH11-130817, JPH11-176575, JPH11-176573, JPH10-189248, JPH10-189247, JPH11-097178, WO1998/008360, JPH11-040360, JPH10-340783, JPH10-330743, JPH10-294179, JPH10-294177, JPH10-088122, JPH10-060427, JPH08-283256, JPH09-053068, JPH08-012600, JPH08-157815, JPH08-048726, JPH08-012967, JPH07-188340, JPH07-138561, JPH07-126330, JPH07-101911, JPH07-026254, JPH06-330032, JPH06-219973, JPH06-009892, JPH05-178810, JPH05-222361, JPH05-263072.

Here, JP indicates a Japanese patent publication, WO indicates an international patent publication, and H indicates Heisei. All the patent publications described in this paragraph are referred to herein as a part of the present description.

The molecular weight of the second organic compound and the third organic compound is, for example, in the case where an organic layer containing the compound is intended to be formed according to a vapor deposition method and used in devices, preferably 1500 or less, more preferably 1200 or less, even more preferably 1000 or less, and further more preferably 800 or less. Irrespective of the molecular weight thereof, the second organic compound and the third organic compound may be formed into a film according to a coating method. When a coating method is employed, even a compound having a relatively large molecular weight can be formed into a film.

Applying the present invention, it is considered to use a compound containing plural structures represented by the above-mentioned general formula in the molecule as a light-emitting material for the second organic compound or the third organic compound.

For example, the general formula (1) is described as an example. It is considered that a polymerizable group is previously introduced into a structure represented by the general formula (1) and the polymerizable group is polymerized to give a polymer, and the polymer is used as the second organic compound. Specifically, a monomer containing a polymerizable functional group in any of L, A and D in the general formula (1) is prepared, and this is homopolymerized or copolymerized with any other monomer to give a polymer having a recurring unit, and the polymer can be used as a light-emitting material. Alternatively, compounds each having a structure represented by the general formula (1) are coupled to give a dimer or a trimer, and it can be used as a light-emitting material.

Examples of the polymer having a recurring unit containing a structure represented by the general formula (1), which is for use for the second organic compound or the third organic compound, include polymers containing a structure represented by the following general formula (23) or (24).

General Formula (23)

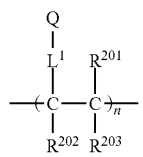

General Formula (24)

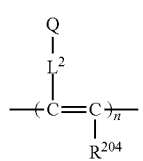

In the general formula (23) or (24), Q represents a group containing a structure represented by the above-mentioned general formula, and $L^1$ and $L^2$ each represent a linking group. The carbon number of the linking group is preferably 0 to 20, more preferably 1 to 15, even more preferably 2 to 10. Preferably, the linking group has a structure represented by —$X^{11}$-$L^{11}$-. Here, $X^{11}$ represents an oxygen atom or a sulfur atom, and is preferably an oxygen atom. $L^{11}$ represents a linking group, and is preferably a substituted or unsubstituted alkylene group, or a substituted or unsubstituted arylene group, more preferably a substituted or unsubstituted alkylene group having 1 to 10 carbon atoms, or a substituted or unsubstituted phenylene group.

In the general formula (23) or (24), $R^{201}$, $R^{202}$, $R^{203}$ and $R^{204}$ each independently represent a substituent. Preferably, the substituent is a substituted or unsubstituted alkyl group having 1 to 6 carbon atoms, a substituted or unsubstituted alkoxy group having 1 to 6 carbon atoms, or a halogen atom, more preferably an unsubstituted alkyl group having 1 to 3 carbon atoms, an unsubstituted alkoxy group having 1 to 3 carbon atoms, a fluorine atom, or a chlorine atom, and even more preferably an unsubstituted alkyl group having 1 to 3 carbon atoms, or an unsubstituted alkoxy group having 1 to 3 carbon atoms.

The linking group represented by $L^1$ and $L^2$ may bond to any of L, A and D in the structure of the general formula (1) constituting Q. Two or more linking groups may bond to one Q to form a crosslinked structure or a network structure.

Specific examples of the structure of the recurring unit include structures represented by the following general formulae (25) to (28).

General Formula (25)

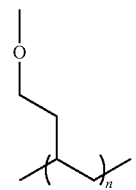

General Formula (26)

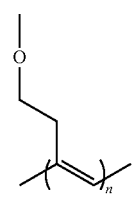

General Formula (27)

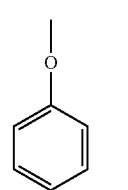

General Formula (28)

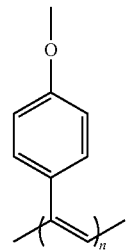

The polymer having the recurring unit containing the structure represented by any of the general formulae (25) to (28) may be synthesized in such a manner that a hydroxyl group is introduced to any of L, A and D in the structure represented by the general formula (1), and the hydroxyl group as a linker is reacted with the following compound to introduce a polymerizable group thereinto, followed by polymerizing the polymerizable group.

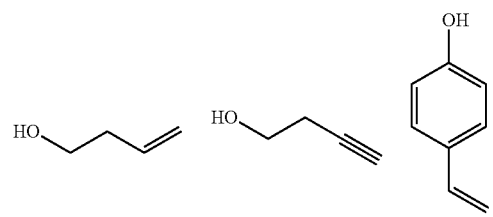

-continued

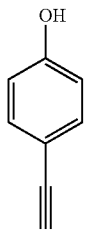

The polymer containing the structure represented by the above-mentioned general formula in the molecule may be a polymer containing only a recurring unit having the structure represented by the general formula, or a polymer further containing a recurring unit having another structure. The recurring unit having the structure represented by the general formula contained in the polymer may be only one kind or two or more kinds. Examples of the recurring unit that does not have the structure represented by the general formula include a recurring unit derived from a monomer that is used for ordinary copolymerization. Examples of the recurring unit include a recurring unit derived from a monomer having an ethylenic unsaturated bond, such as ethylene and styrene.

[Content of Compound and Combination of Compounds]

The content of each organic compound contained in the light-emitting layer is not specifically limited but is preferably such that the content of the second organic compound is smaller than the content of the first organic compound. With that, a higher light emission efficiency can be attained. Specifically, in the case where a total weigh of the first organic compound having a content of W1, the second organic compound having a content of W2 and a third organic compound having a content of W3 is 100% by weight, preferably, the content W1 of the first organic compound is 15% by weight or more and 99.9% by weight or less, the content W2 of the second organic compound is preferably 5.0% by weight or more and 50% by weight or less, and the content W3 of the third organic compound is preferably 0.5% by weight or more and 5.0% by weight or less.

In producing an organic electroluminescent device, the first organic compound, the second organic compound and the third organic compound can be used in one layer alone, or may be used in the other layers. For example, one or more of the first organic compound, the second organic compound and the third organic compound may be used in the above-mentioned injection layer, blocking layer, hole blocking layer electron blocking layer, exciton blocking layer, hole transport layer and an electron transport layer. Film formation methods for forming these layers are not specifically limited, and the layers may be formed according to any of a dry process or a wet process.

Specific examples of a combination of the second organic compound and the third organic compound in producing an organic electroluminescent device are shown in the following Tables. The vertical lines indicate the compounds 1 to 678 exemplified as the second organic compound, and the horizontal lines indicates the compounds D1 to D25 exemplified as the third organic compound. The combinations specified by the second organic compound of the horizontal line and the third organic compound of the vertical line are sequentially numbered as No. 1 to No. 16950.

Preferably, the first organic compound, the second organic compound and the third organic compound for use in the present invention do not contain a metal atom, and are more preferably compounds composed of atoms selected from a carbon atom, a hydrogen atom, a nitrogen atom, an oxygen atom, a sulfur atom, a silicon atom, and a halogen atom (fluorine atom, chlorine atom, bromine atom, iodine atom). For example, it is possible to select compounds composed of atoms alone selected from the group consisting of a carbon atom, a hydrogen atom, a nitrogen atom and a halogen atom (fluorine atom, chlorine atom, bromine atom, iodine atom), or to select compounds composed of atoms alone selected from the group consisting of a carbon atom, a hydrogen atom and a nitrogen atom.

|  |  | Third organic compound | | | | | | | | | | | | |
| --- | --- | --- | --- | --- | --- | --- | --- | --- | --- | --- | --- | --- | --- | --- |
|  |  | D1 | D2 | D3 | D4 | D5 | D6 | D7 | D8 | D9 | D10 | D11 | D12 | D13 |
| Second organic compound | 1 | 1 | 2 | 3 | 4 | 5 | 6 | 7 | 8 | 9 | 10 | 11 | 12 | 13 |
|  | 2 | 26 | 27 | 28 | 29 | 30 | 31 | 32 | 33 | 34 | 35 | 36 | 37 | 38 |
|  | 3 | 51 | 52 | 53 | 54 | 55 | 56 | 57 | 58 | 59 | 60 | 61 | 62 | 63 |
|  | 4 | 76 | 77 | 78 | 79 | 80 | 81 | 82 | 83 | 84 | 85 | 86 | 87 | 88 |
|  | 5 | 101 | 102 | 103 | 104 | 105 | 106 | 107 | 108 | 109 | 110 | 111 | 112 | 113 |
|  | 6 | 126 | 127 | 128 | 129 | 130 | 131 | 132 | 133 | 134 | 135 | 136 | 137 | 138 |
|  | 7 | 151 | 152 | 153 | 154 | 155 | 156 | 157 | 158 | 159 | 160 | 161 | 162 | 163 |
|  | 8 | 176 | 177 | 178 | 179 | 180 | 181 | 182 | 183 | 184 | 185 | 186 | 187 | 188 |
|  | 9 | 201 | 202 | 203 | 204 | 205 | 206 | 207 | 208 | 209 | 210 | 211 | 212 | 213 |
|  | 10 | 226 | 227 | 228 | 229 | 230 | 231 | 232 | 233 | 234 | 235 | 236 | 237 | 238 |
|  | 11 | 251 | 252 | 253 | 254 | 255 | 256 | 257 | 258 | 259 | 260 | 261 | 262 | 263 |
|  | 12 | 276 | 277 | 278 | 279 | 280 | 281 | 282 | 283 | 284 | 285 | 286 | 287 | 288 |
|  | 13 | 301 | 302 | 303 | 304 | 305 | 306 | 307 | 308 | 309 | 310 | 311 | 312 | 313 |
|  | 14 | 326 | 327 | 328 | 329 | 330 | 331 | 332 | 333 | 334 | 335 | 336 | 337 | 338 |
|  | 15 | 351 | 352 | 353 | 354 | 355 | 356 | 357 | 358 | 359 | 360 | 361 | 362 | 363 |
|  | 16 | 376 | 377 | 378 | 379 | 380 | 381 | 382 | 383 | 384 | 385 | 386 | 387 | 388 |
|  | 17 | 401 | 402 | 403 | 404 | 405 | 406 | 407 | 408 | 409 | 410 | 411 | 412 | 413 |
|  | 18 | 426 | 427 | 428 | 429 | 430 | 431 | 432 | 433 | 434 | 435 | 436 | 437 | 438 |
|  | 19 | 451 | 452 | 453 | 454 | 455 | 456 | 157 | 458 | 459 | 460 | 461 | 462 | 463 |
|  | 20 | 476 | 477 | 478 | 479 | 480 | 481 | 482 | 483 | 484 | 485 | 486 | 487 | 488 |
|  | 21 | 501 | 502 | 503 | 504 | 505 | 506 | 507 | 508 | 509 | 510 | 511 | 512 | 513 |
|  | 22 | 526 | 527 | 528 | 529 | 530 | 531 | 532 | 533 | 534 | 535 | 536 | 537 | 538 |
|  | 23 | 551 | 552 | 553 | 554 | 555 | 556 | 557 | 558 | 559 | 560 | 561 | 562 | 563 |
|  | 24 | 576 | 577 | 578 | 579 | 580 | 581 | 582 | 583 | 584 | 585 | 586 | 587 | 588 |
|  | 25 | 601 | 602 | 603 | 604 | 605 | 606 | 607 | 608 | 609 | 610 | 611 | 612 | 613 |
|  | 26 | 626 | 627 | 628 | 629 | 630 | 631 | 632 | 633 | 634 | 635 | 636 | 637 | 638 |
|  | 27 | 651 | 652 | 653 | 654 | 655 | 656 | 657 | 658 | 659 | 660 | 661 | 662 | 663 |

-continued

| | | | | | | | | | | | | | |
|---|---|---|---|---|---|---|---|---|---|---|---|---|---|
| | 28 | 676 | 677 | 678 | 679 | 680 | 681 | 682 | 683 | 684 | 685 | 686 | 687 | 688 |
| | 29 | 701 | 702 | 703 | 704 | 705 | 706 | 707 | 708 | 709 | 710 | 711 | 712 | 713 |
| | 30 | 726 | 727 | 728 | 729 | 730 | 731 | 732 | 733 | 734 | 735 | 736 | 737 | 738 |
| | 31 | 751 | 752 | 753 | 754 | 755 | 756 | 757 | 758 | 759 | 760 | 761 | 762 | 763 |
| | 32 | 776 | 777 | 778 | 779 | 780 | 781 | 782 | 783 | 784 | 785 | 786 | 787 | 788 |
| | 33 | 801 | 802 | 803 | 804 | 805 | 806 | 807 | 808 | 809 | 810 | 811 | 812 | 813 |
| | 34 | 826 | 827 | 828 | 829 | 830 | 831 | 832 | 833 | 834 | 835 | 836 | 837 | 838 |
| | 35 | 851 | 852 | 853 | 854 | 855 | 856 | 857 | 858 | 859 | 860 | 861 | 862 | 863 |
| | 36 | 876 | 877 | 878 | 879 | 880 | 881 | 882 | 883 | 884 | 885 | 886 | 887 | 888 |
| | 37 | 901 | 902 | 903 | 904 | 905 | 906 | 907 | 908 | 909 | 910 | 911 | 912 | 913 |
| | 38 | 926 | 927 | 928 | 929 | 930 | 931 | 932 | 933 | 934 | 935 | 936 | 937 | 938 |
| | 39 | 951 | 952 | 953 | 954 | 955 | 956 | 957 | 958 | 959 | 960 | 961 | 962 | 963 |
| | 40 | 976 | 977 | 978 | 979 | 980 | 981 | 982 | 983 | 984 | 985 | 986 | 987 | 988 |
| | 41 | 1001 | 1002 | 1003 | 1004 | 1005 | 1006 | 1007 | 1008 | 1009 | 1010 | 1011 | 1012 | 1013 |
| | 42 | 1026 | 1027 | 1028 | 1029 | 1030 | 1031 | 1032 | 1033 | 1034 | 1035 | 1036 | 1037 | 1038 |
| | 43 | 1051 | 1052 | 1053 | 1054 | 1055 | 1056 | 1057 | 1058 | 1059 | 1060 | 1061 | 1062 | 1063 |
| | 44 | 1076 | 1077 | 1078 | 1079 | 1080 | 1081 | 1082 | 1083 | 1084 | 1085 | 1086 | 1087 | 1088 |
| | 45 | 1101 | 1102 | 1103 | 1104 | 1105 | 1106 | 1107 | 1108 | 1109 | 1110 | 1111 | 1112 | 1113 |
| | 46 | 1126 | 1127 | 1128 | 1129 | 1130 | 1131 | 1132 | 1133 | 1134 | 1135 | 1136 | 1137 | 1138 |
| | 47 | 1151 | 1152 | 1153 | 1154 | 1155 | 1156 | 1157 | 1158 | 1159 | 1160 | 1161 | 1162 | 1163 |
| | 48 | 1176 | 1177 | 1178 | 1179 | 1180 | 1181 | 1182 | 1183 | 1184 | 1185 | 1186 | 1187 | 1188 |
| | 49 | 1201 | 1202 | 1203 | 1204 | 1205 | 1206 | 1207 | 1208 | 1209 | 1210 | 1211 | 1212 | 1213 |
| | 50 | 1226 | 1227 | 1228 | 1229 | 1230 | 1231 | 1232 | 1233 | 1234 | 1235 | 1236 | 1237 | 1238 |
| | 51 | 1251 | 1252 | 1253 | 1254 | 1255 | 1256 | 1257 | 1258 | 1259 | 1260 | 1261 | 1262 | 1263 |
| | 52 | 1276 | 1277 | 1278 | 1279 | 1280 | 1281 | 1282 | 1283 | 1284 | 1285 | 1286 | 1287 | 1288 |
| | 53 | 1301 | 1302 | 1303 | 1304 | 1305 | 1306 | 1307 | 1308 | 1309 | 1310 | 1311 | 1312 | 1313 |
| | 54 | 1326 | 1327 | 1328 | 1329 | 1330 | 1331 | 1332 | 1333 | 1334 | 1335 | 1336 | 1337 | 1338 |
| | 55 | 1351 | 1352 | 1353 | 1354 | 1355 | 1356 | 1357 | 1358 | 1359 | 1360 | 1361 | 1362 | 1363 |

| | | Third organic compound | | | | | | | | | | | |
|---|---|---|---|---|---|---|---|---|---|---|---|---|---|
| | | D14 | D15 | D16 | D17 | D18 | D19 | D20 | D21 | D22 | D23 | D24 | D25 |
| Second | 1 | 14 | 15 | 16 | 17 | 18 | 19 | 20 | 21 | 22 | 23 | 24 | 25 |
| organic | 2 | 39 | 40 | 41 | 42 | 43 | 44 | 45 | 46 | 47 | 48 | 49 | 50 |
| compound | 3 | 64 | 65 | 66 | 67 | 68 | 69 | 70 | 71 | 72 | 73 | 74 | 75 |
| | 4 | 89 | 90 | 91 | 92 | 93 | 94 | 95 | 96 | 97 | 98 | 99 | 100 |
| | 5 | 14 | 115 | 116 | 117 | 118 | 119 | 120 | 121 | 122 | 123 | 124 | 125 |
| | 6 | 139 | 140 | 141 | 142 | 143 | 144 | 145 | 146 | 147 | 148 | 149 | 150 |
| | 7 | 164 | 165 | 166 | 167 | 168 | 169 | 170 | 171 | 172 | 173 | 174 | 175 |
| | 8 | 189 | 190 | 191 | 192 | 193 | 194 | 195 | 196 | 197 | 198 | 199 | 200 |
| | 9 | 214 | 215 | 216 | 217 | 218 | 219 | 220 | 221 | 222 | 223 | 224 | 225 |
| | 10 | 239 | 240 | 241 | 242 | 243 | 244 | 245 | 246 | 247 | 248 | 249 | 250 |
| | 11 | 264 | 265 | 266 | 267 | 268 | 269 | 270 | 271 | 272 | 273 | 274 | 275 |
| | 12 | 289 | 290 | 291 | 292 | 293 | 294 | 295 | 296 | 297 | 298 | 299 | 300 |
| | 13 | 314 | 315 | 316 | 317 | 318 | 319 | 320 | 321 | 322 | 323 | 324 | 325 |
| | 14 | 339 | 340 | 341 | 342 | 343 | 344 | 345 | 346 | 347 | 348 | 349 | 350 |
| | 15 | 364 | 365 | 366 | 367 | 368 | 369 | 370 | 371 | 372 | 373 | 374 | 375 |
| | 16 | 389 | 390 | 391 | 392 | 393 | 394 | 395 | 396 | 397 | 398 | 399 | 400 |
| | 17 | 414 | 415 | 416 | 417 | 418 | 419 | 420 | 421 | 422 | 423 | 424 | 425 |
| | 18 | 439 | 440 | 441 | 442 | 443 | 444 | 445 | 446 | 447 | 448 | 449 | 450 |
| | 19 | 464 | 465 | 466 | 467 | 468 | 469 | 470 | 471 | 472 | 473 | 474 | 475 |
| | 20 | 489 | 490 | 491 | 492 | 493 | 494 | 495 | 496 | 497 | 498 | 499 | 500 |
| | 21 | 514 | 515 | 516 | 517 | 518 | 519 | 520 | 521 | 522 | 523 | 524 | 525 |
| | 22 | 539 | 540 | 541 | 542 | 543 | 544 | 545 | 546 | 547 | 548 | 549 | 550 |
| | 23 | 564 | 565 | 566 | 567 | 568 | 569 | 570 | 571 | 572 | 573 | 574 | 575 |
| | 24 | 589 | 590 | 591 | 592 | 593 | 594 | 595 | 596 | 597 | 598 | 599 | 600 |
| | 25 | 614 | 615 | 616 | 617 | 618 | 619 | 620 | 621 | 622 | 623 | 624 | 625 |
| | 26 | 639 | 640 | 641 | 642 | 643 | 644 | 645 | 646 | 647 | 648 | 649 | 650 |
| | 27 | 664 | 665 | 666 | 667 | 668 | 669 | 670 | 671 | 672 | 673 | 674 | 675 |
| | 28 | 689 | 690 | 691 | 692 | 693 | 694 | 695 | 696 | 697 | 698 | 699 | 700 |
| | 29 | 714 | 715 | 716 | 717 | 718 | 719 | 720 | 721 | 722 | 723 | 724 | 725 |
| | 30 | 739 | 740 | 741 | 742 | 743 | 744 | 745 | 746 | 747 | 748 | 749 | 750 |
| | 31 | 764 | 765 | 766 | 767 | 768 | 769 | 770 | 771 | 772 | 773 | 774 | 775 |
| | 32 | 789 | 790 | 791 | 792 | 793 | 794 | 795 | 796 | 797 | 798 | 799 | 800 |
| | 33 | 814 | 815 | 816 | 817 | 818 | 819 | 820 | 821 | 822 | 823 | 824 | 825 |
| | 34 | 839 | 840 | 841 | 842 | 843 | 844 | 845 | 846 | 847 | 848 | 849 | 850 |
| | 35 | 864 | 865 | 866 | 867 | 868 | 869 | 870 | 871 | 872 | 873 | 874 | 875 |
| | 36 | 889 | 890 | 891 | 892 | 893 | 894 | 895 | 896 | 897 | 898 | 899 | 900 |
| | 37 | 914 | 915 | 916 | 917 | 918 | 919 | 920 | 921 | 922 | 923 | 924 | 925 |
| | 38 | 939 | 940 | 941 | 942 | 943 | 944 | 945 | 946 | 947 | 948 | 949 | 950 |
| | 39 | 964 | 965 | 966 | 967 | 968 | 969 | 970 | 971 | 972 | 973 | 974 | 975 |
| | 40 | 989 | 990 | 991 | 992 | 993 | 994 | 995 | 996 | 997 | 998 | 999 | 1000 |
| | 41 | 1014 | 1015 | 1016 | 1017 | 1018 | 1019 | 1020 | 1021 | 1022 | 1023 | 1024 | 1025 |
| | 42 | 1039 | 1040 | 1041 | 1042 | 1043 | 1044 | 1045 | 1046 | 1047 | 1048 | 1049 | 1050 |
| | 43 | 1064 | 1065 | 1066 | 1067 | 1068 | 1069 | 1070 | 1071 | 1072 | 1073 | 1074 | 1075 |
| | 44 | 1089 | 1090 | 1091 | 1092 | 1093 | 1094 | 1095 | 1096 | 1097 | 1098 | 1099 | 1100 |
| | 45 | 1114 | 1115 | 1116 | 1117 | 1118 | 1119 | 1120 | 1121 | 1122 | 1123 | 1124 | 1125 |
| | 46 | 1139 | 1140 | 1141 | 1142 | 1143 | 1144 | 1145 | 1146 | 1147 | 1148 | 1149 | 1150 |

-continued

| | | | | | | | | | | | |
|---|---|---|---|---|---|---|---|---|---|---|---|
| 47 | 1164 | 1165 | 1166 | 1167 | 1168 | 169 | 1170 | 1171 | 1172 | 1173 | 1174 | 1175 |
| 48 | 1189 | 1190 | 1191 | 1192 | 1193 | 1194 | 1195 | 1196 | 1197 | 1198 | 1199 | 1200 |
| 49 | 1214 | 1215 | 1216 | 1217 | 1218 | 1219 | 1220 | 1221 | 1222 | 1223 | 1224 | 1225 |
| 50 | 1239 | 1240 | 1241 | 1242 | 1243 | 1244 | 1245 | 1246 | 1247 | 1248 | 1249 | 1250 |
| 51 | 1264 | 1265 | 1266 | 1267 | 1268 | 1269 | 1270 | 1271 | 1272 | 1273 | 1274 | 1275 |
| 52 | 1289 | 1290 | 1291 | 1292 | 1293 | 1294 | 1295 | 1296 | 1297 | 1298 | 1299 | 1300 |
| 53 | 1314 | 1315 | 1316 | 1317 | 1318 | 1319 | 1320 | 1321 | 1322 | 1323 | 1324 | 1325 |
| 54 | 1339 | 1340 | 1341 | 1342 | 1343 | 1344 | 1345 | 1346 | 1347 | 1348 | 1349 | 1350 |
| 55 | 1364 | 1365 | 1366 | 1367 | 1368 | 1369 | 1370 | 1371 | 1372 | 1373 | 1374 | 1375 |

| Third organic compound | | | | | | | | | | | | | |
|---|---|---|---|---|---|---|---|---|---|---|---|---|---|
| | D1 | D2 | D3 | D4 | D5 | D6 | D7 | D8 | D9 | D10 | D11 | D12 | D13 |
| 56 | 1376 | 1377 | 1378 | 1379 | 1380 | 1381 | 1382 | 1383 | 1384 | 1385 | 1386 | 1387 | 1388 |
| 57 | 1401 | 1402 | 1403 | 1404 | 1405 | 1406 | 1407 | 1408 | 1409 | 1410 | 1411 | 1412 | 1413 |
| 58 | 1426 | 1427 | 1428 | 1429 | 1430 | 1431 | 1432 | 1433 | 1434 | 435 | 1436 | 1437 | 1438 |
| 59 | 1451 | 1452 | 1453 | 1454 | 1455 | 1456 | 1457 | 1458 | 1459 | 1460 | 1461 | 1462 | 1463 |
| 60 | 1476 | 1477 | 1478 | 1479 | 1480 | 1481 | 1482 | 1483 | 1484 | 1485 | 1486 | 1487 | 1488 |
| 61 | 1501 | 1502 | 1503 | 504 | 1505 | 506 | 1507 | 1508 | 1509 | 1510 | 1511 | 1512 | 1513 |
| 62 | 1526 | 1527 | 1528 | 1529 | 1530 | 1531 | 1532 | 1533 | 1534 | 1535 | 1536 | 1537 | 1538 |
| 63 | 1551 | 1552 | 1553 | 1554 | 1555 | 1556 | 1557 | 1558 | 1559 | 1560 | 1561 | 1562 | 1563 |
| 64 | 1576 | 1577 | 1578 | 1579 | 1580 | 1581 | 1582 | 1583 | 1584 | 1585 | 1586 | 1587 | 1588 |
| 65 | 1601 | 1602 | 1603 | 1604 | 1605 | 1606 | 1607 | 1608 | 1609 | 1610 | 1611 | 1612 | 1613 |
| 66 | 1626 | 1627 | 1628 | 1629 | 1630 | 1631 | 1632 | 1633 | 1634 | 1635 | 1636 | 1637 | 1638 |
| 67 | 1651 | 1652 | 1653 | 1654 | 1655 | 1656 | 1657 | 1658 | 1659 | 1660 | 1661 | 1662 | 1663 |
| 68 | 1676 | 1677 | 1678 | 1679 | 1680 | 1681 | 1682 | 1683 | 1684 | 1685 | 1686 | 1687 | 1688 |
| 69 | 1701 | 1702 | 1703 | 1704 | 1705 | 1706 | 1707 | 1708 | 1709 | 1710 | 1711 | 1712 | 1713 |
| 70 | 1726 | 1727 | 1728 | 1729 | 1730 | 1731 | 1732 | 1733 | 1734 | 1735 | 1736 | 1737 | 1738 |
| 71 | 1751 | 1752 | 1753 | 1754 | 1755 | 1756 | 1757 | 1758 | 1759 | 1760 | 1761 | 1762 | 1763 |
| 72 | 1776 | 1777 | 1778 | 1779 | 1780 | 1781 | 1782 | 1783 | 1784 | 1785 | 1786 | 1787 | 1788 |
| 73 | 1801 | 1802 | 1803 | 1804 | 1805 | 1806 | 1807 | 1808 | 1809 | 1810 | 1811 | 1812 | 1813 |
| 74 | 1826 | 1827 | 1828 | 829 | 1830 | 1831 | 1832 | 1833 | 1834 | 1835 | 1836 | 1837 | 1838 |
| 75 | 1851 | 1852 | 1853 | 1854 | 1855 | 1856 | 1857 | 1858 | 1859 | 1860 | 1861 | 1862 | 1863 |
| 76 | 1876 | 1877 | 1878 | 1879 | 1880 | 1881 | 1882 | 1883 | 1884 | 1885 | 1886 | 1887 | 1888 |
| 77 | 1901 | 1902 | 1903 | 1904 | 1905 | 1906 | 1907 | 1908 | 1909 | 1910 | 1911 | 1912 | 1913 |
| 78 | 1926 | 1927 | 1928 | 1929 | 1930 | 1931 | 1932 | 1933 | 1934 | 1935 | 1936 | 1937 | 1938 |
| 79 | 1951 | 1952 | 1953 | 1954 | 1955 | 1956 | 1957 | 1958 | 1959 | 1960 | 1961 | 1962 | 1963 |
| 80 | 1976 | 1977 | 1978 | 1979 | 1980 | 1981 | 1982 | 1983 | 1984 | 1985 | 1986 | 1987 | 1988 |
| 81 | 2001 | 2002 | 2003 | 2004 | 2005 | 2006 | 2007 | 2008 | 2009 | 2010 | 2011 | 2012 | 2013 |
| 82 | 2026 | 2027 | 2028 | 2029 | 2030 | 2031 | 2032 | 2033 | 2034 | 2035 | 2036 | 2037 | 2038 |
| 83 | 2051 | 2052 | 2053 | 2054 | 2055 | 2056 | 2057 | 2058 | 2059 | 2060 | 2061 | 2062 | 2063 |
| 84 | 2076 | 2077 | 2078 | 2079 | 2080 | 2081 | 2082 | 2083 | 2084 | 2085 | 2086 | 2087 | 2088 |
| 85 | 2101 | 2102 | 2103 | 2104 | 2105 | 2106 | 2107 | 2108 | 2109 | 2110 | 2111 | 2112 | 2113 |
| 86 | 2126 | 2127 | 2128 | 2129 | 2130 | 2131 | 2132 | 2133 | 2134 | 2135 | 2136 | 2137 | 2138 |
| 87 | 2151 | 2152 | 2153 | 2154 | 2155 | 2156 | 2157 | 2158 | 2159 | 2160 | 2161 | 2162 | 2163 |
| 88 | 2176 | 2177 | 2178 | 2179 | 2180 | 2181 | 2182 | 2183 | 2184 | 2185 | 2186 | 2187 | 2188 |
| 89 | 2201 | 2202 | 2203 | 2204 | 2205 | 2206 | 2207 | 2208 | 2209 | 2210 | 2211 | 2212 | 2213 |
| 90 | 2226 | 2227 | 2228 | 2229 | 2230 | 2231 | 2232 | 2233 | 2234 | 2235 | 2236 | 2237 | 2238 |
| 91 | 2251 | 2252 | 2253 | 2254 | 2255 | 2256 | 2257 | 2258 | 2259 | 2260 | 2261 | 2262 | 2263 |
| 92 | 2276 | 2277 | 2278 | 2279 | 2280 | 2281 | 2282 | 2283 | 2284 | 2285 | 2286 | 2287 | 2288 |
| 93 | 2301 | 2302 | 2303 | 2304 | 2305 | 2306 | 2307 | 2308 | 2309 | 2310 | 2311 | 2312 | 2313 |
| 94 | 2326 | 2327 | 2328 | 2329 | 2330 | 2331 | 2332 | 2333 | 2334 | 2335 | 2336 | 2337 | 2338 |
| 95 | 2351 | 2352 | 2353 | 2354 | 2355 | 2356 | 2357 | 2358 | 2359 | 2360 | 2361 | 2362 | 2363 |
| 96 | 2376 | 2377 | 2378 | 2379 | 2380 | 2381 | 2382 | 2383 | 2384 | 2385 | 2386 | 2387 | 2388 |
| 97 | 2401 | 2402 | 2403 | 2404 | 2405 | 2406 | 2407 | 2408 | 2409 | 2410 | 2411 | 2412 | 2413 |
| 98 | 2426 | 2427 | 2428 | 2429 | 2430 | 2431 | 2432 | 2433 | 2434 | 2435 | 2436 | 2437 | 2438 |
| 99 | 2451 | 2452 | 2453 | 2454 | 2455 | 2456 | 2457 | 2458 | 2459 | 2460 | 2461 | 2462 | 2463 |
| 100 | 2476 | 2477 | 2478 | 2479 | 2480 | 2481 | 2482 | 2483 | 2484 | 2485 | 2486 | 2487 | 2488 |
| 101 | 2501 | 2502 | 2503 | 2504 | 2505 | 2506 | 2507 | 2508 | 2509 | 2510 | 2511 | 2512 | 2513 |
| 102 | 2526 | 2527 | 2528 | 2529 | 2530 | 2531 | 2532 | 2533 | 2534 | 2535 | 2536 | 2537 | 2538 |
| 103 | 2551 | 2552 | 2553 | 2554 | 2555 | 2556 | 2557 | 2558 | 2559 | 2560 | 2561 | 2562 | 2563 |
| 104 | 2576 | 2577 | 2578 | 2579 | 2580 | 2581 | 2582 | 2583 | 2584 | 2585 | 2586 | 2587 | 2588 |
| 105 | 2601 | 2602 | 2603 | 2604 | 2605 | 2606 | 2607 | 2608 | 2609 | 2610 | 2611 | 2612 | 2613 |
| 106 | 2626 | 2627 | 2628 | 2629 | 2630 | 2631 | 2632 | 2633 | 2634 | 2635 | 2636 | 2637 | 2638 |
| 107 | 2651 | 2652 | 2653 | 2654 | 2655 | 2656 | 2657 | 2658 | 2659 | 2660 | 2661 | 2662 | 2663 |
| 108 | 2676 | 2677 | 2678 | 2679 | 2680 | 2681 | 2682 | 2683 | 2684 | 2685 | 2686 | 2687 | 2688 |
| 109 | 2701 | 2702 | 2703 | 2704 | 2705 | 2706 | 2707 | 2708 | 2709 | 2710 | 2711 | 2712 | 2713 |
| 110 | 2726 | 2727 | 2728 | 2729 | 2730 | 2731 | 2732 | 2733 | 2734 | 2735 | 2736 | 2737 | 2738 |

| Third organic compound | | | | | | | | | | | | |
|---|---|---|---|---|---|---|---|---|---|---|---|---|
| | D14 | D15 | D16 | D17 | D18 | D19 | D20 | D21 | D22 | D23 | D24 | D25 |
| 56 | 1389 | 1390 | 1391 | 1392 | 1393 | 1394 | 1395 | 1396 | 1397 | 1398 | 1399 | 1400 |
| 57 | 1414 | 1415 | 1416 | 1417 | 1418 | 1419 | 1420 | 1421 | 1422 | 1423 | 1424 | 1425 |

-continued

| | | | | | | | | | | | |
|---|---|---|---|---|---|---|---|---|---|---|---|
| 58 | 1439 | 1440 | 1441 | 1442 | 1443 | 1444 | 1445 | 1446 | 1447 | 1448 | 1449 | 1450 |
| 59 | 1464 | 1465 | 1466 | 1467 | 1468 | 1469 | 1470 | 1471 | 1472 | 1473 | 1474 | 1475 |
| 60 | 1489 | 1490 | 1491 | 1492 | 493 | 1494 | 1495 | 1496 | 1497 | 1498 | 1499 | 1500 |
| 61 | 1514 | 1515 | 1516 | 1517 | 1518 | 1519 | 1520 | 1521 | 1522 | 1523 | 1524 | 1525 |
| 62 | 1539 | 1540 | 1541 | 1542 | 1543 | 1544 | 1545 | 1546 | 1547 | 1548 | 1549 | 1550 |
| 63 | 1564 | 1565 | 1566 | 1567 | 1568 | 1569 | 1570 | 1571 | 1572 | 1573 | 1574 | 1575 |
| 64 | 1589 | 1590 | 1591 | 1592 | 1593 | 1594 | 1595 | 1596 | 1597 | 1598 | 1599 | 1600 |
| 65 | 1614 | 1615 | 1616 | 1617 | 1618 | 1619 | 1620 | 1621 | 1622 | 1623 | 1624 | 1625 |
| 66 | 1639 | 1640 | 1641 | 1642 | 1643 | 1644 | 1645 | 1646 | 1647 | 1648 | 1649 | 1650 |
| 67 | 1664 | 1665 | 1666 | 1667 | 1668 | 1669 | 1670 | 1671 | 1672 | 1673 | 1674 | 1675 |
| 68 | 1689 | 1690 | 1691 | 1692 | 1693 | 1694 | 1695 | 1696 | 1697 | 1698 | 1699 | 1700 |
| 69 | 1714 | 1715 | 1716 | 1717 | 1718 | 1719 | 1720 | 1721 | 1722 | 1723 | 1724 | 1725 |
| 70 | 1739 | 1740 | 1741 | 1742 | 1743 | 1744 | 1745 | 1746 | 1747 | 1748 | 1749 | 1750 |
| 71 | 1764 | 1765 | 1766 | 1767 | 1768 | 1769 | 1770 | 1771 | 1772 | 1773 | 1774 | 1775 |
| 72 | 1789 | 1790 | 1791 | 1792 | 1793 | 1794 | 1795 | 1796 | 1797 | 1798 | 1799 | 1800 |
| 73 | 1814 | 1815 | 1816 | 1817 | 1818 | 1819 | 1820 | 1821 | 1822 | 1823 | 1824 | 1825 |
| 74 | 1839 | 1840 | 1841 | 1842 | 1843 | 1844 | 1845 | 1846 | 1847 | 1848 | 1849 | 1850 |
| 75 | 1864 | 1865 | 1866 | 1867 | 1868 | 1869 | 1870 | 1871 | 1872 | 1873 | 1874 | 1875 |
| 76 | 1889 | 1890 | 1891 | 1892 | 1893 | 1894 | 1895 | 1896 | 1897 | 1898 | 1899 | 1900 |
| 77 | 1914 | 1915 | 1916 | 1917 | 1918 | 1919 | 1920 | 1921 | 1922 | 1923 | 1924 | 1925 |
| 78 | 1939 | 1940 | 1941 | 1942 | 1943 | 1944 | 1945 | 1946 | 1947 | 1948 | 1949 | 1950 |
| 79 | 1964 | 1965 | 1966 | 1967 | 1968 | 1969 | 1970 | 1971 | 1972 | 1973 | 1974 | 1975 |
| 80 | 1989 | 1990 | 1991 | 1992 | 1993 | 1994 | 1995 | 1996 | 1997 | 1998 | 1999 | 2000 |
| 81 | 2014 | 2015 | 2016 | 2017 | 2018 | 2019 | 2020 | 2021 | 2022 | 2023 | 2024 | 2025 |
| 82 | 2039 | 2040 | 2041 | 2042 | 2043 | 2044 | 2045 | 2046 | 2047 | 2048 | 2049 | 2050 |
| 83 | 2064 | 2065 | 2066 | 2067 | 2068 | 2069 | 2070 | 2071 | 2072 | 2073 | 2074 | 2075 |
| 84 | 2089 | 2090 | 2091 | 2092 | 2093 | 2094 | 2095 | 2096 | 2097 | 2098 | 2099 | 2100 |
| 85 | 2114 | 2115 | 2116 | 2117 | 2118 | 2119 | 2120 | 2121 | 2122 | 2123 | 2124 | 2125 |
| 86 | 2139 | 2140 | 2141 | 2142 | 2143 | 2144 | 2145 | 2146 | 2147 | 2148 | 2149 | 2150 |
| 87 | 2164 | 2165 | 2166 | 2167 | 2168 | 2169 | 2170 | 2171 | 2172 | 2173 | 2174 | 2175 |
| 88 | 2189 | 2190 | 2191 | 2192 | 2193 | 2194 | 2195 | 2196 | 2197 | 2198 | 2199 | 2200 |
| 89 | 2214 | 2215 | 2216 | 2217 | 2218 | 2219 | 2220 | 2221 | 2222 | 2223 | 2224 | 2225 |
| 90 | 2239 | 2240 | 2241 | 2242 | 2243 | 2244 | 2245 | 2246 | 2247 | 2248 | 2249 | 2250 |
| 91 | 2264 | 2265 | 2266 | 2267 | 2268 | 2269 | 2270 | 2271 | 2272 | 2273 | 2274 | 2275 |
| 92 | 2289 | 2290 | 2291 | 2292 | 2293 | 2294 | 2295 | 2296 | 2297 | 2298 | 2299 | 2300 |
| 93 | 2314 | 2315 | 2316 | 2317 | 2318 | 2319 | 2320 | 2321 | 2322 | 2323 | 2324 | 2325 |
| 94 | 2339 | 2340 | 2341 | 2342 | 2343 | 2344 | 2345 | 2346 | 2347 | 2348 | 2349 | 2350 |
| 95 | 2364 | 2365 | 2366 | 2367 | 2368 | 2369 | 2370 | 2371 | 2372 | 2373 | 2374 | 2375 |
| 96 | 2389 | 2390 | 2391 | 2392 | 2393 | 2394 | 2395 | 2396 | 2397 | 2398 | 2399 | 2400 |
| 97 | 2414 | 2415 | 2416 | 2417 | 2418 | 2419 | 2420 | 2421 | 2422 | 2423 | 2424 | 2425 |
| 98 | 2439 | 2440 | 2441 | 2442 | 2443 | 2444 | 2445 | 2446 | 2447 | 2448 | 2449 | 2450 |
| 99 | 2464 | 2465 | 2466 | 2467 | 2468 | 2469 | 2470 | 2471 | 2472 | 2473 | 2474 | 2475 |
| 100 | 2489 | 2490 | 2491 | 2492 | 2493 | 2494 | 2495 | 2496 | 2497 | 2498 | 2499 | 2500 |
| 101 | 2514 | 2515 | 2516 | 2517 | 2518 | 2519 | 2520 | 2521 | 2522 | 2523 | 2524 | 2525 |
| 102 | 2539 | 2540 | 2541 | 2542 | 2543 | 2544 | 2545 | 2546 | 2547 | 2548 | 2549 | 2550 |
| 103 | 2564 | 2565 | 2566 | 2567 | 2568 | 2569 | 2570 | 2571 | 2572 | 2573 | 2574 | 2575 |
| 104 | 2589 | 2590 | 2591 | 2592 | 2593 | 2594 | 2595 | 2596 | 2597 | 2598 | 2599 | 2600 |
| 105 | 2614 | 2615 | 2616 | 2617 | 2618 | 2619 | 2620 | 2621 | 2622 | 2623 | 2624 | 2625 |
| 106 | 2639 | 2640 | 2641 | 2642 | 2643 | 2644 | 2645 | 2646 | 2647 | 2648 | 2649 | 2650 |
| 107 | 2664 | 2665 | 2666 | 2667 | 2668 | 2669 | 2670 | 2671 | 2672 | 2673 | 2674 | 2675 |
| 108 | 2689 | 2690 | 2691 | 2692 | 2693 | 2694 | 2695 | 2696 | 2697 | 2698 | 2699 | 2700 |
| 109 | 2714 | 2715 | 2716 | 2717 | 2718 | 2719 | 2720 | 2721 | 2722 | 2723 | 2724 | 2725 |
| 110 | 2739 | 2740 | 2741 | 2742 | 2743 | 2744 | 2745 | 2746 | 2747 | 2748 | 2749 | 2750 |

| | | Third organic compound | | | | | | | | | | | |
|---|---|---|---|---|---|---|---|---|---|---|---|---|---|
| | | D1 | D2 | D3 | D4 | D5 | D6 | D7 | D8 | D9 | D10 | D11 | D12 | D13 |
| Second organic compound | 111 | 2751 | 2752 | 2753 | 2754 | 2755 | 2756 | 2757 | 2758 | 2759 | 2760 | 2761 | 2762 | 2763 |
| | 112 | 2776 | 2777 | 2778 | 2779 | 2780 | 2781 | 2782 | 2783 | 2784 | 2785 | 2786 | 2787 | 2788 |
| | 113 | 2801 | 2802 | 2803 | 2804 | 2805 | 2806 | 2807 | 2808 | 2809 | 2810 | 2811 | 2812 | 2813 |
| | 114 | 2826 | 2827 | 2828 | 2829 | 2830 | 2831 | 2832 | 2833 | 2834 | 2835 | 2836 | 2837 | 2838 |
| | 115 | 2851 | 2852 | 2853 | 2854 | 2855 | 2856 | 2857 | 2858 | 2859 | 2860 | 2861 | 2862 | 2863 |
| | 116 | 2876 | 2877 | 2878 | 2879 | 2880 | 2881 | 2882 | 2883 | 2884 | 2885 | 2886 | 2887 | 2888 |
| | 117 | 2901 | 2902 | 2903 | 2904 | 2905 | 2906 | 2907 | 2908 | 2909 | 2910 | 2911 | 2912 | 2913 |
| | 118 | 2926 | 2927 | 2928 | 2929 | 2930 | 2931 | 2932 | 2933 | 2934 | 2935 | 2936 | 2937 | 2938 |
| | 119 | 2951 | 2952 | 2953 | 2954 | 2955 | 2956 | 2957 | 2958 | 2959 | 2960 | 2961 | 2962 | 2963 |
| | 120 | 2976 | 2977 | 2978 | 2979 | 2980 | 2981 | 2982 | 2983 | 2984 | 2985 | 2986 | 2987 | 2988 |
| | 121 | 3001 | 3002 | 3003 | 3004 | 3005 | 3006 | 3007 | 3008 | 3009 | 3010 | 3011 | 3012 | 3013 |
| | 122 | 3026 | 3027 | 3028 | 3029 | 3030 | 3031 | 3032 | 3033 | 3034 | 3035 | 3036 | 3037 | 3038 |
| | 123 | 3051 | 3052 | 3053 | 3054 | 3055 | 3056 | 3057 | 3058 | 3059 | 3060 | 3061 | 3062 | 3063 |
| | 124 | 3076 | 3077 | 3078 | 3079 | 3080 | 3081 | 3082 | 3083 | 3084 | 3085 | 3086 | 3087 | 3088 |
| | 125 | 3101 | 3102 | 3103 | 3104 | 3105 | 3106 | 3107 | 3108 | 3109 | 3110 | 3111 | 3112 | 3113 |
| | 126 | 3126 | 3127 | 3128 | 3129 | 3130 | 3131 | 3132 | 3133 | 3134 | 3135 | 3136 | 3137 | 3138 |
| | 127 | 3151 | 3152 | 3153 | 3154 | 3155 | 3156 | 3157 | 3158 | 3159 | 3160 | 3161 | 3162 | 3163 |
| | 128 | 3176 | 3177 | 3178 | 3179 | 3180 | 3181 | 3182 | 3183 | 3184 | 3185 | 3186 | 3187 | 3188 |

-continued

| | | | | | | | | | | | | |
|---|---|---|---|---|---|---|---|---|---|---|---|---|
| 129 | 3201 | 3202 | 3203 | 3204 | 3205 | 3206 | 3207 | 3208 | 3209 | 3210 | 3211 | 3212 | 3213 |
| 130 | 3226 | 3227 | 3228 | 3229 | 3230 | 3231 | 3232 | 3233 | 3234 | 3235 | 3236 | 3237 | 3238 |
| 131 | 3251 | 3252 | 3253 | 3254 | 3255 | 3256 | 3257 | 3258 | 3259 | 3260 | 3261 | 3262 | 3263 |
| 132 | 3276 | 3277 | 3278 | 3279 | 3280 | 3281 | 3282 | 3283 | 3284 | 3285 | 3286 | 3287 | 3288 |
| 133 | 3301 | 3302 | 3303 | 3304 | 3305 | 3306 | 3307 | 3308 | 3309 | 3310 | 3311 | 3312 | 3313 |
| 134 | 3326 | 3327 | 3328 | 3329 | 3330 | 3331 | 3332 | 3333 | 3334 | 3335 | 3336 | 3337 | 3338 |
| 135 | 3351 | 3352 | 3353 | 3354 | 3355 | 3356 | 3357 | 3358 | 3359 | 3360 | 3361 | 3362 | 3363 |
| 136 | 3376 | 3377 | 3378 | 3379 | 3380 | 3381 | 3382 | 3383 | 3384 | 3385 | 3386 | 3387 | 3388 |
| 137 | 3401 | 3402 | 3403 | 3404 | 3405 | 3406 | 3407 | 3408 | 3409 | 3410 | 3411 | 3412 | 3413 |
| 138 | 3426 | 3427 | 3428 | 3429 | 3430 | 3431 | 3432 | 3433 | 3434 | 3435 | 3436 | 3437 | 3438 |
| 139 | 3451 | 3452 | 3453 | 3454 | 3455 | 3456 | 3457 | 3458 | 3459 | 3460 | 3461 | 3462 | 3463 |
| 140 | 3476 | 3477 | 3478 | 3479 | 3480 | 3481 | 3482 | 3483 | 3484 | 3485 | 3486 | 3487 | 3488 |
| 141 | 3501 | 3502 | 3503 | 3504 | 3505 | 3506 | 3507 | 3508 | 3509 | 3510 | 3511 | 3512 | 3513 |
| 142 | 3526 | 3527 | 3528 | 3529 | 3530 | 3531 | 3532 | 3533 | 3534 | 3535 | 3536 | 3537 | 3538 |
| 143 | 3551 | 3552 | 3553 | 3554 | 3555 | 3556 | 3557 | 3558 | 3559 | 3560 | 3561 | 3562 | 3563 |
| 144 | 3576 | 3577 | 3578 | 3579 | 3580 | 3581 | 3582 | 3583 | 3584 | 3585 | 3586 | 3587 | 3588 |
| 145 | 3601 | 3602 | 3603 | 3604 | 3605 | 3606 | 3607 | 3608 | 3609 | 3610 | 3611 | 3612 | 3613 |
| 146 | 3626 | 3627 | 3628 | 3629 | 3630 | 3631 | 3632 | 3633 | 3634 | 3635 | 3636 | 3637 | 3638 |
| 147 | 3651 | 3652 | 3653 | 3654 | 3655 | 3656 | 3657 | 3658 | 3659 | 3660 | 3661 | 3662 | 3663 |
| 148 | 3676 | 3677 | 3678 | 3679 | 3680 | 3681 | 3682 | 3683 | 3684 | 3685 | 3686 | 3687 | 3688 |
| 149 | 3701 | 3702 | 3703 | 3704 | 3705 | 3706 | 3707 | 3708 | 3709 | 3710 | 3711 | 3712 | 3713 |
| 150 | 3726 | 3727 | 3728 | 3729 | 3730 | 3731 | 3732 | 3733 | 3734 | 3735 | 3736 | 3737 | 3738 |
| 151 | 3751 | 3752 | 3753 | 3754 | 3755 | 3756 | 3757 | 3758 | 3759 | 3760 | 3761 | 3762 | 3763 |
| 152 | 3776 | 3777 | 3778 | 3779 | 3780 | 3781 | 3782 | 3783 | 3784 | 3785 | 3786 | 3787 | 3788 |
| 153 | 3801 | 3802 | 3803 | 3804 | 3805 | 3806 | 3807 | 3808 | 3809 | 3810 | 3811 | 3812 | 3813 |
| 154 | 3826 | 3827 | 3828 | 3829 | 3830 | 3831 | 3832 | 3833 | 3834 | 3835 | 3836 | 3837 | 3838 |
| 155 | 3851 | 3852 | 3853 | 3854 | 3855 | 3856 | 3857 | 3858 | 3859 | 3860 | 3861 | 3862 | 3863 |
| 156 | 3876 | 3877 | 3878 | 3879 | 3880 | 3881 | 3882 | 3883 | 3884 | 3885 | 3886 | 3887 | 3888 |
| 157 | 3901 | 3902 | 3903 | 3904 | 3905 | 3906 | 3907 | 3908 | 3909 | 3910 | 3911 | 3912 | 3913 |
| 158 | 3926 | 3927 | 3928 | 3929 | 3930 | 3931 | 3932 | 3933 | 3934 | 3935 | 3936 | 3937 | 3938 |
| 159 | 3951 | 3952 | 3953 | 3954 | 3955 | 3956 | 3957 | 3958 | 3959 | 3960 | 3961 | 3962 | 3963 |
| 160 | 3976 | 3977 | 3978 | 3979 | 3980 | 3981 | 3982 | 3983 | 3984 | 3985 | 3986 | 3987 | 3988 |
| 161 | 4001 | 4002 | 4003 | 4004 | 4005 | 4006 | 4007 | 4008 | 4009 | 4010 | 4011 | 4012 | 4013 |
| 162 | 4026 | 4027 | 4028 | 4029 | 4030 | 4031 | 4032 | 4033 | 4034 | 4035 | 4036 | 4037 | 4038 |
| 163 | 4051 | 4052 | 4053 | 4054 | 4055 | 4056 | 4057 | 4058 | 4059 | 4060 | 4061 | 4062 | 4063 |
| 164 | 4076 | 4077 | 4078 | 4079 | 4080 | 4081 | 4082 | 4083 | 4084 | 4085 | 4086 | 4087 | 4088 |
| 165 | 4101 | 4102 | 4103 | 4104 | 4105 | 4106 | 4107 | 4108 | 4109 | 4110 | 4111 | 4112 | 4113 |

| | | Third organic compound | | | | | | | | | | | |
|---|---|---|---|---|---|---|---|---|---|---|---|---|---|
| | | D14 | D15 | D16 | D17 | D18 | D19 | D20 | D21 | D22 | D23 | D24 | D25 |
| Second organic compound | 111 | 2764 | 2765 | 2766 | 2767 | 2768 | 2769 | 2770 | 2771 | 2772 | 2773 | 2774 | 2775 |
| | 112 | 2789 | 2790 | 2791 | 2792 | 2793 | 2794 | 2795 | 2796 | 2797 | 2798 | 2799 | 2800 |
| | 113 | 2814 | 2815 | 2816 | 2817 | 2818 | 2819 | 2820 | 2821 | 2822 | 2823 | 2824 | 2825 |
| | 114 | 2839 | 2840 | 2841 | 2842 | 2843 | 2844 | 2845 | 2846 | 2847 | 2848 | 2849 | 2850 |
| | 115 | 2864 | 2865 | 2866 | 2867 | 2868 | 2869 | 2870 | 2871 | 2872 | 2873 | 2874 | 2875 |
| | 116 | 2889 | 2890 | 2891 | 2892 | 2893 | 2894 | 2895 | 2896 | 2897 | 2898 | 2899 | 2900 |
| | 117 | 2914 | 2915 | 2916 | 2917 | 2918 | 2919 | 2920 | 2921 | 2922 | 2923 | 2924 | 2925 |
| | 118 | 2939 | 2940 | 2941 | 2942 | 2943 | 2944 | 2945 | 2946 | 2947 | 2948 | 2949 | 2950 |
| | 119 | 2964 | 2965 | 2966 | 2967 | 2968 | 2969 | 2970 | 2971 | 2972 | 2973 | 2974 | 2975 |
| | 120 | 2989 | 2990 | 2991 | 2992 | 2993 | 2994 | 2995 | 2996 | 2997 | 2998 | 2999 | 3000 |
| | 121 | 3014 | 3015 | 3016 | 3017 | 3018 | 3019 | 3020 | 3021 | 3022 | 3023 | 3024 | 3025 |
| | 122 | 3039 | 3040 | 3041 | 3042 | 3043 | 3044 | 3045 | 3046 | 3047 | 3048 | 3049 | 3050 |
| | 123 | 3064 | 3065 | 3066 | 3067 | 3068 | 3069 | 3070 | 3071 | 3072 | 3073 | 3074 | 3075 |
| | 124 | 3089 | 3090 | 3091 | 3092 | 3093 | 3094 | 3095 | 3096 | 3097 | 3098 | 3099 | 3100 |
| | 125 | 3114 | 3115 | 3116 | 3117 | 3118 | 3119 | 3120 | 3121 | 3122 | 3123 | 3124 | 3125 |
| | 126 | 3139 | 3140 | 3141 | 3142 | 3143 | 3144 | 3145 | 3146 | 3147 | 3148 | 3149 | 3150 |
| | 127 | 3164 | 3165 | 3166 | 3167 | 3168 | 3169 | 3170 | 3171 | 3172 | 3173 | 3174 | 3175 |
| | 128 | 3189 | 3190 | 3191 | 3192 | 3193 | 3194 | 3195 | 3196 | 3197 | 3198 | 3199 | 3200 |
| | 129 | 3214 | 3215 | 3216 | 3217 | 3218 | 3219 | 3220 | 3221 | 3222 | 3223 | 3224 | 3225 |
| | 130 | 3239 | 3240 | 3241 | 3242 | 3243 | 3244 | 3245 | 3246 | 3247 | 3248 | 3249 | 3250 |
| | 131 | 3264 | 3265 | 3266 | 3267 | 3268 | 3269 | 3270 | 3271 | 3272 | 3273 | 3274 | 3275 |
| | 132 | 3289 | 3290 | 3291 | 3292 | 3293 | 3294 | 3295 | 3296 | 3297 | 3298 | 3299 | 3300 |
| | 133 | 3314 | 3315 | 3316 | 3317 | 3318 | 3319 | 3320 | 3321 | 3322 | 3323 | 3324 | 3325 |
| | 134 | 3339 | 3340 | 3341 | 3342 | 3343 | 3344 | 3345 | 3346 | 3347 | 3348 | 3349 | 3350 |
| | 135 | 3364 | 3365 | 3366 | 3367 | 3368 | 3369 | 3370 | 3371 | 3372 | 3373 | 3374 | 3375 |
| | 136 | 3389 | 3390 | 3391 | 3392 | 3393 | 3394 | 3395 | 3396 | 3397 | 3398 | 3399 | 3400 |
| | 137 | 3414 | 3415 | 3416 | 3417 | 3418 | 3419 | 3420 | 3421 | 3422 | 3423 | 3424 | 3425 |
| | 138 | 3439 | 3440 | 3441 | 3442 | 3443 | 3444 | 3445 | 3446 | 3447 | 3448 | 3449 | 3450 |
| | 139 | 3464 | 3465 | 3466 | 3467 | 3468 | 3469 | 3470 | 3471 | 3472 | 3473 | 3474 | 3475 |
| | 140 | 3489 | 3490 | 3491 | 3492 | 3493 | 3494 | 3495 | 3496 | 3497 | 3498 | 3499 | 3500 |
| | 141 | 3514 | 3515 | 3516 | 3517 | 3518 | 3519 | 3520 | 3521 | 3522 | 3523 | 3524 | 3525 |
| | 142 | 3539 | 3540 | 3541 | 3542 | 3543 | 3544 | 3545 | 3546 | 3547 | 3548 | 3549 | 3550 |
| | 143 | 3564 | 3565 | 3566 | 3567 | 3568 | 3569 | 3570 | 3571 | 3572 | 3573 | 3574 | 3575 |
| | 144 | 3589 | 3590 | 3591 | 3592 | 3593 | 3594 | 3595 | 3596 | 3597 | 3598 | 3599 | 3600 |
| | 145 | 3614 | 3615 | 3616 | 3617 | 3618 | 3619 | 3620 | 3621 | 3622 | 3623 | 3624 | 3625 |
| | 146 | 3639 | 3640 | 3641 | 3642 | 3643 | 3644 | 3645 | 3646 | 3647 | 3648 | 3649 | 3650 |
| | 147 | 3664 | 3665 | 3666 | 3667 | 3668 | 3669 | 3670 | 3671 | 3672 | 3673 | 3674 | 3675 |

|     | C2   | C3   | C4   | C5   | C6   | C7   | C8   | C9   | C10  | C11  | C12  | C13  | C14  |
|-----|------|------|------|------|------|------|------|------|------|------|------|------|------|
| 148 | 3689 | 3690 | 3691 | 3692 | 3693 | 3694 | 3695 | 3696 | 3697 | 3698 | 3699 | 3700 |      |
| 149 | 3714 | 3715 | 3716 | 3717 | 3718 | 3719 | 3720 | 3721 | 3722 | 3723 | 3724 | 3725 |      |
| 150 | 3739 | 3740 | 3741 | 3742 | 3743 | 3744 | 3745 | 3746 | 3747 | 3748 | 3749 | 3750 |      |
| 151 | 3764 | 3765 | 3766 | 3767 | 3768 | 3769 | 3770 | 3771 | 3772 | 3773 | 3774 | 3775 |      |
| 152 | 3789 | 3790 | 3791 | 3792 | 3793 | 3794 | 3795 | 3796 | 3797 | 3798 | 3799 | 3800 |      |
| 153 | 3814 | 3815 | 3816 | 3817 | 3818 | 3819 | 3820 | 3821 | 3822 | 3823 | 3824 | 3825 |      |
| 154 | 3839 | 3840 | 3841 | 3842 | 3843 | 3844 | 3845 | 3846 | 3847 | 3848 | 3849 | 3850 |      |
| 155 | 3864 | 3865 | 3866 | 3867 | 3868 | 3869 | 3870 | 3871 | 3872 | 3873 | 3874 | 3875 |      |
| 156 | 3889 | 3890 | 3891 | 3892 | 3893 | 3894 | 3895 | 3896 | 3897 | 3898 | 3899 | 3900 |      |
| 157 | 3914 | 3915 | 3916 | 3917 | 3918 | 3919 | 3920 | 3921 | 3922 | 3923 | 3924 | 3925 |      |
| 158 | 3939 | 3940 | 3941 | 3942 | 3943 | 3944 | 3945 | 3946 | 3947 | 3948 | 3949 | 3950 |      |
| 159 | 3964 | 3965 | 3966 | 3967 | 3968 | 3969 | 3970 | 3971 | 3972 | 3973 | 3974 | 3975 |      |
| 160 | 3989 | 3990 | 3991 | 3992 | 3993 | 3994 | 3995 | 3996 | 3997 | 3998 | 3999 | 4000 |      |
| 161 | 4014 | 4015 | 4016 | 4017 | 4018 | 4019 | 4020 | 4021 | 4022 | 4023 | 4024 | 4025 |      |
| 162 | 4039 | 4040 | 4041 | 4042 | 4043 | 4044 | 4045 | 4046 | 4047 | 4048 | 4049 | 4050 |      |
| 163 | 4064 | 4065 | 4066 | 4067 | 4068 | 4069 | 4070 | 4071 | 4072 | 4073 | 4074 | 4075 |      |
| 164 | 4089 | 4090 | 4091 | 4092 | 4093 | 4094 | 4095 | 4096 | 4097 | 4098 | 4099 | 4100 |      |
| 165 | 4114 | 4115 | 4116 | 4117 | 4118 | 4119 | 4120 | 4121 | 4122 | 4123 | 4124 | 4125 |      |

| Third organic compound | | | | | | | | | | | | | |
|-----|------|------|------|------|------|------|------|------|------|------|------|------|------|
|     | D1   | D2   | D3   | D4   | D5   | D6   | D7   | D8   | D9   | D10  | D11  | D12  | D13  |
| 166 | 4126 | 4127 | 4128 | 4129 | 4130 | 4131 | 4132 | 4133 | 4134 | 4135 | 4136 | 4137 | 4138 |
| 167 | 4151 | 4152 | 4153 | 4154 | 4155 | 4156 | 4157 | 4158 | 4159 | 4160 | 4161 | 4162 | 4163 |
| 168 | 4176 | 4177 | 4178 | 4179 | 4180 | 4181 | 4182 | 4183 | 4184 | 4185 | 4186 | 4187 | 4188 |
| 169 | 4201 | 4202 | 4203 | 4204 | 4205 | 4206 | 4207 | 4208 | 4209 | 4210 | 4211 | 4212 | 4213 |
| 170 | 4226 | 4227 | 4228 | 4229 | 4230 | 4231 | 4232 | 4233 | 4234 | 4235 | 4236 | 4237 | 4238 |
| 171 | 4251 | 4252 | 4253 | 4254 | 4255 | 4256 | 4257 | 4258 | 4259 | 4260 | 4261 | 4262 | 4263 |
| 172 | 4276 | 4277 | 4278 | 4279 | 4280 | 4281 | 4282 | 4283 | 4284 | 4285 | 4286 | 4287 | 4288 |
| 173 | 4301 | 4302 | 4303 | 4304 | 4305 | 4306 | 4307 | 4308 | 4309 | 4310 | 4311 | 4312 | 4313 |
| 174 | 4326 | 4327 | 4328 | 4329 | 4330 | 4331 | 4332 | 4333 | 4334 | 4335 | 4336 | 4337 | 4338 |
| 175 | 4351 | 4352 | 4353 | 4354 | 4355 | 4356 | 4357 | 4358 | 4359 | 4360 | 4361 | 4362 | 4363 |
| 176 | 4376 | 4377 | 4378 | 4379 | 4380 | 4381 | 4382 | 4383 | 4384 | 4385 | 4386 | 4387 | 4388 |
| 177 | 4401 | 4402 | 4403 | 4404 | 4405 | 4406 | 4407 | 4408 | 4409 | 4410 | 4411 | 4412 | 4413 |
| 178 | 4426 | 4427 | 4428 | 4429 | 4430 | 4431 | 4432 | 4433 | 4434 | 4435 | 4436 | 4437 | 4438 |
| 179 | 4451 | 4452 | 4453 | 4454 | 4455 | 4456 | 4457 | 4458 | 4459 | 4460 | 4461 | 4462 | 4463 |
| 180 | 4476 | 4477 | 4478 | 4479 | 4480 | 4481 | 4482 | 4483 | 4484 | 4485 | 4486 | 4487 | 4488 |
| 181 | 4501 | 4502 | 4503 | 4504 | 4505 | 4506 | 4507 | 4508 | 4509 | 4510 | 4511 | 4512 | 4513 |
| 182 | 4526 | 4527 | 4528 | 4529 | 4530 | 4531 | 4532 | 4533 | 4534 | 4535 | 4536 | 4537 | 4538 |
| 183 | 4551 | 4552 | 4553 | 4554 | 4555 | 4556 | 4557 | 4558 | 4559 | 4560 | 4561 | 4562 | 4563 |
| 184 | 4576 | 4577 | 4578 | 4579 | 4580 | 4581 | 4582 | 4583 | 4584 | 4585 | 4586 | 4587 | 4588 |
| 185 | 4601 | 4602 | 4603 | 4604 | 4605 | 4606 | 4607 | 4608 | 4609 | 4610 | 4611 | 4612 | 4613 |
| 186 | 4626 | 4627 | 4628 | 4629 | 4630 | 4631 | 4632 | 4633 | 4634 | 4635 | 4636 | 4637 | 4638 |
| 187 | 4651 | 4652 | 4653 | 4654 | 4655 | 4656 | 4657 | 4658 | 4659 | 4660 | 4661 | 4662 | 4663 |
| 188 | 4676 | 4677 | 4678 | 4679 | 4680 | 4681 | 4682 | 4683 | 4684 | 4685 | 4686 | 4687 | 4688 |
| 189 | 4701 | 4702 | 4703 | 4704 | 4705 | 4706 | 4707 | 4708 | 4709 | 4710 | 4711 | 4712 | 4713 |
| 190 | 4726 | 4727 | 4728 | 4729 | 4730 | 4731 | 4732 | 4733 | 4734 | 4735 | 4736 | 4737 | 4738 |
| 191 | 4751 | 4752 | 4753 | 4754 | 4755 | 4756 | 4757 | 4758 | 4759 | 4760 | 4761 | 4762 | 4763 |
| 192 | 4776 | 4777 | 4778 | 4779 | 4780 | 4781 | 4782 | 4783 | 4784 | 4785 | 4786 | 4787 | 4788 |
| 193 | 4801 | 4802 | 4803 | 4804 | 4805 | 4806 | 4807 | 4808 | 4809 | 4810 | 4811 | 4812 | 4813 |
| 194 | 4826 | 4827 | 4828 | 4829 | 4830 | 4831 | 4832 | 4833 | 4834 | 4835 | 4836 | 4837 | 4838 |
| 195 | 4851 | 4852 | 4853 | 4854 | 4855 | 4856 | 4857 | 4858 | 4859 | 4860 | 4861 | 4862 | 4863 |
| 196 | 4876 | 4877 | 4878 | 4879 | 4880 | 4881 | 4882 | 4883 | 4884 | 4885 | 4886 | 4887 | 4888 |
| 197 | 4901 | 4902 | 4903 | 4904 | 4905 | 4906 | 4907 | 4908 | 4909 | 4910 | 4911 | 4912 | 4913 |
| 198 | 4926 | 4927 | 4928 | 4929 | 4930 | 4931 | 4932 | 4933 | 4934 | 4935 | 4936 | 4937 | 4938 |
| 199 | 4951 | 4952 | 4953 | 4954 | 4955 | 4956 | 4957 | 4958 | 4959 | 4960 | 4961 | 4962 | 4963 |
| 200 | 4976 | 4977 | 4978 | 1979 | 4980 | 4981 | 4982 | 4983 | 4984 | 4985 | 4986 | 4987 | 4988 |
| 201 | 5001 | 5002 | 5003 | 5004 | 5005 | 5006 | 5007 | 5008 | 5009 | 5010 | 5011 | 5012 | 5013 |
| 202 | 5026 | 5027 | 5028 | 5029 | 5030 | 5031 | 5032 | 5033 | 5034 | 5035 | 5036 | 5037 | 5038 |
| 203 | 5051 | 5052 | 5053 | 5054 | 5055 | 5056 | 5057 | 5058 | 5059 | 5060 | 5061 | 5062 | 5063 |
| 204 | 5076 | 5077 | 5078 | 5079 | 5080 | 5081 | 5082 | 5083 | 5084 | 5085 | 5086 | 5087 | 5088 |
| 205 | 5101 | 5102 | 5103 | 5104 | 5105 | 5106 | 5107 | 5108 | 5109 | 5110 | 5111 | 5112 | 5113 |
| 206 | 5126 | 5127 | 5128 | 5129 | 5130 | 5131 | 5132 | 5133 | 5134 | 5135 | 5136 | 5137 | 5138 |
| 207 | 5151 | 5152 | 5153 | 5154 | 5155 | 5156 | 5157 | 5158 | 5159 | 5160 | 5161 | 5162 | 5163 |
| 208 | 5176 | 5177 | 5178 | 5179 | 5180 | 5181 | 5182 | 5183 | 5184 | 5185 | 5186 | 5187 | 5188 |
| 209 | 5201 | 5202 | 5203 | 5204 | 5205 | 5206 | 5207 | 5208 | 5209 | 5210 | 5211 | 5212 | 5213 |
| 210 | 5226 | 5227 | 5228 | 5229 | 5230 | 5231 | 5232 | 5233 | 5234 | 5235 | 5236 | 5237 | 5238 |
| 211 | 5251 | 5252 | 5253 | 5254 | 5255 | 5256 | 5257 | 5258 | 5259 | 5260 | 5261 | 5262 | 5263 |
| 212 | 5276 | 5277 | 5278 | 5279 | 5280 | 5281 | 5282 | 5283 | 5284 | 5285 | 5286 | 5287 | 5288 |
| 213 | 5301 | 5302 | 5303 | 5304 | 5305 | 5306 | 5307 | 5308 | 5309 | 5310 | 5311 | 5312 | 5313 |
| 214 | 5326 | 5327 | 5328 | 5329 | 5330 | 5331 | 5332 | 5333 | 5334 | 5335 | 5336 | 5337 | 5338 |
| 215 | 5351 | 5352 | 5353 | 5354 | 5355 | 5356 | 5357 | 5358 | 5359 | 5360 | 5361 | 5362 | 5363 |
| 216 | 5376 | 5377 | 5378 | 5379 | 5380 | 5381 | 5382 | 5383 | 5384 | 5385 | 5386 | 5387 | 5388 |
| 217 | 5401 | 5402 | 5403 | 5404 | 5405 | 5406 | 5407 | 5408 | 5409 | 5410 | 5411 | 5412 | 5413 |
| 218 | 5426 | 5427 | 5428 | 5429 | 5430 | 5431 | 5432 | 5433 | 5434 | 5435 | 5436 | 5437 | 5438 |

-continued

| | | | | | | | | | | | | |
|---|---|---|---|---|---|---|---|---|---|---|---|---|
| 219 | 5451 | 5452 | 5453 | 5454 | 5455 | 5456 | 5457 | 5458 | 5459 | 5460 | 5461 | 5462 | 5463 |
| 220 | 5476 | 5477 | 5478 | 5479 | 5480 | 5481 | 5482 | 5483 | 5484 | 5485 | 5486 | 5487 | 5488 |

| | Third organic compound | | | | | | | | | | | |
|---|---|---|---|---|---|---|---|---|---|---|---|---|
| | D14 | D15 | D16 | D17 | D18 | D19 | D20 | D21 | D22 | D23 | D24 | D25 |
| 166 | 4139 | 4140 | 4141 | 4142 | 4143 | 4144 | 4145 | 4146 | 4147 | 4148 | 4149 | 4150 |
| 167 | 4164 | 4165 | 4166 | 4167 | 4168 | 4169 | 4170 | 4171 | 4172 | 4173 | 4174 | 4175 |
| 168 | 4189 | 4190 | 4191 | 4192 | 4193 | 4194 | 4195 | 4196 | 4197 | 4198 | 4199 | 4200 |
| 169 | 4214 | 4215 | 4216 | 4217 | 4218 | 4219 | 4220 | 4221 | 4222 | 4223 | 4224 | 4225 |
| 170 | 4239 | 4240 | 4241 | 4242 | 4243 | 4244 | 4245 | 4246 | 4247 | 1248 | 4249 | 4250 |
| 171 | 4264 | 4265 | 4266 | 4267 | 4268 | 4269 | 4270 | 4271 | 4272 | 4273 | 4274 | 4275 |
| 172 | 4289 | 4290 | 4291 | 4292 | 4293 | 4294 | 4295 | 4296 | 4297 | 4298 | 4299 | 4300 |
| 173 | 4314 | 4315 | 4316 | 4317 | 4318 | 4319 | 4320 | 4321 | 4322 | 4323 | 4324 | 4325 |
| 174 | 4339 | 4340 | 4341 | 4342 | 4343 | 4344 | 4345 | 4346 | 4347 | 4348 | 4349 | 4350 |
| 175 | 4364 | 4365 | 4366 | 4367 | 4368 | 4369 | 4370 | 4371 | 4372 | 4373 | 4374 | 4375 |
| 176 | 4389 | 4390 | 4391 | 4392 | 4393 | 4394 | 4395 | 4396 | 4397 | 4398 | 4399 | 4400 |
| 177 | 4414 | 4415 | 4416 | 4417 | 4418 | 4419 | 4420 | 4421 | 4422 | 4423 | 4424 | 4425 |
| 178 | 4439 | 4440 | 4441 | 4442 | 4443 | 4444 | 4445 | 4446 | 4447 | 4448 | 4449 | 4450 |
| 179 | 4464 | 4465 | 4466 | 4467 | 4468 | 4469 | 4470 | 4471 | 4472 | 4473 | 4474 | 4475 |
| 180 | 4489 | 4490 | 4491 | 4492 | 4493 | 4494 | 4495 | 4496 | 4497 | 4498 | 4499 | 4500 |
| 181 | 4514 | 4515 | 4516 | 4517 | 4518 | 4519 | 4520 | 4521 | 4522 | 4523 | 4524 | 4525 |
| 182 | 4539 | 4540 | 4541 | 4542 | 4543 | 4544 | 4545 | 4546 | 4547 | 4548 | 4549 | 4550 |
| 183 | 4564 | 4565 | 4566 | 4567 | 4568 | 4569 | 4570 | 4571 | 4572 | 4573 | 4574 | 4575 |
| 184 | 4589 | 4590 | 4591 | 4592 | 4593 | 4594 | 4595 | 4596 | 4597 | 4598 | 4599 | 4600 |
| 185 | 4614 | 4615 | 4616 | 4617 | 4618 | 4619 | 4620 | 4621 | 4622 | 4623 | 4624 | 4625 |
| 186 | 4639 | 4640 | 4641 | 4642 | 4643 | 4644 | 4645 | 4646 | 4647 | 4648 | 4649 | 4650 |
| 187 | 4664 | 4665 | 4666 | 4667 | 4668 | 4669 | 4670 | 4671 | 4672 | 4673 | 4674 | 4675 |
| 188 | 4689 | 4690 | 4691 | 4692 | 4693 | 4694 | 4695 | 4696 | 4697 | 4698 | 4699 | 4700 |
| 189 | 4714 | 4715 | 4716 | 4717 | 4718 | 4719 | 4720 | 4721 | 4722 | 4723 | 4724 | 4725 |
| 190 | 4739 | 4740 | 4741 | 4742 | 4743 | 4744 | 4745 | 4746 | 4747 | 4748 | 4749 | 4750 |
| 191 | 4764 | 4765 | 4766 | 4767 | 4768 | 4769 | 4770 | 4771 | 4772 | 4773 | 4774 | 4775 |
| 192 | 4789 | 4790 | 4791 | 4792 | 4793 | 4794 | 4795 | 4796 | 4797 | 4798 | 4799 | 4800 |
| 193 | 4814 | 4815 | 4816 | 4817 | 4818 | 4819 | 4820 | 4821 | 4822 | 4823 | 4824 | 4825 |
| 194 | 4839 | 4840 | 4841 | 4842 | 4843 | 4844 | 4845 | 4846 | 4847 | 4848 | 4849 | 4850 |
| 195 | 4864 | 4865 | 4866 | 4867 | 4868 | 4869 | 4870 | 4871 | 4872 | 4873 | 4874 | 4875 |
| 196 | 4889 | 4890 | 4891 | 4892 | 4893 | 4894 | 4895 | 4896 | 4897 | 4898 | 4899 | 4900 |
| 197 | 4914 | 4915 | 4916 | 4917 | 4918 | 4919 | 4920 | 4921 | 4922 | 4923 | 4924 | 4925 |
| 198 | 4939 | 4940 | 4941 | 4942 | 4943 | 4944 | 4945 | 4946 | 4947 | 4948 | 4949 | 4950 |
| 199 | 4964 | 4965 | 4966 | 4967 | 4968 | 4969 | 4970 | 4971 | 4972 | 4973 | 4974 | 4975 |
| 200 | 4989 | 4990 | 4991 | 4992 | 4993 | 4994 | 4995 | 4996 | 4997 | 4998 | 4999 | 5000 |
| 201 | 5014 | 5015 | 5016 | 5017 | 5018 | 5019 | 5020 | 5021 | 5022 | 5023 | 5024 | 5025 |
| 202 | 5039 | 5040 | 5041 | 5042 | 5043 | 5044 | 5045 | 5046 | 5047 | 5048 | 5049 | 5050 |
| 203 | 5064 | 5065 | 5066 | 5067 | 5068 | 5069 | 5070 | 5071 | 5072 | 5073 | 5074 | 5075 |
| 204 | 5089 | 5090 | 5091 | 5092 | 5093 | 5094 | 5095 | 5096 | 5097 | 5098 | 5099 | 5100 |
| 205 | 5114 | 5115 | 5116 | 5117 | 5118 | 5119 | 5120 | 5121 | 5122 | 5123 | 5124 | 5125 |
| 206 | 5139 | 5140 | 5141 | 5142 | 5143 | 5144 | 5145 | 5146 | 5147 | 5148 | 5149 | 5150 |
| 207 | 5164 | 5165 | 5166 | 5167 | 5168 | 5169 | 5170 | 5171 | 5172 | 5173 | 5174 | 5175 |
| 208 | 5189 | 5190 | 5191 | 5192 | 5193 | 5194 | 5195 | 5196 | 5197 | 5198 | 5199 | 5200 |
| 209 | 5214 | 5215 | 5216 | 5217 | 5218 | 5219 | 5220 | 5221 | 5222 | 5223 | 5224 | 5225 |
| 210 | 5239 | 5240 | 5241 | 5242 | 5243 | 5244 | 5245 | 5246 | 5247 | 5248 | 5249 | 5250 |
| 211 | 5264 | 5265 | 5266 | 5267 | 5268 | 5269 | 5270 | 5271 | 5272 | 5273 | 5274 | 5275 |
| 212 | 5289 | 5290 | 5291 | 5292 | 5293 | 5294 | 5295 | 5296 | 5297 | 5298 | 5299 | 5300 |
| 213 | 5314 | 5315 | 5316 | 5317 | 5318 | 5319 | 5320 | 5321 | 5322 | 5323 | 5324 | 5325 |
| 214 | 5339 | 5340 | 5341 | 5342 | 5343 | 5344 | 5345 | 5346 | 5347 | 5348 | 5349 | 5350 |
| 215 | 5364 | 5365 | 5366 | 5367 | 5368 | 5369 | 5370 | 5371 | 5372 | 5373 | 5374 | 5375 |
| 216 | 5389 | 5390 | 5391 | 5392 | 5393 | 5394 | 5395 | 5396 | 5397 | 5398 | 5399 | 5400 |
| 217 | 5414 | 5415 | 5416 | 5417 | 5418 | 5419 | 5420 | 5421 | 5422 | 5423 | 5424 | 5425 |
| 218 | 5439 | 5440 | 5441 | 5442 | 5443 | 5444 | 5445 | 5446 | 5447 | 5448 | 5449 | 5450 |
| 219 | 5464 | 5465 | 5466 | 5467 | 5468 | 5469 | 5470 | 5471 | 5472 | 5473 | 5474 | 5475 |
| 220 | 5489 | 5490 | 5491 | 5492 | 5493 | 5494 | 5495 | 5496 | 5497 | 5498 | 5499 | 5500 |

| | | Third organic compound | | | | | | | | | | | | |
|---|---|---|---|---|---|---|---|---|---|---|---|---|---|---|
| | | D1 | D2 | D3 | D4 | D5 | D6 | D7 | D8 | D9 | D10 | D11 | D12 | D13 |
| Second organic compound | 221 | 5501 | 5502 | 5503 | 5504 | 5505 | 5506 | 5507 | 5508 | 5509 | 5510 | 5511 | 5512 | 5513 |
| | 222 | 5526 | 5527 | 5528 | 5529 | 5530 | 5531 | 5532 | 5533 | 5534 | 5535 | 5536 | 5537 | 5538 |
| | 223 | 5551 | 5552 | 5553 | 5554 | 5555 | 5556 | 5557 | 5558 | 5559 | 5560 | 5561 | 5562 | 5563 |
| | 224 | 5576 | 5577 | 5578 | 5579 | 5580 | 5581 | 5582 | 5583 | 5584 | 5585 | 5586 | 5587 | 5588 |
| | 225 | 5601 | 5602 | 5603 | 5604 | 5605 | 5606 | 5607 | 5608 | 5609 | 5610 | 5611 | 5612 | 5613 |
| | 226 | 5626 | 5627 | 5628 | 5629 | 5630 | 5631 | 5632 | 5633 | 5634 | 5635 | 5636 | 5637 | 5638 |
| | 227 | 5651 | 5652 | 5653 | 5654 | 5655 | 5656 | 5657 | 5658 | 5659 | 5660 | 5661 | 5662 | 5663 |
| | 228 | 5676 | 5677 | 5678 | 5679 | 5680 | 5681 | 5682 | 5683 | 5684 | 5685 | 5686 | 5687 | 5688 |
| | 229 | 5701 | 5702 | 5703 | 5704 | 5705 | 5706 | 5707 | 5708 | 5709 | 5710 | 5711 | 5712 | 5713 |

-continued

| | | | | | | | | | | | | | |
|---|---|---|---|---|---|---|---|---|---|---|---|---|---|
| 230 | 5726 | 5727 | 5728 | 5729 | 5730 | 5731 | 5732 | 5733 | 5734 | 5735 | 5736 | 5737 | 5738 |
| 231 | 5751 | 5752 | 5753 | 5754 | 5755 | 5756 | 5757 | 5758 | 5759 | 5760 | 5761 | 5762 | 5763 |
| 232 | 5776 | 5777 | 5778 | 5779 | 5780 | 5781 | 5782 | 5783 | 5784 | 5785 | 5786 | 5787 | 5788 |
| 233 | 5801 | 5802 | 5803 | 5804 | 5805 | 5806 | 5807 | 5808 | 5809 | 5810 | 5811 | 5812 | 5813 |
| 234 | 5826 | 5827 | 5828 | 5829 | 5830 | 5831 | 5832 | 5833 | 5834 | 5835 | 5836 | 5837 | 5838 |
| 235 | 5851 | 5852 | 5853 | 5854 | 5855 | 5856 | 5857 | 5858 | 5859 | 5860 | 5861 | 5862 | 5863 |
| 236 | 5876 | 5877 | 5878 | 5879 | 5880 | 5881 | 5882 | 5883 | 5884 | 5885 | 5886 | 5887 | 5888 |
| 237 | 5901 | 5902 | 5903 | 5904 | 5905 | 5906 | 5907 | 5908 | 5909 | 5910 | 5911 | 5912 | 5913 |
| 238 | 5926 | 5927 | 5928 | 5929 | 5930 | 5931 | 5932 | 5933 | 5934 | 5935 | 5936 | 5937 | 5938 |
| 239 | 5951 | 5952 | 5953 | 5954 | 5955 | 5956 | 5957 | 5958 | 5959 | 5960 | 5961 | 5962 | 5963 |
| 240 | 5976 | 5977 | 5978 | 5979 | 5980 | 5981 | 5982 | 5983 | 5984 | 5985 | 5986 | 5987 | 5988 |
| 241 | 6001 | 6002 | 6003 | 6004 | 6005 | 6006 | 6007 | 6008 | 6009 | 6010 | 6011 | 6012 | 6013 |
| 242 | 6026 | 6027 | 6028 | 6029 | 6030 | 6031 | 6032 | 6033 | 6034 | 6035 | 6036 | 6037 | 6038 |
| 243 | 6051 | 6052 | 6053 | 6054 | 6055 | 6056 | 6057 | 6058 | 6059 | 6060 | 6061 | 6062 | 6063 |
| 244 | 6076 | 6077 | 6078 | 6079 | 6080 | 6081 | 6082 | 6083 | 6084 | 6085 | 6086 | 6087 | 6088 |
| 245 | 6101 | 6102 | 6103 | 6104 | 6105 | 6106 | 6107 | 6108 | 6109 | 6110 | 6111 | 6112 | 6113 |
| 246 | 6126 | 6127 | 6128 | 6129 | 6130 | 6131 | 6132 | 6133 | 6134 | 6135 | 6136 | 6137 | 6138 |
| 247 | 6151 | 6152 | 6153 | 6154 | 6155 | 6156 | 6157 | 6158 | 6159 | 6160 | 6161 | 6162 | 6163 |
| 248 | 6176 | 6177 | 6178 | 6179 | 6180 | 6181 | 6182 | 6183 | 6184 | 6185 | 6186 | 6181 | 6188 |
| 249 | 6201 | 6202 | 6203 | 6204 | 6205 | 6206 | 6207 | 6208 | 6209 | 6210 | 6211 | 6212 | 6213 |
| 250 | 6226 | 6227 | 6228 | 6229 | 6230 | 6231 | 6232 | 6233 | 6234 | 6235 | 6236 | 6237 | 6238 |
| 251 | 6251 | 6252 | 6253 | 6254 | 6255 | 6256 | 6257 | 6258 | 6259 | 6260 | 6261 | 6262 | 6263 |
| 252 | 6276 | 6277 | 6278 | 6279 | 6280 | 6281 | 6282 | 6283 | 6284 | 6285 | 6286 | 6287 | 6288 |
| 253 | 6301 | 6302 | 6303 | 6304 | 6305 | 6306 | 6307 | 6308 | 6309 | 6310 | 6311 | 6312 | 6313 |
| 254 | 6326 | 6327 | 6328 | 6329 | 6330 | 6331 | 6332 | 6333 | 6334 | 6335 | 6336 | 6337 | 6338 |
| 255 | 6351 | 6352 | 6353 | 6354 | 6355 | 6356 | 6357 | 6358 | 6359 | 6360 | 6361 | 6362 | 6363 |
| 256 | 6376 | 6377 | 6378 | 6379 | 6380 | 6381 | 6382 | 6383 | 6384 | 6385 | 6386 | 6387 | 6388 |
| 257 | 6401 | 6402 | 6403 | 6404 | 6405 | 6406 | 6407 | 6408 | 6409 | 6410 | 6411 | 6412 | 6413 |
| 258 | 6426 | 6427 | 6428 | 6429 | 6430 | 6431 | 6432 | 6433 | 6434 | 6435 | 6436 | 6437 | 6438 |
| 259 | 6451 | 6452 | 6453 | 6454 | 6455 | 6456 | 6457 | 6458 | 6459 | 6460 | 6461 | 6462 | 6463 |
| 260 | 6476 | 6477 | 6478 | 6479 | 6480 | 6481 | 6482 | 6483 | 6484 | 6485 | 6486 | 6487 | 6488 |
| 261 | 6501 | 6502 | 6503 | 6504 | 6505 | 6506 | 6507 | 6508 | 6509 | 6510 | 6511 | 6512 | 6513 |
| 262 | 6526 | 6527 | 6528 | 6529 | 6530 | 6531 | 6532 | 6533 | 6534 | 6535 | 6536 | 6537 | 6538 |
| 263 | 6551 | 6552 | 6553 | 6554 | 6555 | 6556 | 6557 | 6558 | 6559 | 6560 | 6561 | 6562 | 6563 |
| 264 | 6576 | 6577 | 6578 | 6579 | 6580 | 6581 | 6582 | 6583 | 6584 | 6585 | 6586 | 6587 | 6588 |
| 265 | 6601 | 6602 | 6603 | 6604 | 6605 | 6606 | 6607 | 6608 | 6609 | 6610 | 6611 | 6612 | 6613 |
| 266 | 6626 | 6627 | 6628 | 6629 | 6630 | 6631 | 6632 | 6633 | 6634 | 6635 | 6636 | 6637 | 6638 |
| 267 | 6651 | 6652 | 6653 | 6654 | 6655 | 6656 | 6657 | 6658 | 6659 | 6660 | 6661 | 6662 | 6663 |
| 268 | 6676 | 6677 | 6678 | 6679 | 6680 | 6681 | 6682 | 6683 | 6684 | 6685 | 6686 | 6687 | 6688 |
| 269 | 6701 | 6702 | 6703 | 6704 | 6705 | 6706 | 6707 | 6708 | 6709 | 6710 | 6711 | 6712 | 6713 |
| 270 | 6726 | 6727 | 6728 | 6729 | 6730 | 6731 | 6732 | 6733 | 5734 | 6735 | 6736 | 6737 | 6738 |
| 271 | 6751 | 6752 | 6753 | 6754 | 6755 | 6756 | 6757 | 6758 | 6759 | 6760 | 6761 | 6762 | 6763 |
| 272 | 6776 | 6777 | 6778 | 6779 | 6780 | 6781 | 6782 | 6783 | 6784 | 6785 | 6786 | 6787 | 6788 |
| 273 | 6801 | 6802 | 6803 | 6804 | 6805 | 6806 | 6807 | 6808 | 6809 | 6810 | 6811 | 6812 | 6813 |
| 274 | 6826 | 6827 | 6828 | 6829 | 6830 | 6831 | 6832 | 6833 | 6834 | 6835 | 6836 | 6837 | 6838 |
| 275 | 6851 | 6852 | 6853 | 6854 | 6855 | 6856 | 6857 | 6858 | 6859 | 6860 | 6861 | 6862 | 6863 |

| | | Third organic compound | | | | | | | | | | | |
|---|---|---|---|---|---|---|---|---|---|---|---|---|---|
| | | D14 | D15 | D16 | D17 | D18 | D19 | D20 | D21 | D22 | D23 | D24 | D25 |
| Second organic compound | 221 | 5514 | 5515 | 5516 | 5517 | 5518 | 5519 | 5520 | 5521 | 5522 | 5523 | 5524 | 5525 |
| | 222 | 5539 | 5540 | 5541 | 5542 | 5543 | 5544 | 5545 | 5546 | 5547 | 5548 | 5549 | 5550 |
| | 223 | 5564 | 5565 | 5566 | 5567 | 5568 | 5569 | 5570 | 5571 | 5572 | 5573 | 5574 | 5575 |
| | 224 | 5589 | 5590 | 5591 | 5592 | 5593 | 5594 | 5595 | 5596 | 5597 | 5598 | 5599 | 5600 |
| | 225 | 5614 | 5615 | 5616 | 5617 | 5618 | 5619 | 5620 | 5621 | 5622 | 5623 | 5624 | 5625 |
| | 226 | 5639 | 5640 | 5641 | 5642 | 5643 | 5644 | 5645 | 5646 | 5647 | 5648 | 5649 | 5650 |
| | 227 | 5664 | 5665 | 5666 | 5667 | 5668 | 5669 | 5670 | 5671 | 5672 | 5673 | 5674 | 5675 |
| | 228 | 5689 | 5690 | 5691 | 5692 | 5693 | 5694 | 5695 | 5696 | 5697 | 5698 | 5699 | 5700 |
| | 229 | 5714 | 5715 | 5716 | 5717 | 5718 | 5719 | 5720 | 5721 | 5722 | 5723 | 5724 | 5725 |
| | 230 | 5739 | 5740 | 5741 | 5742 | 5743 | 5744 | 5745 | 5746 | 5747 | 5748 | 5749 | 5750 |
| | 231 | 5764 | 5765 | 5766 | 5767 | 5768 | 5769 | 5770 | 5771 | 5772 | 5773 | 5774 | 5775 |
| | 232 | 5789 | 5790 | 5791 | 5792 | 5793 | 5794 | 5795 | 5796 | 5797 | 5798 | 5799 | 5800 |
| | 233 | 5814 | 5815 | 5816 | 5817 | 5818 | 5819 | 5820 | 5821 | 5822 | 5823 | 5824 | 5825 |
| | 234 | 5839 | 5840 | 5841 | 5842 | 5843 | 5844 | 5845 | 5846 | 5847 | 5848 | 5849 | 5850 |
| | 235 | 5864 | 5865 | 5866 | 5867 | 5868 | 5869 | 5870 | 5871 | 5872 | 5873 | 5874 | 5875 |
| | 236 | 5889 | 5890 | 5891 | 5892 | 5893 | 5894 | 5895 | 5896 | 5897 | 5898 | 5899 | 5900 |
| | 237 | 5914 | 5915 | 5916 | 5917 | 5918 | 5919 | 5920 | 5921 | 5922 | 5923 | 5924 | 5925 |
| | 238 | 5939 | 5940 | 5941 | 5942 | 5943 | 5944 | 5945 | 5946 | 5947 | 5948 | 5949 | 5950 |
| | 239 | 5964 | 5965 | 5966 | 5967 | 5968 | 5969 | 5970 | 5971 | 5972 | 5973 | 5974 | 5975 |
| | 240 | 5989 | 5990 | 5991 | 5992 | 5993 | 5994 | 5995 | 5996 | 5997 | 5998 | 5999 | 6000 |
| | 241 | 6014 | 6015 | 6016 | 6017 | 6018 | 6019 | 6020 | 6021 | 6022 | 6023 | 6024 | 6025 |
| | 242 | 6039 | 6040 | 6041 | 6042 | 6043 | 6044 | 6045 | 6046 | 6047 | 6048 | 6049 | 6050 |
| | 243 | 6064 | 6065 | 6066 | 6067 | 6068 | 6069 | 6070 | 6071 | 6072 | 6073 | 6074 | 6075 |
| | 244 | 6089 | 6090 | 6091 | 6092 | 6093 | 6094 | 6095 | 6096 | 6097 | 6098 | 6099 | 6100 |
| | 245 | 6114 | 6115 | 6116 | 6117 | 6118 | 6119 | 6120 | 6121 | 6122 | 6123 | 6124 | 6125 |
| | 246 | 6139 | 6140 | 6141 | 6142 | 6143 | 6144 | 6145 | 6146 | 6147 | 6148 | 6149 | 6150 |
| | 247 | 6164 | 6165 | 6166 | 6167 | 6168 | 6169 | 6170 | 6171 | 6172 | 6173 | 6174 | 6175 |
| | 248 | 6189 | 6190 | 6191 | 6192 | 6193 | 6194 | 6195 | 6196 | 6197 | 6198 | 6199 | 6200 |

|  |  |  |  |  |  |  |  |  |  |  |  |  |
|---|---|---|---|---|---|---|---|---|---|---|---|---|
| 249 | 6214 | 6215 | 6216 | 6217 | 6218 | 6219 | 6220 | 6221 | 6222 | 6223 | 6224 | 6225 |
| 250 | 6239 | 6240 | 6241 | 6242 | 6243 | 6244 | 6245 | 6246 | 6247 | 6248 | 6249 | 6250 |
| 251 | 6264 | 6265 | 6266 | 6267 | 6268 | 6269 | 6270 | 6271 | 6272 | 6273 | 6274 | 6275 |
| 252 | 6289 | 6290 | 6291 | 6292 | 6293 | 6294 | 6295 | 6296 | 6297 | 6298 | 6299 | 6300 |
| 253 | 6314 | 6315 | 6316 | 6317 | 6318 | 6319 | 6320 | 6321 | 6322 | 6323 | 6324 | 6325 |
| 254 | 6339 | 6340 | 6341 | 6342 | 6343 | 6344 | 6345 | 6346 | 6347 | 6348 | 6349 | 6350 |
| 255 | 6364 | 6365 | 6366 | 6367 | 6368 | 6369 | 6370 | 6371 | 6372 | 6373 | 6374 | 6375 |
| 256 | 6389 | 6390 | 6391 | 6392 | 6393 | 6394 | 6395 | 6396 | 6397 | 6398 | 6399 | 6400 |
| 257 | 6414 | 6415 | 6416 | 6417 | 6418 | 6419 | 6420 | 6421 | 6422 | 6423 | 6424 | 6425 |
| 258 | 6439 | 6440 | 6441 | 6442 | 6443 | 6444 | 6445 | 6446 | 6447 | 6448 | 6449 | 6450 |
| 259 | 6464 | 6465 | 6466 | 6467 | 6468 | 6469 | 6470 | 6471 | 6472 | 6473 | 6474 | 6475 |
| 260 | 6489 | 6490 | 6491 | 6492 | 6493 | 6494 | 6495 | 6496 | 6497 | 6498 | 6499 | 6500 |
| 261 | 6514 | 6515 | 6516 | 6517 | 6518 | 6519 | 6520 | 6521 | 6522 | 6523 | 6524 | 6525 |
| 262 | 6539 | 6540 | 6541 | 6542 | 6543 | 6544 | 6545 | 6546 | 6547 | 6548 | 6549 | 6550 |
| 263 | 6564 | 6565 | 6566 | 6567 | 6568 | 6569 | 6570 | 6571 | 6572 | 6573 | 6574 | 6575 |
| 264 | 6589 | 6590 | 6591 | 6592 | 6593 | 6594 | 6595 | 6596 | 6597 | 6598 | 6599 | 6600 |
| 265 | 6614 | 6615 | 6616 | 6617 | 6618 | 6619 | 6620 | 6621 | 6622 | 6623 | 6624 | 6625 |
| 266 | 6639 | 6640 | 6641 | 6642 | 6643 | 6644 | 6645 | 6646 | 6647 | 6648 | 6649 | 6650 |
| 267 | 6664 | 6665 | 6666 | 6667 | 6668 | 6669 | 6670 | 6671 | 6672 | 6673 | 6674 | 6675 |
| 268 | 6689 | 6690 | 6691 | 6692 | 6693 | 6694 | 6695 | 6696 | 6697 | 6698 | 6699 | 6700 |
| 269 | 6714 | 6715 | 6716 | 6717 | 6718 | 6719 | 6720 | 6721 | 6722 | 6723 | 6724 | 6725 |
| 270 | 6739 | 6740 | 6741 | 6742 | 6743 | 6744 | 6745 | 6746 | 6747 | 6748 | 6749 | 6750 |
| 271 | 6764 | 6765 | 6766 | 6767 | 6768 | 6769 | 6770 | 6771 | 6772 | 6773 | 6774 | 6775 |
| 272 | 6789 | 6790 | 6791 | 6792 | 6793 | 6794 | 6795 | 6796 | 6797 | 6798 | 6799 | 6800 |
| 273 | 6814 | 6815 | 6816 | 6817 | 6818 | 6819 | 6820 | 6821 | 6822 | 6823 | 6824 | 6825 |
| 274 | 6839 | 6840 | 6841 | 6842 | 6843 | 6844 | 6845 | 6846 | 6847 | 6848 | 6849 | 6850 |
| 275 | 6864 | 6865 | 6866 | 6867 | 6868 | 6869 | 6870 | 6871 | 6872 | 6873 | 6874 | 6875 |

| Third organic compound | | | | | | | | | | | | | |
|---|---|---|---|---|---|---|---|---|---|---|---|---|---|
|  | D1 | D2 | D3 | D4 | D5 | D6 | D7 | D8 | D9 | D10 | D11 | D12 | D13 |
| 276 | 6876 | 6877 | 6878 | 6879 | 6880 | 6881 | 6882 | 6883 | 6884 | 6885 | 6886 | 6887 | 6888 |
| 277 | 6901 | 6902 | 6903 | 6904 | 6905 | 6906 | 6907 | 6908 | 6909 | 6910 | 6911 | 6912 | 6913 |
| 278 | 6926 | 6927 | 6928 | 6929 | 6930 | 6931 | 6932 | 6933 | 6934 | 6935 | 6936 | 6937 | 6938 |
| 279 | 6951 | 6952 | 6953 | 6954 | 6955 | 6956 | 6957 | 6958 | 6959 | 6960 | 6961 | 6962 | 6963 |
| 280 | 6976 | 6977 | 6978 | 6979 | 6980 | 6981 | 6982 | 6983 | 6984 | 6985 | 6986 | 6987 | 6988 |
| 281 | 7001 | 7002 | 7003 | 7004 | 7005 | 7006 | 7007 | 7008 | 7009 | 7010 | 7011 | 7012 | 7013 |
| 282 | 7026 | 7027 | 7028 | 7029 | 7030 | 7031 | 7032 | 7033 | 7034 | 7035 | 7036 | 7037 | 7038 |
| 283 | 7051 | 7052 | 7053 | 7054 | 7055 | 7056 | 7057 | 7058 | 7059 | 7060 | 7061 | 7062 | 7063 |
| 284 | 7076 | 7077 | 7078 | 7079 | 7080 | 7081 | 7082 | 7083 | 7084 | 7085 | 7086 | 7087 | 7088 |
| 285 | 7101 | 7102 | 7103 | 7104 | 7105 | 7106 | 7107 | 7108 | 7109 | 7110 | 7111 | 7112 | 7113 |
| 286 | 7126 | 7127 | 7128 | 7129 | 7130 | 7131 | 7132 | 7133 | 7134 | 7135 | 7136 | 7137 | 7138 |
| 287 | 7151 | 7152 | 7153 | 7154 | 7155 | 7156 | 7157 | 7158 | 7159 | 7160 | 7161 | 7162 | 7163 |
| 288 | 7176 | 7177 | 7178 | 7179 | 7180 | 7181 | 7182 | 7183 | 7184 | 7185 | 7186 | 7187 | 7188 |
| 289 | 7201 | 7202 | 7203 | 7204 | 7205 | 7206 | 7207 | 7208 | 7209 | 7210 | 7211 | 7212 | 7213 |
| 290 | 7226 | 7227 | 7228 | 7229 | 7230 | 7231 | 7232 | 7233 | 7234 | 7235 | 7236 | 7237 | 7238 |
| 291 | 7251 | 7252 | 7253 | 7254 | 7255 | 7256 | 7257 | 7258 | 7259 | 7260 | 7261 | 7262 | 7263 |
| 292 | 7276 | 7277 | 7278 | 7279 | 7280 | 7281 | 7282 | 7283 | 7284 | 7285 | 7286 | 7287 | 7288 |
| 293 | 7301 | 7302 | 7303 | 7304 | 7305 | 7306 | 7307 | 7308 | 7309 | 7310 | 7311 | 7312 | 7313 |
| 294 | 7326 | 7327 | 7328 | 7329 | 7330 | 7331 | 7332 | 7333 | 7334 | 7335 | 7336 | 7337 | 7338 |
| 295 | 7351 | 7352 | 7353 | 7354 | 7355 | 7356 | 7357 | 7358 | 7359 | 7360 | 7361 | 7362 | 7363 |
| 296 | 7376 | 7377 | 7378 | 7379 | 7380 | 7381 | 7382 | 7383 | 7384 | 7385 | 7386 | 7387 | 7388 |
| 297 | 7401 | 7402 | 7403 | 7404 | 7405 | 7406 | 7407 | 7408 | 7409 | 7410 | 7411 | 7412 | 7413 |
| 298 | 7426 | 7427 | 7428 | 7429 | 7430 | 7431 | 7432 | 7433 | 7434 | 7435 | 7436 | 7437 | 7438 |
| 299 | 7451 | 7452 | 7453 | 7454 | 7455 | 7456 | 7457 | 7458 | 7459 | 7460 | 7461 | 7462 | 7463 |
| 300 | 7476 | 7477 | 7478 | 7479 | 7480 | 7481 | 7482 | 7483 | 7484 | 7485 | 7486 | 7487 | 7488 |
| 301 | 7501 | 7502 | 7503 | 7504 | 7505 | 7506 | 7507 | 7508 | 7509 | 7510 | 7511 | 7512 | 7513 |
| 302 | 7526 | 7527 | 7528 | 7529 | 7530 | 7531 | 7532 | 7533 | 7534 | 7535 | 7536 | 7537 | 7538 |
| 303 | 7551 | 7552 | 7553 | 7554 | 7555 | 7556 | 7557 | 7558 | 7559 | 7560 | 7561 | 7562 | 7563 |
| 304 | 7576 | 7577 | 7578 | 7579 | 7580 | 7581 | 7582 | 7583 | 7584 | 7585 | 7586 | 7587 | 7588 |
| 305 | 7601 | 7602 | 7603 | 7604 | 7605 | 7606 | 7607 | 7608 | 7609 | 7610 | 7611 | 7612 | 7613 |
| 306 | 7626 | 7627 | 7628 | 7629 | 7630 | 7631 | 7632 | 7633 | 7634 | 7635 | 7636 | 7637 | 7638 |
| 307 | 7651 | 7652 | 7653 | 7654 | 7655 | 7656 | 7657 | 7658 | 7659 | 7660 | 7661 | 7662 | 7663 |
| 308 | 7676 | 7677 | 7678 | 7679 | 7680 | 7681 | 7682 | 7683 | 7684 | 7685 | 7686 | 7687 | 7688 |
| 309 | 7701 | 7702 | 7703 | 7704 | 7705 | 7706 | 7707 | 7708 | 7709 | 7710 | 7711 | 7712 | 7713 |
| 310 | 7726 | 7727 | 7728 | 7729 | 7730 | 7731 | 7732 | 7733 | 7734 | 7735 | 7736 | 7737 | 7738 |
| 311 | 7751 | 7752 | 7753 | 7754 | 7755 | 7756 | 7757 | 7758 | 7759 | 7760 | 7761 | 7762 | 7763 |
| 312 | 7776 | 7777 | 7778 | 7779 | 7780 | 7781 | 7782 | 7783 | 7784 | 7785 | 7786 | 7787 | 7788 |
| 313 | 7801 | 7802 | 7803 | 7804 | 7805 | 7806 | 7807 | 7808 | 7809 | 7810 | 7811 | 7812 | 7813 |
| 314 | 7826 | 7827 | 7828 | 7829 | 7830 | 7831 | 7832 | 7833 | 7834 | 7835 | 7836 | 7837 | 7838 |
| 315 | 7851 | 7852 | 7853 | 7854 | 7855 | 7856 | 7857 | 7858 | 7859 | 7860 | 7861 | 7862 | 7863 |
| 316 | 7876 | 7877 | 7878 | 7879 | 7880 | 7881 | 7882 | 7883 | 7884 | 7885 | 7886 | 7887 | 7888 |
| 317 | 7901 | 7902 | 7903 | 7904 | 7905 | 7906 | 7907 | 7908 | 7909 | 7910 | 7911 | 7912 | 7913 |
| 318 | 7926 | 7927 | 7928 | 7929 | 7930 | 7931 | 7932 | 7933 | 7934 | 7935 | 7936 | 7937 | 7938 |
| 319 | 7951 | 7952 | 7953 | 7954 | 7955 | 7956 | 7957 | 7958 | 7959 | 7960 | 7961 | 7962 | 7963 |

-continued

| | | | | | | | | | | | | | |
|---|---|---|---|---|---|---|---|---|---|---|---|---|---|
| 320 | 7976 | 7977 | 7978 | 7979 | 7980 | 7981 | 7982 | 7983 | 7984 | 7985 | 7986 | 7987 | 7988 |
| 321 | 8001 | 8002 | 8003 | 8004 | 8005 | 8006 | 8007 | 8008 | 8009 | 8010 | 8011 | 8012 | 8013 |
| 322 | 8026 | 8027 | 8028 | 8029 | 8030 | 8031 | 8032 | 8033 | 8034 | 8035 | 8036 | 8037 | 8038 |
| 323 | 8051 | 8052 | 8053 | 8054 | 8055 | 8056 | 8057 | 8058 | 8059 | 8060 | 8061 | 8062 | 8063 |
| 324 | 8076 | 8077 | 8078 | 8079 | 8080 | 8081 | 8082 | 8083 | 8084 | 8085 | 8086 | 8087 | 8088 |
| 325 | 8101 | 8102 | 8103 | 8104 | 8105 | 8106 | 8107 | 8108 | 8109 | 8110 | 8111 | 8112 | 8113 |
| 326 | 8126 | 8127 | 8128 | 8129 | 8130 | 8131 | 8132 | 8133 | 8134 | 8135 | 8136 | 8137 | 8138 |
| 327 | 8151 | 8152 | 8153 | 8154 | 8155 | 8156 | 8157 | 8158 | 8159 | 8160 | 8161 | 8162 | 8163 |
| 328 | 8176 | 8177 | 8178 | 8179 | 8180 | 8181 | 8182 | 8183 | 8184 | 8185 | 8186 | 8187 | 8188 |
| 329 | 8201 | 8202 | 8203 | 8204 | 8205 | 8206 | 8207 | 8208 | 8209 | 8210 | 8211 | 8212 | 8213 |
| 330 | 8226 | 8227 | 8228 | 8229 | 8230 | 8231 | 8232 | 8233 | 8234 | 8235 | 8236 | 8237 | 8238 |

| | Third organic compound | | | | | | | | | | | |
|---|---|---|---|---|---|---|---|---|---|---|---|---|
| | D14 | D15 | D16 | D17 | D18 | D19 | D20 | D21 | D22 | D23 | D24 | D25 |
| 276 | 6889 | 6890 | 6891 | 6892 | 6893 | 6894 | 6895 | 6896 | 6897 | 6898 | 6899 | 6900 |
| 277 | 6914 | 6915 | 6916 | 6917 | 6918 | 6919 | 6920 | 6921 | 6922 | 6923 | 6924 | 6925 |
| 278 | 6939 | 6940 | 6941 | 6942 | 6943 | 6944 | 6945 | 6946 | 6947 | 6948 | 6949 | 6950 |
| 279 | 6964 | 6965 | 6966 | 6967 | 6968 | 6969 | 6970 | 6971 | 6972 | 6973 | 6974 | 6975 |
| 280 | 6989 | 6990 | 6991 | 6992 | 6993 | 6994 | 6995 | 6996 | 6997 | 6998 | 6999 | 7000 |
| 281 | 7014 | 7015 | 7016 | 7017 | 7018 | 7019 | 7020 | 7021 | 7022 | 7023 | 7024 | 7025 |
| 282 | 7039 | 7040 | 7041 | 7042 | 7043 | 7044 | 7045 | 7046 | 7047 | 7048 | 7049 | 7050 |
| 283 | 7064 | 7065 | 7066 | 7067 | 7068 | 7069 | 7070 | 7071 | 7072 | 7073 | 7074 | 7075 |
| 284 | 7089 | 7090 | 7091 | 7092 | 7093 | 7094 | 7095 | 7096 | 7097 | 7098 | 7099 | 7100 |
| 285 | 7114 | 7115 | 7116 | 7117 | 7118 | 7119 | 7120 | 7121 | 7122 | 7123 | 7124 | 7125 |
| 286 | 7139 | 7140 | 7141 | 7142 | 7143 | 7144 | 7145 | 7146 | 7147 | 7148 | 7149 | 7150 |
| 287 | 7164 | 7165 | 7166 | 7167 | 7168 | 7169 | 7170 | 7171 | 7172 | 7173 | 7174 | 7175 |
| 288 | 7189 | 7190 | 7191 | 7192 | 7193 | 7194 | 7195 | 7196 | 7197 | 7198 | 7199 | 7200 |
| 289 | 7214 | 7215 | 7216 | 7217 | 7218 | 7219 | 7220 | 7221 | 7222 | 7223 | 7224 | 7225 |
| 290 | 7239 | 7240 | 7241 | 7242 | 7243 | 7244 | 7245 | 7246 | 7247 | 7248 | 7249 | 7250 |
| 291 | 7264 | 7265 | 7266 | 7267 | 7268 | 7269 | 7270 | 7271 | 7272 | 7273 | 7274 | 7275 |
| 292 | 7289 | 7290 | 7291 | 7292 | 7293 | 7294 | 7295 | 7296 | 7297 | 7298 | 7299 | 7300 |
| 293 | 7314 | 7315 | 7316 | 7317 | 7318 | 7319 | 7320 | 7321 | 7322 | 7323 | 7324 | 7325 |
| 294 | 7339 | 7340 | 7341 | 7342 | 7343 | 7344 | 7345 | 7346 | 7347 | 7348 | 7349 | 7350 |
| 295 | 7364 | 7365 | 7366 | 7367 | 7368 | 7369 | 7370 | 7371 | 7372 | 7373 | 7374 | 7375 |
| 296 | 7389 | 7390 | 7391 | 7392 | 7393 | 7394 | 7395 | 7396 | 7397 | 7398 | 7399 | 7400 |
| 297 | 7414 | 7415 | 7416 | 7417 | 7418 | 7419 | 7420 | 7421 | 7422 | 7423 | 7424 | 7425 |
| 298 | 7439 | 7440 | 7441 | 7442 | 7443 | 7444 | 7445 | 7446 | 7447 | 7448 | 7449 | 7450 |
| 299 | 7464 | 7465 | 7466 | 7467 | 7468 | 7469 | 7470 | 7471 | 7472 | 7473 | 7474 | 7475 |
| 300 | 7489 | 7490 | 7491 | 7492 | 7493 | 7494 | 7495 | 7496 | 7497 | 7498 | 7499 | 7500 |
| 301 | 7514 | 7515 | 7516 | 7517 | 7518 | 7519 | 7520 | 7521 | 7522 | 7523 | 7524 | 7525 |
| 302 | 7539 | 7540 | 7541 | 7542 | 7543 | 7544 | 7545 | 7546 | 7547 | 7548 | 7549 | 7550 |
| 303 | 7564 | 7565 | 7566 | 7567 | 7568 | 7569 | 7570 | 7571 | 7572 | 7573 | 7574 | 7575 |
| 304 | 7589 | 7590 | 7591 | 7592 | 7593 | 7594 | 7595 | 7596 | 7597 | 7598 | 7599 | 7600 |
| 305 | 7614 | 7615 | 7616 | 7617 | 7618 | 7619 | 7620 | 7621 | 7622 | 7623 | 7624 | 7625 |
| 306 | 7639 | 7640 | 7641 | 7642 | 7643 | 7644 | 7645 | 7646 | 7647 | 7648 | 7649 | 7650 |
| 307 | 7664 | 7665 | 7666 | 7667 | 7668 | 7669 | 7670 | 7671 | 7672 | 7673 | 7674 | 7675 |
| 308 | 7689 | 7690 | 7691 | 7692 | 7693 | 7694 | 7695 | 7696 | 7697 | 7698 | 7699 | 7700 |
| 309 | 7714 | 7715 | 7716 | 7717 | 7718 | 7719 | 7720 | 7721 | 7722 | 7723 | 7724 | 7725 |
| 310 | 7739 | 7740 | 7741 | 7742 | 7743 | 7744 | 7745 | 7746 | 7747 | 7748 | 7749 | 7750 |
| 311 | 7764 | 7765 | 7766 | 7767 | 7768 | 7769 | 7770 | 7771 | 7772 | 7773 | 7774 | 7775 |
| 312 | 7789 | 7790 | 7791 | 7792 | 7793 | 7794 | 7795 | 7796 | 7797 | 7798 | 7799 | 7800 |
| 313 | 7814 | 7815 | 7816 | 7817 | 7818 | 7819 | 7820 | 7821 | 7822 | 7823 | 7824 | 7825 |
| 314 | 7839 | 7840 | 7841 | 7842 | 7843 | 7844 | 7845 | 7846 | 7847 | 7848 | 7849 | 7850 |
| 315 | 7864 | 7865 | 7866 | 7867 | 7868 | 7869 | 7870 | 7871 | 7872 | 7873 | 7874 | 7875 |
| 316 | 7889 | 7890 | 7891 | 7892 | 7893 | 7894 | 7895 | 7896 | 7897 | 7898 | 7899 | 7900 |
| 317 | 7914 | 7915 | 7916 | 7917 | 7918 | 7919 | 7920 | 7921 | 7922 | 7923 | 7924 | 7925 |
| 318 | 7939 | 7940 | 7941 | 7942 | 7943 | 7944 | 7945 | 7946 | 7947 | 7948 | 7949 | 7950 |
| 319 | 7964 | 7965 | 7966 | 7967 | 7968 | 7969 | 7970 | 7971 | 7972 | 7973 | 7974 | 7975 |
| 320 | 7989 | 7990 | 7991 | 7992 | 7993 | 7994 | 7995 | 7996 | 7997 | 7998 | 7999 | 8000 |
| 321 | 8014 | 8015 | 8016 | 8017 | 8018 | 8019 | 8020 | 8021 | 8022 | 8023 | 8024 | 8025 |
| 322 | 8039 | 8040 | 8041 | 8042 | 8043 | 8044 | 8045 | 8046 | 8047 | 8048 | 8049 | 8050 |
| 323 | 8064 | 8065 | 8066 | 8067 | 8068 | 8069 | 8070 | 8071 | 8072 | 8073 | 8074 | 8075 |
| 324 | 8089 | 8090 | 8091 | 8092 | 8093 | 8094 | 8095 | 8096 | 8097 | 8098 | 8099 | 8100 |
| 325 | 8114 | 8115 | 8116 | 8117 | 8118 | 8119 | 8120 | 8121 | 8122 | 8123 | 8124 | 8125 |
| 326 | 8139 | 8140 | 8141 | 8142 | 8143 | 8144 | 8145 | 8146 | 8147 | 8148 | 8149 | 8150 |
| 327 | 8164 | 8165 | 8166 | 8167 | 8168 | 8169 | 8170 | 8171 | 8172 | 8173 | 8174 | 8175 |
| 328 | 8189 | 8190 | 8191 | 8192 | 8193 | 8194 | 8195 | 8196 | 8197 | 8198 | 8199 | 8200 |
| 329 | 8214 | 8215 | 8216 | 8217 | 8218 | 8219 | 8220 | 8221 | 8222 | 8223 | 8224 | 8225 |
| 330 | 8239 | 8240 | 8241 | 8242 | 8243 | 8244 | 8245 | 8246 | 8247 | 8248 | 8249 | 8250 |

|  |  | Third organic compound | | | | | | | | | | | | |
| --- | --- | --- | --- | --- | --- | --- | --- | --- | --- | --- | --- | --- | --- | --- |
|  |  | D1 | D2 | D3 | D4 | D5 | D6 | D7 | D8 | D9 | D10 | D11 | D12 | D13 |
| Second organic compound | 331 | 8251 | 8252 | 8253 | 8254 | 8255 | 8256 | 8257 | 8258 | 8259 | 8260 | 8261 | 8262 | 8263 |
|  | 332 | 8276 | 8277 | 8278 | 8279 | 8280 | 8281 | 8282 | 8283 | 8284 | 8285 | 8286 | 8287 | 8288 |
|  | 333 | 8301 | 8302 | 8303 | 8304 | 8305 | 8306 | 8307 | 8308 | 8309 | 8310 | 8311 | 8312 | 8313 |
|  | 334 | 8326 | 8327 | 8328 | 8329 | 8330 | 8331 | 8332 | 8333 | 8334 | 8335 | 8336 | 8337 | 8338 |
|  | 335 | 8351 | 8352 | 8353 | 8354 | 8355 | 8356 | 8357 | 8358 | 8359 | 8360 | 8361 | 8362 | 8363 |
|  | 336 | 8376 | 8377 | 8378 | 8379 | 8380 | 8381 | 8382 | 8383 | 8384 | 8385 | 8386 | 8387 | 8388 |
|  | 337 | 8401 | 8402 | 8403 | 8404 | 8405 | 8406 | 8407 | 8408 | 8409 | 8410 | 8411 | 8412 | 8413 |
|  | 338 | 8426 | 8427 | 8428 | 8429 | 8430 | 8431 | 8432 | 8433 | 8434 | 8435 | 8436 | 8437 | 8438 |
|  | 339 | 8451 | 8452 | 8453 | 8454 | 8455 | 8456 | 8457 | 8458 | 8459 | 8460 | 8461 | 8462 | 8463 |
|  | 340 | 8476 | 8477 | 8478 | 8479 | 8480 | 8481 | 8482 | 8483 | 8484 | 8485 | 8486 | 8487 | 8488 |
|  | 341 | 8501 | 8502 | 8503 | 8504 | 8505 | 8506 | 8507 | 8508 | 8509 | 8510 | 8511 | 8512 | 8513 |
|  | 342 | 8526 | 8527 | 8528 | 8529 | 8530 | 8531 | 8532 | 8533 | 8534 | 8535 | 8536 | 8537 | 8538 |
|  | 343 | 8551 | 8552 | 8553 | 8554 | 8555 | 8556 | 8557 | 8558 | 8559 | 8560 | 8561 | 8562 | 8563 |
|  | 344 | 8576 | 8577 | 8578 | 8579 | 8580 | 8581 | 8582 | 8583 | 8584 | 8585 | 8586 | 8587 | 8588 |
|  | 345 | 8601 | 8602 | 8603 | 8604 | 8605 | 8606 | 8607 | 8608 | 8609 | 8610 | 8611 | 8612 | 8613 |
|  | 346 | 8626 | 8627 | 8628 | 8629 | 8630 | 8631 | 8632 | 8633 | 8634 | 8635 | 8636 | 8637 | 8638 |
|  | 347 | 8651 | 8652 | 8653 | 8654 | 8655 | 8656 | 8657 | 8658 | 8659 | 8660 | 8661 | 8662 | 8663 |
|  | 348 | 8676 | 8677 | 8678 | 8679 | 8680 | 8681 | 8682 | 8683 | 8684 | 8685 | 8686 | 8687 | 8688 |
|  | 349 | 8701 | 8702 | 8703 | 8704 | 8705 | 8706 | 8707 | 8708 | 8709 | 8710 | 8711 | 8712 | 8713 |
|  | 350 | 8726 | 8727 | 8728 | 8729 | 8730 | 8731 | 8732 | 8733 | 8734 | 8735 | 8736 | 8737 | 8738 |
|  | 351 | 8751 | 8752 | 8753 | 8754 | 8755 | 8756 | 8757 | 8758 | 8759 | 8760 | 8761 | 8762 | 8763 |
|  | 352 | 8776 | 8777 | 8778 | 8779 | 8780 | 8781 | 8782 | 8783 | 8784 | 8785 | 8786 | 8787 | 8788 |
|  | 353 | 8801 | 8802 | 8803 | 8804 | 8805 | 8806 | 8807 | 8808 | 8809 | 8810 | 8811 | 8812 | 8813 |
|  | 354 | 8826 | 8827 | 8828 | 8829 | 8830 | 8831 | 8832 | 8833 | 8834 | 8835 | 8836 | 8837 | 8838 |
|  | 355 | 8851 | 8852 | 8853 | 8854 | 8855 | 8856 | 8857 | 8858 | 8859 | 8860 | 8861 | 8862 | 8863 |
|  | 356 | 8876 | 8877 | 8878 | 8879 | 8880 | 8881 | 8882 | 8883 | 8884 | 8885 | 8886 | 8887 | 8888 |
|  | 357 | 8901 | 8902 | 8903 | 8904 | 8905 | 8906 | 8907 | 8908 | 8909 | 8910 | 8911 | 8912 | 8913 |
|  | 358 | 8926 | 8927 | 8928 | 8929 | 8930 | 8931 | 8932 | 8933 | 8934 | 8935 | 8936 | 8937 | 8938 |
|  | 359 | 8951 | 8952 | 8953 | 8954 | 8955 | 8956 | 8957 | 8958 | 8959 | 8960 | 8961 | 8962 | 8963 |
|  | 360 | 8976 | 8977 | 8978 | 8979 | 8980 | 8981 | 8982 | 8983 | 8984 | 8985 | 8986 | 8987 | 8988 |
|  | 361 | 9001 | 9002 | 9003 | 9004 | 9005 | 9006 | 9007 | 9008 | 9009 | 9010 | 9011 | 9012 | 9013 |
|  | 362 | 9026 | 9027 | 9028 | 9029 | 9030 | 9031 | 9032 | 9033 | 9034 | 9035 | 9036 | 9037 | 9038 |
|  | 363 | 9051 | 9052 | 9053 | 9054 | 9055 | 9056 | 9057 | 9058 | 9059 | 9060 | 9061 | 9062 | 9063 |
|  | 364 | 9076 | 9077 | 9078 | 9079 | 9080 | 9081 | 9082 | 9083 | 9084 | 9085 | 9086 | 9087 | 9088 |
|  | 365 | 9101 | 9102 | 9103 | 9104 | 9105 | 9106 | 9107 | 9108 | 9109 | 9110 | 9111 | 9112 | 9113 |
|  | 366 | 9126 | 9127 | 9128 | 9129 | 9130 | 9131 | 9132 | 9133 | 9134 | 9135 | 9136 | 9137 | 9138 |
|  | 367 | 9151 | 9152 | 9153 | 9154 | 9155 | 9156 | 9157 | 9158 | 9159 | 9160 | 9161 | 9162 | 9163 |
|  | 368 | 9176 | 9177 | 9178 | 9179 | 9180 | 9181 | 9182 | 9183 | 9184 | 9185 | 9186 | 9187 | 9188 |
|  | 369 | 9201 | 9202 | 9203 | 9204 | 9205 | 9206 | 9207 | 9208 | 9209 | 9210 | 9211 | 9212 | 9213 |
|  | 370 | 9226 | 9227 | 9228 | 9229 | 9230 | 9231 | 9232 | 9233 | 9234 | 9235 | 9236 | 9237 | 9238 |
|  | 371 | 9251 | 9252 | 9253 | 9254 | 9255 | 9256 | 9257 | 9258 | 9259 | 9260 | 9261 | 9262 | 9263 |
|  | 372 | 9276 | 9277 | 9278 | 9279 | 9280 | 9281 | 9282 | 9283 | 9284 | 9285 | 9286 | 9287 | 9288 |
|  | 373 | 9301 | 9302 | 9303 | 9304 | 9305 | 9306 | 9307 | 9308 | 9309 | 9310 | 9311 | 9312 | 9313 |
|  | 374 | 9326 | 9327 | 9328 | 9329 | 9330 | 9331 | 9332 | 9333 | 9334 | 9335 | 9336 | 9337 | 9338 |
|  | 375 | 9351 | 9352 | 9353 | 9354 | 9355 | 9356 | 9357 | 9358 | 9359 | 9360 | 9361 | 9362 | 9363 |
|  | 376 | 9376 | 9377 | 9378 | 9379 | 9380 | 9381 | 9382 | 9383 | 9384 | 9385 | 9386 | 9387 | 9388 |
|  | 377 | 9401 | 9402 | 9403 | 9404 | 9405 | 9406 | 9407 | 9408 | 9409 | 9410 | 9411 | 9412 | 9413 |
|  | 378 | 9426 | 9427 | 9428 | 9429 | 9430 | 9431 | 9432 | 9433 | 9434 | 9435 | 9436 | 9437 | 9438 |
|  | 379 | 9451 | 9452 | 9453 | 9454 | 9455 | 9456 | 9457 | 9458 | 9459 | 9460 | 9461 | 9462 | 9463 |
|  | 380 | 9476 | 9477 | 9478 | 9479 | 9480 | 9481 | 9482 | 9483 | 9484 | 9485 | 9486 | 9487 | 9488 |
|  | 381 | 9501 | 9502 | 9503 | 9504 | 9505 | 9506 | 9507 | 9508 | 9509 | 9510 | 9511 | 9512 | 9513 |
|  | 382 | 9526 | 9527 | 9528 | 9529 | 9530 | 9531 | 9532 | 9533 | 9534 | 9535 | 9536 | 9537 | 9538 |
|  | 383 | 9551 | 9552 | 9553 | 9554 | 9555 | 9556 | 9557 | 9558 | 9559 | 9560 | 9561 | 9562 | 9563 |
|  | 384 | 9576 | 9577 | 9578 | 9579 | 9580 | 9581 | 9582 | 9583 | 9584 | 9585 | 9586 | 9587 | 9588 |
|  | 385 | 9601 | 9602 | 9603 | 9604 | 9605 | 9606 | 9607 | 9608 | 9609 | 9610 | 9611 | 9612 | 9613 |

|  |  | Third organic compound | | | | | | | | | | | |
| --- | --- | --- | --- | --- | --- | --- | --- | --- | --- | --- | --- | --- | --- |
|  |  | D14 | D15 | D16 | D17 | D18 | D19 | D20 | D21 | D22 | D23 | D24 | D25 |
| Second organic compound | 331 | 8264 | 8265 | 8266 | 8267 | 8268 | 8269 | 8270 | 8271 | 8272 | 8273 | 8274 | 8275 |
|  | 332 | 8289 | 8290 | 8291 | 8292 | 8293 | 8294 | 8295 | 8296 | 8297 | 8298 | 8299 | 8300 |
|  | 333 | 8314 | 8315 | 8316 | 8317 | 8318 | 8319 | 8320 | 8321 | 8322 | 8323 | 8324 | 8325 |
|  | 334 | 8339 | 8340 | 8341 | 8342 | 8343 | 8344 | 8345 | 8346 | 8347 | 8348 | 8349 | 8350 |
|  | 335 | 8364 | 8365 | 8366 | 8367 | 8368 | 8369 | 8370 | 8371 | 8372 | 8373 | 8374 | 8375 |
|  | 336 | 8389 | 8390 | 8391 | 8392 | 8393 | 8394 | 8395 | 8396 | 8397 | 8398 | 8399 | 8400 |
|  | 337 | 8414 | 8415 | 8416 | 8417 | 8418 | 8419 | 8420 | 8421 | 8422 | 8423 | 8424 | 8425 |
|  | 338 | 8439 | 8440 | 8441 | 8442 | 8443 | 8444 | 8445 | 8446 | 8447 | 8448 | 8449 | 8450 |
|  | 339 | 8464 | 8465 | 8466 | 8467 | 8468 | 8469 | 8470 | 8471 | 8472 | 8473 | 8474 | 8475 |
|  | 340 | 8489 | 8490 | 8491 | 8492 | 8493 | 8494 | 8495 | 8496 | 8497 | 8498 | 8499 | 8500 |
|  | 341 | 8514 | 8515 | 8516 | 8517 | 8518 | 8519 | 8520 | 8521 | 8522 | 8523 | 8524 | 8525 |
|  | 342 | 8539 | 8540 | 8541 | 8542 | 8543 | 8544 | 8545 | 8546 | 8547 | 8548 | 8549 | 8550 |
|  | 343 | 8564 | 8565 | 8566 | 8567 | 8568 | 8569 | 8570 | 8571 | 8572 | 8573 | 8574 | 8575 |
|  | 344 | 8589 | 8590 | 8591 | 8592 | 8593 | 8594 | 8595 | 8596 | 8597 | 8598 | 8599 | 8600 |
|  | 345 | 8614 | 8615 | 8616 | 8617 | 8618 | 8619 | 8620 | 8621 | 8622 | 8623 | 8624 | 8625 |
|  | 346 | 8639 | 8640 | 8641 | 8642 | 8643 | 8644 | 8645 | 8646 | 8647 | 8648 | 8649 | 8650 |
|  | 347 | 8664 | 8665 | 8666 | 8667 | 8668 | 8669 | 8670 | 8671 | 8672 | 8673 | 8674 | 8675 |

-continued

|     |      |      |      |      |      |      |      |      |      |      |      |      |
|-----|------|------|------|------|------|------|------|------|------|------|------|------|
| 348 | 8689 | 8690 | 8691 | 8692 | 8693 | 8694 | 8695 | 8696 | 8697 | 8698 | 8699 | 8700 |
| 349 | 8714 | 8715 | 8716 | 8717 | 8718 | 8719 | 8720 | 8721 | 8722 | 8723 | 8724 | 8725 |
| 350 | 8739 | 8740 | 8741 | 8742 | 8743 | 8744 | 8745 | 8746 | 8747 | 8748 | 8749 | 8750 |
| 351 | 8764 | 8765 | 8766 | 8767 | 8768 | 8769 | 8770 | 8771 | 8772 | 8773 | 8774 | 8775 |
| 352 | 8789 | 8790 | 8791 | 8792 | 8793 | 8794 | 8795 | 8796 | 8797 | 8798 | 8799 | 8800 |
| 353 | 8814 | 8815 | 8816 | 8817 | 8818 | 8819 | 8820 | 8821 | 8822 | 8823 | 8824 | 8825 |
| 354 | 8839 | 8840 | 8841 | 8842 | 8843 | 8844 | 8845 | 8846 | 8847 | 8848 | 8849 | 8850 |
| 355 | 8864 | 8865 | 8866 | 8867 | 8868 | 8869 | 8870 | 8871 | 8872 | 8873 | 8874 | 8875 |
| 356 | 8889 | 8890 | 8891 | 8892 | 8893 | 8894 | 8895 | 8896 | 8897 | 8898 | 8899 | 8900 |
| 357 | 8914 | 8915 | 8916 | 8917 | 8918 | 8919 | 8920 | 8921 | 8922 | 8923 | 8924 | 8925 |
| 358 | 8939 | 8940 | 8941 | 8942 | 8943 | 8944 | 8945 | 8946 | 8947 | 8948 | 8949 | 8950 |
| 359 | 8964 | 8965 | 8966 | 8967 | 8968 | 8969 | 8970 | 8971 | 8972 | 8973 | 8974 | 8975 |
| 360 | 8989 | 8990 | 8991 | 8992 | 8993 | 8994 | 8995 | 8996 | 8997 | 8998 | 8999 | 9000 |
| 361 | 9014 | 9015 | 9016 | 9017 | 9018 | 9019 | 9020 | 9021 | 9022 | 9023 | 9024 | 9025 |
| 362 | 9039 | 9040 | 9041 | 9042 | 9043 | 9044 | 9045 | 9046 | 9047 | 9048 | 9049 | 9050 |
| 363 | 9064 | 9065 | 9066 | 9067 | 9068 | 9069 | 9070 | 9071 | 9072 | 9073 | 9074 | 9075 |
| 364 | 9089 | 9090 | 9091 | 9092 | 9093 | 9094 | 9095 | 9096 | 9097 | 9098 | 9099 | 9100 |
| 365 | 9114 | 9115 | 9116 | 9117 | 9118 | 9119 | 9120 | 9121 | 9122 | 9123 | 9124 | 9125 |
| 366 | 9139 | 9140 | 9141 | 9142 | 9143 | 9144 | 9145 | 9146 | 9147 | 9148 | 9149 | 9150 |
| 367 | 9164 | 9165 | 9166 | 9167 | 9168 | 9169 | 9170 | 9171 | 9172 | 9173 | 9174 | 9175 |
| 368 | 9189 | 9190 | 9191 | 9192 | 9193 | 9194 | 9195 | 9196 | 9197 | 9198 | 9199 | 9200 |
| 369 | 9214 | 9215 | 9216 | 9217 | 9218 | 9219 | 9220 | 9221 | 9222 | 9223 | 9224 | 9225 |
| 370 | 9239 | 9240 | 9241 | 9242 | 9243 | 9244 | 9245 | 9246 | 9247 | 9248 | 9249 | 9250 |
| 371 | 9264 | 9265 | 9266 | 9267 | 9268 | 9269 | 9270 | 9271 | 9272 | 9273 | 9274 | 9275 |
| 372 | 9289 | 9290 | 9291 | 9292 | 9293 | 9294 | 9295 | 9296 | 9297 | 9298 | 9299 | 9300 |
| 373 | 9314 | 9315 | 9316 | 9317 | 9318 | 9319 | 9320 | 9321 | 9322 | 9323 | 9324 | 9325 |
| 374 | 9339 | 9340 | 9341 | 9342 | 9343 | 9344 | 9345 | 9346 | 9347 | 9348 | 9349 | 9350 |
| 375 | 9364 | 9365 | 9366 | 9367 | 9368 | 9369 | 9370 | 9371 | 9372 | 9373 | 9374 | 9375 |
| 376 | 9389 | 9390 | 939] | 9392 | 9393 | 9394 | 9395 | 9396 | 9397 | 9398 | 9399 | 9400 |
| 377 | 9414 | 9415 | 9416 | 9417 | 9418 | 9419 | 9420 | 9421 | 9422 | 9423 | 9424 | 9425 |
| 378 | 9439 | 9440 | 9441 | 9442 | 9443 | 9444 | 9445 | 9446 | 9447 | 9448 | 9449 | 9450 |
| 379 | 9464 | 9465 | 9466 | 9467 | 9468 | 9469 | 9470 | 9471 | 9472 | 9473 | 9474 | 9475 |
| 380 | 9489 | 9490 | 9491 | 9492 | 9493 | 9494 | 9495 | 9496 | 9497 | 9498 | 9499 | 9500 |
| 381 | 9514 | 9515 | 9516 | 9517 | 9518 | 9519 | 9520 | 9521 | 9522 | 9523 | 9524 | 9525 |
| 382 | 9539 | 9540 | 9541 | 9542 | 9543 | 9544 | 9545 | 9546 | 9547 | 9548 | 9549 | 9550 |
| 383 | 9564 | 9565 | 9566 | 9567 | 9568 | 9569 | 9570 | 9571 | 9572 | 9573 | 9574 | 9575 |
| 384 | 9589 | 9590 | 9591 | 9592 | 9593 | 9594 | 9595 | 9596 | 9597 | 9598 | 9599 | 9600 |
| 385 | 9614 | 9615 | 9616 | 9617 | 9618 | 9619 | 9620 | 9621 | 9622 | 9623 | 9624 | 9625 |

| | Third organic compound | | | | | | | | | | | | |
|---|---|---|---|---|---|---|---|---|---|---|---|---|
| | D1 | D2 | D3 | D4 | D5 | D6 | D7 | D8 | D9 | D10 | D11 | D12 | D13 |
| 386 | 9626 | 9627 | 9628 | 9629 | 9630 | 9631 | 9632 | 9633 | 9634 | 9635 | 9636 | 9637 | 9638 |
| 387 | 9651 | 9652 | 9653 | 9654 | 9655 | 9656 | 9657 | 9658 | 9659 | 9660 | 9661 | 9662 | 9663 |
| 388 | 9676 | 9677 | 9678 | 9679 | 9680 | 9681 | 9682 | 9683 | 9684 | 9685 | 9686 | 9687 | 9688 |
| 389 | 9701 | 9702 | 9703 | 9704 | 9705 | 9706 | 9707 | 9708 | 9709 | 9710 | 9711 | 9712 | 9713 |
| 390 | 9726 | 9727 | 9728 | 9729 | 9730 | 9731 | 9732 | 9733 | 9734 | 9735 | 9736 | 9737 | 9738 |
| 391 | 9751 | 9752 | 9753 | 9754 | 9755 | 9756 | 9757 | 9758 | 9759 | 9760 | 9761 | 9762 | 9763 |
| 392 | 9776 | 9777 | 9778 | 9779 | 9780 | 9781 | 9782 | 9783 | 9784 | 9785 | 9786 | 9787 | 9788 |
| 393 | 9801 | 9802 | 9803 | 9804 | 9805 | 9806 | 9807 | 9808 | 9809 | 9810 | 9811 | 9812 | 9813 |
| 394 | 9826 | 9827 | 9828 | 9829 | 9830 | 9831 | 9832 | 9833 | 9834 | 9835 | 9836 | 9837 | 9838 |
| 395 | 9851 | 9852 | 9853 | 9854 | 9855 | 9856 | 9857 | 9858 | 9859 | 9860 | 9861 | 9862 | 9863 |
| 396 | 9876 | 9877 | 9878 | 9879 | 9880 | 9881 | 9882 | 9883 | 9884 | 9885 | 9886 | 9887 | 9888 |
| 397 | 9901 | 9902 | 9903 | 9904 | 9905 | 9906 | 9907 | 9908 | 9909 | 9910 | 9911 | 9912 | 9913 |
| 398 | 9926 | 9927 | 9928 | 9929 | 9930 | 9931 | 9932 | 9933 | 9934 | 9935 | 9936 | 9937 | 9938 |
| 399 | 9951 | 9952 | 9953 | 9954 | 9955 | 9956 | 9957 | 9958 | 9959 | 9960 | 9961 | 9962 | 9963 |
| 400 | 9976 | 9977 | 9978 | 9979 | 9980 | 9981 | 9982 | 9983 | 9984 | 9985 | 9986 | 9987 | 9988 |
| 401 | 10001 | 10002 | 10003 | 10004 | 10005 | 10006 | 10007 | 10008 | 10009 | 10010 | 10011 | 10012 | 10013 |
| 402 | 10026 | 10027 | 10028 | 10029 | 10030 | 10031 | 10032 | 10033 | 10034 | 10035 | 10036 | 10037 | 10038 |
| 403 | 10051 | 10052 | 10053 | 10054 | 10055 | 10056 | 10057 | 10058 | 10059 | 10060 | 10061 | 10062 | 10063 |
| 404 | 10076 | 10077 | 10078 | 10079 | 10080 | 10081 | 10082 | 10083 | 10084 | 10085 | 10086 | 10087 | 10088 |
| 405 | 10101 | 10102 | 10103 | 10104 | 10105 | 10106 | 10107 | 10108 | 10109 | 10110 | 10111 | 10112 | 10113 |
| 406 | 10126 | 10127 | 10128 | 10129 | 10130 | 10131 | 10132 | 10133 | 10134 | 10135 | 10136 | 10137 | 10138 |
| 407 | 10151 | 10152 | 10153 | 10154 | 10155 | 10156 | 10157 | 10158 | 10159 | 10160 | 10161 | 10162 | 10163 |
| 408 | 10176 | 10177 | 10178 | 10179 | 10180 | 10181 | 10182 | 10183 | 10184 | 10185 | 10186 | 10187 | 10188 |
| 409 | 10201 | 10202 | 10203 | 10204 | 10205 | 10206 | 10207 | 10208 | 10209 | 10210 | 10211 | 10212 | 10213 |
| 410 | 10226 | 10227 | 10228 | 10229 | 10230 | 10231 | 10232 | 10233 | 10234 | 10235 | 10236 | 10237 | 10238 |
| 411 | 10251 | 10252 | 10253 | 10254 | 10255 | 10256 | 10257 | 10258 | 10259 | 10260 | 10261 | 10262 | 10263 |
| 412 | 10276 | 10277 | 10278 | 10279 | 10280 | 10281 | 10282 | 10283 | 10284 | 10285 | 10286 | 10287 | 10288 |
| 413 | 10301 | 10302 | 10303 | 10304 | 10305 | 10306 | 10307 | 10308 | 10309 | 10310 | 10311 | 10312 | 10313 |
| 414 | 10326 | 10327 | 10328 | 10329 | 10330 | 10331 | 10332 | 10333 | 10334 | 10335 | 10336 | 10337 | 10338 |
| 415 | 10351 | 10352 | 10353 | 10354 | 10355 | 10356 | 10357 | 10358 | 10359 | 10360 | 10361 | 10362 | 10363 |
| 416 | 10376 | 10377 | 10378 | 10379 | 10380 | 10381 | 10382 | 10383 | 10384 | 10385 | 10386 | 10387 | 10388 |
| 417 | 10401 | 10402 | 10403 | 10404 | 10405 | 10406 | 10407 | 10408 | 10409 | 10410 | 10411 | 10412 | 10413 |
| 418 | 10426 | 10427 | 10428 | 10429 | 10430 | 10431 | 10432 | 10433 | 10434 | 10435 | 10436 | 10437 | 10438 |

-continued

| | | | | | | | | | | | | |
|---|---|---|---|---|---|---|---|---|---|---|---|---|
| 419 | 10451 | 10452 | 10453 | 10454 | 10455 | 10456 | 10457 | 10458 | 10459 | 10460 | 10461 | 10462 | 10463 |
| 420 | 10476 | 10477 | 10478 | 10479 | 10480 | 10481 | 10482 | 10483 | 10484 | 10485 | 10486 | 10487 | 10488 |
| 421 | 10501 | 10502 | 10503 | 10504 | 10505 | 10506 | 10507 | 10508 | 10509 | 10510 | 10511 | 10512 | 10513 |
| 422 | 10526 | 10527 | 10528 | 10529 | 10530 | 10531 | 10532 | 10533 | 10534 | 10535 | 10536 | 10537 | 10538 |
| 423 | 10551 | 10552 | 10553 | 10554 | 10555 | 10556 | 10557 | 10558 | 10559 | 10560 | 10561 | 10562 | 10563 |
| 424 | 10576 | 10577 | 10578 | 10579 | 10580 | 10581 | 10582 | 10583 | 10584 | 10585 | 10586 | 10587 | 10588 |
| 425 | 10601 | 10602 | 10603 | 10604 | 10605 | 10606 | 10607 | 10608 | 10609 | 10610 | 10611 | 10612 | 10613 |
| 426 | 10626 | 10627 | 10628 | 10629 | 10630 | 10631 | 10632 | 10633 | 10634 | 10635 | 10636 | 10637 | 10638 |
| 427 | 10651 | 10652 | 10653 | 10654 | 10655 | 10656 | 10657 | 10658 | 10659 | 10660 | 10661 | 10662 | 10663 |
| 428 | 10676 | 10677 | 10678 | 10679 | 10680 | 10681 | 10682 | 10683 | 10684 | 10685 | 10686 | 10687 | 10688 |
| 429 | 10701 | 10702 | 10703 | 10704 | 10705 | 10706 | 10707 | 10708 | 10709 | 10710 | 10711 | 10712 | 10713 |
| 430 | 10726 | 10727 | 10728 | 10729 | 10730 | 10731 | 10732 | 10733 | 10734 | 10735 | 10736 | 10737 | 10738 |
| 431 | 10751 | 10752 | 10753 | 10754 | 10755 | 10756 | 10757 | 10758 | 10759 | 10760 | 10761 | 10762 | 10763 |
| 432 | 10776 | 10777 | 10778 | 10779 | 10780 | 10781 | 10782 | 10783 | 10784 | 10785 | 10786 | 10787 | 10788 |
| 433 | 10801 | 10802 | 10803 | 10804 | 10805 | 10806 | 10807 | 10808 | 10809 | 10810 | 10811 | 10812 | 10813 |
| 434 | 10826 | 10827 | 10828 | 10829 | 10830 | 10831 | 10832 | 10833 | 10834 | 10835 | 10836 | 10837 | 10838 |
| 435 | 10851 | 10852 | 10853 | 10854 | 10855 | 10856 | 10857 | 10858 | 10859 | 10860 | 10861 | 10862 | 10863 |
| 436 | 10876 | 10877 | 10878 | 10879 | 10880 | 10881 | 10882 | 10883 | 10884 | 10885 | 10886 | 10887 | 10888 |
| 437 | 10901 | 10902 | 10903 | 10904 | 10905 | 10906 | 10907 | 10908 | 10909 | 10910 | 10911 | 10912 | 10913 |
| 438 | 10926 | 10927 | 10928 | 10929 | 10930 | 10931 | 10932 | 10933 | 10934 | 10935 | 10936 | 10937 | 10938 |
| 439 | 10951 | 10952 | 10953 | 10954 | 10955 | 10956 | 10957 | 10958 | 10959 | 10960 | 10961 | 10962 | 10963 |
| 440 | 10976 | 10977 | 10978 | 10979 | 10980 | 10981 | 10982 | 10983 | 10984 | 10985 | 10986 | 10987 | 10988 |

| | Third organic compound | | | | | | | | | | | |
|---|---|---|---|---|---|---|---|---|---|---|---|---|
| | D14 | D15 | D16 | D17 | D18 | D19 | D20 | D21 | D22 | D23 | D24 | D25 |
| 386 | 9639 | 9640 | 9641 | 9642 | 9643 | 9644 | 9645 | 9646 | 9647 | 9648 | 9649 | 9650 |
| 387 | 9664 | 9665 | 9666 | 9667 | 9668 | 9669 | 9670 | 9671 | 9672 | 9673 | 9674 | 9675 |
| 388 | 9689 | 9690 | 9691 | 9692 | 9693 | 9694 | 9695 | 9696 | 9697 | 9698 | 9699 | 9700 |
| 389 | 9714 | 9715 | 9716 | 9717 | 9718 | 9719 | 9720 | 9721 | 9722 | 9723 | 9724 | 9725 |
| 390 | 9739 | 9740 | 9741 | 9742 | 9743 | 9744 | 9745 | 9746 | 9747 | 9748 | 9749 | 9750 |
| 391 | 9764 | 9765 | 9766 | 9767 | 9768 | 9769 | 9770 | 9771 | 9772 | 9773 | 9774 | 9775 |
| 392 | 9789 | 9790 | 9791 | 9792 | 9793 | 9794 | 9795 | 9796 | 9797 | 9798 | 9799 | 9800 |
| 393 | 9814 | 9815 | 9816 | 9817 | 9818 | 9819 | 9820 | 9821 | 9822 | 9823 | 9824 | 9825 |
| 394 | 9839 | 9840 | 9841 | 9842 | 9843 | 9844 | 9845 | 9846 | 9847 | 9848 | 9849 | 9850 |
| 395 | 9864 | 9865 | 9866 | 9867 | 9868 | 9869 | 9870 | 9871 | 9872 | 9873 | 9874 | 9875 |
| 396 | 9889 | 9890 | 9891 | 9892 | 9893 | 9894 | 9895 | 9896 | 9897 | 9898 | 9899 | 9900 |
| 397 | 9914 | 9915 | 9916 | 9917 | 9918 | 9919 | 9920 | 9921 | 9922 | 9923 | 9924 | 9925 |
| 398 | 9939 | 9940 | 9941 | 9942 | 9943 | 9944 | 9945 | 9946 | 9947 | 9948 | 9949 | 9950 |
| 399 | 9964 | 9965 | 9966 | 9967 | 9968 | 9969 | 9970 | 9971 | 9972 | 9973 | 9974 | 9975 |
| 400 | 9989 | 9990 | 9991 | 9992 | 9993 | 9994 | 9995 | 9996 | 9997 | 9998 | 9999 | 10000 |
| 401 | 10014 | 10015 | 10016 | 10017 | 10018 | 10019 | 10020 | 10021 | 10022 | 10023 | 10024 | 10025 |
| 402 | 10039 | 10040 | 10041 | 10042 | 10043 | 10044 | 10045 | 10046 | 10047 | 10048 | 10049 | 10050 |
| 403 | 10064 | 10065 | 10066 | 10067 | 10068 | 10069 | 10070 | 10071 | 10072 | 10073 | 10074 | 10075 |
| 404 | 10089 | 10090 | 10091 | 10092 | 10093 | 10094 | 10095 | 10096 | 10097 | 10098 | 10099 | 10100 |
| 405 | 10114 | 10115 | 10116 | 10117 | 10118 | 10119 | 10120 | 10121 | 10122 | 10123 | 10124 | 10125 |
| 406 | 10139 | 10140 | 10141 | 10142 | 10143 | 10144 | 10145 | 10146 | 10147 | 10148 | 10149 | 10150 |
| 407 | 10164 | 10165 | 10166 | 10167 | 10168 | 10169 | 10170 | 10171 | 10172 | 10173 | 10174 | 10175 |
| 408 | 10189 | 10190 | 10191 | 10192 | 10193 | 10194 | 10195 | 10196 | 10197 | 10198 | 10199 | 10200 |
| 409 | 10214 | 10215 | 10216 | 10217 | 10218 | 10219 | 10220 | 10221 | 10222 | 10223 | 10224 | 10225 |
| 410 | 10239 | 10240 | 10241 | 10242 | 10243 | 10244 | 10245 | 10246 | 10247 | 10248 | 10249 | 10250 |
| 411 | 10264 | 10265 | 10266 | 10267 | 10268 | 10269 | 10270 | 10271 | 10272 | 10273 | 10274 | 10275 |
| 412 | 10289 | 10290 | 10291 | 10292 | 10293 | 10294 | 10295 | 10296 | 10297 | 10298 | 10299 | 10300 |
| 413 | 10314 | 10315 | 10316 | 10317 | 10318 | 10319 | 10320 | 10321 | 10322 | 10323 | 10324 | 10325 |
| 414 | 10339 | 10340 | 10341 | 10342 | 10343 | 10344 | 10345 | 10346 | 10347 | 10348 | 10349 | 10350 |
| 415 | 10364 | 10365 | 10366 | 10367 | 10368 | 10369 | 10370 | 10371 | 10372 | 10373 | 10374 | 10375 |
| 416 | 10389 | 10390 | 10391 | 10392 | 10393 | 10394 | 10395 | 10396 | 10397 | 10398 | 10399 | 10400 |
| 417 | 10414 | 10415 | 10416 | 10417 | 10418 | 10419 | 10420 | 10421 | 10422 | 10423 | 10424 | 10425 |
| 418 | 10439 | 10440 | 10441 | 10442 | 10443 | 10444 | 10445 | 10446 | 10447 | 10448 | 10449 | 10450 |
| 419 | 10464 | 10465 | 10466 | 10467 | 10468 | 10469 | 10470 | 10471 | 10472 | 10473 | 10474 | 10475 |
| 420 | 10489 | 10490 | 10491 | 10492 | 10493 | 10494 | 10495 | 10496 | 10497 | 10498 | 10499 | 10500 |
| 421 | 10514 | 10515 | 10516 | 10517 | 10518 | 10519 | 10520 | 10521 | 10522 | 10523 | 10524 | 10525 |
| 422 | 10539 | 10540 | 10541 | 10542 | 10543 | 10544 | 10545 | 10546 | 10547 | 10548 | 10549 | 10550 |
| 423 | 10564 | 10565 | 10566 | 10567 | 10568 | 10569 | 10570 | 10571 | 10572 | 10573 | 10574 | 10575 |
| 424 | 10589 | 10590 | 10591 | 10592 | 10593 | 10594 | 10595 | 10596 | 10597 | 10598 | 10599 | 10600 |
| 425 | 10614 | 10615 | 10616 | 10617 | 10618 | 10619 | 10620 | 10621 | 10622 | 10623 | 10624 | 10625 |
| 426 | 10639 | 10640 | 10641 | 10642 | 10643 | 10644 | 10645 | 10646 | 10647 | 10648 | 10649 | 10650 |
| 427 | 10664 | 10665 | 10666 | 10667 | 10668 | 10669 | 10670 | 10671 | 10672 | 10673 | 10674 | 10675 |
| 428 | 10689 | 10690 | 10691 | 10692 | 10693 | 10694 | 10695 | 10696 | 10697 | 10698 | 10699 | 10700 |
| 429 | 10714 | 10715 | 10716 | 10717 | 10718 | 10719 | 10720 | 10721 | 10722 | 10723 | 10724 | 10725 |
| 430 | 10739 | 10740 | 10741 | 10742 | 10743 | 10744 | 10745 | 10746 | 10747 | 10748 | 10749 | 10750 |
| 431 | 10764 | 10765 | 10766 | 10767 | 10768 | 10769 | 10770 | 10771 | 10772 | 10773 | 10774 | 10775 |
| 432 | 10789 | 10790 | 10791 | 10792 | 10793 | 10794 | 10795 | 10796 | 10797 | 10798 | 10799 | 10800 |
| 433 | 10814 | 10815 | 10816 | 10817 | 10818 | 10819 | 10820 | 10821 | 10822 | 10823 | 10824 | 10825 |
| 434 | 10839 | 10840 | 10841 | 10842 | 10843 | 10844 | 10845 | 10846 | 10847 | 10848 | 10849 | 10850 |
| 435 | 10864 | 10865 | 10866 | 10867 | 10868 | 10869 | 10870 | 10871 | 10872 | 10873 | 10874 | 10875 |
| 436 | 10889 | 10890 | 10891 | 10892 | 10893 | 10894 | 10895 | 10896 | 10897 | 10898 | 10899 | 10900 |
| 437 | 10914 | 10915 | 10916 | 10917 | 10918 | 10919 | 10920 | 10921 | 10922 | 10923 | 10924 | 10925 |

-continued

| | | | | | | | | | | | | |
|---|---|---|---|---|---|---|---|---|---|---|---|---|
| 438 | 10939 | 10940 | 10941 | 10942 | 10943 | 10944 | 10945 | 10946 | 10947 | 10948 | 10949 | 10950 |
| 439 | 10964 | 10965 | 10966 | 10967 | 10968 | 10969 | 10970 | 10971 | 10972 | 10973 | 10974 | 10975 |
| 440 | 10989 | 10990 | 10991 | 10992 | 10993 | 10994 | 10995 | 10996 | 10997 | 10998 | 10999 | 11000 |

| | | Third organic compound | | | | | | | | | | | | |
|---|---|---|---|---|---|---|---|---|---|---|---|---|---|---|
| | | D1 | D2 | D3 | D4 | D5 | D6 | D7 | D8 | D9 | D10 | D11 | D12 | D13 |
| Second organic compound | 441 | 11001 | 11002 | 11003 | 11004 | 11005 | 11006 | 11007 | 11008 | 11009 | 11010 | 11011 | 11012 | 11013 |
| | 442 | 11026 | 11027 | 11028 | 11029 | 11030 | 11031 | 11032 | 11033 | 11034 | 11035 | 11036 | 11037 | 11038 |
| | 443 | 11051 | 11052 | 11053 | 11054 | 11055 | 11056 | 11057 | 11058 | 11059 | 11060 | 11061 | 11062 | 11063 |
| | 444 | 11076 | 11077 | 11078 | 11079 | 11080 | 11081 | 11082 | 1083 | 11084 | 11085 | 11086 | 11087 | 11088 |
| | 445 | 11101 | 11102 | 11103 | 11104 | 11105 | 11106 | 11107 | 11108 | 11109 | 11110 | 11111 | 11112 | 11113 |
| | 446 | 11126 | 11127 | 11128 | 11129 | 11130 | 11131 | 11132 | 11133 | 11134 | 11135 | 11136 | 11137 | 11138 |
| | 447 | 11151 | 11152 | 11153 | 11154 | 11155 | 11156 | 11157 | 11158 | 11159 | 11160 | 11161 | 11162 | 11163 |
| | 448 | 11176 | 11177 | 11178 | 11179 | 11180 | 11181 | 11182 | 11183 | 11184 | 11185 | 11186 | 11187 | 11188 |
| | 449 | 11201 | 11202 | 11203 | 11204 | 11205 | 11206 | 11207 | 11208 | 11209 | 11210 | 11211 | 11212 | 11213 |
| | 450 | 11226 | 11227 | 11228 | 11229 | 11230 | 11231 | 11232 | 11233 | 11234 | 11235 | 11236 | 11237 | 11238 |
| | 451 | 11251 | 11252 | 11253 | 11254 | 11255 | 11256 | 11257 | 11258 | 11259 | 11260 | 11261 | 11262 | 11263 |
| | 452 | 11276 | 11277 | 11278 | 11279 | 11280 | 11281 | 11282 | 11283 | 11284 | 11285 | 11286 | 11287 | 11288 |
| | 453 | 11301 | 11302 | 11303 | 11304 | 11305 | 11306 | 11307 | 11308 | 11309 | 11310 | 11311 | 11312 | 11313 |
| | 454 | 11326 | 11327 | 11328 | 11329 | 11330 | 11331 | 11332 | 11333 | 11334 | 11335 | 11336 | 11337 | 11338 |
| | 455 | 11351 | 11352 | 11353 | 11354 | 11355 | 11356 | 11357 | 11358 | 11359 | 11360 | 11361 | 11362 | 11363 |
| | 456 | 11376 | 11377 | 11378 | 11379 | 11380 | 11381 | 11382 | 11383 | 11384 | 11385 | 11386 | 11387 | 11388 |
| | 457 | 11401 | 11402 | 11403 | 11404 | 11405 | 11406 | 11407 | 11408 | 11409 | 11410 | 11411 | 11412 | 11413 |
| | 458 | 11426 | 11427 | 11428 | 11429 | 11430 | 11431 | 11432 | 11433 | 11434 | 11435 | 11436 | 11437 | 11438 |
| | 459 | 11451 | 11452 | 11453 | 11454 | 11455 | 11456 | 11457 | 11458 | 11459 | 11460 | 11461 | 11462 | 11463 |
| | 460 | 11476 | 11477 | 11478 | 11479 | 11480 | 11481 | 11482 | 11483 | 11484 | 11485 | 11486 | 11487 | 11488 |
| | 461 | 11501 | 11502 | 11503 | 11504 | 11505 | 11506 | 11507 | 11508 | 11509 | 11510 | 11511 | 11512 | 11513 |
| | 462 | 11526 | 11527 | 11528 | 11529 | 11530 | 11531 | 11532 | 11533 | 11534 | 11535 | 11536 | 11537 | 11538 |
| | 463 | 11551 | 11552 | 11553 | 11554 | 11555 | 11556 | 11557 | 11558 | 11559 | 11560 | 11561 | 11562 | 11563 |
| | 464 | 11576 | 11577 | 11578 | 11579 | 11580 | 11581 | 11582 | 11583 | 11584 | 11585 | 11586 | 11587 | 11588 |
| | 465 | 11601 | 11602 | 11603 | 11604 | 11605 | 11606 | 11607 | 11608 | 11609 | 11610 | 11611 | 11612 | 11613 |
| | 466 | 11626 | 11627 | 11628 | 11629 | 11630 | 11631 | 11632 | 11633 | 11634 | 11635 | 11636 | 11637 | 11638 |
| | 467 | 11651 | 11652 | 11653 | 11654 | 11655 | 11656 | 11657 | 11658 | 11659 | 11660 | 11661 | 11662 | 11663 |
| | 468 | 11676 | 11677 | 11678 | 11679 | 11680 | 11681 | 11682 | 11683 | 11684 | 11685 | 11686 | 11687 | 11688 |
| | 469 | 11701 | 11702 | 11703 | 11704 | 11705 | 11706 | 11707 | 11708 | 11709 | 11710 | 11711 | 11712 | 11713 |
| | 470 | 11726 | 11727 | 11728 | 11729 | 11730 | 11731 | 11732 | 11733 | 11734 | 11735 | 11736 | 11737 | 11738 |
| | 471 | 11751 | 11752 | 11753 | 11754 | 11755 | 11756 | 11757 | 11758 | 11759 | 11760 | 11761 | 11762 | 11763 |
| | 472 | 11776 | 11777 | 11778 | 11779 | 11780 | 11781 | 11782 | 11783 | 11784 | 11785 | 11786 | 11787 | 11788 |
| | 473 | 11801 | 11802 | 11803 | 11804 | 11805 | 11806 | 11807 | 11808 | 11809 | 11810 | 11811 | 11812 | 11813 |
| | 474 | 11826 | 11827 | 11828 | 11829 | 11830 | 11831 | 11832 | 11833 | 11834 | 11835 | 1836 | 11837 | 11838 |
| | 475 | 11851 | 11852 | 11853 | 11854 | 11855 | 11856 | 11857 | 11858 | 11859 | 11860 | 11861 | 11862 | 11863 |
| | 476 | 11876 | 11877 | 11878 | 11879 | 11880 | 11881 | 11882 | 11883 | 11884 | 11885 | 11886 | 11887 | 11888 |
| | 477 | 11901 | 11902 | 11903 | 11904 | 11905 | 11906 | 11907 | 11908 | 11909 | 11910 | 11911 | 11912 | 11913 |
| | 478 | 11926 | 11927 | 11928 | 11929 | 11930 | 11931 | 11932 | 11933 | 11934 | 11935 | 11936 | 11937 | 11938 |
| | 479 | 11951 | 11952 | 11953 | 11954 | 11955 | 11956 | 11957 | 11958 | 11959 | 11960 | 11961 | 11962 | 11963 |
| | 480 | 11976 | 11977 | 11978 | 11979 | 11980 | 11981 | 11982 | 11983 | 11984 | 11985 | 11986 | 11987 | 11988 |
| | 481 | 12001 | 12002 | 12003 | 12004 | 12005 | 12006 | 12007 | 12008 | 12009 | 12010 | 12011 | 12012 | 12013 |
| | 482 | 12026 | 12027 | 12028 | 12029 | 12030 | 12031 | 12032 | 12033 | 12034 | 12035 | 12036 | 12037 | 12038 |
| | 483 | 12051 | 12052 | 12053 | 12054 | 12055 | 12056 | 12057 | 12058 | 12059 | 12060 | 12061 | 12062 | 12063 |
| | 484 | 12076 | 12077 | 12078 | 12079 | 12080 | 12081 | 12082 | 12083 | 12084 | 12085 | 12086 | 12087 | 12088 |
| | 485 | 12101 | 12102 | 12103 | 12104 | 12105 | 12106 | 12107 | 12108 | 12109 | 12110 | 12111 | 12112 | 12113 |
| | 486 | 12126 | 12127 | 12128 | 12129 | 12130 | 12131 | 12132 | 12133 | 12134 | 12135 | 12136 | 12137 | 12138 |
| | 487 | 12151 | 12152 | 12153 | 12154 | 12155 | 12156 | 12157 | 12158 | 12159 | 12160 | 12161 | 12162 | 12163 |
| | 488 | 12176 | 12177 | 12178 | 12179 | 12180 | 12181 | 12182 | 12183 | 12184 | 12185 | 12186 | 12187 | 12188 |
| | 489 | 12201 | 12202 | 12203 | 12204 | 12205 | 12206 | 12207 | 12208 | 12209 | 12210 | 12211 | 2212 | 12213 |
| | 490 | 12226 | 12227 | 12228 | 12229 | 12230 | 12231 | 12232 | 12233 | 12234 | 12235 | 12236 | 12237 | 12238 |
| | 491 | 12251 | 12252 | 12253 | 12254 | 12255 | 12256 | 12257 | 12258 | 12259 | 12260 | 12261 | 12262 | 12263 |
| | 492 | 12276 | 12277 | 12278 | 12279 | 12280 | 12281 | 12282 | 12283 | 12284 | 12285 | 12286 | 12287 | 12288 |
| | 493 | 12301 | 12302 | 12303 | 12304 | 12305 | 12306 | 12307 | 12308 | 12309 | 12310 | 12311 | 12312 | 12313 |
| | 494 | 12326 | 12327 | 12328 | 12329 | 12330 | 12331 | 12332 | 12333 | 12334 | 12335 | 12336 | 12337 | 12338 |
| | 495 | 12351 | 12352 | 12353 | 12354 | 12355 | 12356 | 12357 | 12358 | 12359 | 12360 | 12361 | 12362 | 12363 |

| | | Third organic compound | | | | | | | | | | | |
|---|---|---|---|---|---|---|---|---|---|---|---|---|---|
| | | D14 | D15 | D16 | D17 | D18 | D19 | D20 | D21 | D22 | D23 | D24 | D25 |
| Second organic compound | 441 | 11014 | 11015 | 11016 | 11017 | 11018 | 11019 | 11020 | 11021 | 11022 | 11023 | 11024 | 11025 |
| | 442 | 11039 | 11040 | 11041 | 11042 | 11043 | 11044 | 11045 | 11046 | 11047 | 11048 | 11049 | 11050 |
| | 443 | 11064 | 11065 | 11066 | 11067 | 11068 | 11069 | 11070 | 11071 | 11072 | 11073 | 11074 | 11075 |
| | 444 | 11089 | 11090 | 11091 | 11092 | 11093 | 11094 | 11095 | 11096 | 11097 | 11098 | 11099 | 11100 |
| | 445 | 11114 | 11115 | 11116 | 11117 | 11118 | 11119 | 11120 | 11121 | 11122 | 11123 | 11124 | 11125 |
| | 446 | 11139 | 11140 | 11141 | 11142 | 11143 | 11144 | 11145 | 11146 | 11147 | 11148 | 11149 | 11150 |
| | 447 | 11164 | 11165 | 11166 | 11167 | 11168 | 11169 | 11170 | 11171 | 11172 | 11173 | 11174 | 11175 |
| | 448 | 11189 | 11190 | 11191 | 11192 | 11193 | 11194 | 11195 | 11196 | 11197 | 11198 | 11199 | 11200 |

-continued

| | | | | | | | | | | | | |
|---|---|---|---|---|---|---|---|---|---|---|---|---|
| 449 | 11214 | 11215 | 11216 | 11217 | 11218 | 11219 | 11220 | 11221 | 11222 | 11223 | 11224 | 11225 |
| 450 | 11239 | 11240 | 11241 | 11242 | 11243 | 11244 | 11245 | 11246 | 11247 | 11248 | 11249 | 11250 |
| 451 | 11264 | 11265 | 11266 | 11267 | 11268 | 11269 | 11270 | 11271 | 11272 | 11273 | 11274 | 11275 |
| 452 | 11289 | 11290 | 11291 | 11292 | 11293 | 11294 | 11295 | 11296 | 11297 | 11298 | 11299 | 11300 |
| 453 | 11314 | 11315 | 11316 | 11317 | 11318 | 11319 | 11320 | 11321 | 11322 | 11323 | 11324 | 11325 |
| 454 | 11339 | 11340 | 11341 | 11342 | 11343 | 11344 | 11345 | 11346 | 11347 | 11348 | 11349 | 11350 |
| 455 | 11364 | 11365 | 11366 | 11367 | 11368 | 11369 | 11370 | 11371 | 11372 | 11373 | 11374 | 11375 |
| 456 | 11389 | 11390 | 11391 | 11392 | 11393 | 11394 | 11395 | 11396 | 11397 | 11398 | 11399 | 11400 |
| 457 | 11414 | 11415 | 11416 | 11417 | 11418 | 11419 | 11420 | 11421 | 11422 | 11423 | 11424 | 11425 |
| 458 | 11439 | 11440 | 11441 | 11442 | 11443 | 11444 | 11445 | 11446 | 11447 | 11448 | 11449 | 11450 |
| 459 | 11464 | 11465 | 11466 | 11467 | 11468 | 11469 | 11470 | 11471 | 11472 | 11473 | 11474 | 11475 |
| 460 | 11489 | 11490 | 11491 | 11492 | 11493 | 11494 | 11495 | 11496 | 11497 | 11498 | 11499 | 11500 |
| 461 | 11514 | 11515 | 11516 | 11517 | 11518 | 11519 | 11520 | 11521 | 11522 | 11523 | 11524 | 11525 |
| 462 | 11539 | 11540 | 11541 | 11542 | 11543 | 11544 | 11545 | 11546 | 11547 | 11548 | 11549 | 11550 |
| 463 | 11564 | 11565 | 11566 | 11567 | 11568 | 11569 | 11570 | 11571 | 11572 | 11573 | 11574 | 11575 |
| 464 | 11589 | 11590 | 11591 | 11592 | 11593 | 11594 | 11595 | 11596 | 11597 | 11598 | 11599 | 11600 |
| 465 | 11614 | 11615 | 11616 | 11617 | 11618 | 11619 | 11620 | 11621 | 11622 | 11623 | 11624 | 11625 |
| 466 | 11639 | 11640 | 11641 | 11642 | 11643 | 11644 | 11645 | 11646 | 11647 | 11648 | 11649 | 11650 |
| 467 | 11664 | 11665 | 11666 | 11667 | 11668 | 11669 | 11670 | 11671 | 11672 | 11673 | 11674 | 11675 |
| 468 | 11689 | 11690 | 11691 | 11692 | 11693 | 11694 | 11695 | 11696 | 11697 | 11698 | 11699 | 11700 |
| 469 | 11714 | 11715 | 11716 | 11717 | 11718 | 11719 | 11720 | 11721 | 11722 | 11723 | 11724 | 11725 |
| 470 | 11739 | 11740 | 11741 | 11742 | 11743 | 11744 | 11745 | 11746 | 11747 | 11748 | 11749 | 11750 |
| 471 | 11764 | 11765 | 11766 | 11767 | 11768 | 11769 | 11770 | 11771 | 11772 | 11773 | 11774 | 11775 |
| 472 | 11789 | 11790 | 11791 | 11792 | 11793 | 11794 | 11795 | 11796 | 11797 | 11798 | 11799 | 11800 |
| 473 | 11814 | 11815 | 11816 | 11817 | 11818 | 11819 | 11820 | 11821 | 11822 | 11823 | 11824 | 11825 |
| 474 | 11839 | 11840 | 11841 | 11842 | 11843 | 11844 | 1845 | 11846 | 11847 | 11848 | 11849 | 11850 |
| 475 | 11864 | 11865 | 11866 | 11867 | 11868 | 11869 | 11870 | 11871 | 11872 | 11873 | 11874 | 11875 |
| 476 | 11889 | 11890 | 11891 | 11892 | 11893 | 11894 | 11895 | 11896 | 11897 | 11898 | 11899 | 11900 |
| 477 | 11914 | 11915 | 11916 | 11917 | 11918 | 11919 | 11920 | 11921 | 11922 | 11923 | 11924 | 11925 |
| 478 | 11939 | 11940 | 11941 | 11942 | 11943 | 11944 | 11945 | 11946 | 11947 | 11948 | 11949 | 11950 |
| 479 | 11964 | 11965 | 11966 | 11967 | 11968 | 11969 | 11970 | 11971 | 11972 | 11973 | 11974 | 11975 |
| 480 | 11989 | 11990 | 11991 | 11992 | 11993 | 11994 | 11995 | 11996 | 11997 | 11998 | 11999 | 12000 |
| 481 | 12014 | 12015 | 12016 | 12017 | 12018 | 12019 | 12020 | 12021 | 12022 | 12023 | 12024 | 12025 |
| 482 | 12039 | 12040 | 12041 | 12042 | 12043 | 12044 | 12045 | 12046 | 12047 | 12048 | 12049 | 12050 |
| 483 | 12064 | 12065 | 12066 | 12067 | 12068 | 12069 | 12070 | 12071 | 12072 | 12073 | 12074 | 12075 |
| 484 | 12089 | 12090 | 12091 | 12092 | 12093 | 12094 | 12095 | 12096 | 12097 | 12098 | 12099 | 12100 |
| 485 | 12114 | 12115 | 12116 | 12117 | 12118 | 12119 | 12120 | 12121 | 12122 | 12123 | 12124 | 12125 |
| 486 | 12139 | 12140 | 12141 | 12142 | 12143 | 12144 | 12145 | 12146 | 12147 | 12148 | 12149 | 12150 |
| 487 | 12164 | 12165 | 12166 | 12167 | 12168 | 12169 | 12170 | 12171 | 12172 | 12173 | 12174 | 12175 |
| 488 | 12189 | 12190 | 12191 | 12192 | 12193 | 12194 | 12195 | 12196 | 12197 | 12198 | 12199 | 12200 |
| 489 | 12214 | 12215 | 12216 | 12217 | 12218 | 12219 | 12220 | 12221 | 12222 | 12223 | 12224 | 12225 |
| 490 | 12239 | 12240 | 12241 | 12242 | 12243 | 12244 | 12245 | 12246 | 12247 | 12248 | 12249 | 12250 |
| 491 | 12264 | 12265 | 12266 | 12267 | 12268 | 12269 | 12270 | 12271 | 12272 | 12273 | 12274 | 12275 |
| 492 | 12289 | 12290 | 12291 | 12292 | 12293 | 12294 | 12295 | 12296 | 12297 | 12298 | 12299 | 12300 |
| 493 | 12314 | 12315 | 12316 | 12317 | 12318 | 12319 | 12320 | 12321 | 12322 | 12323 | 12324 | 12325 |
| 494 | 12339 | 12340 | 12341 | 12342 | 12343 | 12344 | 12345 | 12346 | 12347 | 12348 | 12349 | 12350 |
| 495 | 12364 | 12365 | 12366 | 12367 | 12368 | 12369 | 12370 | 12371 | 12372 | 12373 | 12374 | 12375 |

| | Third organic compound | | | | | | | | | | | |
|---|---|---|---|---|---|---|---|---|---|---|---|---|
| | D1 | D2 | D3 | D4 | D5 | D6 | D7 | D8 | D9 | D10 | D11 | D12 | D13 |
| 496 | 12376 | 12377 | 12378 | 12379 | 12380 | 12381 | 12382 | 12383 | 12384 | 12385 | 12386 | 12387 | 12388 |
| 497 | 12401 | 12402 | 12403 | 12404 | 12405 | 12406 | 12407 | 12408 | 12409 | 12410 | 12411 | 12412 | 12413 |
| 498 | 12426 | 12427 | 12428 | 12429 | 12430 | 12431 | 12432 | 12433 | 12434 | 12435 | 12436 | 12437 | 12438 |
| 499 | 12451 | 12452 | 12453 | 12454 | 12455 | 12456 | 12457 | 12458 | 12459 | 12460 | 12461 | 12462 | 12463 |
| 500 | 12476 | 12477 | 12478 | 12479 | 12480 | 12481 | 12482 | 12483 | 12484 | 12485 | 12486 | 12487 | 12488 |
| 501 | 12501 | 12502 | 12503 | 12504 | 12505 | 12506 | 12507 | 12508 | 2509 | 12510 | 12511 | 12512 | 12513 |
| 502 | 12526 | 12527 | 12528 | 12529 | 12530 | 12531 | 12532 | 12533 | 12534 | 12535 | 12536 | 12537 | 12538 |
| 503 | 12551 | 12552 | 12553 | 12554 | 12555 | 12556 | 12557 | 12558 | 12559 | 12560 | 12561 | 12562 | 12563 |
| 504 | 12576 | 12577 | 12578 | 12579 | 12580 | 12581 | 12582 | 12583 | 12584 | 12585 | 12586 | 12587 | 12588 |
| 505 | 12601 | 12602 | 12603 | 12604 | 12605 | 12606 | 12607 | 12608 | 12609 | 12610 | 12611 | 12612 | 12613 |
| 506 | 12626 | 12627 | 12628 | 12629 | 12630 | 12631 | 12632 | 12633 | 12634 | 12635 | 12636 | 12637 | 12638 |
| 507 | 12651 | 12652 | 12653 | 12654 | 12655 | 12656 | 12657 | 12658 | 12659 | 12660 | 12661 | 12662 | 12663 |
| 508 | 12676 | 12677 | 12678 | 12679 | 12680 | 12681 | 12682 | 12683 | 12684 | 12685 | 12686 | 12687 | 12688 |
| 509 | 12701 | 12702 | 12703 | 12704 | 12705 | 12706 | 12707 | 12708 | 12709 | 12710 | 12711 | 12712 | 12713 |
| 510 | 12726 | 12727 | 12728 | 12729 | 12730 | 12731 | 12732 | 12733 | 12734 | 12735 | 12736 | 12737 | 12738 |
| 511 | 12751 | 12752 | 12753 | 12754 | 12755 | 12756 | 12757 | 12758 | 12759 | 12760 | 12761 | 12762 | 12763 |
| 512 | 12776 | 12777 | 12778 | 12779 | 12780 | 12781 | 12782 | 12783 | 12784 | 12785 | 12786 | 12787 | 12788 |
| 513 | 12801 | 12802 | 12803 | 12804 | 12805 | 12806 | 12807 | 12808 | 12809 | 12810 | 12811 | 12812 | 12813 |
| 514 | 12826 | 12827 | 12828 | 12829 | 12830 | 12831 | 12832 | 12833 | 12834 | 12835 | 12836 | 12837 | 12838 |
| 515 | 12851 | 12852 | 12853 | 12854 | 12855 | 12856 | 12857 | 12858 | 12859 | 12860 | 12861 | 12862 | 12863 |
| 516 | 12876 | 12877 | 12878 | 12879 | 12880 | 12881 | 12882 | 12883 | 12884 | 12885 | 12886 | 12887 | 12888 |
| 517 | 12901 | 12902 | 12903 | 12904 | 12905 | 12906 | 12907 | 12908 | 12909 | 12910 | 12911 | 12912 | 12913 |
| 518 | 12926 | 12927 | 12928 | 12929 | 12930 | 12931 | 12932 | 12933 | 12934 | 12935 | 12936 | 12937 | 12938 |
| 519 | 12951 | 12952 | 12953 | 12954 | 12955 | 12956 | 12957 | 12958 | 12959 | 12960 | 12961 | 12962 | 12963 |

-continued

| | | | | | | | | | | | | |
|---|---|---|---|---|---|---|---|---|---|---|---|---|
| 520 | 12976 | 12977 | 12978 | 12979 | 12980 | 12981 | 12982 | 12983 | 12984 | 12985 | 12986 | 12987 | 12988 |
| 521 | 13001 | 13002 | 13003 | 13004 | 13005 | 13006 | 13007 | 13008 | 13009 | 13010 | 13011 | 13012 | 13013 |
| 522 | 13026 | 13027 | 13028 | 13029 | 13030 | 13031 | 13032 | 13033 | 13034 | 13035 | 13036 | 13037 | 13038 |
| 523 | 13051 | 13052 | 13053 | 13054 | 13055 | 13056 | 13057 | 13058 | 13059 | 13060 | 13061 | 13062 | 13063 |
| 524 | 13076 | 13077 | 13078 | 13079 | 13080 | 13081 | 13082 | 13083 | 13084 | 13085 | 13086 | 13087 | 13088 |
| 525 | 13101 | 13102 | 13103 | 13104 | 13105 | 13106 | 13107 | 13108 | 13109 | 13110 | 13111 | 13112 | 13113 |
| 526 | 13126 | 13127 | 13128 | 13129 | 13130 | 13131 | 13132 | 13133 | 13134 | 13135 | 13136 | 13137 | 13138 |
| 527 | 13151 | 13152 | 13153 | 13154 | 13155 | 13156 | 13157 | 13158 | 13159 | 13160 | 13161 | 13162 | 13163 |
| 528 | 13176 | 13177 | 13178 | 13179 | 13180 | 13181 | 13182 | 13183 | 13184 | 13185 | 13186 | 13187 | 13188 |
| 529 | 13201 | 13202 | 13203 | 13204 | 13205 | 13206 | 13207 | 13208 | 13209 | 13210 | 13211 | 13212 | 13213 |
| 530 | 13226 | 13227 | 13228 | 13229 | 13230 | 13231 | 13232 | 13233 | 13234 | 13235 | 13236 | 13237 | 13238 |
| 531 | 13251 | 13252 | 13253 | 13254 | 13255 | 13256 | 13257 | 13258 | 13259 | 13260 | 13261 | 13262 | 13263 |
| 532 | 13276 | 13277 | 13278 | 13279 | 13280 | 13281 | 13282 | 13283 | 13284 | 13285 | 13286 | 13287 | 13288 |
| 533 | 13301 | 13302 | 13303 | 13304 | 13305 | 13306 | 13307 | 13308 | 13309 | 13310 | 13311 | 13312 | 13313 |
| 534 | 13326 | 13327 | 13328 | 13329 | 13330 | 13331 | 13332 | 13333 | 13334 | 13335 | 13336 | 13337 | 13338 |
| 535 | 13351 | 13352 | 13353 | 13354 | 13355 | 13356 | 13357 | 13358 | 13359 | 13360 | 13361 | 13362 | 13363 |
| 536 | 13376 | 13377 | 13378 | 13379 | 13380 | 13381 | 13382 | 13383 | 13384 | 13385 | 13386 | 13387 | 13388 |
| 537 | 13401 | 13402 | 13403 | 13404 | 13405 | 13406 | 13407 | 13408 | 13409 | 13410 | 13411 | 13412 | 13413 |
| 538 | 13426 | 13427 | 13428 | 13429 | 13430 | 13431 | 13432 | 13433 | 13434 | 13435 | 13436 | 13437 | 13438 |
| 539 | 13451 | 13452 | 13453 | 13454 | 13455 | 13456 | 13457 | 13458 | 13459 | 13460 | 13461 | 13462 | 13463 |
| 540 | 13476 | 13477 | 13478 | 13479 | 13480 | 13481 | 13482 | 13483 | 13484 | 13485 | 13486 | 13487 | 13488 |
| 541 | 13501 | 13502 | 13503 | 13504 | 13505 | 13506 | 13507 | 13508 | 13509 | 13510 | 13511 | 13512 | 13513 |
| 542 | 13526 | 13527 | 13528 | 13529 | 13530 | 13531 | 13532 | 13533 | 13534 | 13535 | 13536 | 13537 | 13538 |
| 543 | 13551 | 13552 | 13553 | 13554 | 13555 | 13556 | 13557 | 13558 | 13559 | 13560 | 13561 | 13562 | 13563 |
| 544 | 13576 | 13577 | 13578 | 13579 | 13580 | 13581 | 13582 | 13583 | 13584 | 13585 | 13586 | 13587 | 13588 |
| 545 | 13601 | 13602 | 13603 | 13604 | 13605 | 13606 | 13607 | 13608 | 13609 | 13610 | 13611 | 13612 | 13613 |
| 546 | 13626 | 13627 | 13628 | 13629 | 13630 | 13631 | 13632 | 13633 | 13634 | 13635 | 13636 | 13637 | 13638 |
| 547 | 13651 | 13652 | 13653 | 13654 | 13655 | 13656 | 13657 | 13658 | 13659 | 13660 | 13661 | 13662 | 13663 |
| 548 | 13676 | 13677 | 13678 | 13679 | 13680 | 13681 | 13682 | 13683 | 13684 | 13685 | 13686 | 13687 | 13688 |
| 549 | 13701 | 13702 | 13703 | 13704 | 13705 | 13706 | 13707 | 13708 | 13709 | 13710 | 13711 | 13712 | 13713 |
| 550 | 13726 | 13727 | 13728 | 13729 | 13730 | 13731 | 13732 | 13733 | 13734 | 13735 | 13736 | 13737 | 13738 |

| | Third organic compound | | | | | | | | | | | |
|---|---|---|---|---|---|---|---|---|---|---|---|---|
| | D14 | D15 | D16 | D17 | D18 | D19 | D20 | D21 | D22 | D23 | D24 | D25 |
| 496 | 12389 | 12390 | 12391 | 12392 | 12393 | 12394 | 12395 | 12396 | 12397 | 12398 | 12399 | 12400 |
| 497 | 12414 | 12415 | 12416 | 12417 | 12418 | 12419 | 12420 | 12421 | 12422 | 12423 | 12424 | 12425 |
| 498 | 12439 | 12440 | 12441 | 12442 | 12443 | 12444 | 12445 | 12446 | 12447 | 12448 | 12449 | 12450 |
| 499 | 12464 | 12465 | 12466 | 12467 | 12468 | 12469 | 12470 | 12471 | 12472 | 12473 | 12474 | 12475 |
| 500 | 12489 | 12490 | 12491 | 12492 | 12493 | 12494 | 12495 | 12496 | 12497 | 12498 | 12499 | 12500 |
| 501 | 12514 | 12515 | 12516 | 12517 | 12518 | 12519 | 12520 | 12521 | 12522 | 12523 | 12524 | 12525 |
| 502 | 12539 | 12540 | 12541 | 12542 | 12543 | 12544 | 12545 | 12546 | 12547 | 12548 | 12549 | 12550 |
| 503 | 12564 | 12565 | 12566 | 12567 | 12568 | 12569 | 12570 | 12571 | 12572 | 12573 | 12574 | 12575 |
| 504 | 12589 | 12590 | 12591 | 12592 | 12593 | 12594 | 12595 | 12596 | 12597 | 12598 | 12599 | 12600 |
| 505 | 12614 | 12615 | 12616 | 12617 | 12618 | 12619 | 12620 | 12621 | 12622 | 12623 | 12624 | 12625 |
| 506 | 12639 | 12640 | 12641 | 12642 | 12643 | 12644 | 12645 | 12646 | 12647 | 12648 | 12649 | 12650 |
| 507 | 12664 | 12665 | 12666 | 12667 | 12668 | 12669 | 12670 | 12671 | 12672 | 12673 | 12674 | 12675 |
| 508 | 12689 | 12690 | 12691 | 12692 | 12693 | 12694 | 12695 | 12696 | 12697 | 12698 | 12699 | 12700 |
| 509 | 12714 | 12715 | 12716 | 12717 | 12718 | 12719 | 12720 | 12721 | 12722 | 12723 | 12724 | 12725 |
| 510 | 12739 | 12740 | 12741 | 12742 | 12743 | 12744 | 12745 | 12746 | 12747 | 12748 | 12749 | 12750 |
| 511 | 12764 | 12765 | 12766 | 12767 | 12768 | 12769 | 12770 | 12771 | 12772 | 12773 | 12774 | 12775 |
| 512 | 12789 | 12790 | 12791 | 12792 | 12793 | 12794 | 12795 | 12796 | 12797 | 12798 | 12799 | 12800 |
| 513 | 12814 | 12815 | 12816 | 12817 | 12818 | 12819 | 12820 | 12821 | 12822 | 12823 | 12824 | 12825 |
| 514 | 12839 | 12840 | 12841 | 12842 | 12843 | 12844 | 12845 | 12846 | 12847 | 12848 | 12849 | 12850 |
| 515 | 12864 | 12865 | 12866 | 12867 | 12868 | 12869 | 12870 | 12871 | 12872 | 12873 | 12874 | 12875 |
| 516 | 12889 | 12890 | 12891 | 12892 | 12893 | 12894 | 12895 | 12896 | 12897 | 12898 | 12899 | 12900 |
| 517 | 12914 | 12915 | 12916 | 12917 | 12918 | 12919 | 12920 | 12921 | 12922 | 12923 | 12924 | 12925 |
| 518 | 12939 | 12940 | 12941 | 12942 | 12943 | 12944 | 12945 | 12946 | 12947 | 12948 | 12949 | 12950 |
| 519 | 12964 | 12965 | 12966 | 12967 | 12968 | 12969 | 12970 | 12971 | 12972 | 12973 | 12974 | 12975 |
| 520 | 12989 | 12990 | 12991 | 12992 | 12993 | 12994 | 12995 | 12996 | 12997 | 12998 | 12999 | 13000 |
| 521 | 13014 | 13015 | 13016 | 13017 | 13018 | 13019 | 13020 | 13021 | 13022 | 13023 | 13024 | 13025 |
| 522 | 13039 | 13040 | 13041 | 13042 | 13043 | 13044 | 13045 | 13046 | 13047 | 13048 | 13049 | 13050 |
| 523 | 13064 | 13065 | 13066 | 13067 | 13068 | 13069 | 13070 | 13071 | 13072 | 13073 | 13074 | 13075 |
| 524 | 13089 | 13090 | 13091 | 13092 | 13093 | 13094 | 13095 | 13096 | 13097 | 13098 | 13099 | 13100 |
| 525 | 13114 | 13115 | 13116 | 13117 | 13118 | 13119 | 13120 | 13121 | 13122 | 13123 | 13124 | 13125 |
| 526 | 13139 | 13140 | 13141 | 13142 | 13143 | 13144 | 13145 | 13146 | 13147 | 13148 | 13149 | 13150 |
| 527 | 13164 | 13165 | 13166 | 13167 | 13168 | 13169 | 13170 | 13171 | 13172 | 13173 | 13174 | 13175 |
| 528 | 13189 | 13190 | 13191 | 13192 | 13193 | 13194 | 13195 | 13196 | 13197 | 13198 | 13199 | 13200 |
| 529 | 13214 | 13215 | 13216 | 13217 | 13218 | 13219 | 13220 | 13221 | 13222 | 13223 | 13224 | 13225 |
| 530 | 13239 | 13240 | 13241 | 13242 | 13243 | 13244 | 13245 | 13246 | 13247 | 13248 | 13249 | 13250 |
| 531 | 13264 | 13265 | 13266 | 13267 | 13268 | 13269 | 13270 | 13271 | 13272 | 13273 | 13274 | 13275 |
| 532 | 13289 | 13290 | 13291 | 13292 | 13293 | 13294 | 13295 | 3296 | 13297 | 13298 | 13299 | 13300 |
| 533 | 13314 | 13315 | 13316 | 13317 | 13318 | 13319 | 13320 | 13321 | 13322 | 13323 | 13324 | 13325 |
| 534 | 13339 | 13340 | 13341 | 13342 | 13343 | 13344 | 13345 | 13346 | 13347 | 13348 | 13349 | 13350 |
| 535 | 13364 | 13365 | 13366 | 13367 | 13368 | 13369 | 13370 | 13371 | 13372 | 13373 | 13374 | 13375 |
| 536 | 13389 | 13390 | 13391 | 13392 | 13393 | 13394 | 13395 | 13396 | 13397 | 13398 | 13399 | 13400 |
| 537 | 13414 | 13415 | 13416 | 13417 | 13418 | 13419 | 13420 | 13421 | 13422 | 13423 | 13424 | 13425 |
| 538 | 13439 | 13440 | 13441 | 13442 | 13443 | 13444 | 13445 | 13446 | 13447 | 13448 | 13449 | 13450 |

-continued

| | | | | | | | | | | | | |
|---|---|---|---|---|---|---|---|---|---|---|---|---|
| 539 | 13464 | 13465 | 13466 | 13467 | 13468 | 13469 | 13470 | 13471 | 13472 | 13473 | 13474 | 13475 |
| 540 | 13489 | 13490 | 13491 | 13492 | 13493 | 13494 | 13495 | 13496 | 13497 | 13498 | 13499 | 13500 |
| 541 | 13514 | 13515 | 13516 | 13517 | 13518 | 13519 | 13520 | 13521 | 13522 | 13523 | 13524 | 13525 |
| 542 | 13539 | 13540 | 13541 | 13542 | 13543 | 13544 | 13545 | 13546 | 13547 | 13548 | 13549 | 13550 |
| 543 | 13564 | 13565 | 13566 | 13567 | 13568 | 13569 | 13570 | 13571 | 13572 | 13573 | 13574 | 13575 |
| 544 | 13589 | 13590 | 13591 | 13592 | 13593 | 13594 | 13595 | 13596 | 13597 | 13598 | 13599 | 13600 |
| 545 | 13614 | 13615 | 13616 | 13617 | 13618 | 13619 | 13620 | 13621 | 13622 | 13623 | 13624 | 13625 |
| 546 | 13639 | 13640 | 13641 | 13642 | 13643 | 13644 | 13645 | 13646 | 13647 | 13648 | 13649 | 13650 |
| 547 | 13664 | 13665 | 13666 | 13667 | 13668 | 13669 | 13670 | 13671 | 13672 | 13673 | 13674 | 13675 |
| 548 | 13689 | 13690 | 13691 | 13692 | 13693 | 13694 | 13695 | 13696 | 13697 | 13698 | 13699 | 13700 |
| 549 | 13714 | 13715 | 13716 | 13717 | 13718 | 13719 | 13720 | 13721 | 13722 | 13723 | 13724 | 13725 |
| 550 | 13739 | 13740 | 13741 | 13742 | 13743 | 13744 | 13745 | 13746 | 13747 | 13748 | 13749 | 13750 |

| | | Third organic compound | | | | | | | | | | | | |
|---|---|---|---|---|---|---|---|---|---|---|---|---|---|---|
| | | D1 | D2 | D3 | D4 | D5 | D6 | D7 | D8 | D9 | D10 | D11 | D12 | D13 |
| Second organic compound | 551 | 13751 | 13752 | 13753 | 13754 | 13755 | 13756 | 13757 | 13758 | 13759 | 13760 | 13761 | 13762 | 13763 |
| | 552 | 13776 | 13777 | 13778 | 13779 | 13780 | 13781 | 13782 | 13783 | 13784 | 13785 | 13786 | 13787 | 13788 |
| | 553 | 13801 | 13802 | 13803 | 13804 | 13805 | 13806 | 13807 | 13808 | 13809 | 13810 | 13811 | 13812 | 13813 |
| | 554 | 13826 | 13827 | 13828 | 13829 | 13830 | 13831 | 13832 | 13833 | 13834 | 13835 | 13836 | 13837 | 13838 |
| | 555 | 13851 | 13852 | 13853 | 13854 | 13855 | 13856 | 13857 | 13858 | 13859 | 13860 | 13861 | 13862 | 13863 |
| | 556 | 13876 | 13877 | 13878 | 13879 | 13880 | 13881 | 13882 | 13883 | 13884 | 13885 | 13886 | 13887 | 13888 |
| | 557 | 13901 | 13902 | 13903 | 13904 | 13905 | 13906 | 13907 | 13908 | 13909 | 13910 | 13911 | 13912 | 13913 |
| | 558 | 13926 | 13927 | 13928 | 13929 | 13930 | 13931 | 13932 | 13933 | 13934 | 13935 | 13936 | 13937 | 13938 |
| | 559 | 13951 | 13952 | 13953 | 13954 | 13955 | 13956 | 13957 | 13958 | 13959 | 13960 | 13961 | 13962 | 13963 |
| | 560 | 13976 | 13977 | 13978 | 13979 | 13980 | 13981 | 13982 | 13983 | 13984 | 13985 | 13986 | 13987 | 13988 |
| | 561 | 14001 | 14002 | 14003 | 14004 | 14005 | 14006 | 14007 | 14008 | 14009 | 14010 | 14011 | 14012 | 14013 |
| | 562 | 14026 | 14027 | 14028 | 14029 | 14030 | 14031 | 14032 | 14033 | 14034 | 14035 | 14036 | 14037 | 14038 |
| | 563 | 14051 | 14052 | 14053 | 14054 | 14055 | 14056 | 14057 | 14058 | 14059 | 14060 | 14061 | 14062 | 14063 |
| | 564 | 14076 | 14077 | 14078 | 14079 | 14080 | 14081 | 14082 | 14083 | 14084 | 14085 | 14086 | 14087 | 14088 |
| | 565 | 14101 | 14102 | 14103 | 14104 | 14105 | 14106 | 14107 | 14108 | 14109 | 14110 | 14111 | 14112 | 14113 |
| | 566 | 14126 | 14127 | 14128 | 14129 | 14130 | 14131 | 14132 | 14133 | 14134 | 14135 | 14136 | 14137 | 14138 |
| | 567 | 14151 | 14152 | 14153 | 14154 | 14155 | 14156 | 14157 | 14158 | 14159 | 14160 | 14161 | 14162 | 14163 |
| | 568 | 14176 | 14177 | 14178 | 14179 | 14180 | 14181 | 14182 | 14183 | 14184 | 14185 | 14186 | 14187 | 14188 |
| | 569 | 14201 | 14202 | 14203 | 14204 | 14205 | 14206 | 14207 | 14208 | 14209 | 14210 | 14211 | 14212 | 14213 |
| | 570 | 14226 | 14227 | 14228 | 14229 | 14230 | 14231 | 14232 | 14233 | 14234 | 14235 | 14236 | 14237 | 14238 |
| | 571 | 14251 | 14252 | 14253 | 14254 | 14255 | 14256 | 14257 | 14258 | 14259 | 14260 | 14261 | 14262 | 14263 |
| | 572 | 14276 | 14277 | 14278 | 14279 | 14280 | 14281 | 14282 | 14283 | 14284 | 14285 | 14286 | 14287 | 14288 |
| | 573 | 14301 | 14302 | 14303 | 4304 | 14305 | 14306 | 14307 | 14308 | 14309 | 14310 | 14311 | 14312 | 14313 |
| | 574 | 14326 | 14327 | 14328 | 14329 | 14330 | 14331 | 14332 | 14333 | 14334 | 14335 | 14336 | 14337 | 14338 |
| | 575 | 14351 | 14352 | 14353 | 14354 | 14355 | 14356 | 14357 | 14358 | 14359 | 14360 | 14361 | 14362 | 14363 |
| | 576 | 14376 | 14377 | 14378 | 14379 | 14380 | 14381 | 14382 | 14383 | 14384 | 14385 | 14386 | 14387 | 14388 |
| | 577 | 14401 | 14402 | 14403 | 14404 | 14405 | 14406 | 14407 | 14408 | 14409 | 14410 | 14411 | 14412 | 14413 |
| | 578 | 14426 | 14427 | 14428 | 14429 | 14430 | 14431 | 14432 | 14433 | 14434 | 14435 | 14436 | 14437 | 14438 |
| | 579 | 14451 | 14452 | 14453 | 14454 | 14455 | 14456 | 14457 | 14458 | 14459 | 14460 | 14461 | 14462 | 14463 |
| | 580 | 14476 | 14477 | 14478 | 14479 | 14480 | 14481 | 14482 | 14483 | 14484 | 14485 | 14486 | 14487 | 14488 |
| | 581 | 14501 | 14502 | 14503 | 14504 | 14505 | 14506 | 14507 | 14508 | 14509 | 14510 | 14511 | 14512 | 14513 |
| | 582 | 14526 | 14527 | 14528 | 14529 | 14530 | 14531 | 14532 | 14533 | 14534 | 14535 | 14536 | 14537 | 14538 |
| | 583 | 14551 | 14552 | 14553 | 14554 | 14555 | 14556 | 14557 | 14558 | 14559 | 14560 | 14561 | 14562 | 14563 |
| | 584 | 14576 | 14577 | 14578 | 14579 | 14580 | 14581 | 14582 | 14583 | 14584 | 14585 | 14586 | 14587 | 14588 |
| | 585 | 14601 | 14602 | 14603 | 14604 | 14605 | 14606 | 14607 | 14608 | 14609 | 14610 | 14611 | 14612 | 14613 |
| | 586 | 14626 | 14627 | 14628 | 14629 | 14630 | 14631 | 14632 | 14633 | 14634 | 14635 | 14636 | 14637 | 14638 |
| | 587 | 14651 | 14652 | 14653 | 14654 | 14655 | 14656 | 14657 | 14658 | 14659 | 14660 | 14661 | 14662 | 14663 |
| | 588 | 14676 | 14677 | 14678 | 14679 | 14680 | 14681 | 14682 | 14683 | 14684 | 14685 | 14686 | 14687 | 14688 |
| | 589 | 14701 | 14702 | 14703 | 14704 | 14705 | 14706 | 14707 | 14708 | 14709 | 14710 | 14711 | 14712 | 14713 |
| | 590 | 14726 | 14727 | 14728 | 14729 | 14730 | 14731 | 14732 | 14733 | 14734 | 14735 | 14736 | 14737 | 14738 |
| | 591 | 14751 | 14752 | 14753 | 14754 | 14755 | 14756 | 14757 | 14758 | 14759 | 14760 | 14761 | 14762 | 14763 |
| | 592 | 14776 | 14777 | 14778 | 14779 | 14780 | 14781 | 14782 | 14783 | 14784 | 14785 | 14786 | 14787 | 14788 |
| | 593 | 14801 | 14802 | 14803 | 14804 | 14805 | 14806 | 14807 | 14808 | 14809 | 14810 | 14811 | 14812 | 14813 |
| | 594 | 14826 | 14827 | 14828 | 14829 | 14830 | 14831 | 14832 | 14833 | 14834 | 14835 | 14836 | 14837 | 14838 |
| | 595 | 14851 | 14852 | 14853 | 14854 | 14855 | 14856 | 14857 | 14858 | 14859 | 14860 | 14861 | 14862 | 14863 |
| | 596 | 14876 | 14877 | 14878 | 14879 | 14880 | 14881 | 14882 | 14883 | 14884 | 14885 | 14886 | 14887 | 14888 |
| | 597 | 14901 | 14902 | 14903 | 14904 | 14905 | 14906 | 14907 | 14908 | 14909 | 14910 | 14911 | 14912 | 14913 |
| | 598 | 14926 | 14927 | 14928 | 14929 | 14930 | 14931 | 14932 | 14933 | 14934 | 14935 | 14936 | 14937 | 14938 |
| | 599 | 14951 | 14952 | 14953 | 14954 | 14955 | 14956 | 14957 | 14958 | 14959 | 14960 | 14961 | 14962 | 14963 |
| | 600 | 14976 | 14977 | 14978 | 14979 | 14980 | 14981 | 14982 | 14983 | 14984 | 14985 | 14986 | 14987 | 14988 |
| | 601 | 15001 | 15002 | 15003 | 15004 | 15005 | 15006 | 15007 | 15008 | 15009 | 15010 | 15011 | 15012 | 15013 |
| | 602 | 15026 | 15027 | 15028 | 15029 | 15030 | 15031 | 15032 | 15033 | 15034 | 15035 | 15036 | 15037 | 15038 |
| | 603 | 15051 | 15052 | 15053 | 15054 | 15055 | 15056 | 15057 | 15058 | 15059 | 15060 | 15061 | 15062 | 15063 |
| | 604 | 15076 | 15077 | 15078 | 15079 | 15080 | 15081 | 15082 | 15083 | 15084 | 15085 | 15086 | 15087 | 15088 |
| | 605 | 15101 | 15102 | 15103 | 15104 | 15105 | 15106 | 15107 | 15108 | 15109 | 15110 | 15111 | 15112 | 15113 |

-continued

|  |  | Third organic compound | | | | | | | | | | | |
|---|---|---|---|---|---|---|---|---|---|---|---|---|
|  |  | D14 | D15 | D16 | D17 | D18 | D19 | D20 | D21 | D22 | D23 | D24 | D25 |
| Second | 551 | 13764 | 13765 | 13766 | 13767 | 13768 | 13769 | 13770 | 13771 | 13772 | 13773 | 13774 | 13775 |
| organic | 552 | 13789 | 13790 | 13791 | 13792 | 13793 | 13794 | 13795 | 13796 | 13797 | 13798 | 13799 | 13800 |
| compound | 553 | 13814 | 13815 | 13816 | 13817 | 13818 | 13819 | 13820 | 13821 | 13822 | 13823 | 13824 | 13825 |
|  | 554 | 13839 | 13840 | 13841 | 13842 | 13843 | 13844 | 13845 | 13846 | 13847 | 13848 | 13849 | 13850 |
|  | 555 | 13864 | 13865 | 13866 | 13867 | 13868 | 13869 | 13870 | 13871 | 13872 | 13873 | 13874 | 13875 |
|  | 556 | 13889 | 13890 | 13891 | 13892 | 13893 | 13894 | 13895 | 13896 | 13897 | 13898 | 13899 | 13900 |
|  | 557 | 13914 | 13915 | 13916 | 13917 | 13918 | 13919 | 13920 | 13921 | 13922 | 13923 | 13924 | 13925 |
|  | 558 | 13939 | 13940 | 13941 | 13942 | 13943 | 13944 | 13945 | 13946 | 13947 | 13948 | 13949 | 13950 |
|  | 559 | 13964 | 13965 | 13966 | 13967 | 13968 | 13969 | 13970 | 13971 | 13972 | 13973 | 13974 | 13975 |
|  | 560 | 13989 | 13990 | 13991 | 13992 | 13993 | 13994 | 13995 | 13996 | 13997 | 13998 | 13999 | 14000 |
|  | 561 | 14014 | 14015 | 14016 | 14017 | 14018 | 14019 | 14020 | 14021 | 14022 | 14023 | 14024 | 14025 |
|  | 562 | 14039 | 14040 | 14041 | 14042 | 14043 | 14044 | 14045 | 14046 | 14047 | 14048 | 14049 | 14050 |
|  | 563 | 14064 | 14065 | 14066 | 14067 | 14068 | 14069 | 14070 | 14071 | 14072 | 14073 | 14074 | 14075 |
|  | 564 | 14089 | 14090 | 14091 | 14092 | 14093 | 14094 | 14095 | 14096 | 14097 | 14098 | 14099 | 14100 |
|  | 565 | 14114 | 14115 | 14116 | 14117 | 14118 | 14119 | 14120 | 14121 | 14122 | 14123 | 14124 | 14125 |
|  | 566 | 14139 | 14140 | 14141 | 14142 | 14143 | 14144 | 14145 | 14146 | 14147 | 14148 | 14149 | 14150 |
|  | 567 | 14164 | 14165 | 14166 | 14167 | 14168 | 14169 | 14170 | 14171 | 14172 | 14173 | 14174 | 14175 |
|  | 568 | 14189 | 14190 | 14191 | 14192 | 14193 | 14194 | 14195 | 14196 | 14197 | 14198 | 14199 | 14200 |
|  | 569 | 14214 | 14215 | 14216 | 14217 | 14218 | 14219 | 14220 | 14221 | 14222 | 14223 | 14224 | 14225 |
|  | 570 | 14239 | 14240 | 14241 | 14242 | 14243 | 14244 | 14245 | 14246 | 14247 | 14248 | 14249 | 14250 |
|  | 571 | 14264 | 14265 | 14266 | 14267 | 14268 | 14269 | 14270 | 14271 | 14272 | 14273 | 14274 | 14275 |
|  | 572 | 14289 | 14290 | 14291 | 14292 | 14293 | 14294 | 14295 | 14296 | 14297 | 14298 | 14299 | 14300 |
|  | 573 | 14314 | 14315 | 14316 | 14317 | 14318 | 14319 | 14320 | 14321 | 14322 | 14323 | 14324 | 14325 |
|  | 574 | 14339 | 14340 | 14341 | 14342 | 14343 | 14344 | 14345 | 14346 | 14347 | 14348 | 14349 | 14350 |
|  | 575 | 14364 | 14365 | 14366 | 14367 | 14368 | 14369 | 14370 | 14371 | 14372 | 14373 | 14374 | 14375 |
|  | 576 | 14389 | 14390 | 14391 | 14392 | 14393 | 14394 | 14395 | 14396 | 14397 | 14398 | 14399 | 14400 |
|  | 577 | 14414 | 14415 | 14416 | 14417 | 14418 | 14419 | 14420 | 14421 | 14422 | 14423 | 14424 | 14425 |
|  | 578 | 14439 | 14440 | 14441 | 14442 | 14443 | 14444 | 14445 | 14446 | 14447 | 14448 | 14449 | 14450 |
|  | 579 | 14464 | 14465 | 14466 | 14467 | 14468 | 14469 | 14470 | 14471 | 14472 | 14473 | 14474 | 14475 |
|  | 580 | 14489 | 14490 | 14491 | 14492 | 14493 | 14494 | 14495 | 14496 | 14497 | 14498 | 14499 | 14500 |
|  | 581 | 14514 | 14515 | 14516 | 14517 | 14518 | 14519 | 14520 | 14521 | 14522 | 14523 | 14524 | 14525 |
|  | 582 | 14539 | 14540 | 14541 | 14542 | 14543 | 14544 | 14545 | 14546 | 14547 | 14548 | 14549 | 14550 |
|  | 583 | 14564 | 14565 | 14566 | 14567 | 14568 | 14569 | 14570 | 14571 | 14572 | 14573 | 14574 | 14575 |
|  | 584 | 14589 | 14590 | 14591 | 14592 | 14593 | 14594 | 14595 | 14596 | 14597 | 14598 | 14599 | 14600 |
|  | 585 | 14614 | 14615 | 14616 | 14617 | 14618 | 14619 | 14620 | 14621 | 14622 | 14623 | 14624 | 14625 |
|  | 586 | 14639 | 14640 | 14641 | 14642 | 14643 | 14644 | 14645 | 14646 | 14647 | 14648 | 14649 | 14650 |
|  | 587 | 14664 | 14665 | 14666 | 14667 | 14668 | 14669 | 14670 | 14671 | 14672 | 14673 | 14674 | 14675 |
|  | 588 | 14689 | 14690 | 14691 | 14692 | 14693 | 14694 | 14695 | 14696 | 14697 | 14698 | 14699 | 14700 |
|  | 589 | 14714 | 14715 | 14716 | 14717 | 14718 | 14719 | 14720 | 14721 | 14722 | 14723 | 14724 | 14725 |
|  | 590 | 14739 | 14740 | 14741 | 14742 | 14743 | 14744 | 14745 | 14746 | 14747 | 14748 | 14749 | 14750 |
|  | 591 | 14764 | 14765 | 14766 | 14767 | 14768 | 14769 | 14770 | 14771 | 14772 | 14773 | 14774 | 14775 |
|  | 592 | 14789 | 14790 | 14791 | 14792 | 14793 | 14794 | 14795 | 14796 | 14797 | 14798 | 14799 | 14800 |
|  | 593 | 14814 | 14815 | 14816 | 14817 | 14818 | 14819 | 14820 | 14821 | 14822 | 14823 | 14824 | 14825 |
|  | 594 | 14839 | 14840 | 14841 | 14842 | 14843 | 14844 | 14845 | 14846 | 14847 | 14848 | 14849 | 14850 |
|  | 595 | 14864 | 14865 | 14866 | 14867 | 14868 | 14869 | 14870 | 14871 | 14872 | 14873 | 14874 | 14875 |
|  | 596 | 14889 | 14890 | 14891 | 14892 | 14893 | 14894 | 14895 | 14896 | 14897 | 14898 | 14899 | 14900 |
|  | 597 | 14914 | 14915 | 14916 | 14917 | 14918 | 14919 | 14920 | 14921 | 14922 | 14923 | 14924 | 14925 |
|  | 598 | 14939 | 14940 | 14941 | 14942 | 14943 | 14944 | 14945 | 14946 | 14947 | 14948 | 14949 | 14950 |
|  | 599 | 14964 | 14965 | 14966 | 14967 | 14968 | 14969 | 14970 | 14971 | 14972 | 14973 | 14974 | 14975 |
|  | 600 | 14989 | 14990 | 14991 | 14992 | 14993 | 14994 | 14995 | 14996 | 14997 | 14998 | 14999 | 15000 |
|  | 601 | 15014 | 15015 | 15016 | 15017 | 15018 | 15019 | 15020 | 15021 | 15022 | 15023 | 15024 | 15025 |
|  | 602 | 15039 | 15040 | 15041 | 15042 | 15043 | 15044 | 15045 | 15046 | 15047 | 15048 | 15049 | 15050 |
|  | 603 | 15064 | 15065 | 15066 | 15067 | 15068 | 15069 | 15070 | 15071 | 15072 | 15073 | 15074 | 15075 |
|  | 604 | 15089 | 15090 | 15091 | 15092 | 15093 | 15094 | 15095 | 15096 | 15097 | 15098 | 15099 | 15100 |
|  | 605 | 15114 | 15115 | 15116 | 15117 | 15118 | 15119 | 15120 | 15121 | 15122 | 15123 | 15124 | 15125 |

| | Third organic compound | | | | | | | | | | | |
|---|---|---|---|---|---|---|---|---|---|---|---|---|
| | D1 | D2 | D3 | D4 | D5 | D6 | D7 | D8 | D9 | D10 | D11 | D12 | D13 |
| 606 | 15126 | 15127 | 15128 | 15129 | 15130 | 15131 | 15132 | 15133 | 15134 | 15135 | 15136 | 15137 | 15138 |
| 607 | 15151 | 15152 | 15153 | 15154 | 15155 | 15156 | 15157 | 15158 | 15159 | 15160 | 15161 | 15162 | 15163 |
| 608 | 15176 | 15177 | 15178 | 15179 | 15180 | 15181 | 15182 | 15183 | 15184 | 15185 | 15186 | 15187 | 15188 |
| 609 | 15201 | 15202 | 15203 | 15204 | 15205 | 15206 | 15207 | 15208 | 15209 | 15210 | 15211 | 15212 | 15213 |
| 610 | 15226 | 15227 | 15228 | 15229 | 15230 | 15231 | 15232 | 15233 | 15234 | 15235 | 15236 | 15237 | 15238 |
| 611 | 15251 | 15252 | 15253 | 15254 | 15255 | 15256 | 15257 | 15258 | 15259 | 15260 | 15261 | 15262 | 15263 |
| 612 | 15276 | 15277 | 15278 | 15279 | 15280 | 15281 | 15282 | 15283 | 15284 | 15285 | 15286 | 15287 | 15288 |
| 613 | 15301 | 15302 | 15303 | 15304 | 15305 | 15306 | 15307 | 15308 | 15309 | 15310 | 15311 | 15312 | 15313 |
| 614 | 15326 | 15327 | 15328 | 15329 | 15330 | 15331 | 15332 | 15333 | 15334 | 15335 | 15336 | 15337 | 15338 |
| 615 | 15351 | 15352 | 15353 | 15354 | 15355 | 15356 | 15357 | 15358 | 15359 | 15360 | 15361 | 15362 | 15363 |
| 616 | 15376 | 15377 | 15378 | 15379 | 15380 | 15381 | 15382 | 15383 | 15384 | 15385 | 15386 | 15387 | 15388 |
| 617 | 15401 | 15402 | 15403 | 15404 | 15405 | 15406 | 15407 | 15408 | 15409 | 15410 | 15411 | 15412 | 15413 |

-continued

| | | | | | | | | | | | | |
|---|---|---|---|---|---|---|---|---|---|---|---|---|
| 618 | 15426 | 15427 | 15428 | 15429 | 15430 | 15431 | 15432 | 15433 | 15434 | 15435 | 15436 | 15437 | 15438 |
| 619 | 15451 | 15452 | 15453 | 15454 | 15455 | 15456 | 15457 | 15458 | 15459 | 15460 | 15461 | 15462 | 15463 |
| 620 | 15476 | 15477 | 15478 | 15479 | 15480 | 15481 | 15482 | 15483 | 15484 | 15485 | 15486 | 15487 | 15488 |
| 621 | 15501 | 15502 | 15503 | 15504 | 15505 | 15506 | 15507 | 15508 | 15509 | 15510 | 15511 | 15512 | 15513 |
| 622 | 15526 | 15527 | 15528 | 15529 | 15530 | 15531 | 15532 | 15533 | 15534 | 15535 | 15536 | 15537 | 15538 |
| 623 | 15551 | 15552 | 15553 | 15554 | 15555 | 15556 | 15557 | 15558 | 15559 | 15560 | 15561 | 15562 | 15563 |
| 624 | 15576 | 15577 | 15578 | 15579 | 15580 | 15581 | 15582 | 15583 | 15584 | 15585 | 15586 | 15587 | 15588 |
| 625 | 15601 | 15602 | 15603 | 15604 | 15605 | 15606 | 15607 | 15608 | 15609 | 15610 | 15611 | 15612 | 15613 |
| 626 | 15626 | 15627 | 15628 | 15629 | 15630 | 15631 | 15632 | 15633 | 15634 | 15635 | 15636 | 15637 | 15638 |
| 627 | 15651 | 15652 | 15653 | 15654 | 15655 | 15656 | 15657 | 15658 | 15659 | 15660 | 15661 | 15662 | 15663 |
| 628 | 15676 | 15677 | 15678 | 15679 | 15680 | 15681 | 15682 | 15683 | 15684 | 15685 | 15686 | 15687 | 15688 |
| 629 | 15701 | 15702 | 15703 | 15704 | 15705 | 15706 | 15707 | 15708 | 15709 | 15710 | 15711 | 15712 | 15713 |
| 630 | 15726 | 15727 | 15728 | 15729 | 15730 | 15731 | 15732 | 15733 | 15734 | 15735 | 15736 | 15737 | 15738 |
| 631 | 15751 | 15752 | 15753 | 15754 | 15755 | 15756 | 15757 | 15758 | 15759 | 15760 | 15761 | 15762 | 15763 |
| 632 | 15776 | 15777 | 15778 | 15779 | 15780 | 15781 | 15782 | 15783 | 15784 | 15785 | 15786 | 15787 | 15788 |
| 633 | 15801 | 15802 | 15803 | 15804 | 15805 | 15806 | 15807 | 15808 | 15809 | 15810 | 15811 | 15812 | 15813 |
| 634 | 15826 | 15827 | 15828 | 15829 | 15830 | 15831 | 15832 | 15833 | 15834 | 15835 | 15836 | 15837 | 15838 |
| 635 | 15851 | 15852 | 15853 | 15854 | 15855 | 15856 | 15857 | 15858 | 15859 | 15860 | 15861 | 15862 | 15863 |
| 636 | 15876 | 15877 | 15878 | 15879 | 15880 | 15881 | 15882 | 15883 | 15884 | 15885 | 15886 | 15887 | 15888 |
| 637 | 15901 | 15902 | 15903 | 15904 | 15905 | 15906 | 15907 | 15908 | 15909 | 15910 | 15911 | 15912 | 15913 |
| 638 | 15926 | 15927 | 15928 | 15929 | 15930 | 15931 | 15932 | 15933 | 15934 | 15935 | 15936 | 15937 | 15938 |
| 639 | 15951 | 15952 | 15953 | 15954 | 15955 | 15956 | 15957 | 5958 | 5959 | 15960 | 15961 | 15962 | 15963 |
| 640 | 15976 | 15977 | 15978 | 15979 | 15980 | 15981 | 15982 | 15983 | 15984 | 15985 | 15986 | 15987 | 15988 |
| 641 | 16001 | 16002 | 16003 | 16004 | 16005 | 16006 | 16007 | 16008 | 16009 | 16010 | 16011 | 16012 | 16013 |
| 642 | 16026 | 16027 | 16028 | 16029 | 16030 | 16031 | 16032 | 16033 | 16034 | 16035 | 16036 | 16037 | 16038 |
| 643 | 16051 | 16052 | 16053 | 16054 | 16055 | 16056 | 16057 | 16058 | 16059 | 16060 | 16061 | 16062 | 16063 |
| 644 | 16076 | 16077 | 16078 | 16079 | 16080 | 16081 | 16082 | 16083 | 16084 | 16085 | 16086 | 16087 | 16088 |
| 645 | 16101 | 16102 | 16103 | 16104 | 16105 | 16106 | 16107 | 16108 | 16109 | 16110 | 16111 | 16112 | 16113 |
| 646 | 16126 | 16127 | 16128 | 16129 | 16130 | 16131 | 16132 | 16133 | 16134 | 16135 | 16136 | 16137 | 16138 |
| 647 | 16151 | 16152 | 16153 | 16154 | 16155 | 16156 | 16157 | 16158 | 16159 | 16160 | 16161 | 16162 | 16163 |
| 648 | 16176 | 16177 | 16178 | 16179 | 16180 | 16181 | 16182 | 16183 | 16184 | 16185 | 16186 | 16187 | 16188 |
| 649 | 16201 | 16202 | 16203 | 16204 | 16205 | 16206 | 16207 | 16208 | 16209 | 16210 | 16211 | 16212 | 16213 |
| 650 | 16226 | 16227 | 16228 | 16229 | 16230 | 16231 | 16232 | 16233 | 16234 | 16235 | 16236 | 16237 | 16238 |
| 651 | 16251 | 16252 | 16253 | 16254 | 16255 | 16256 | 16257 | 16258 | 16259 | 16260 | 16261 | 16262 | 16263 |
| 652 | 16276 | 16277 | 16278 | 16279 | 16280 | 16281 | 16282 | 16283 | 16284 | 16285 | 16286 | 16287 | 16288 |
| 653 | 16301 | 16302 | 16303 | 16304 | 16305 | 16306 | 16307 | 16308 | 16309 | 16310 | 16311 | 16312 | 16313 |
| 654 | 16326 | 16327 | 16328 | 16329 | 16330 | 16331 | 16332 | 16333 | 16334 | 16335 | 16336 | 16337 | 16338 |
| 655 | 16351 | 16352 | 16353 | 16354 | 16355 | 16356 | 16357 | 16358 | 16359 | 16360 | 16361 | 16362 | 16363 |
| 656 | 16376 | 16377 | 16378 | 16379 | 16380 | 16381 | 16382 | 16383 | 16384 | 16385 | 16386 | 16387 | 16388 |
| 657 | 16401 | 16402 | 16403 | 16404 | 16405 | 16406 | 16407 | 16408 | 16409 | 16410 | 16411 | 16412 | 16413 |
| 658 | 16426 | 16427 | 16428 | 16429 | 16430 | 16431 | 16432 | 16433 | 16434 | 16435 | 16436 | 16437 | 16438 |
| 659 | 16451 | 16452 | 16453 | 16454 | 16455 | 16456 | 16457 | 16458 | 16459 | 16460 | 16461 | 16462 | 16463 |
| 660 | 16476 | 16477 | 16478 | 16479 | 16480 | 16481 | 16482 | 16483 | 16484 | 16485 | 16486 | 16487 | 16488 |

| | Third organic compound | | | | | | | | | | | |
|---|---|---|---|---|---|---|---|---|---|---|---|---|
| | D14 | D15 | D16 | D17 | D18 | D19 | D20 | D21 | D22 | D23 | D24 | D25 |
| 606 | 15139 | 15140 | 15141 | 15142 | 15143 | 15144 | 15145 | 15146 | 15147 | 15148 | 15149 | 15150 |
| 607 | 15164 | 15165 | 15166 | 15167 | 15168 | 15169 | 15170 | 15171 | 15172 | 15173 | 15174 | 15175 |
| 608 | 15189 | 15190 | 15191 | 15192 | 15193 | 15194 | 15195 | 15196 | 15197 | 15198 | 15199 | 15200 |
| 609 | 15214 | 15215 | 15216 | 15217 | 15218 | 15219 | 15220 | 15221 | 15222 | 15223 | 15224 | 15225 |
| 610 | 15239 | 15240 | 15241 | 15242 | 15243 | 15244 | 15245 | 15246 | 15247 | 15248 | 15249 | 15250 |
| 611 | 15264 | 15265 | 15266 | 15267 | 15268 | 15269 | 15270 | 15271 | 15272 | 15273 | 15274 | 15275 |
| 612 | 15289 | 15290 | 15291 | 15292 | 15293 | 15294 | 15295 | 15296 | 15297 | 15298 | 15299 | 15300 |
| 613 | 15314 | 15315 | 15316 | 15317 | 15318 | 15319 | 15320 | 15321 | 15322 | 15323 | 15324 | 15325 |
| 614 | 15339 | 15340 | 15341 | 15342 | 15343 | 15344 | 15345 | 15346 | 15347 | 15348 | 15349 | 15350 |
| 615 | 15364 | 15365 | 15366 | 15367 | 15368 | 15369 | 15370 | 15371 | 15372 | 15373 | 15374 | 15375 |
| 616 | 15389 | 15390 | 15391 | 15392 | 15393 | 15394 | 15395 | 15396 | 15397 | 15398 | 15399 | 15400 |
| 617 | 15414 | 15415 | 15416 | 15417 | 15418 | 15419 | 15420 | 15421 | 15422 | 15423 | 15424 | 15425 |
| 618 | 15439 | 15440 | 15441 | 15442 | 15443 | 15444 | 15445 | 15446 | 15447 | 15448 | 15449 | 15450 |
| 619 | 15464 | 15465 | 15466 | 15467 | 15468 | 15469 | 15470 | 15471 | 15472 | 15473 | 15474 | 15475 |
| 620 | 15489 | 15490 | 15491 | 15492 | 15493 | 15494 | 15495 | 15496 | 15497 | 15498 | 15499 | 15500 |
| 621 | 15514 | 15515 | 15516 | 15517 | 15518 | 15519 | 15520 | 15521 | 15522 | 15523 | 15524 | 15525 |
| 622 | 15539 | 15540 | 15541 | 15542 | 15543 | 15544 | 15545 | 15546 | 15547 | 15548 | 15549 | 15550 |
| 623 | 15564 | 15565 | 15566 | 15567 | 15568 | 15569 | 15570 | 15571 | 15572 | 15573 | 15574 | 15575 |
| 624 | 15589 | 15590 | 15591 | 15592 | 15593 | 15594 | 15595 | 15596 | 15597 | 15598 | 15599 | 15600 |
| 625 | 15614 | 15615 | 15616 | 15617 | 15618 | 15619 | 15620 | 15621 | 15622 | 15623 | 15624 | 15625 |
| 626 | 15639 | 15640 | 15641 | 15642 | 15643 | 15644 | 15645 | 15646 | 15647 | 15648 | 15649 | 15650 |
| 627 | 15664 | 15665 | 15666 | 15667 | 15668 | 15669 | 15670 | 15671 | 15672 | 15673 | 15674 | 15675 |
| 628 | 15689 | 15690 | 15691 | 15692 | 15693 | 15694 | 15695 | 15696 | 15697 | 15698 | 15699 | 15700 |
| 629 | 15714 | 15715 | 15716 | 15717 | 15718 | 15719 | 15720 | 15721 | 15722 | 15723 | 15724 | 15725 |
| 630 | 15739 | 15740 | 15741 | 15742 | 15743 | 15744 | 15745 | 15746 | 15747 | 15748 | 15749 | 15750 |
| 631 | 15764 | 15765 | 15766 | 15767 | 15768 | 15769 | 15770 | 15771 | 15772 | 15773 | 15774 | 15775 |
| 632 | 15789 | 15790 | 15791 | 15792 | 15793 | 15794 | 15795 | 15796 | 15797 | 15798 | 15799 | 15800 |
| 633 | 15814 | 15815 | 15816 | 15817 | 15818 | 15819 | 15820 | 15821 | 15822 | 15823 | 15824 | 15825 |
| 634 | 15839 | 15840 | 15841 | 15842 | 15843 | 15844 | 15845 | 15846 | 15847 | 15848 | 15849 | 15850 |
| 635 | 15864 | 15865 | 15866 | 15867 | 15868 | 15869 | 15870 | 15871 | 15872 | 15873 | 15874 | 15875 |
| 636 | 15889 | 15890 | 15891 | 15892 | 15893 | 15894 | 15895 | 15896 | 15897 | 15898 | 15899 | 15900 |

-continued

| | | | | | | | | | | | | |
|---|---|---|---|---|---|---|---|---|---|---|---|---|
| 637 | 15914 | 15915 | 15916 | 15917 | 15918 | 15919 | 15920 | 15921 | 15922 | 15923 | 15924 | 15925 |
| 638 | 15939 | 15940 | 15941 | 15942 | 15943 | 15944 | 15945 | 15946 | 15947 | 15948 | 15949 | 15950 |
| 639 | 15964 | 15965 | 15966 | 15967 | 15968 | 15969 | 15970 | 15971 | 15972 | 15973 | 15974 | 15975 |
| 640 | 15989 | 15990 | 15991 | 15992 | 15993 | 15994 | 15995 | 15996 | 15997 | 15998 | 15999 | 16000 |
| 641 | 16014 | 16015 | 16016 | 16017 | 16018 | 16019 | 16020 | 16021 | 16022 | 16023 | 16024 | 16025 |
| 642 | 16039 | 16040 | 16041 | 16042 | 16043 | 16044 | 16045 | 16046 | 16047 | 16048 | 16049 | 16050 |
| 643 | 16064 | 16065 | 16066 | 16067 | 16068 | 16069 | 16070 | 16071 | 16072 | 16073 | 16074 | 16075 |
| 644 | 16089 | 16090 | 16091 | 16092 | 16093 | 16094 | 16095 | 16096 | 16097 | 16098 | 16099 | 16100 |
| 645 | 16114 | 16115 | 16116 | 16117 | 16118 | 16119 | 16120 | 16121 | 16122 | 16123 | 16124 | 16125 |
| 646 | 16139 | 16140 | 16141 | 16142 | 16143 | 16144 | 16145 | 16146 | 16147 | 16148 | 16149 | 16150 |
| 647 | 16164 | 16165 | 16166 | 16167 | 16168 | 16169 | 16170 | 16171 | 16172 | 16173 | 16174 | 16175 |
| 648 | 16189 | 16190 | 16191 | 16192 | 16193 | 16194 | 6195 | 16196 | 16197 | 16198 | 16199 | 16200 |
| 649 | 16214 | 16215 | 16216 | 16217 | 16218 | 16219 | 16220 | 16221 | 16222 | 16223 | 16224 | 16225 |
| 650 | 16239 | 16240 | 16241 | 16242 | 16243 | 16244 | 16245 | 16246 | 16247 | 16248 | 16249 | 16250 |
| 651 | 16264 | 16265 | 16266 | 16267 | 16268 | 16269 | 16270 | 16271 | 16272 | 16273 | 16274 | 16275 |
| 652 | 16289 | 16290 | 16291 | 16292 | 16293 | 16294 | 16295 | 16296 | 16297 | 16298 | 16299 | 16300 |
| 653 | 16314 | 16315 | 16316 | 16317 | 16318 | 16319 | 16320 | 16321 | 16322 | 16323 | 16324 | 16325 |
| 654 | 16339 | 16340 | 16341 | 16342 | 16343 | 16344 | 16345 | 16346 | 16347 | 16348 | 16349 | 16350 |
| 655 | 16364 | 16365 | 16366 | 16367 | 16368 | 16369 | 16370 | 16371 | 16372 | 16373 | 16374 | 16375 |
| 656 | 16389 | 16390 | 16391 | 16392 | 16393 | 16394 | 16395 | 16396 | 16397 | 16398 | 16399 | 16400 |
| 657 | 16414 | 16415 | 16416 | 16417 | 16418 | 16419 | 16420 | 16421 | 16422 | 16423 | 16424 | 16425 |
| 658 | 16439 | 16440 | 16441 | 16442 | 16443 | 16444 | 16445 | 16446 | 16447 | 16448 | 16449 | 16450 |
| 659 | 16464 | 16465 | 16466 | 16467 | 16468 | 16469 | 16470 | 16471 | 16472 | 16473 | 16474 | 16475 |
| 660 | 16489 | 16490 | 16491 | 16492 | 16493 | 16494 | 16495 | 16496 | 16497 | 16498 | 16499 | 16500 |

TABLE 9-13

Third organic compound

| | D1 | D2 | D3 | D4 | D5 | D6 | D7 | D8 | D9 | D10 | D11 | D12 | D13 |
|---|---|---|---|---|---|---|---|---|---|---|---|---|---|
| 661 | 16501 | 16502 | 16503 | 16504 | 16505 | 16506 | 16507 | 16508 | 16509 | 16510 | 16511 | 16512 | 16513 |
| 662 | 16526 | 16527 | 16528 | 16529 | 16530 | 16531 | 16532 | 16533 | 16534 | 16535 | 16536 | 16537 | 16538 |
| 663 | 16551 | 16552 | 16553 | 16554 | 16555 | 16556 | 16557 | 16558 | 16559 | 16560 | 16561 | 16562 | 16563 |
| 664 | 16576 | 16577 | 16578 | 16579 | 16580 | 16581 | 16582 | 16583 | 16584 | 16585 | 16586 | 16587 | 16588 |
| 665 | 16601 | 16602 | 16603 | 16604 | 16605 | 16606 | 16607 | 16608 | 16609 | 16610 | 16611 | 16612 | 16613 |
| 666 | 16626 | 16627 | 16628 | 16629 | 16630 | 16631 | 16632 | 16633 | 16634 | 16635 | 16636 | 16637 | 16638 |
| 667 | 16651 | 16652 | 16653 | 16654 | 16655 | 16656 | 16657 | 16658 | 16659 | 16660 | 16661 | 16662 | 16663 |
| 668 | 16676 | 16677 | 16678 | 16679 | 16680 | 16681 | 16682 | 16683 | 16684 | 16685 | 16686 | 16687 | 16688 |
| 669 | 16701 | 16702 | 16703 | 16704 | 16705 | 16706 | 16707 | 16708 | 16709 | 16710 | 16711 | 16712 | 16713 |
| 670 | 16726 | 16727 | 16728 | 16729 | 16730 | 16731 | 16732 | 16733 | 16734 | 16735 | 16736 | 16737 | 16738 |
| 671 | 16751 | 16752 | 16753 | 16754 | 16755 | 16756 | 16757 | 16758 | 16759 | 16760 | 16761 | 16762 | 16763 |
| 672 | 16776 | 16777 | 16778 | 16779 | 16780 | 16781 | 16782 | 16783 | 16784 | 16785 | 16786 | 16787 | 16788 |
| 673 | 16801 | 16802 | 16803 | 16804 | 16805 | 16806 | 16807 | 16808 | 16809 | 16810 | 16811 | 16812 | 16813 |
| 674 | 16826 | 16827 | 16828 | 16829 | 16830 | 16831 | 16832 | 16833 | 16834 | 16835 | 16836 | 16837 | 16838 |
| 675 | 16851 | 16852 | 16853 | 16854 | 16855 | 16856 | 16857 | 16858 | 16859 | 16860 | 16861 | 16862 | 16863 |
| 676 | 16876 | 16877 | 16878 | 16879 | 16880 | 16881 | 16882 | 16883 | 16884 | 16885 | 16886 | 16887 | 16888 |
| 677 | 16901 | 16902 | 16903 | 16904 | 16905 | 16906 | 16907 | 16908 | 16909 | 16910 | 16911 | 16912 | 16913 |
| 678 | 16926 | 16927 | 16928 | 16929 | 16930 | 16931 | 16932 | 16933 | 16934 | 16935 | 16936 | 16937 | 16938 |

Third organic compound

| | D14 | D15 | D16 | D17 | D18 | D19 | D20 | D21 | D22 | D23 | D24 | D25 |
|---|---|---|---|---|---|---|---|---|---|---|---|---|
| 661 | 16514 | 16515 | 16516 | 16517 | 16518 | 16519 | 16520 | 16521 | 16522 | 16523 | 16524 | 16525 |
| 662 | 16539 | 16540 | 16541 | 16542 | 16543 | 16544 | 16545 | 16546 | 16547 | 16548 | 16549 | 16550 |
| 663 | 16564 | 16565 | 16566 | 16567 | 16568 | 16569 | 16570 | 16571 | 16572 | 16573 | 16574 | 16575 |
| 664 | 16589 | 16590 | 16591 | 16592 | 16593 | 16594 | 16595 | 16596 | 16597 | 16598 | 16599 | 16600 |
| 665 | 16614 | 16615 | 16616 | 16617 | 16618 | 16619 | 16620 | 16621 | 16622 | 16623 | 16624 | 16625 |
| 666 | 16639 | 16640 | 16641 | 16642 | 16643 | 16644 | 16645 | 16646 | 16647 | 16648 | 16649 | 16650 |
| 667 | 16664 | 16665 | 16666 | 16667 | 16668 | 16669 | 16670 | 16671 | 16672 | 16673 | 16674 | 16675 |
| 668 | 16689 | 16690 | 16691 | 16692 | 16693 | 16694 | 16695 | 16696 | 16697 | 16698 | 16699 | 16700 |
| 669 | 16714 | 16715 | 16716 | 16717 | 16718 | 16719 | 16720 | 16721 | 16722 | 16723 | 16724 | 16725 |
| 670 | 16739 | 16740 | 16741 | 16742 | 16743 | 16744 | 16745 | 16746 | 16747 | 16748 | 16749 | 16750 |
| 671 | 16764 | 16765 | 16766 | 16767 | 16768 | 16769 | 16770 | 16771 | 16772 | 16773 | 16774 | 16775 |
| 672 | 16789 | 16790 | 16791 | 16792 | 16793 | 16794 | 16795 | 16796 | 16797 | 16798 | 16799 | 16800 |
| 673 | 16814 | 16815 | 16816 | 16817 | 16818 | 16819 | 16820 | 16821 | 16822 | 16823 | 16824 | 16825 |
| 674 | 16839 | 16840 | 16841 | 16842 | 16843 | 16844 | 16845 | 16846 | 16847 | 16848 | 16849 | 16850 |
| 675 | 16864 | 16865 | 16866 | 16867 | 16868 | 16869 | 16870 | 16871 | 16872 | 16873 | 16874 | 16875 |
| 676 | 16889 | 16890 | 16891 | 16892 | 16893 | 16894 | 16895 | 16896 | 16897 | 16898 | 16899 | 16900 |
| 677 | 16914 | 16915 | 16916 | 16917 | 16918 | 16919 | 16920 | 16921 | 16922 | 16923 | 16924 | 16925 |
| 678 | 16939 | 16940 | 16941 | 16942 | 16943 | 16944 | 16945 | 16946 | 16947 | 16948 | 16949 | 16950 |

[Other Organic Compounds]

The light-emitting layer may be composed of only the first organic compound to the third organic compound, and may contain any other organic compound than the first organic compound to the third organic compound. Examples of the other organic compound than the first organic compound to the third organic compound include an organic compound having hole transport competence, and an organic compound having electron transport competence. Regarding the organic compound having hole transport competence, and the organic compound having electron transport competence, reference may be made to the hole transport material and the electron transport material mentioned hereinunder.

[Substrate]

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

[Anode]

The anode of the organic electroluminescent device used is preferably formed of, as an electrode material, a metal, an alloy, or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being coated, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ω/sq or less. The thickness of the anode may be generally selected from a range of from 10 to 1,000 nm, and preferably from 10 to 200 nm, while depending on the material used.

[Cathode]

The cathode is preferably formed of, as an electrode material, a metal (which is referred to as an electron injection metal), an alloy, or an electroconductive compound, having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, is preferred from the standpoint of the electron injection property and the durability against oxidation and the like. The cathode may be produced by forming the electrode material into a thin film by such a method as vapor deposition or sputtering. The cathode preferably has a sheet resistance of several hundred Ω/sq or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

[Injection Layer]

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transport layer and between the cathode and the light emitting layer or the electron transport layer. The injection layer may be provided depending on necessity.

[Blocking Layer]

The blocking layer is a layer that is capable of inhibiting charges (electrons or holes) and/or excitons present in the light-emitting layer from being diffused outside the light-emitting layer. The electron blocking layer may be disposed between the light-emitting layer and the hole transport layer, and inhibits electrons from passing through the light-emitting layer toward the hole transport layer. Similarly, the hole blocking layer may be disposed between the light-emitting layer and the electron transport layer, and inhibits holes from passing through the light-emitting layer toward the electron transport layer. The blocking layer may also be used for inhibiting excitons from being diffused outside the light-emitting layer. Thus, the electron blocking layer and the hole blocking layer each may also have a function as an exciton blocking layer. The term "the electron blocking layer" or "the exciton blocking layer" referred to herein is intended to include a layer that has both the functions of an electron blocking layer and an exciton blocking layer by one layer.

[Hole Blocking Layer]

The hole blocking layer has the function of an electron transport layer in a broad sense. The hole blocking layer has a role of inhibiting holes from reaching the electron transport layer while transporting electrons, and thereby enhances the recombination probability of electrons and holes in the light-emitting layer. As the material for the hole blocking layer, the material for the electron transport layer to be mentioned below may be used optionally.

[Electron Blocking Layer]

The electron blocking layer has the function of transporting holes in a broad sense. The electron blocking layer has a role of inhibiting electrons from reaching the hole transport layer while transporting holes, and thereby enhances the recombination probability of electrons and holes in the light-emitting layer.

[Exciton Blocking Layer]

The exciton blocking layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton blocking layer may be adjacent to the light-emitting layer to be inserted on any of the side of the anode and the side of the cathode, and on both the sides. Specifically, in the case where the exciton blocking layer is present on the side of the anode, the layer may be inserted between the hole transport layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton blocking layer that is adjacent to the light-emitting layer on the side of the anode, a hole injection layer, an electron blocking layer and the like may be provided, and between the cathode and the exciton blocking layer that is adjacent to the light-emitting layer on the side of the cathode, an electron injection layer, an electron transport layer, a hole blocking layer and the like may be provided. In the case where the blocking layer is provided, preferably, at least one of the excited singlet energy and the excited triplet energy of the material used as the blocking layer is higher than the excited singlet energy and the excited triplet energy of the light-emitting layer of the light-emitting material.

[Hole Transport Layer]

The hole transport layer is formed of a hole transport material having a function of transporting holes, and the hole transport layer may be provided as a single layer or plural layers.

The hole transport material has one of injection or transporting property of holes and blocking property of electrons, and may be any of an organic material and an inorganic material. Examples of known hole transport materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. A porphyrin compound, an aromatic tertiary amine compound and a styrylamine compound are preferably used, and an aromatic tertiary amine compound is more preferably used.

[Electron Transport Layer]

The electron transport layer is formed of a material having a function of transporting electrons, and the electron transport layer may be a single layer or may be formed of plural layers.

The electron transport material (often also acting as a hole blocking material) may have a function of transmitting the electrons injected from a cathode to a light-emitting layer. The electron transport layer usable here includes, for example, nitro-substituted fluorene derivatives, diphenylquinone derivatives, thiopyran dioxide derivatives, carbodiimides, fluorenylidenemethane derivatives, anthraquinodimethane and anthrone derivatives, oxadiazole derivatives, etc. Further, thiadiazole derivatives derived from the above-mentioned oxadiazole derivatives by substituting the oxygen atom in the oxadiazole ring with a sulfur atom, and quinoxaline derivatives having a quinoxaline ring known as an electron-attractive group are also usable as the electron transport material. Further, polymer materials prepared by introducing these materials into the polymer chain, or having these material in the polymer main chain are also usable.

[Exemplification of Materials Usable in Organic Electroluminescent Device]

Preferred materials for use for the organic electroluminescent device are concretely exemplified below. However, the materials for use in the present invention are not limitatively interpreted by the following exemplary compounds. Compounds, even though exemplified as materials having a specific function, can also be used as other materials having any other function. R, and $R_2$ to $R_7$ in the structural formulae of the following exemplary compounds each independently represent a hydrogen atom or a substituent. n represents an integer of 3 to 5.

First, preferred compounds for use as a hole injection material are mentioned below.

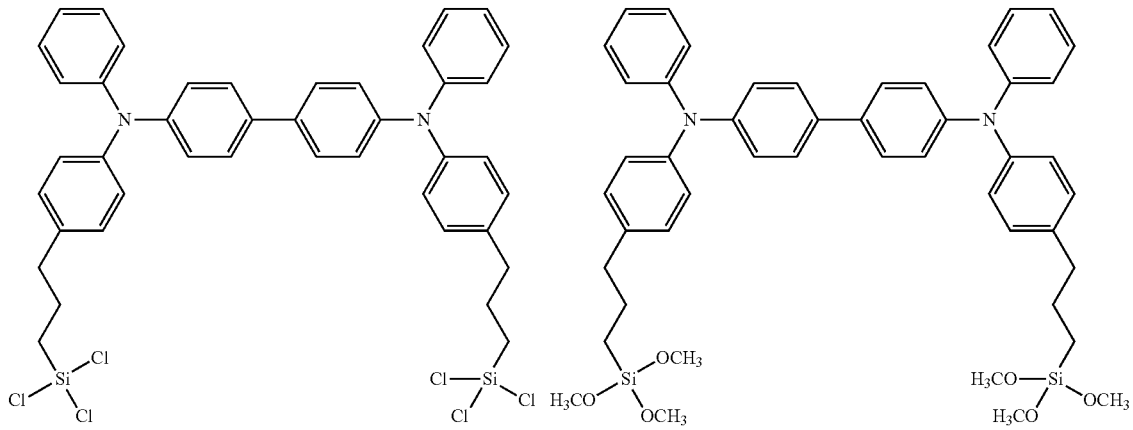

-continued
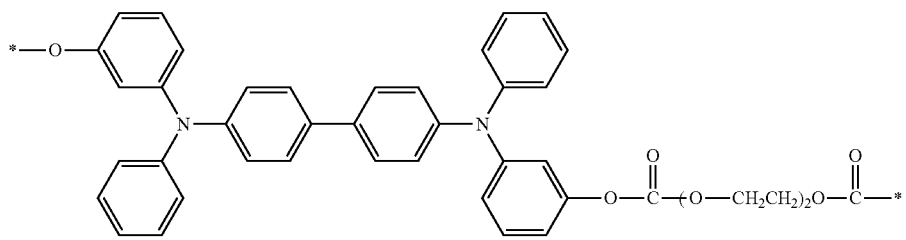
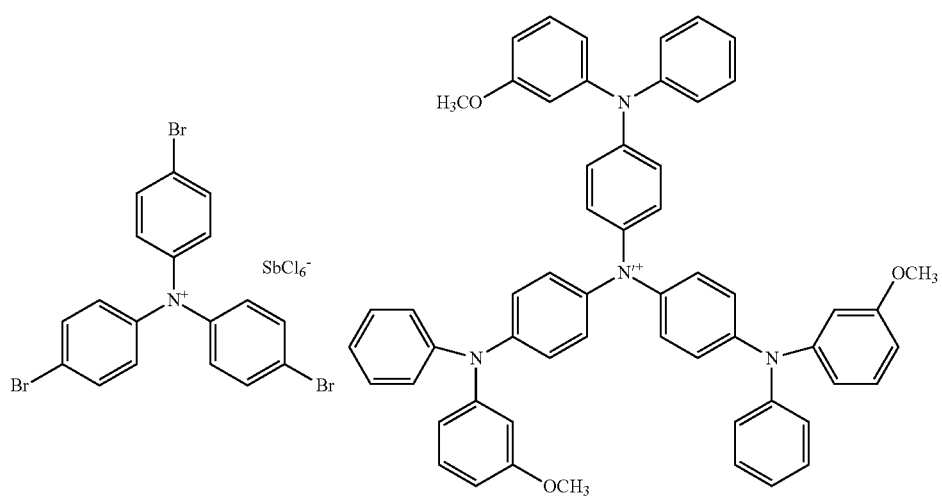
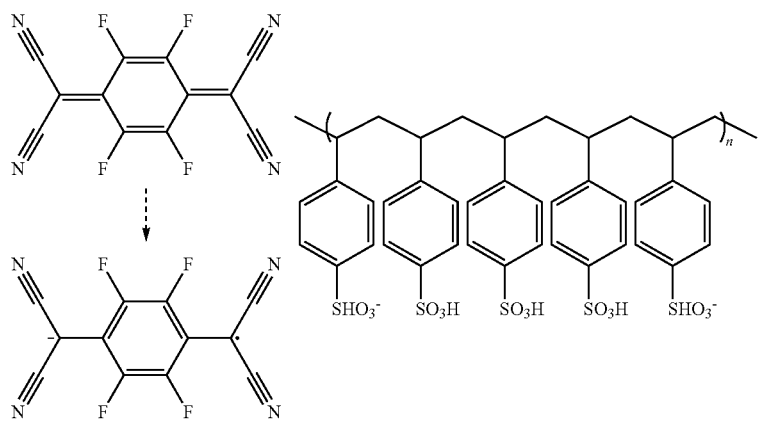
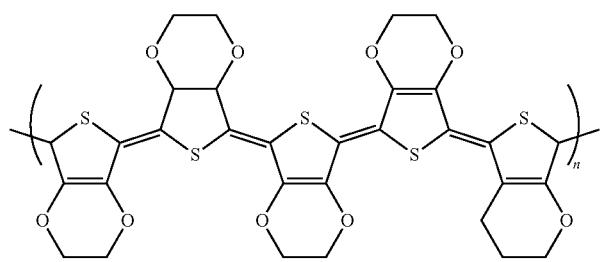

Next, preferred compounds for use as a hole transport material are mentioned below.
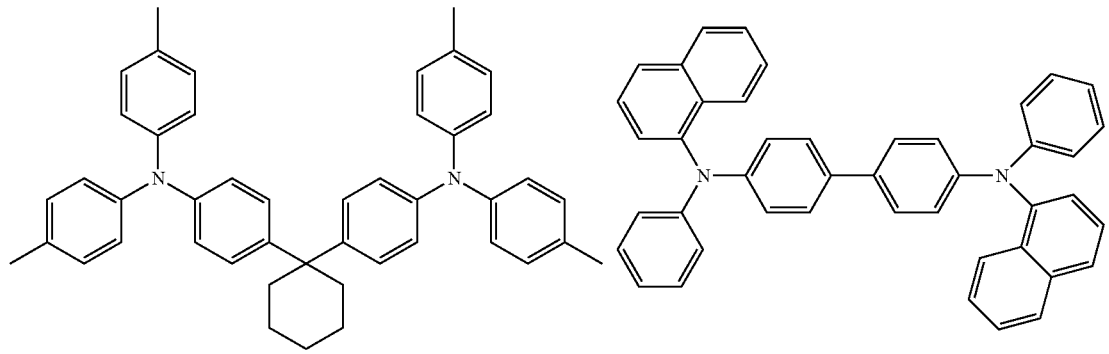
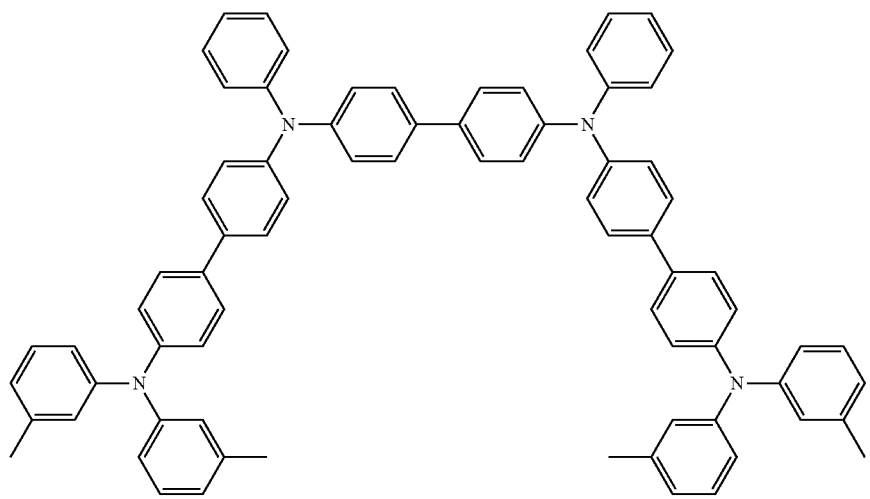
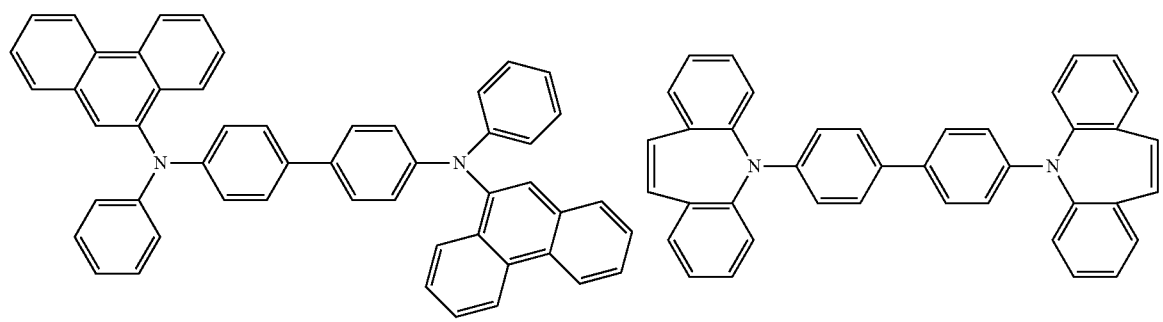

205
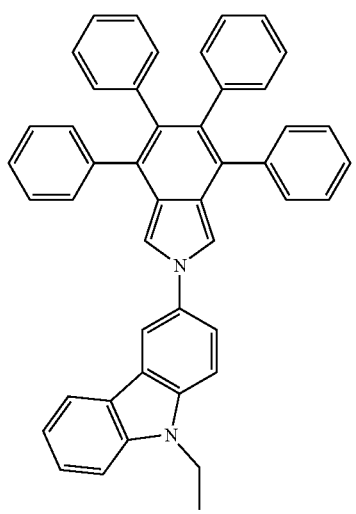
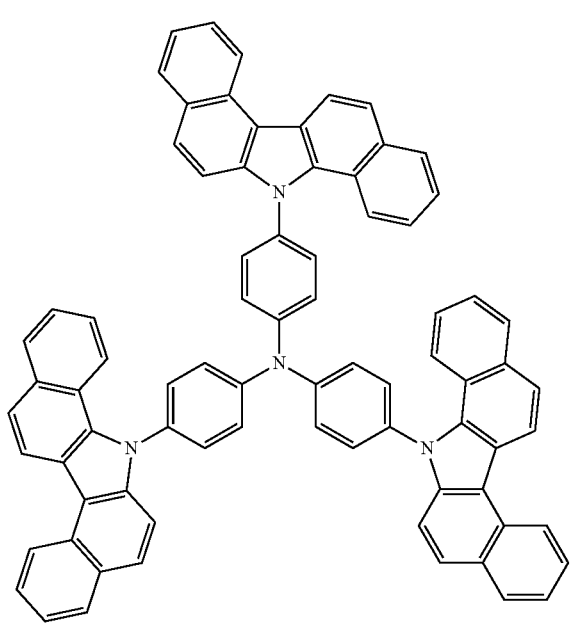
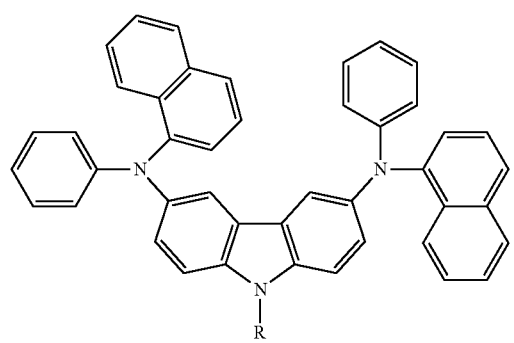
206
-continued
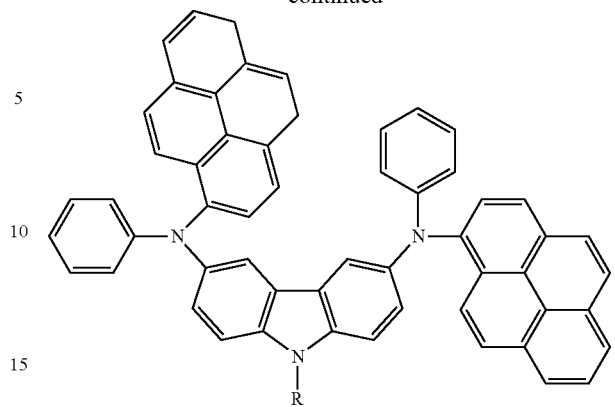
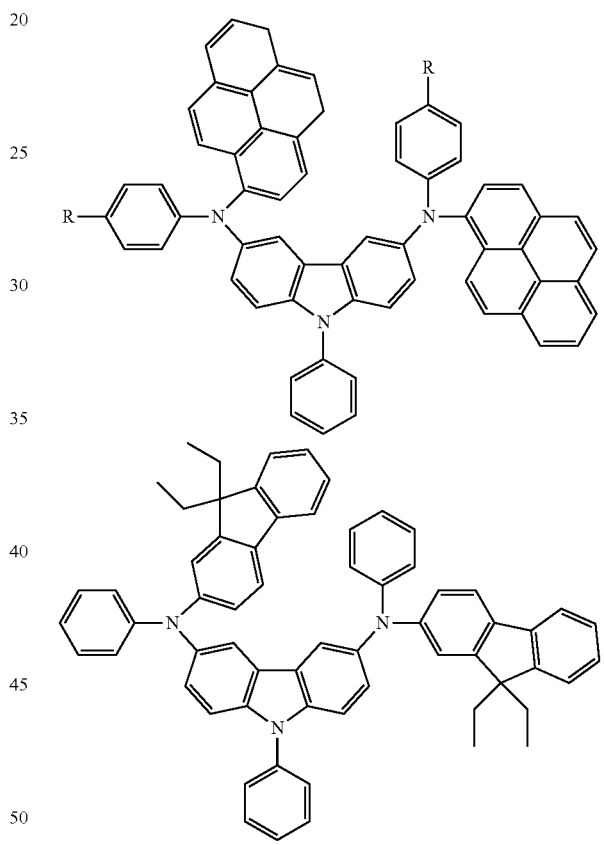

207
-continued
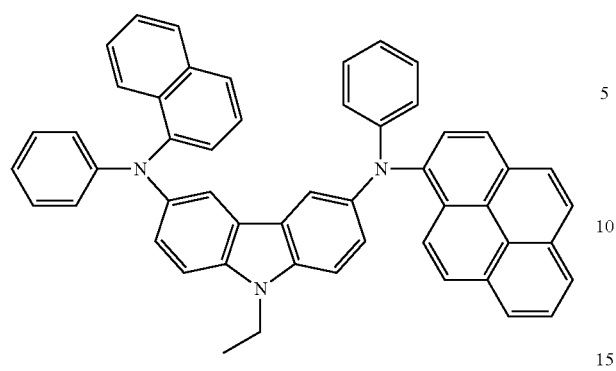
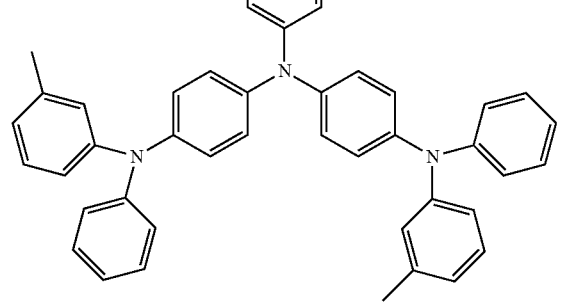
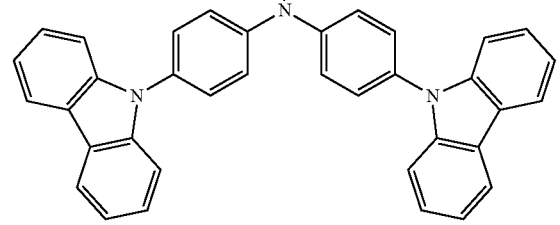
208
-continued
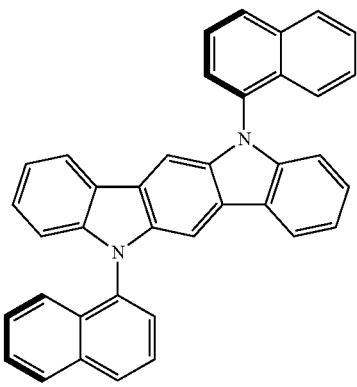
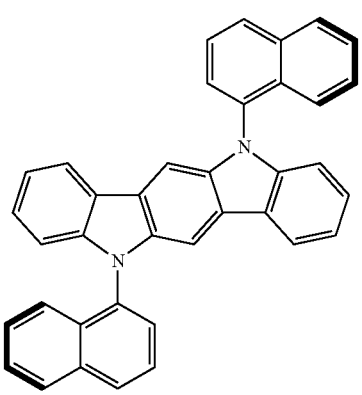
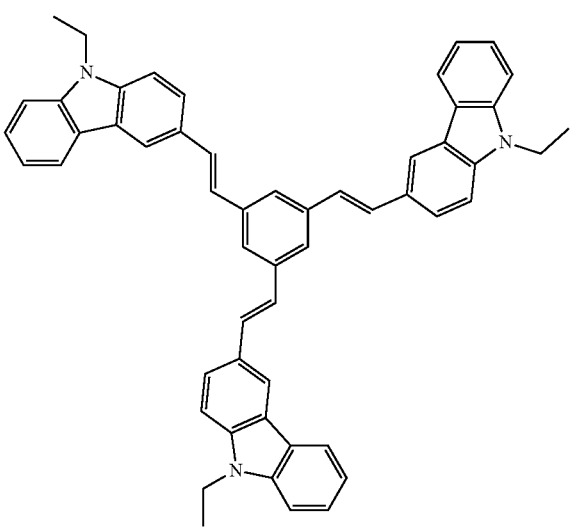

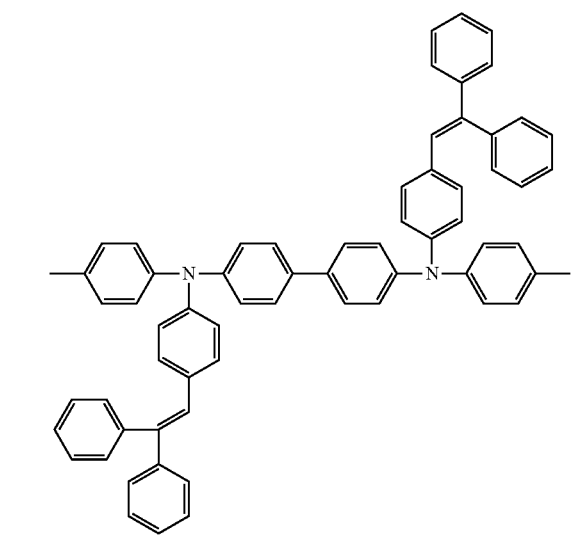
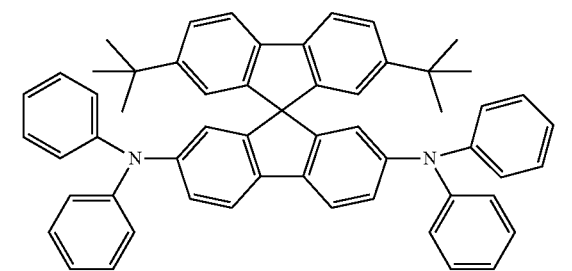
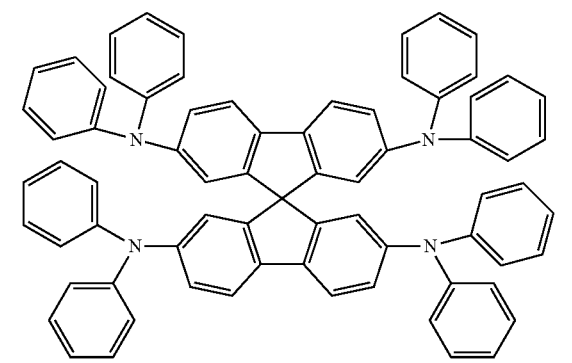
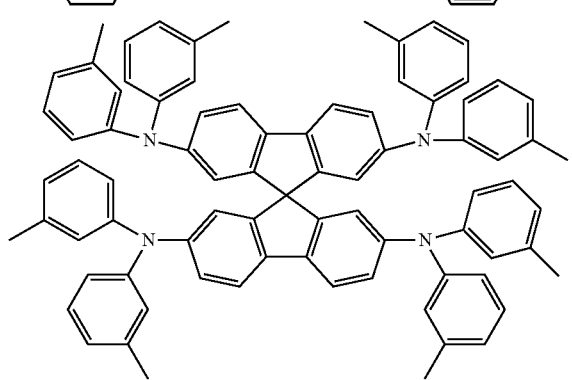
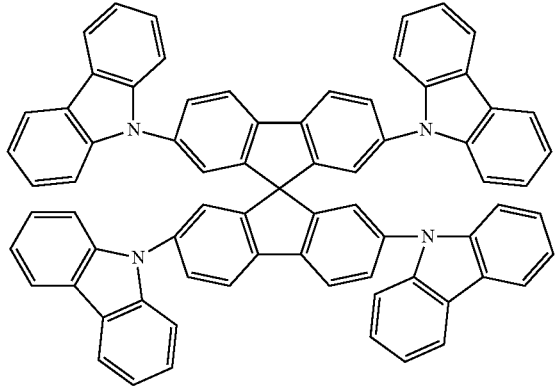
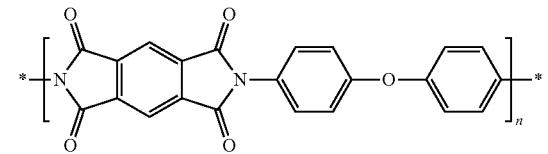
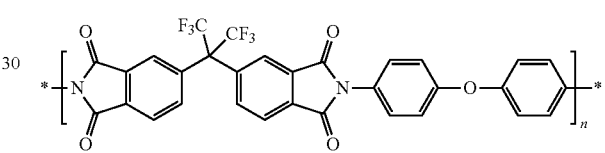
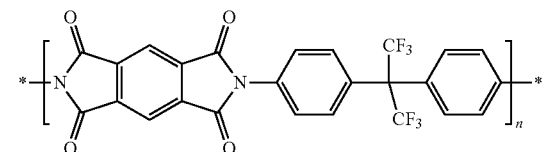
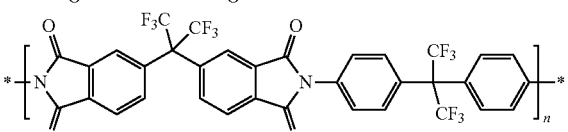
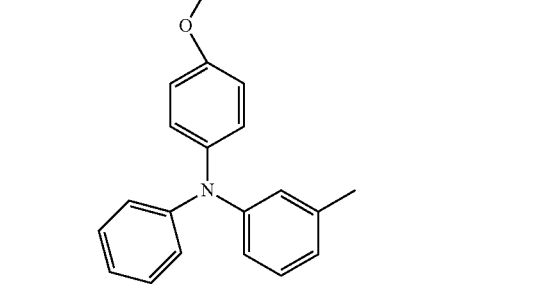

211
-continued
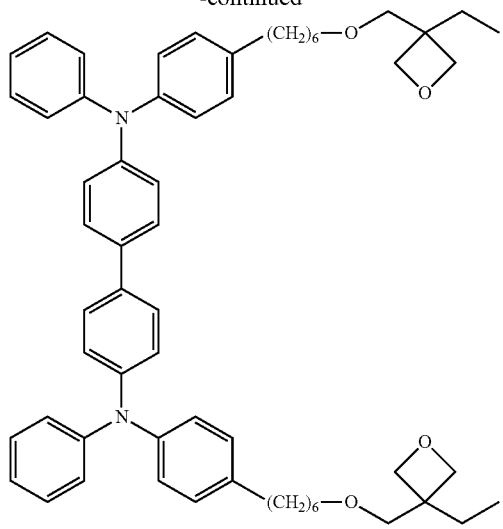
212
-continued
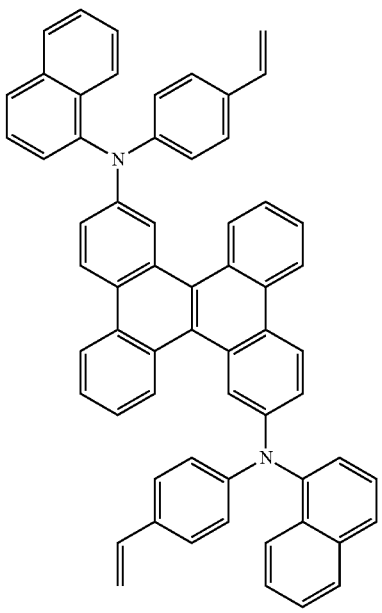
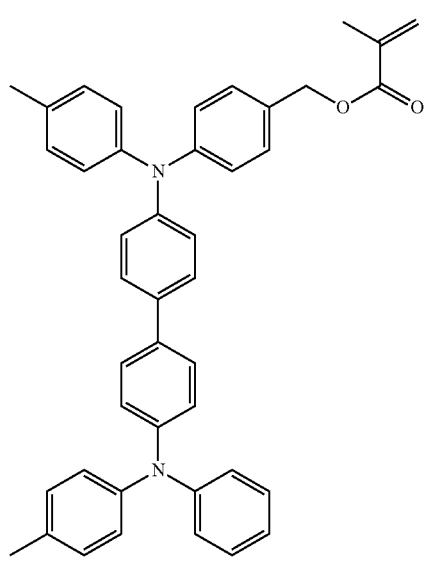
R =
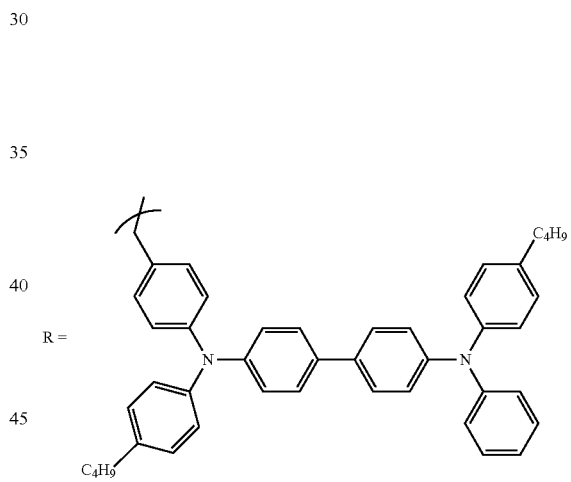
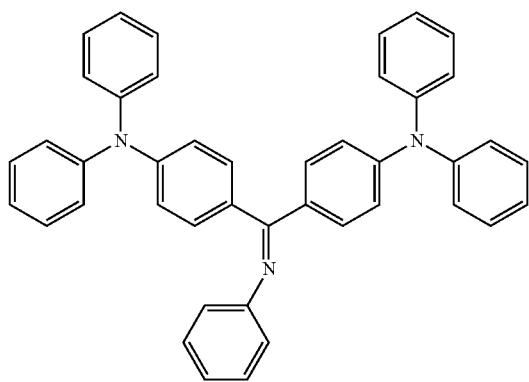

-continued
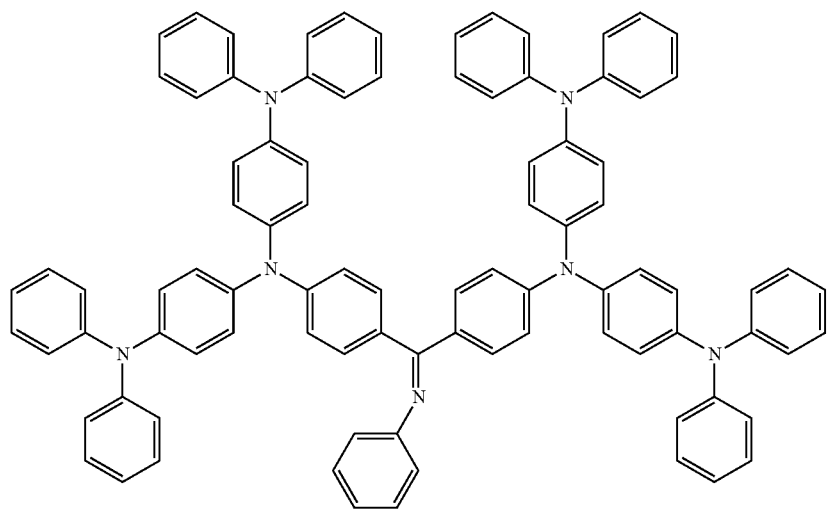
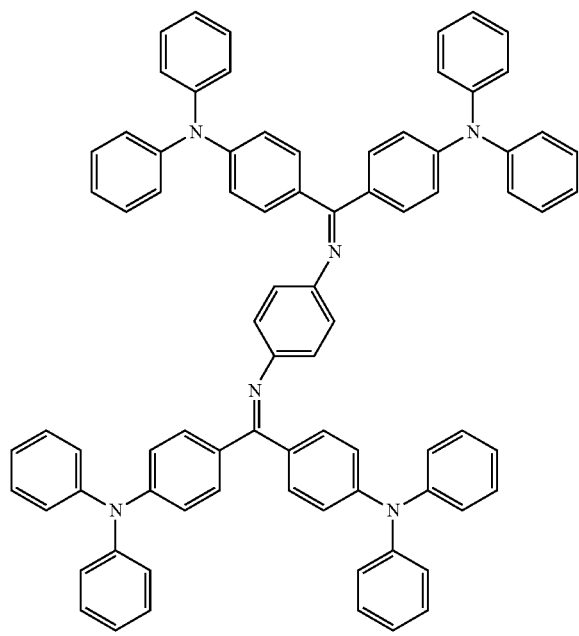

-continued
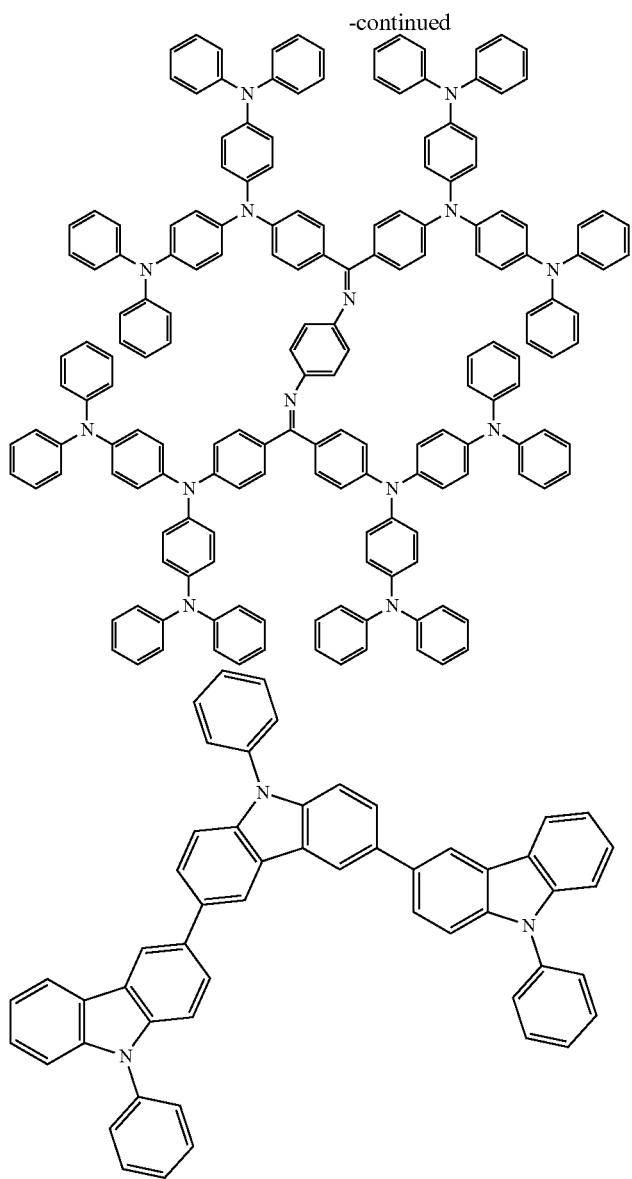
Next, preferred compounds for use as an electron blocking material are mentioned below.
-continued
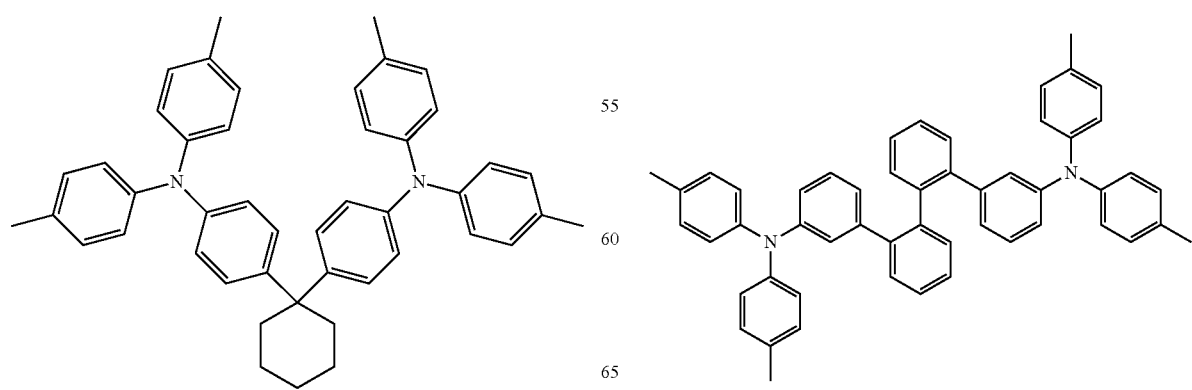

217
-continued
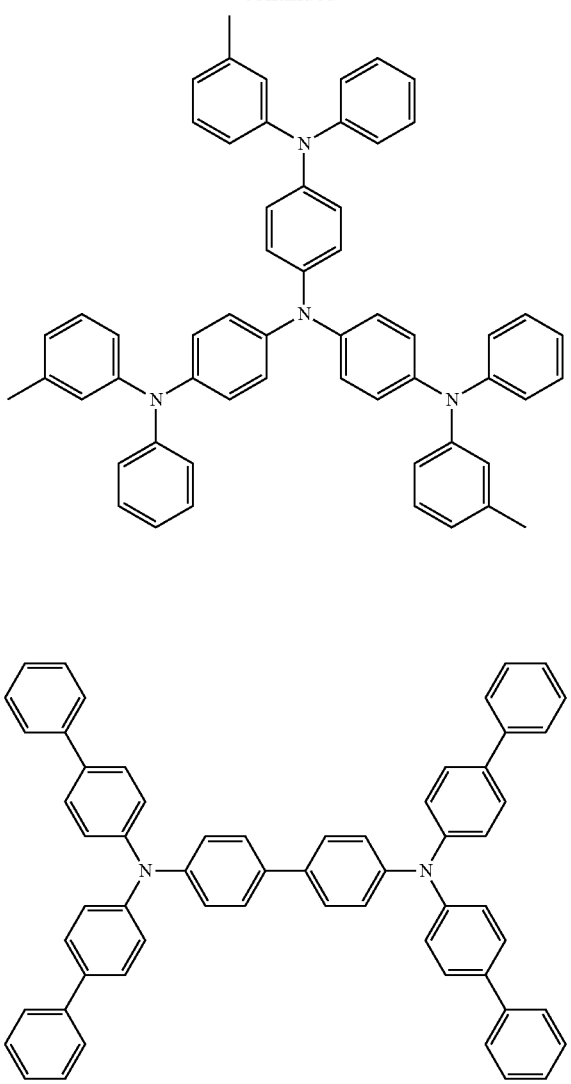
218
-continued
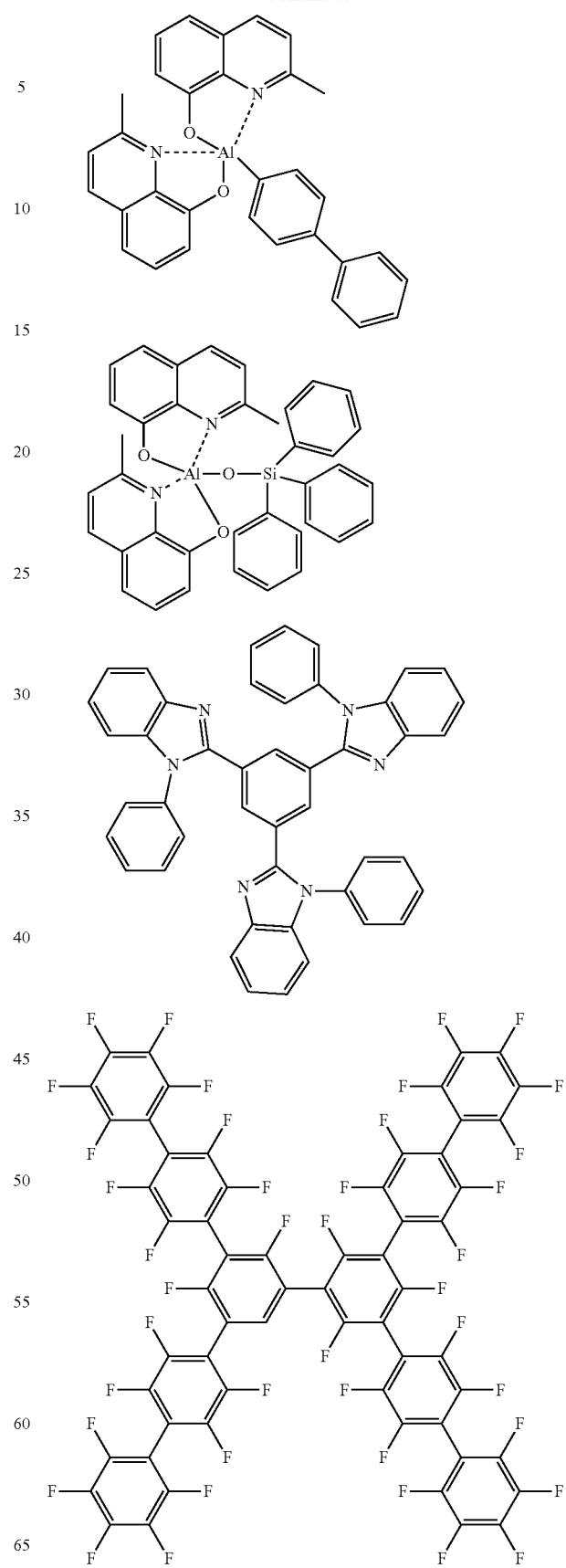
Next, preferred compounds for use as a hole blocking material are mentioned below.
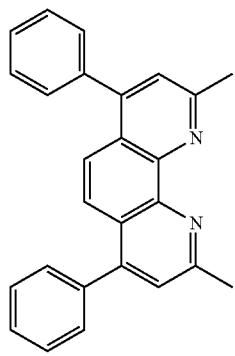

219
-continued
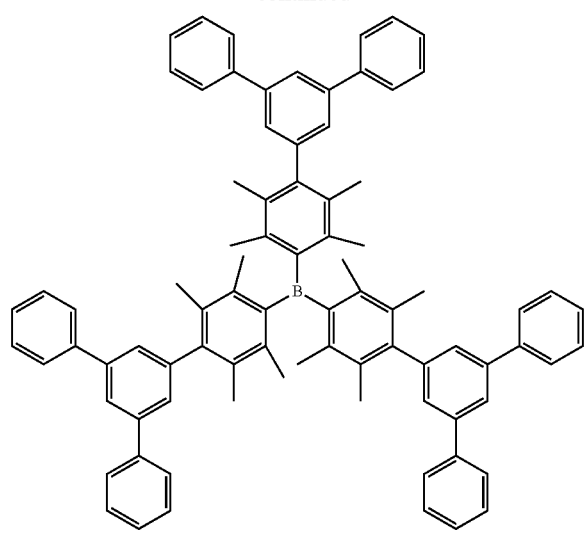
220
-continued
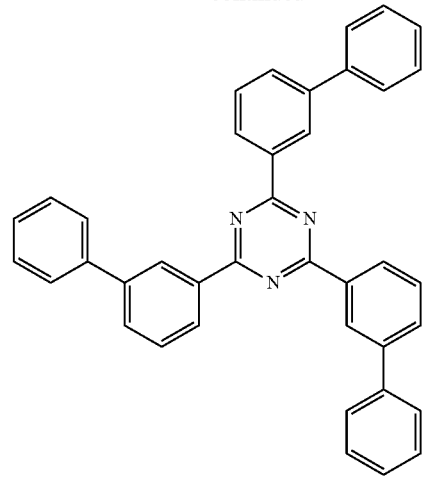
Next, preferred compounds for use as a hole blocking material are mentioned below.
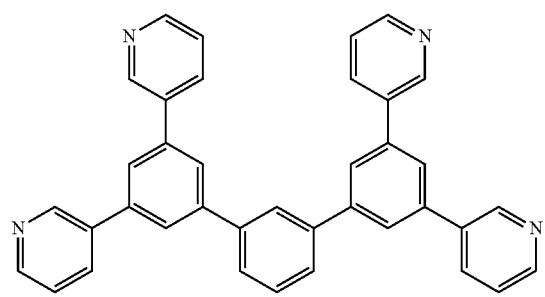
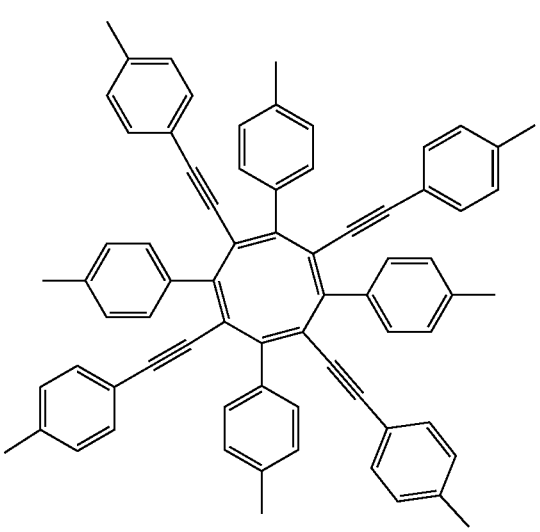
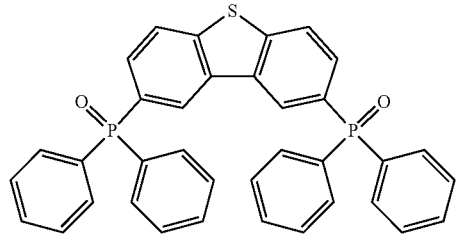
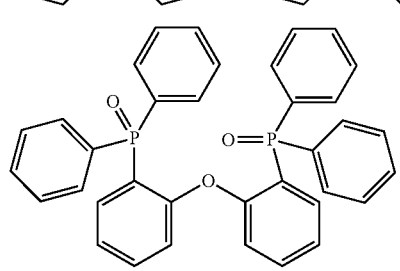
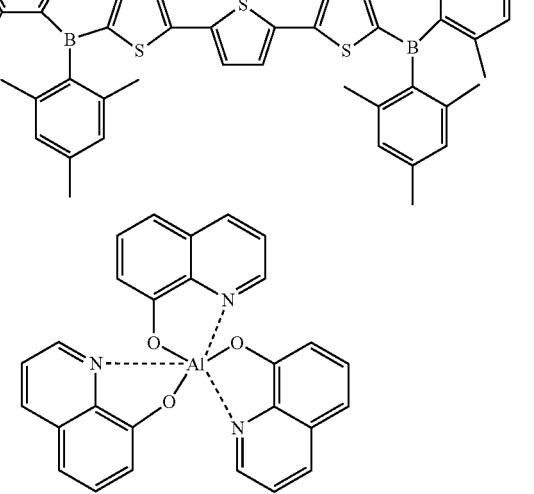

221
-continued
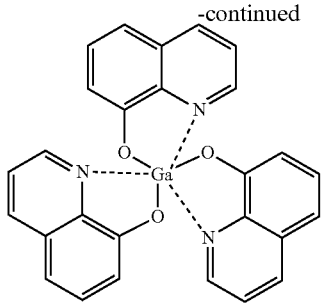
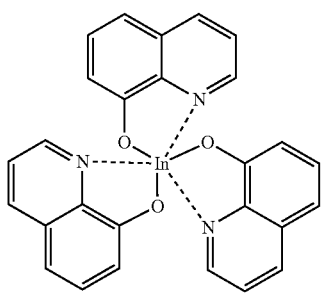
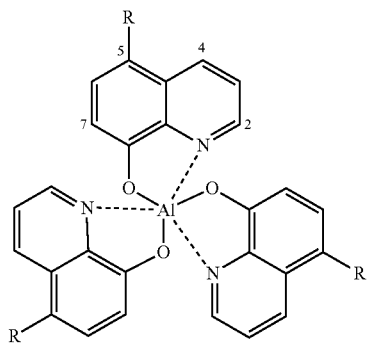
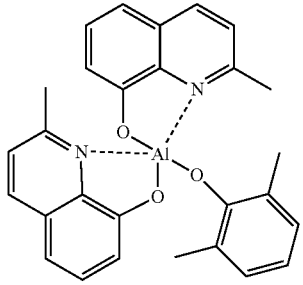
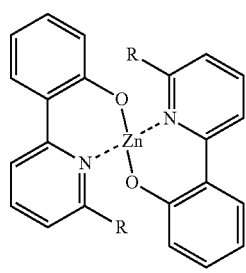
R = H
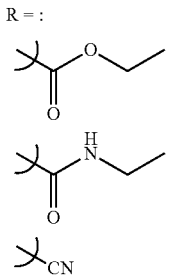
R =:
222
-continued
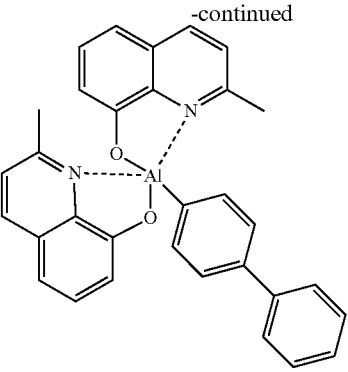
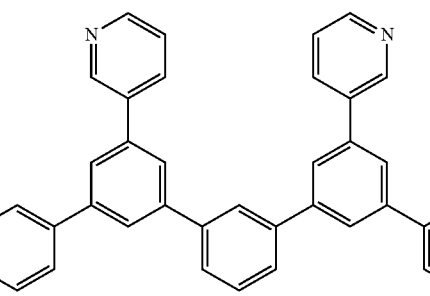
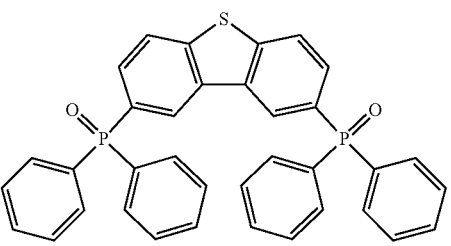
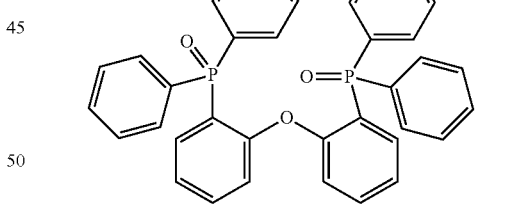
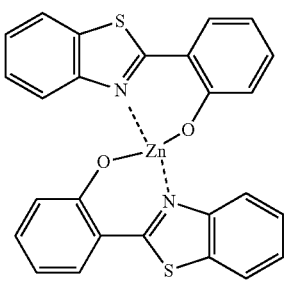
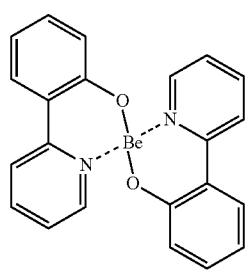

-continued
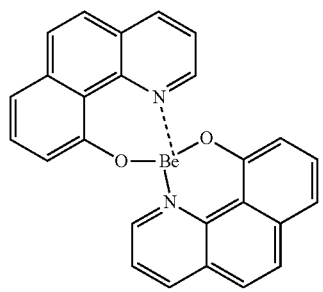 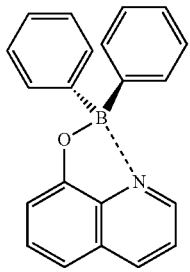 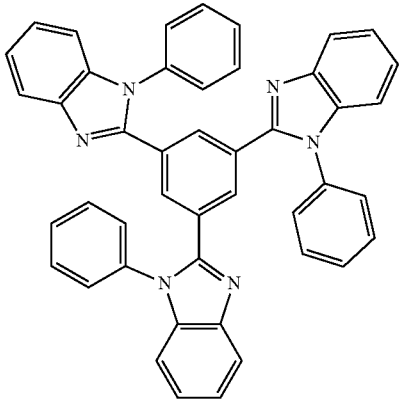
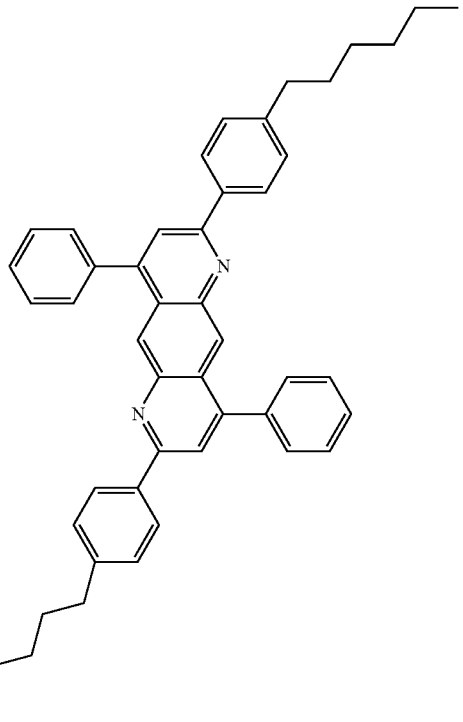 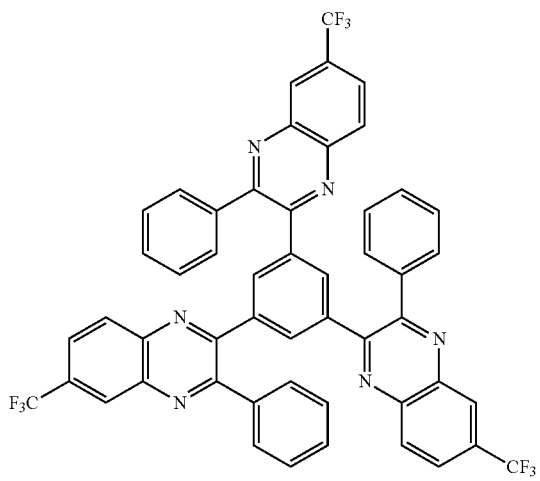
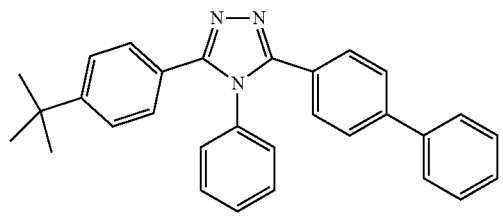
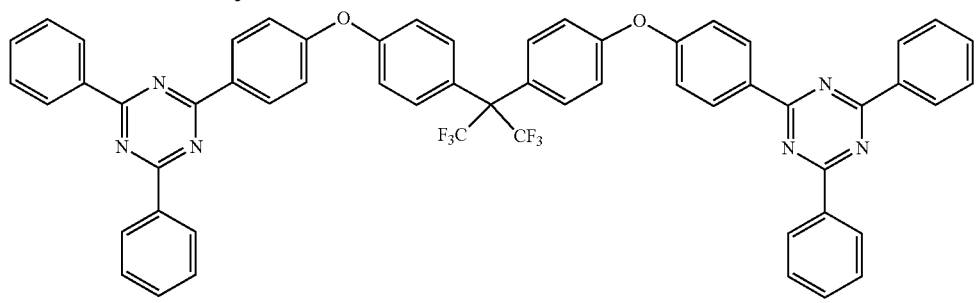

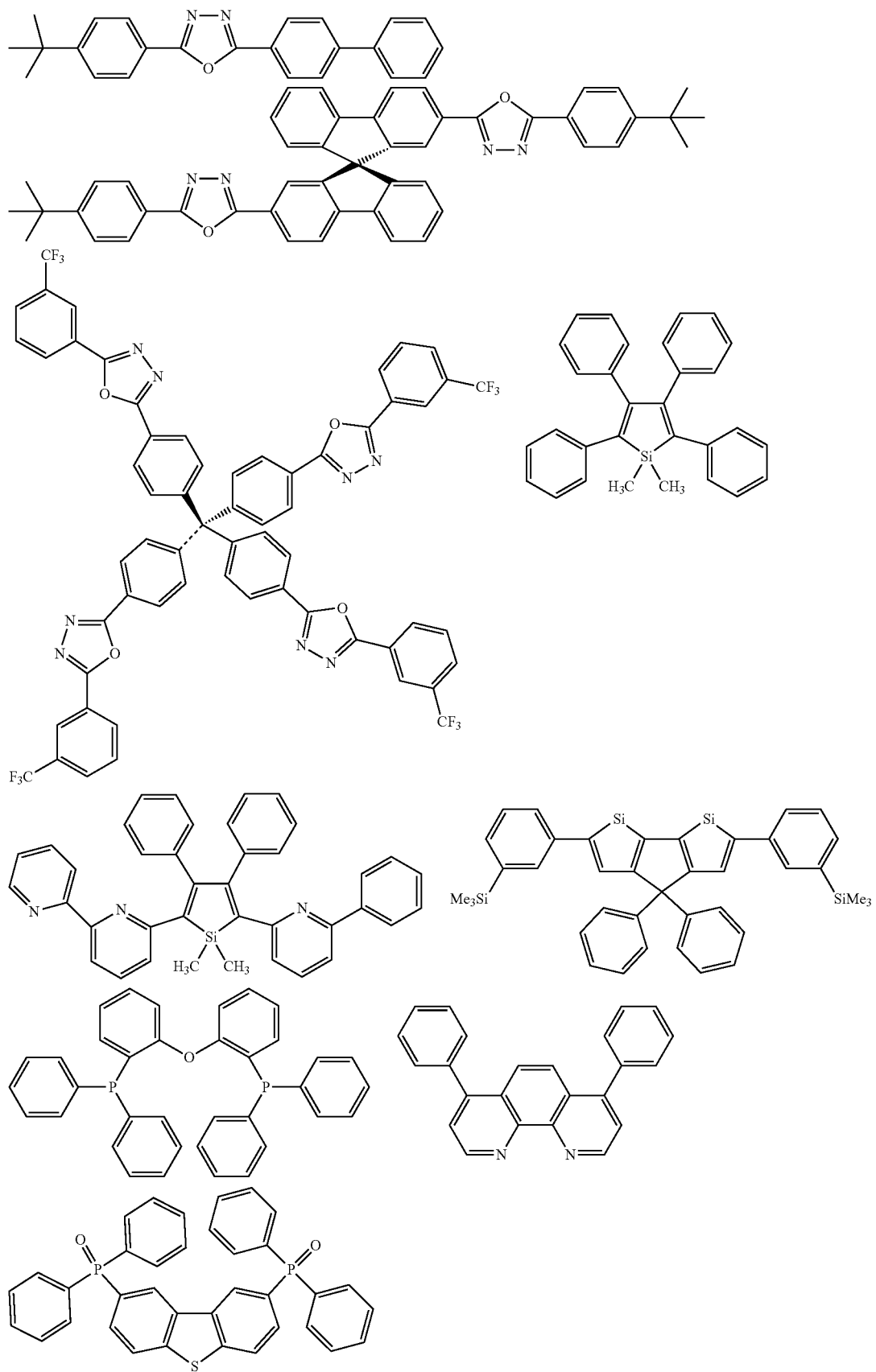

Next, preferred compounds for use as an electron injection material are mentioned below.

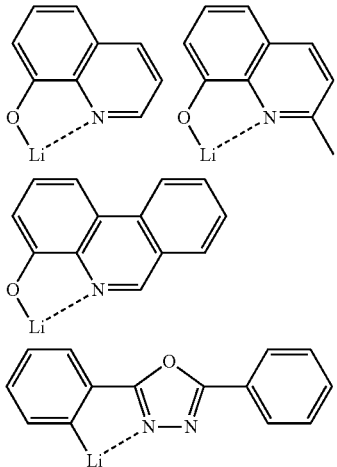

Further, preferred compounds for use as additional materials are mentioned below. For example, these are considered to be added as a stabilization material.

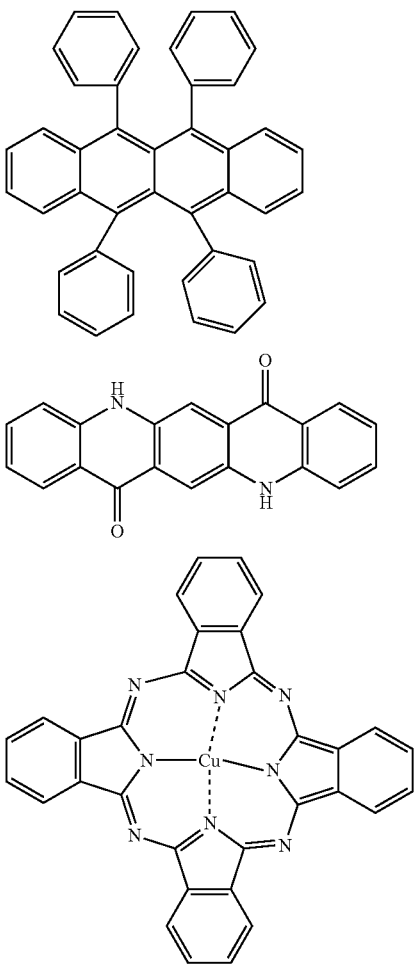

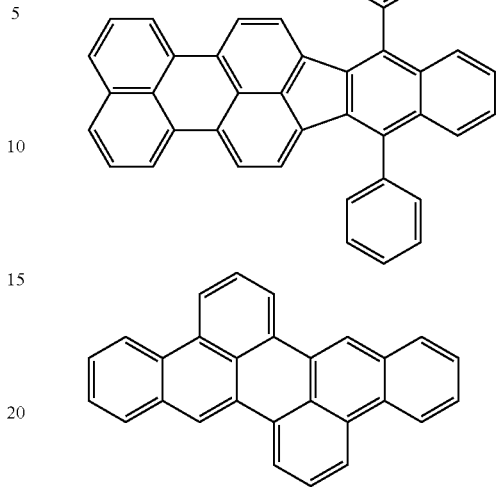

[Light Emission]

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

On the other hand, the phosphorescent light may substantially not be observed with an ordinary organic compound such as the compounds of the present invention at room temperature since the excited triplet energy thereof is unstable and is converted into heat or the like, that is, the lifetime is short and the compound may immediately deactivate. The excited triplet energy of an ordinary organic compound may be measured by observing light emission under an extremely low temperature condition.

[Application]

The organic electroluminescent device of the invention may be applied to any of a single device, a structure with plural devices disposed in an array, and a structure having anodes and cathodes disposed in an X-Y matrix. According to the present invention using the first organic compound, the second organic compound and the third organic compound satisfying the requirement in the present invention, in a light-emitting layer, an organic light-emitting device having a markedly improved light emission efficiency can be obtained. The organic light-emitting device such as the organic electroluminescent device of the present invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLES

The features of the present invention will be described more specifically with reference to Examples given below. The materials, processes, procedures and the like shown below may be appropriately modified unless they deviate from the substance of the invention. Accordingly, the scope of the invention is not construed as being limited to the specific examples shown below. The light emission characteristics were evaluated using a high-performance UV-visible light-near IR spectrophotometer (available from Perkin Elmer, Lambda 950), a fluorescence spectrophotometer (available from Horiba, Ltd., FluoroMax-4), an absolute PL quantum yield meter (available from Hamamatsu Photonics K.K., C11347), a source meter (available from Keithley Instruments Corporation: 2400 series), a semiconductor parameter analyzer (available from Agilent Technologies, E5273A), an optical power meter device (available from Newport Corporation, 1930C), an optical spectroscope (available from Ocean Optics Corporation, USB2000), a spectroradiometer (available from Topcon Corporation, SR-3), and a streak camera (available from Hamamatsu Photonics K.K., Model C4334).

Synthesis of Compounds (Synthesis Example 1) Synthesis of Compound 1

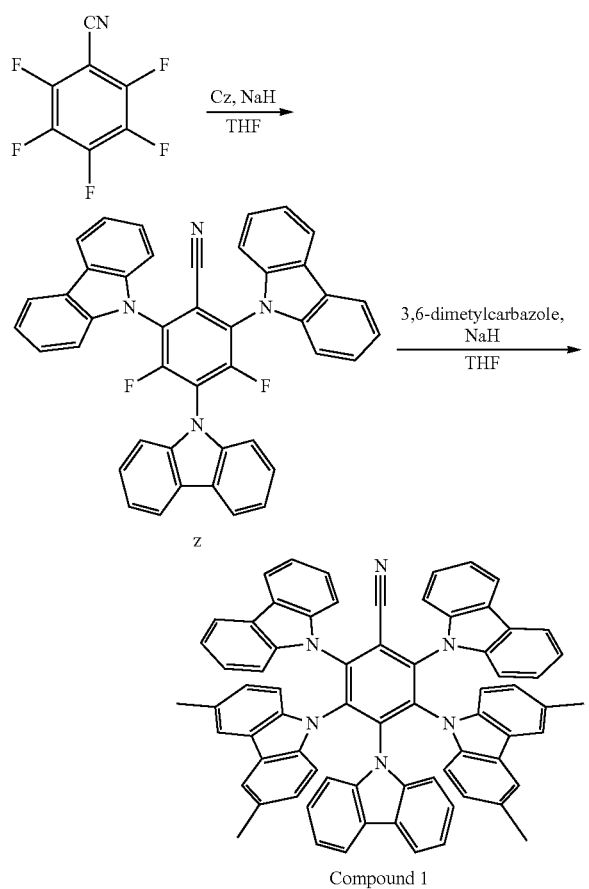

Compound 1

The compound (z) was synthesized according to the same method as in Adv. Opt. Mater. 4, 688-693 (2016).

Next, in a nitrogen stream atmosphere, 3,6-dimethylcarbazole (0.39 g, 1.98 mmol) was added to a tetrahydrofuran solution (20 mL) of sodium hydride (60% mineral oil dispersion, 0.08 g, 1.98 mmol), and stirred at room temperature for 1 hour. The mixture was cooled to 0° C., and the compound (z) (0.5 g, 0.79 mmol) was added thereto and stirred at 50° ° C. for 12 hours. The reaction mixture was quenched by adding it to water with ice, and then filtered to give a crude product. The resultant crude product was purified through silica gel column chromatography (toluene/hexane=3:2) to give a yellow solid of the compound 1 (0.79 g, 0.75 mmol, yield 95%).

$^1$H NMR: (500 MHz, acetone-d6): δ (ppm)=7.83 (d, J=8.2 Hz, 4H), 7.71 (d, J=7.1 Hz, 4H), 7.64 (d, J=8.3 Hz, 2H), 7.45 (d, J=8.4 Hz, 2H), 7.34 (d, J=7.2 Hz, 2H), 7.09 (m, 12H), 6.72 (t, J=7.9 Hz, 2H), 6.62 (d, J=8.4 Hz, 2H), 6.45 (d, J=8.3 Hz, 4H), 2.11 (s, 12H)

(Synthesis Example 2) Synthesis of Compound 2

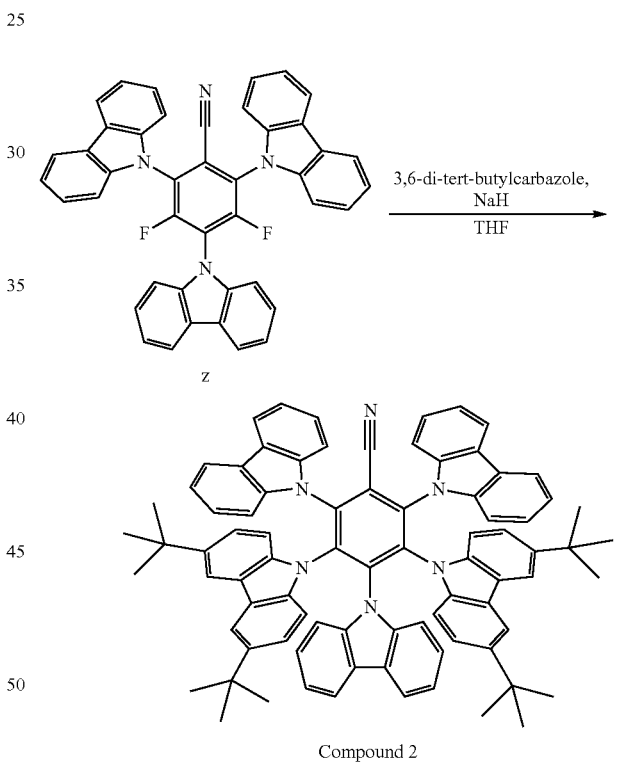

Compound 2

In a nitrogen stream atmosphere, 3,6-di-tert-butylcarbazole (1 g, 3.58 mmol) was added to a tetrahydrofuran solution (20 mL) of sodium hydride (60% mineral oil dispersion, 0.14 g, 3.58 mmol), and stirred at room temperature for 1 hour. The mixture was cooled to 0° C., and the compound (z) (1.04 g, 1.63 mmol) was added thereto and stirred at 50° C. for 12 hours. The reaction mixture was quenched by adding it to water with ice, and then filtered to give a crude product. The resultant crude product was purified through silica gel column chromatography (toluene/hexane=1:1) to give a yellow solid of the compound 2 (1.8 g, 1.56 mmol, yield 96%).

(Synthesis Example 3) Synthesis of Compound 3

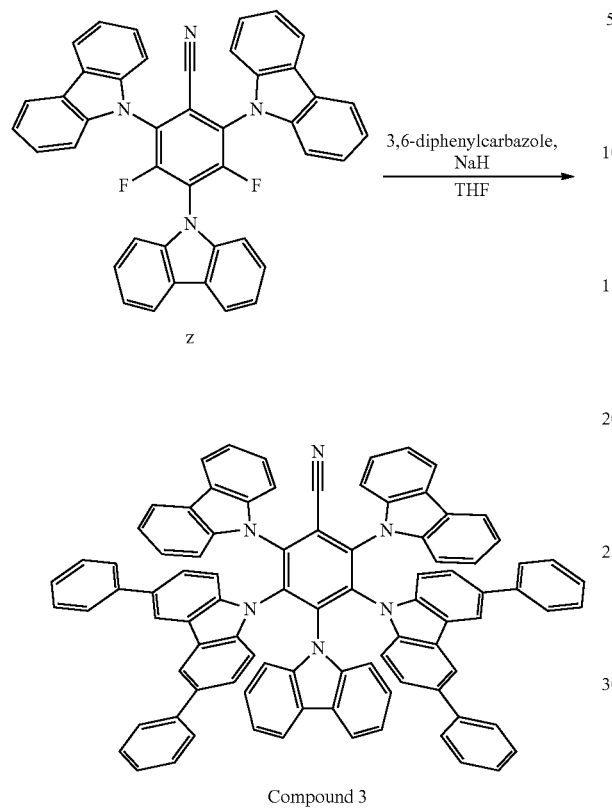

Compound 3

In a nitrogen stream atmosphere, 3,6-diphenylcarbazole (1 g, 3.15 mmol) was added to a tetrahydrofuran solution (20 mL) of sodium hydride (60% mineral oil dispersion, 0.13 g, 3.15 mmol), and stirred at room temperature for 1 hour. The mixture was cooled to 0° C., and the compound (z) (0.8 g, 1.26 mmol) was added thereto and stirred at 50° C. for 12 hours. The reaction mixture was quenched by adding it to water with ice, and then filtered to give a crude product. The resultant crude product was purified through silica gel column chromatography (toluene/hexane=3:2) to give a yellow solid of the compound 3 (1.36 g, 1.10 mmol, yield 87%).

$^1$H NMR: (500 MHz, acetone-d6): δ (ppm)=7.82 (m, 14H), 7.72 (d, J=8.7 Hz, 4H), 7.45 (m, 8H), 7.35 (m, 10H), 7.26 (t, J=8.6 Hz, 4H), 7.16 (t, J=8.3 Hz, 4H), 7.10 (t, J=7.9 Hz, 4H), 6.98 (d, J=8.6 Hz, 4H), 6.75 (m, 4H)

(Synthesis Example 4) Synthesis of Compound 4

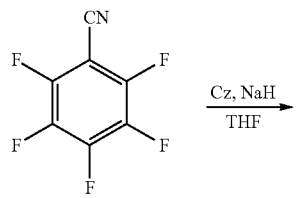

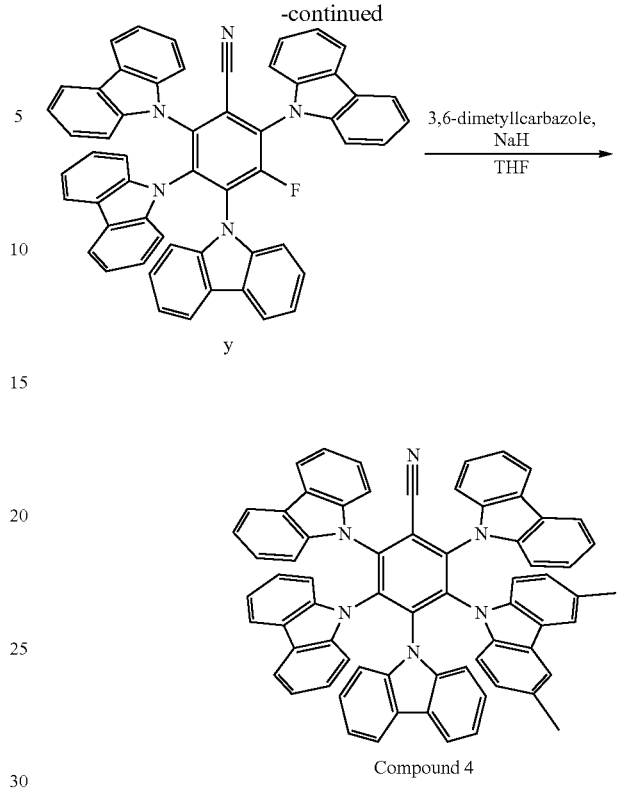

Compound 4

The compound (y) was synthesized according to the same method as in Adv. Opt. Mater. 4, 688-693 (2016).

Next, in a nitrogen stream atmosphere, 3,6-dimethylcarbazole (0.37 g, 1.92 mmol) was added to a tetrahydrofuran solution (20 mL) of sodium hydride (60% mineral oil dispersion, 0.08 g, 1.92 mmol), and stirred at room temperature for 1 hour. The mixture was cooled to 0° C., and the compound (y) (1.0 g, 1.28 mmol) was added thereto and stirred at 50° C. for 12 hours. The reaction mixture was quenched by adding it to water with ice, and then filtered to give a crude product. The resultant crude product was purified through silica gel column chromatography (toluene/hexane=3:2) to give a yellow solid of the compound 4 (1.08 g, 1.13 mmol, yield 88%).

(Synthesis Example 5) Synthesis of Compound 5

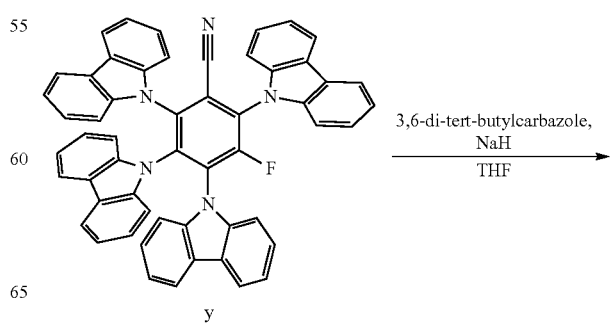

-continued

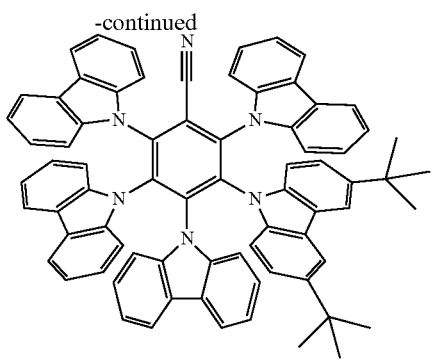

Compound 5

In a nitrogen stream atmosphere, 3,6-di-tert-butylcarbazole (0.54 g, 1.92 mmol) was added to a tetrahydrofuran solution (20 mL) of sodium hydride (60% mineral oil dispersion, 0.08 g, 1.92 mmol), and stirred at room temperature for 1 hour. The mixture was cooled to 0° C., and the compound (y) (1.0 g, 1.28 mmol) was added thereto and stirred at 50° C. for 12 hours. The reaction mixture was quenched by adding it to water with ice, and then filtered to give a crude product. The resultant crude product was purified through silica gel column chromatography (toluene/hexane=3:2) to give a yellow solid of the compound 5 (1.16 g, 1.11 mmol, yield 87%).

(Synthesis Example 6) Synthesis of Compound 6

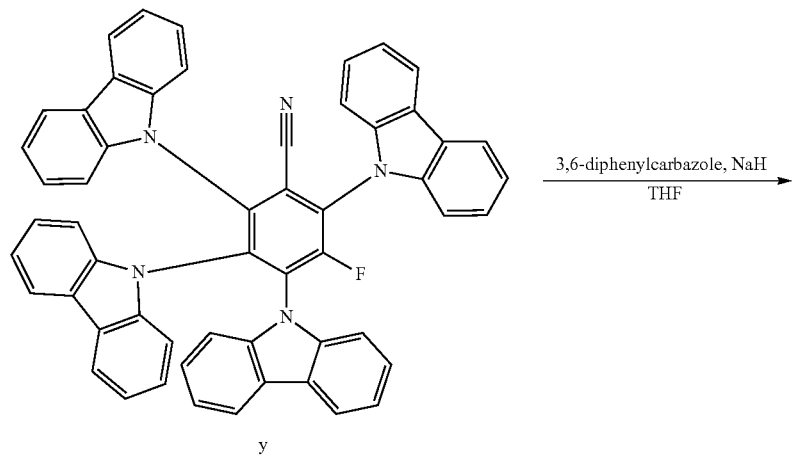

y

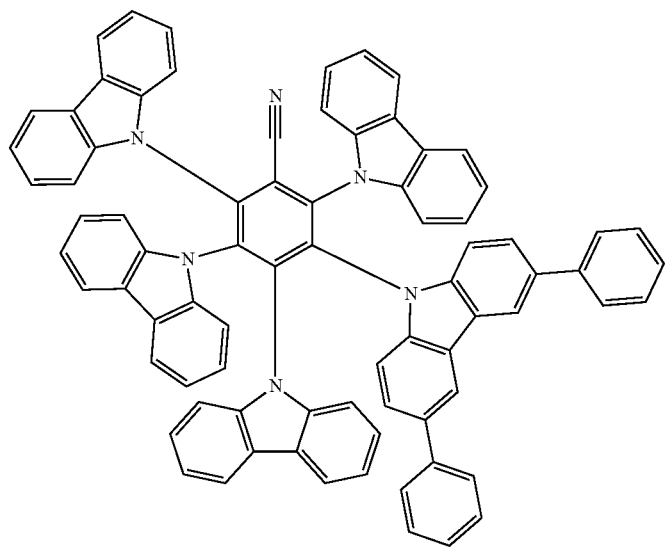

Compound 6

In a nitrogen stream atmosphere, 3,6-diphenylcarbazole (0.61 g, 1.92 mmol) was added to a tetrahydrofuran solution (20 mL) of sodium hydride (60% mineral oil dispersion, 0.08 g, 1.92 mmol), and stirred at room temperature for 1 hour. The mixture was cooled to 0° C., and the compound (y) (1.0 g, 1.28 mmol) was added thereto and stirred at 50° C. for 12 hours. The reaction mixture was quenched by adding it to water with ice, and then filtered to give a crude product. The resultant crude product was purified through silica gel column chromatography (toluene/hexane=3:2) to give a yellow solid of the compound 6 (1.18 g, 1.09 mmol, yield 85%).

$^1$H NMR: (500 MHz, acetone-d6): δ (ppm)=7.82 (m, 8H), 7.75 (m, 4H), 7.67 (t, J=7.8 Hz, 4H), 7.45 (m, 4H), 7.35 (m, 8H), 7.25 (t, J=8.0 Hz, 2H), 7.11 (m, 8H), 6.95 (d, J=8.6 Hz, 2H), 6.74 (m, 4H), 6.66 (t, J=7.8 Hz, 4H)

(Synthesis Example 7) Synthesis of Compound 7

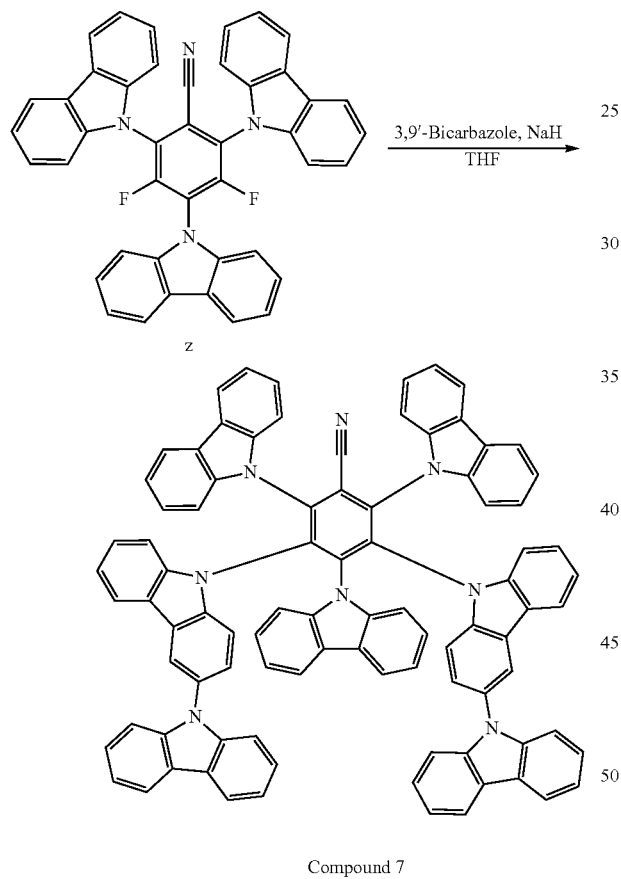

Compound 7

In a nitrogen stream atmosphere, 3,9'-bicarbazole (0.66 g, 1.98 mmol) was added to a tetrahydrofuran solution (15 mL) of sodium hydride (60% mineral oil dispersion, 0.08 g, 1.98 mmol), and stirred at room temperature for 1 hour. The mixture was cooled to 0° C., and the compound (z) (0.5 g, 0.79 mmol) was added thereto and stirred at 50° C. for 12 hours. The reaction mixture was quenched by adding it to water with ice, and then filtered to give a crude product. The resultant crude product was purified through silica gel column chromatography (toluene/hexane=1:1) to give a yellow solid of the compound 7 (0.54 g, 0.43 mmol, yield 54%).

(Synthesis Example 8) Synthesis of Compound 11

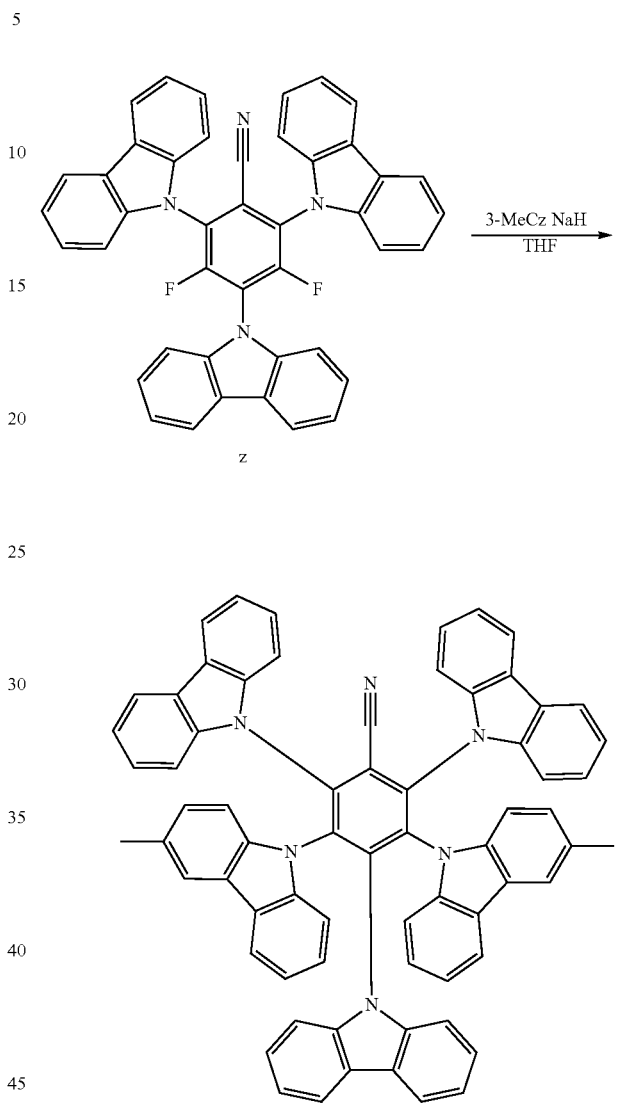

Compound 11

In a nitrogen stream atmosphere, 3-methyl-9H-carbazole (0.51 g, 0.83 mmol) was added to a tetrahydrofuran solution (15 mL) of sodium hydride (60% mineral oil dispersion, 0.15 g, 3.78 mmol), and stirred at room temperature for 1 hour. The mixture was cooled to 50° C., and the compound (z) (0.6 g, 0.95 mmol) was added thereto and stirred at 50° C. for 12 hours. Water was added to the reaction mixture for precipitation, and the resultant precipitate was taken out through filtration. The filtered mixture was purified through silica gel column chromatography (toluene) to give the compound 11 (0.65 g, 0.68 mmol, yield 71.9%).

$^1$H-NMR (500 MHz, CDCl$_3$, δ): 7.76-7.72 (m, 4H), 7.30-7.12 (m, 10H), 7.10-7.02 (m, 10H), 6.98 (t, J=8.5 Hz, 2H), 6.91 (t, J=8.5 Hz, 2H), 6.76-6.71 (m, 4H), 6.61-6.53 (m, 4H), 6.41 (t, J=8.5 Hz, 2H), 2.17-2.16 (m, 6H)

ASAP Mass Spectrometry: Theoretical 956.4, Found 957.3

(Synthesis Example 9) Synthesis of Compound 35

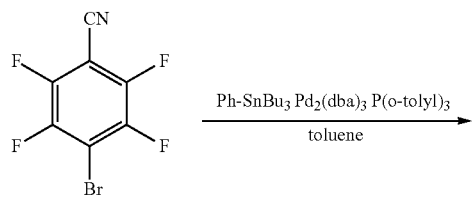

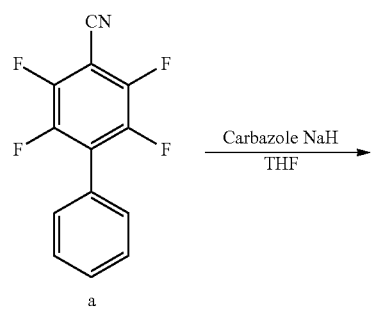

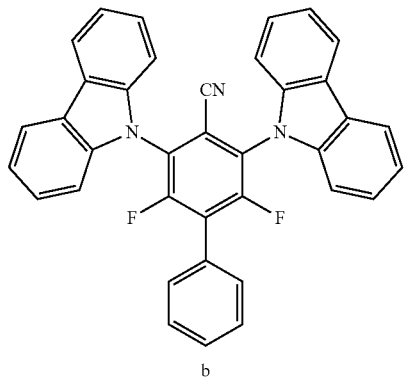

In a nitrogen stream atmosphere, tri(o-tolyl) phosphine (0.525 g, 1.72 mmol) and tris(dibenzylideneacetone)palladium(0) (1.57 g, 1.72 mmol) were added to a toluene solution (50 mL) of tributyltin chloride (5.06 g, 4.45 ml, 13.78 mmol) and 4-bromo-2,3,5,6-tetrafluorobenzonitrile (2.92 g, 11.50 mmol), heated up to 100° C., and stirred for 21 hours. The mixture was restored to room temperature, then quenched by adding water thereto, extracted with ethyl acetate, and filtered through Celite. Next, the organic layer was washed with saturated saline water, and dried with anhydrous magnesium sulfate. This was concentrated under reduced pressure, and the resultant mixture was purified through silica gel column chromatography (dichloromethane/hexane=1:2) to give a white solid of the compound (a) (2.42 g, 9.63 mmol, yield 83.7%).

$^1$H-NMR (500 MHz, CDCl$_3$, δ): 7.56-7.51 (m, 3H), 7.48-7.45 (m, 2H)

ASAP Mass Spectrometry: Theoretical 251.0, Found 251.1

In a nitrogen stream atmosphere, 9H-carbazole (0.397 g, 2.38 mmol) was added to a tetrahydrofuran solution (10 mL) of sodium hydride (60% mineral oil dispersion, 0.125 g, 3.14 mmol), and stirred at room temperature for 1 hour. The mixture was cooled to −50° C., and the compound (a) (0.3 g, 1.19 mmol) was added thereto, then the cooling bath was removed, and with gradually restoring to room temperature, this was stirred for 22 hours. The reaction mixture was quenched by adding it to water with ice, then extracted with ethyl acetate, and the organic layer was washed with saturated saline water, and dried with anhydrous magnesium sulfate. This was concentrated under reduced pressure, and the resultant mixture was purified through silica gel column chromatography (chloroform/hexane=1:2) to give a yellow solid of the compound (b) (0.486 g, 0.89 mmol, yield 74.8%).

$^1$H-NMR (500 MHz, CDCl$_3$, δ): 8.16 (d, J=7.5 Hz, 4H), 7.62-7.59 (m, 2H), 7.54-7.49 (m, 7H), 7.38 (dt, J=7.5 Hz, 1.0 Hz, 4H), 7.30 (d, J=7.5 Hz, 4H)

ASAP Mass Spectrometry: Theoretical 545.2, Found 545.2

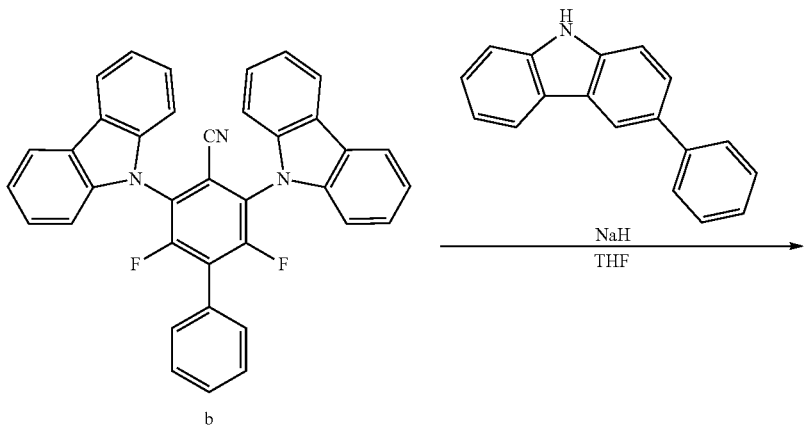

-continued

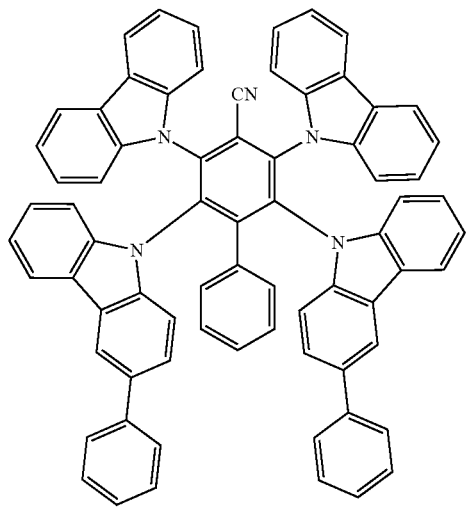

Compound 35

3-Phenyl-9H-carbazole (0.575 g, 2.36 mmol), potassium carbonate (0.702 g, 3.94 mmol) and the compound (b) (0.5 g, 0.788 mmol) were put into a 100-mL three-neck flask, which was then purged with nitrogen. Dewatered 1-methyl-2-pyrrolidone (10 mL) was added to the mixture, and then stirred in a nitrogen atmosphere under heat at 100° C. for 12 hours. After the stirring, the mixture was restored to room temperature, and then water was added and filtered under suction. The resultant solid was dissolved in toluene and purified through silica gel column chromatography. The resultant fraction was concentrated and recrystallized with a mixed solvent of chloroform and acetonitrile to give a pale yellow solid of the compound 35 (yield; 0.60 g, 77%).

$^1$H NMR (500 MHz, CDCl$_3$, δ): 7.77 (d, J=1.2, 2H), 7.55-7.69 (m, 4H), 7.60 (d, J=7.5 Hz, 2H), 7.51 (dd, J=8.5 Hz, 4H), 7.42 (td, J=8.0, J=2.0, 4H), 7.32-6.94 (m, 24H), 6.75 (d, J=7.5, 2H), 6.55 (td, J=7.51, J=1.2, 1H), 6.46 (t, J=7.5, 2H)

ASAP Mass Spectrometry: Theoretical 991.37, Found 992.39

(Synthesis Example 10) Synthesis of Compound 38

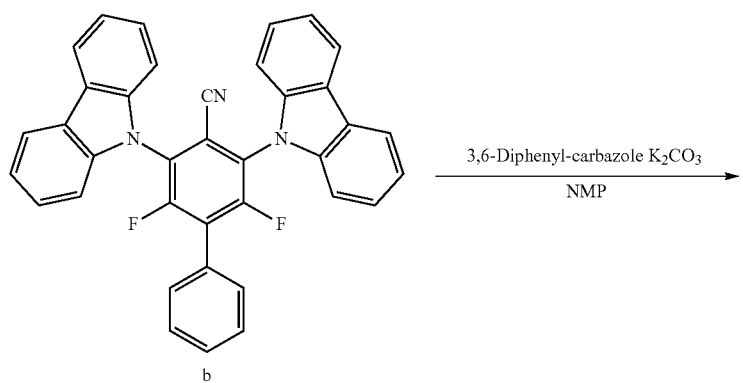

b

-continued

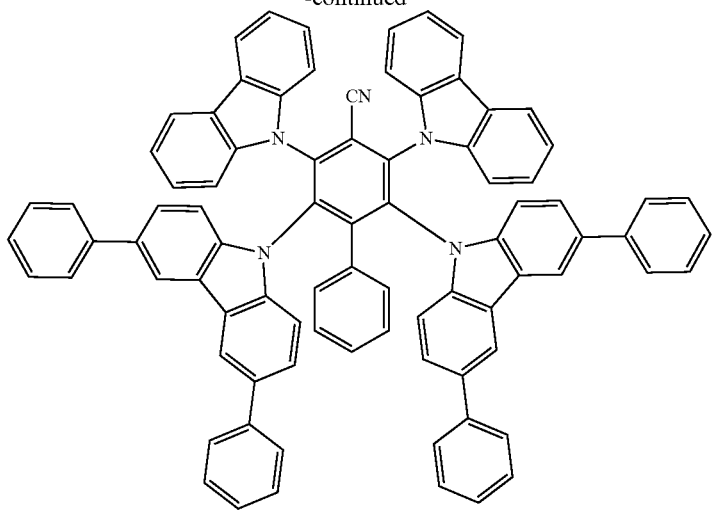

Compound 38

In a nitrogen stream atmosphere, the compound (b) (0.45 g, 0.825 mmol) prepared in Synthesis Example 9 was added to a 1-methyl-2-pyrrolidone solution (10 mL) of 3,6-diphenylcarbazole (0.66 g, 2.06 mmol) and potassium carbonate (0.43 g, 3.11 mmol), and stirred at 100° C. for 48 hours. The mixture was restored to room temperature, then quenched by adding water thereto, extracted with ethyl acetate, and the organic layer was washed with saturated saline water, and dried with anhydrous magnesium sulfate. This was concentrated under reduced pressure, and the resultant mixture was purified through silica gel column chromatography (chloroform/hexane=1:1) to give a yellow solid of the compound 38 (0.575 g, 0.502 mmol, yield 60.9%).

$^1$H-NMR (500 MHz, CDCl$_3$, δ): 7.81 (d, J=1.5 Hz, 4H), 7.72-7.70 (m, 4H), 7.54-7.52 (m, 8H), 7.43 (t, J=7.5 Hz, 8H), 7.32 (t, J=7.5 Hz, 4H), 7.29-7.06 (m, 20H), 6.86-6.83 (m, 2H), 6.61-6.58 (m, 1H), 6.56-6.52 (m, 2H)

ASAP Mass Spectrometry: Theoretical 1143.4, Found 1143.4

(Synthesis Example 11) Synthesis of Compound 48

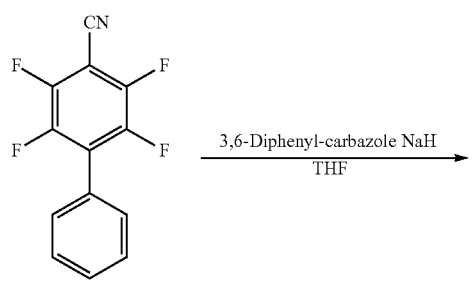

3,6-Diphenyl-carbazole NaH
THF
⟶

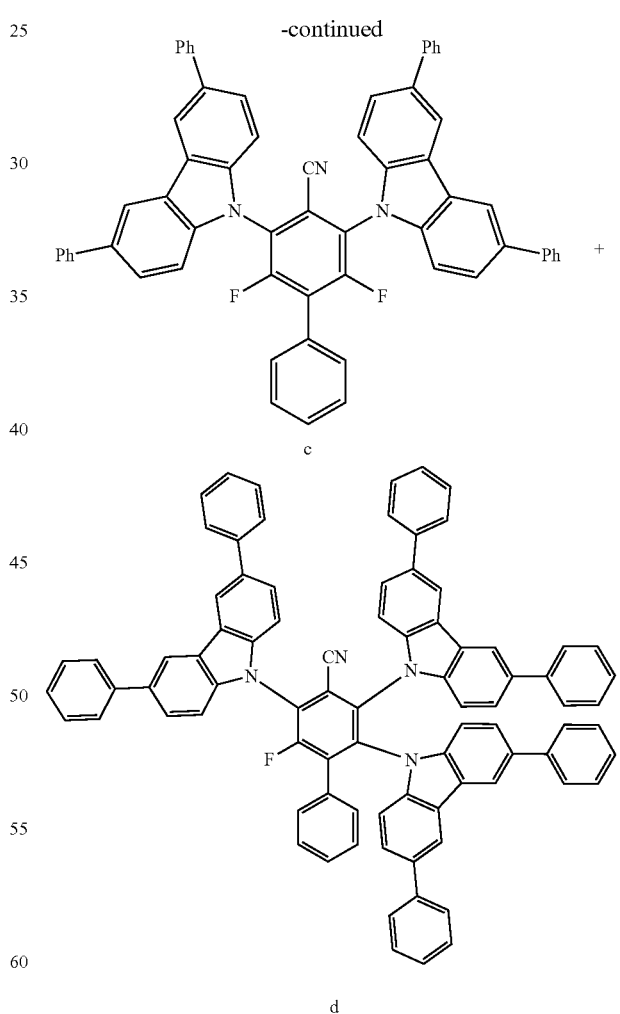

In a nitrogen stream atmosphere, 3,6-diphenylcarbazole (0.95 g, 2.97 mmol) was added to a tetrahydrofuran solution (10 mL) of sodium hydride (60% mineral oil dispersion, 0.315 g, 7.88 mmol), and stirred at room temperature for 1 hour. The mixture was cooled to −50° C., and the compound (a) (0.3 g, 1.19 mmol) prepared in Synthesis Example 9 was added thereto, then the cooling bath was removed, and with gradually restoring to room temperature, this was stirred for 17 hours. The reaction mixture was quenched by adding it to water with ice, then extracted with ethyl acetate, and the organic layer was washed with saturated saline water, and dried with anhydrous magnesium sulfate. This was concentrated under reduced pressure, and the resultant mixture was purified through silica gel column chromatography (chloroform/hexane=1:2) to give a yellow solid of the compound (c) (0.308 g, 0.362 mmol, yield 30.4%), and a yellow solid of the compound (d) (0.70 g, 0.609 mmol, yield 51.2%).

Compound (c):
$^1$H-NMR (500 MHz, CDCl$_3$, δ): 8.42 (d, J=1.0 Hz, 4H), 7.80 (dd, J=7.0 Hz, 2.0 Hz, 4H), 7.74 (dd, J=8.0 Hz, 1.0 Hz, 8H), 7.68-7.65 (m, 2H), 7.58-7.48 (m, 11H), 7.42 (d, J=8.0 Hz, 4H), 7.40-7.36 (m, 4H)

ASAP Mass Spectrometry: Theoretical 849.3, Found 849.3

Compound (d):
$^1$H-NMR (500 MHz, CDCl$_3$, δ): 8.47 (d, J=1.5 Hz, 2H), 7.89 (dd, J=8.5 Hz, 2.0 Hz, 2H), 7.83 (d, J=1.5 Hz, 2H), 7.80-7.78 (m, 4H), 7.74 (d, J=1.5 Hz, 2H), 7.66 (d, J=8.0 Hz, 2H), 7.54-7.52 (m, 4H), 7.48-7.44 (m, 8H), 7.42-7.27 (m, 18H), 7.19-7.16 (m, 7H), 7.01 (d, J=8.0 Hz, 2H)

ASAP Mass Spectrometry: Theoretical 1148.4, Found 1148.4

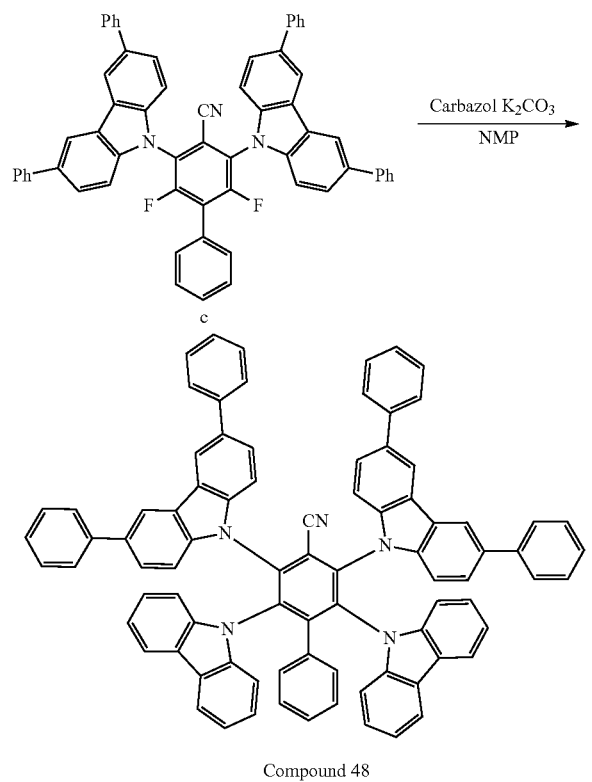

Compound 48

In a nitrogen stream atmosphere, the compound (c) (0.30 g, 0.35 mmol) was added to a 1-methyl-2-pyrrolidone solution (10 mL) of 9H-carbazole (0.175 g, 1.05 mmol) and potassium carbonate (0.184 g, 1.33 mmol), and stirred at 100° C. for 20 hours. The mixture was restored to room temperature, then quenched by adding water thereto, extracted with ethyl acetate, and the organic layer was washed with saturated saline water, and dried with anhydrous magnesium sulfate. This was concentrated under reduced pressure, and the resultant mixture was purified through silica gel column chromatography (chloroform/hexane=1:2) to give a yellow solid of the compound 48 (0.317 g, 0.277 mmol, yield 79.1%).

$^1$H-NMR (500 MHz, CDCl$_3$, δ): 7.96 (d, J=1.5 Hz, 4H), 7.59-7.55 (m, 12H), 7.45 (t, J=7.5 Hz, 8H), 7.35-7.31 (m, 12H), 7.07-7.01 (m, 4H), 7.00-6.94 (m, 8H), 6.76-6.74 (m, 2H), 6.58-6.54 (m, 1H), 6.45 (t, J=8.0 Hz, 2H)

ASAP Mass Spectrometry: Theoretical 1143.4, Found 1143.3

(Synthesis Example 12) Synthesis of Compound 55

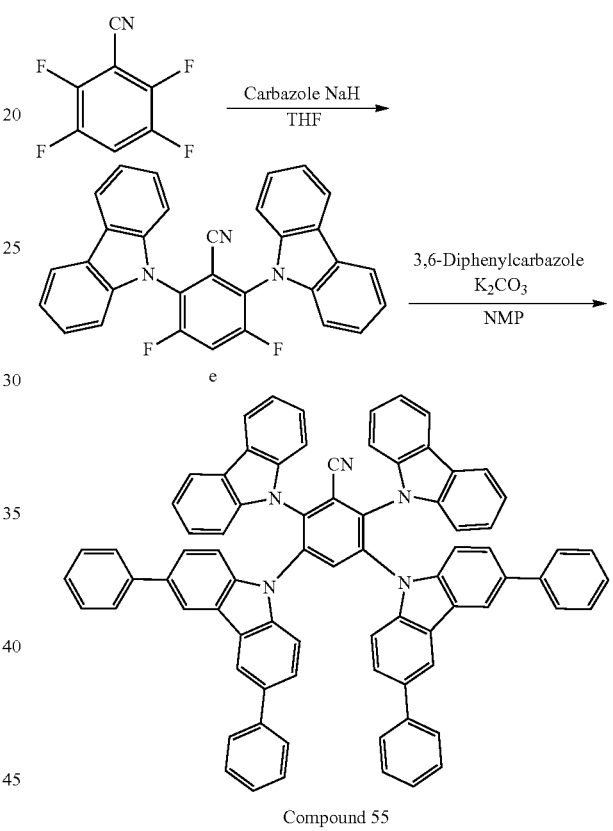

Compound 55

In a nitrogen stream atmosphere, 9H-carbazole (4.78 g, 28.59 mmol) was added to a tetrahydrofuran solution (120 mL) of sodium hydride (60% mineral oil dispersion, 0.90 g, 22.51 mmol), and stirred for 1 hour. The mixture was cooled to −50° C., and 2,3,5,6-tetrafluorobenzonitrile (2.50 g, 14.28 mmol) was added thereto, then the cooling bath was removed, and with gradually restoring to room temperature, this was stirred for 110 hours. The reaction mixture was quenched by adding it to water with ice, then extracted with ethyl acetate, and the organic layer was washed with saturated saline water, and dried with anhydrous magnesium sulfate. This was concentrated under reduced pressure, and the resultant mixture was purified through silica gel column chromatography (toluene/hexane=1:1) to give a pale yellow solid of the compound (e) (2.42 g, 5.15 mmol, yield 36.1%).

$^1$H-NMR (500 MHz, CDCl$_3$, δ): 8.16 (d, J=7.5 Hz, 4H), 7.68 (t, J$_{H-F}$=9.0 Hz, 1H), 7.51 (dt, J=7.5 Hz, 1.0 Hz, 4H), 7.38 (dt, J=7.5 Hz, 1.0 Hz, 4H), 7.23 (d, J=7.5 Hz, 4H)

ASAP Mass Spectrometry: Theoretical 469.1, Found 469.1

In a nitrogen stream atmosphere, the compound (e) (0.34 g, 0.724 mmol) was added to a 1-methyl-2-pyrrolidone solution (9 mL) of 3,6-diphenylcarbazole (0.57 g, 1.81 mmol) and potassium carbonate (0.38 g, 2.75 mmol), and stirred at 100° C. for 24 hours. The mixture was restored to room temperature, then quenched by adding water thereto, extracted with ethyl acetate, and the organic layer was washed with saturated saline water, and dried with anhydrous magnesium sulfate. This was concentrated under reduced pressure, and the resultant mixture was purified through silica gel column chromatography (toluene/hexane=1:1) to give a yellow solid of the compound 55 (0.515 g, 0.482 mmol, yield 66.6%).

$^1$H-NMR (500 MHz, CDCl$_3$, δ): 8.54 (s, 1H), 8.04 (s, 4H), 7.81 (d, J=7.5 Hz, 4H), 7.61-7.59 (m, 8H), 7.47-7.39 (m, 20H), 7.36-7.33 (m, 4H), 7.25-7.22 (m, 4H), 7.18-7.15 (m, 4H)

ASAP Mass Spectrometry: Theoretical 1067.4, Found 1067.4

(Synthesis Example 13) Synthesis of Compound 108

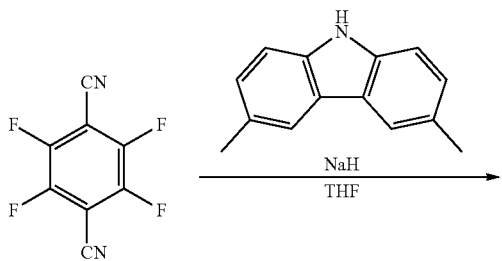

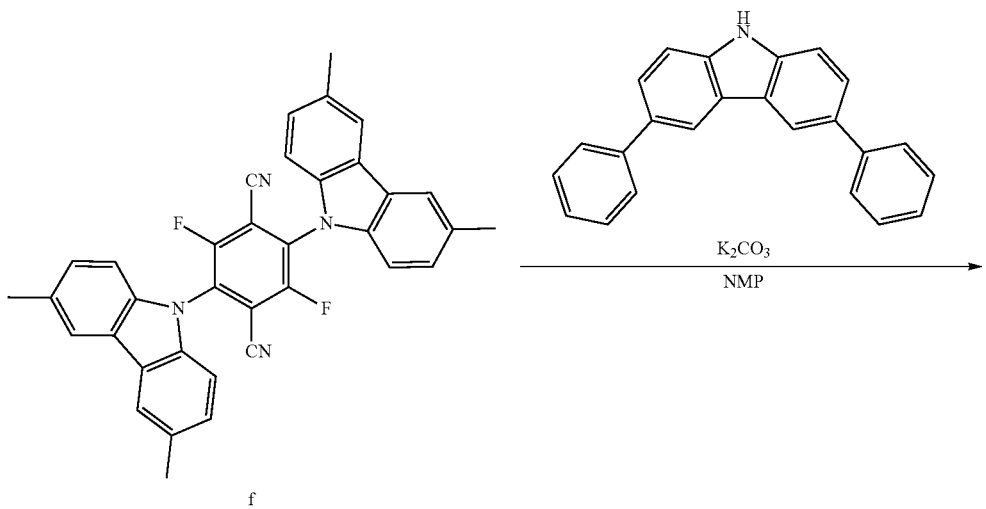

f

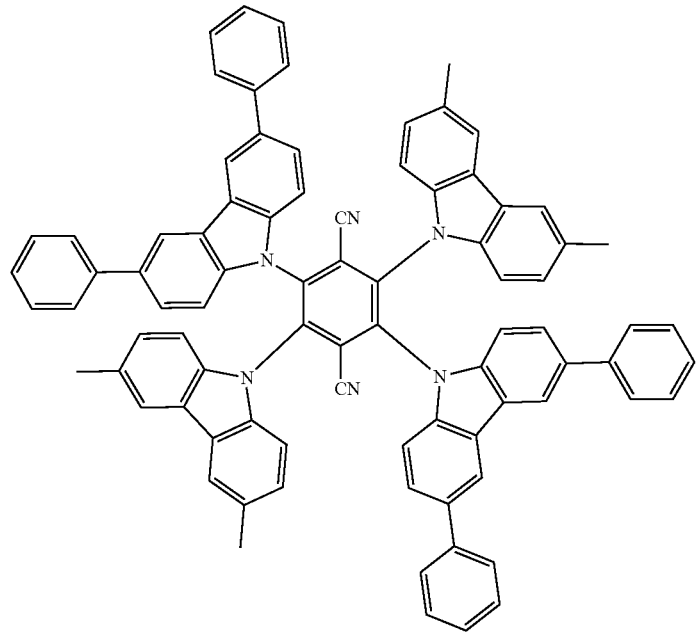

Compound 108

3,6-Dimethyl-9H-carbazole (1.56 g, 9.00 mmol) and sodium hydride (0.400 g, 60% mineral oil dispersion, 1.00 mmol) were put into a 100-mL three-neck flask, which was then purged with nitrogen. Dewatered tetrahydrofuran (80 mL) was added to the mixture, then stirred in a nitrogen atmosphere for 1 hour, and tetrafluoroterephthalonitrile (0.8 g, 4.00 mmol) was added thereto. The mixture was stirred under heat at 50° C. for 12 hours, then restored to room temperature, and water was added and filtered under suction to give a solid. The resultant solid was purified through sublimation to give a red solid of the compound (f) (yield: 0.8 g, 36%).

3,6-Diphenyl-9H-carbazole (0.696 g, 2.18 mmol), potassium carbonate (0.647 g, 3.63 mmol) and the compound (f) (0.4 g, 0.726 mmol) were put into a 100-mL three-neck flask, which was then purged with nitrogen. Dewatered 1-methyl-2-pyrrolidone (10 mL) was added to the mixture, then stirred in a nitrogen atmosphere under heat at 100° C. for 12 hour. After the stirring, the mixture was restored to room temperature, and water was added thereto and filtered under suction. The resultant solid was recrystallized with a mixed solvent of chloroform and acetonitrile to give a red solid of the compound 108 (yield: 0.62 g, 74%).

$^1$H NMR (500 MHz, CDCl$_3$, δ): 8.01 (d, J=1.5 Hz, 4H), 7.62 (dd, J=8.0 Hz, J=1.0 Hz, 8H), 7.50-7.43 (m, 12H), 7.41 (dd, J=7.5, J=1.5, 4H), 7.37 (t, J=7.5, 4H), 7.33 (d, J=8.5 Hz, 4H), 7.17 (d, J=8 Hz, 4H), 6.99 (dd, J=8 Hz, J=1.5 Hz, 4H), 2.41 (s, 12H)

ASAP Mass Spectrometry: Theoretical 1148.46, Found 1150.51

(Synthesis Example 14) Synthesis of Compound 149
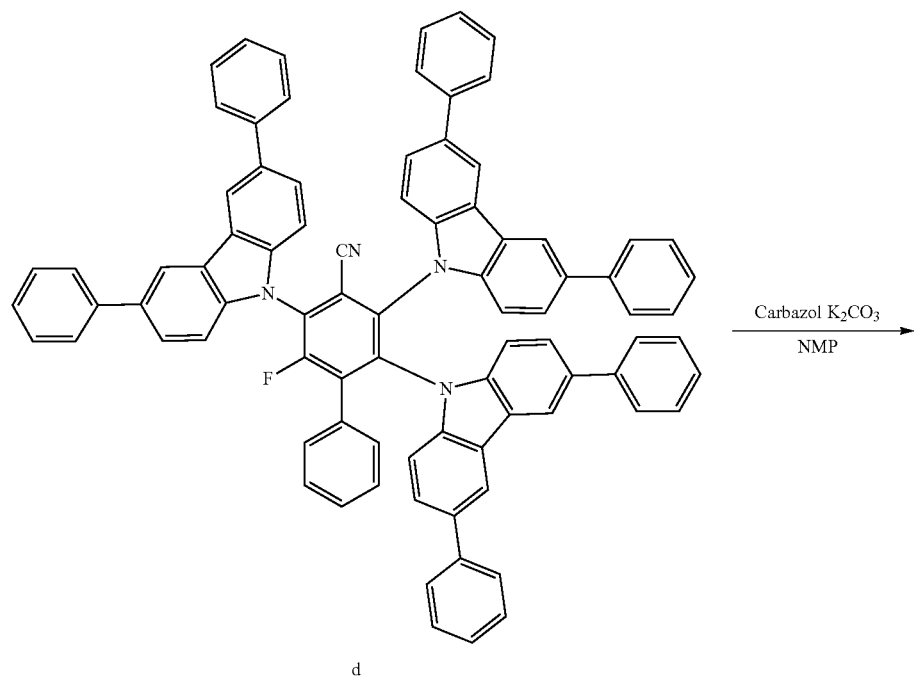
d
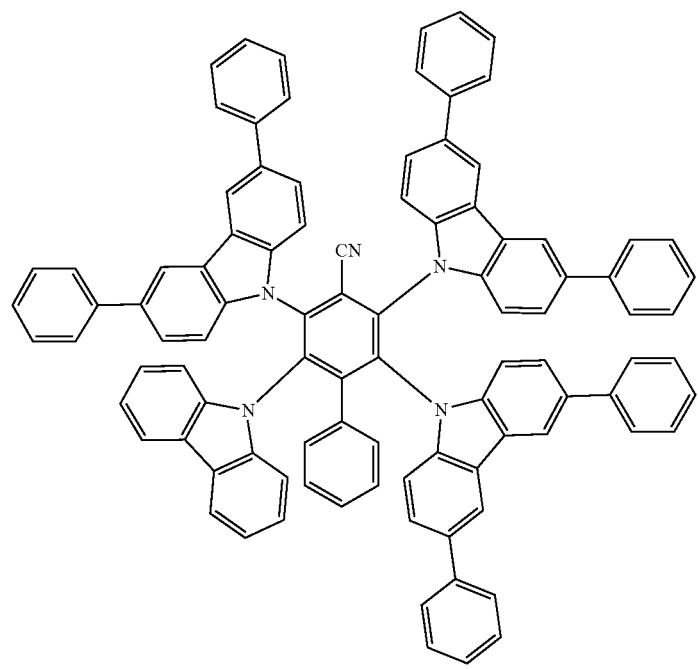
Compound 149

In a nitrogen stream atmosphere, the compound (d) (0.65 g, 0.566 mmol) was added to a 1-methyl-2-pyrrolidone solution (10 mL) of 9H-carbazole (0.142 g, 0.849 mmol) and potassium carbonate (0.18 g, 1.30 mmol), and stirred at 100° C. for 120 hours. The mixture was restored to room temperature, and quenched by adding water thereto. The resultant precipitate was washed with methanol, and this was purified through silica gel column chromatography (toluene/hexane=3:2) to give an orange solid of the compound 149 (0.284 g, 0.219 mmol, yield 38.7%).

$^1$H-NMR (500 MHz, CDCl$_3$, δ): 7.98 (d, J=1.0 Hz, 2H), 7.85 (d, J=1.0 Hz, 2H), 7.73 (d, J=2.0 Hz, 2H), 7.60-7.58 (m, 6H), 7.49-7.44 (m, 12H), 7.39-7.24 (m, 20H), 7.19-7.16 (m, 4H), 7.12-7.09 (m, 2H), 7.05-6.97 (m, 6H), 6.93 (d, J=8.0 Hz, 2H), 6.64 (t, J=8.0 Hz, 1H), 6.58 (t, J=8.0 Hz, 2H)

ASAP Mass Spectrometry: Theoretical 1295.5, Found 1295.2

(Synthesis Example 15) Synthesis of Compound 150

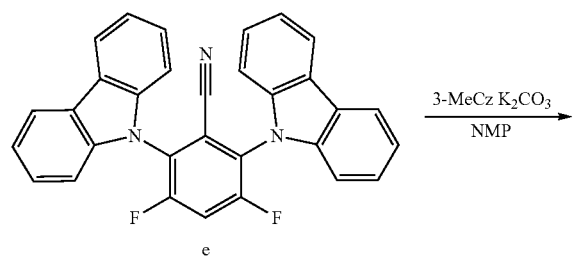

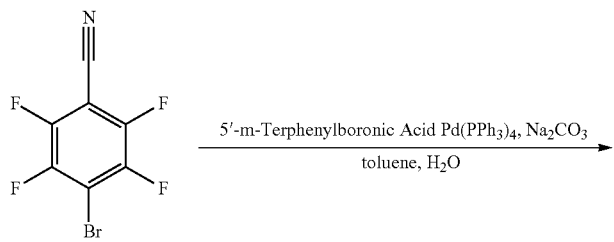

Compound 150

In a nitrogen stream atmosphere, the compound (e) (0.50 g, 1.07 mmol) was added to a 1-methyl-2-pyrrolidone solution (10 mL) of 3-methyl-9H-carbazole (0.57 g, 3.20 mmol) and potassium carbonate (0.95 g, 5.33 mmol), and stirred at 120° C. for 36 hours. The mixture was restored to room temperature, then precipitated by adding water thereto, and the precipitate was taken out through filtration. The filtered mixture was purified through silica gel column chromatography (toluene) to give the compound 150 (0.40 g, 0.51 mmol, yield 47.4%).

$^1$H-NMR (500 MHz, CDCl$_3$, δ): 8.38 (s, 1H), 7.83-7.79 (m, 4H), 7.75-7.72 (m, 2H), 7.58 (d, J=4.0 Hz, 2H), 7.43-7.33 (m, 4H), 7.30-7.11 (m, 12H), 7.10-7.03 (m, 4H), 7.00-6.93 (m, 2H), 2.41 (s, 3H), 2.39 (s, 3H)

ASAP Mass Spectrometry: Theoretical 791.3, Found 792.4

(Synthesis Example 16) Synthesis of Compound 151

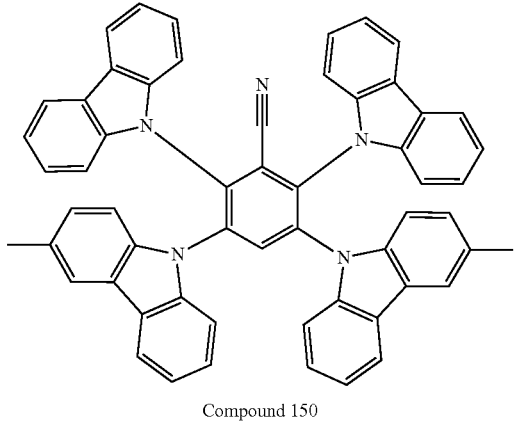

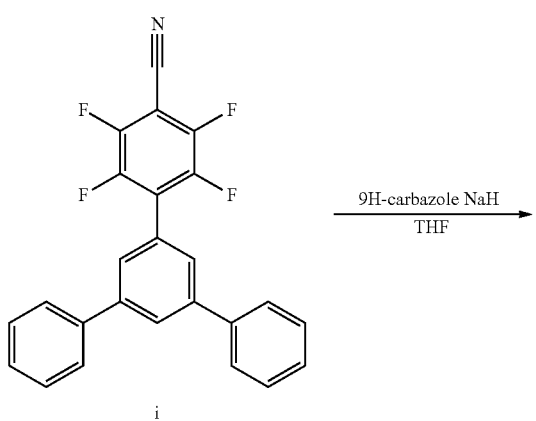

-continued

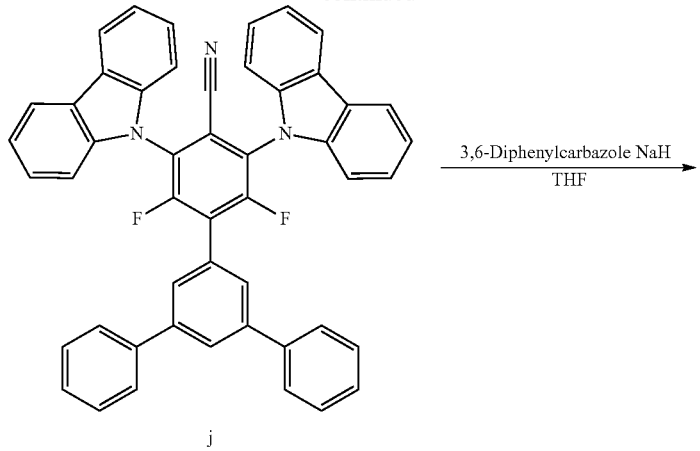

j 3,6-Diphenylcarbazole NaH / THF →

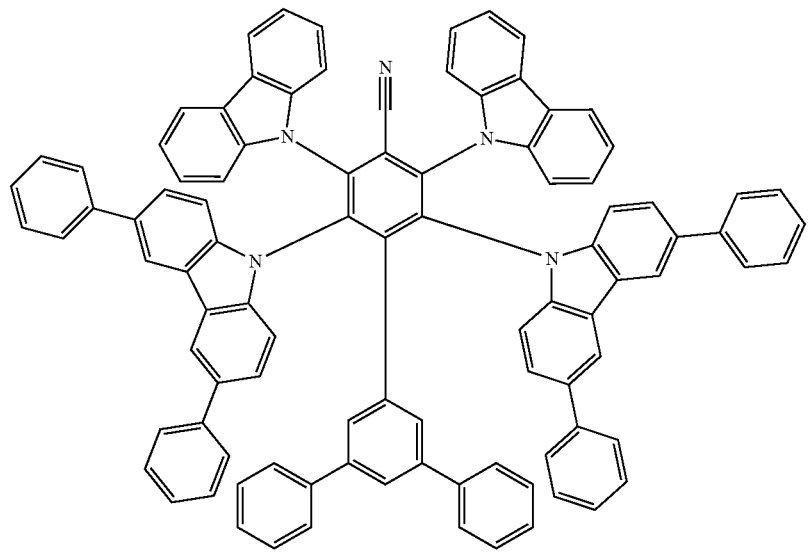

Compound 151

In an argon stream atmosphere, 4-bromo-2,3,5,6-tetrafluorobenzonitrile (3 g, 11.9 mmol) was dissolved in toluene (100 mL), and an aqueous 0.3 M sodium carbonate solution (67 mL) was added thereto. Pd(PPh$_3$)$_4$ (1.38 g, 1.19 mmol) and 5'-m-tetraphenylboronic acid (3.92 g, 14.3 mmol) were added, and heated overnight under reflux. This was cooled to room temperature, then the organic layer was separated, and the aqueous layer was extracted with dichloromethane. The organic layers were combined, and dried with anhydrous sodium sulfate. The desiccant was filtered out, and the filtrate was concentrated by distillation under reduced pressure to give a crude product. The resultant crude product was purified through silica gel column chromatography (hexane/chloroform=4:1) to give a white powder of the compound (i) (2.37 g, 5.88 mmol, yield 49.4%).

In an argon stream atmosphere, 9H-carbazole (0.83 g, 4.96 mmol) was added to a tetrahydrofuran solution (50 mL) of sodium hydride (60% mineral oil dispersion, 0.2 g, 4.96 mmol), and stirred at room temperature for 1 hour. The mixture was cooled to −50° C., and the compound (i) (1.0 g, 2.48 mmol) was added thereto, then the cooling bath was removed, and with gradually restoring to room temperature, this was stirred for 2 hours. The reaction mixture was quenched by adding it to water with ice, then extracted with dichloromethane, and the organic layer was washed with saturated saline water, and dried with anhydrous magnesium sulfate. This was concentrated under reduced pressure, and the resultant mixture was purified through silica gel column chromatography (hexane/toluene=3:2) to give a white solid of the compound (j) (0.96 g, 1.38 mmol, yield 55.6%).

In an argon stream atmosphere, 3,6-diphenylcarbazole (1.32 g, 4.14 mmol) was added to a tetrahydrofuran solution (30 mL) of sodium hydride (60% mineral oil dispersion, 0.17 g, 4.14 mmol), and stirred at room temperature for 1 hour. The compound (j) (0.96 g, 1.38 mmol) was added thereto, and heated overnight at 50° C. The reaction mixture was quenched by adding it to water with ice to collect a solid. The resultant solid was purified through silica gel column chromatography (toluene) to give a yellow solid of the compound 151 (1.10 g, 0.85 mmol, yield 61.5%).

(Synthesis Example 17) Synthesis of Compound 152

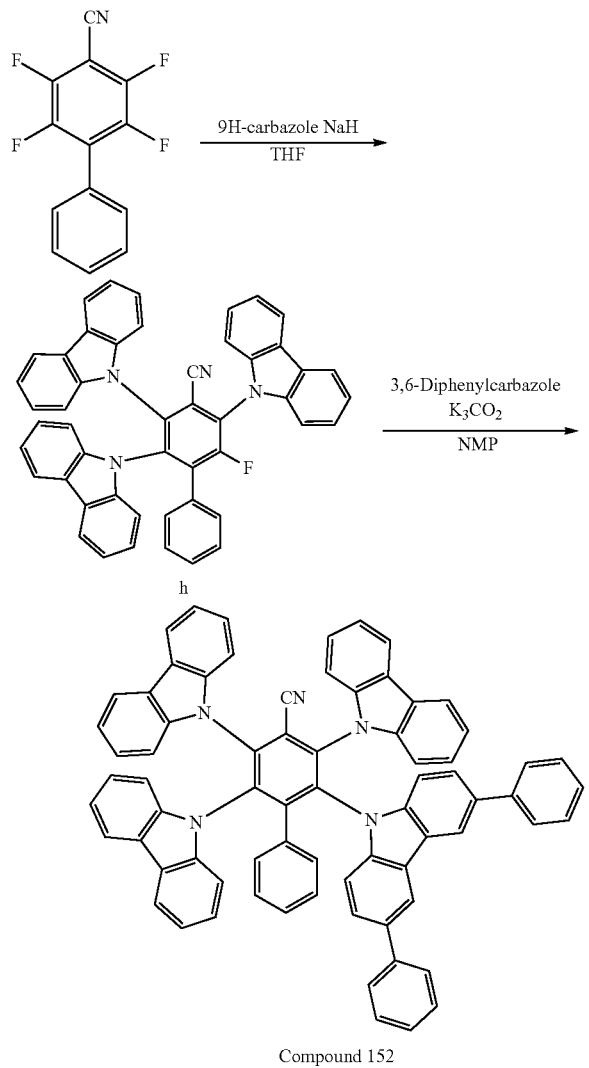

Compound 152

In a nitrogen stream atmosphere, 9H-carbazole (0.80 g, 4.78 mmol) was added to a tetrahydrofuran solution (15 mL) of sodium hydride (60% mineral oil dispersion, 0.17 g, 7.17 mmol), and stirred at room temperature for 1 hour. The mixture was cooled to −50° C., and the compound 1 (0.4 g, 1.59 mmol) was added thereto, then the cooling bath was removed, and with gradually restoring to room temperature, this was stirred for 24 hours. The reaction mixture was quenched by adding it to water with ice, then extracted with ethyl acetate, and the organic layer was washed with saturated saline water, and dried with anhydrous magnesium sulfate. This was concentrated under reduced pressure, and the resultant mixture was purified through silica gel column chromatography (hexane/toluene=2:1) to give a yellow solid of the compound (h) (0.69 g, 1.00 mmol, yield 62.9%).

$^1$H-NMR (500 MHz, CDCl$_3$, δ): 8.20 (d, J=8.5 Hz, 2H), 7.72-7.68 (m, 2H), 7.61-7.56 (m, 4H), 7.51 (d, J=8.5 Hz, 2H), 7.44 (t, J=8.5 Hz, 2H), 7.16-7.11 (m, 4H), 7.10-6.94 (m, 13H)

ASAP Mass Spectrometry: Theoretical 692.2, Found 692.1

In a nitrogen stream atmosphere, the compound (h) (0.50 g, 0.72 mmol) was added to a 1-methyl-2-pyrrolidone solution (10 mL) of 3,6-diphenylcarbazole (0.35 g, 1.08 mmol) and potassium carbonate (0.20 g, 1.44 mmol), and stirred at room temperature for 48 hours. The mixture was restored to room temperature, quenched by adding water thereto, and the resultant precipitate was washed with methanol. This was reprecipitated in chloroform/methanol to give a yellow solid of the compound 152 (0.56 g, 0.564 mmol, yield 77.6%).

$^1$H-NMR (500 MHz, CDCl$_3$, δ): 7.80 (d, J=1.5 Hz, 2H), 7.73-7.68 (m, 4H), 7.59-7.57 (m, 2H), 7.52 (dd, J=8.0 Hz, J=1.5 Hz, 4H), 7.42 (t, J=8.0 Hz, 4H), 7.33-7.22 (m, 6H), 7.19 (dd, J=8.0 Hz, J=1.5 Hz, 2H), 7.14-6.92 (m, 16H), 6.74 (dd, J=8.0 Hz, J=1.5 Hz, 2H), 6.55 (t, J=8.0 Hz, 1H), 6.48 (t, J=8.0 Hz, 2H)

ASAP Mass Spectrometry: Theoretical 991.4, Found 991.8

(Synthesis Example 18) Synthesis of Compound 313

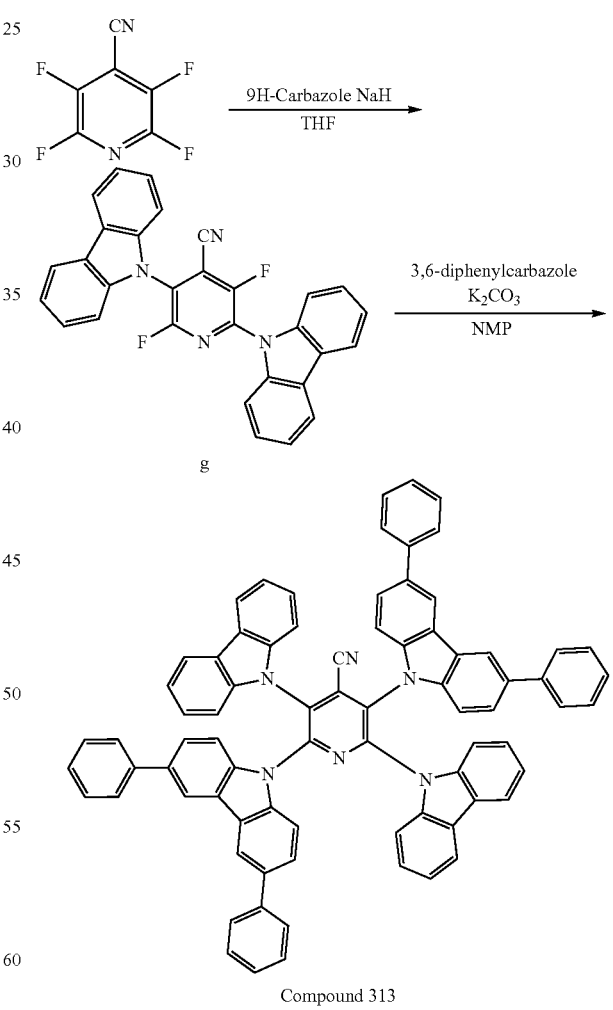

Compound 313

In a nitrogen stream atmosphere, 9H-carbazole (1.42 g, 8.49 mmol) was added to a tetrahydrofuran solution (45 mL) of sodium hydride (60% mineral oil dispersion, 0.265 g, 6.63 mmol), and stirred at room temperature for 1 hour. The mixture was cooled to −50° C., and 2,3,5,6-tetrafluoro-4-pyridinecarbonitrile (0.749 g, 4.25 mmol) was added thereto, then the cooling bath was removed, and with gradually restoring to room temperature, this was stirred for 24 hours. The reaction mixture was quenched by adding it to water with ice, then extracted with ethyl acetate, and the organic layer was washed with saturated saline water, and dried with anhydrous magnesium sulfate. This was concentrated under reduced pressure, and the resultant mixture was reprecipitated in ethyl acetate/methanol to give an orange solid of the compound (g) (0.989 g, 2.10 mmol, yield 49.4%).

$^1$H-NMR (500 MHz, CDCl$_3$, δ): 8.19 (d, J=7.5 Hz, 2H), 8.15 (d, J=7.5 Hz, 2H), 7.69-7.67 (m, 2H), 7.54 (dt, J=7.5, 1.0 Hz, 4H), 7.44 (dt, J=7.5, 1.5 Hz, 4H), 7.30 (d, J=8.0 Hz, 2H)

$^3$C-NMR (125 MHz, CDCl$_3$, δ): 154.66, 154.64, 152.67, 152.65, 150.66, 150.62, 148.47, 148.43, 139.63, 138.59, 126.80, 126.76, 125.14, 124.55, 122.71, 122.14, 120.98, 120.54, 120.02, 119.75, 115.74, 115.69, 115.62, 115.57, 111.53, 111.50, 109.74, 108.76, 108.73

ASAP Mass Spectrometry: Theoretical 470.1, Found 470.1

In a nitrogen stream atmosphere, the compound (g) (0.50 g, 1.06 mmol) was added to a 1-methyl-2-pyrrolidone solution (13 mL) of 3,6-diphenylcarbazole (0.849 g, 2.66 mmol) and potassium carbonate (0.55 g, 3.99 mmol), and stirred at 100° C. for 48 hours. The mixture was restored to room temperature, quenched by adding water thereto, extracted with ethyl acetate, and the organic layer was washed with saturated saline water, and dried with anhydrous magnesium sulfate. This was concentrated under reduced pressure, and the resultant mixture was purified through silica gel column chromatography (toluene/hexane=1:1) to give an orange solid of the compound 313 (0.963 g, 0.901 mmol, yield 84.7%).

$^1$H-NMR (500 MHz, CDCl$_3$, δ): 8.07 (d, J=1.5 Hz, 2H), 8.00 (d, J=1.5 Hz, 2H), 7.84 (d, J=7.0 Hz, 2H), 7.76 (d, J=7.0 Hz, 2H), 7.63 (d, J=8.0 Hz, 4H) 7.58 (d, J=8.0 Hz, 4H), 7.54-7.43 (m, 14H), 7.38-7.32 (m, 8H), 7.30-7.07 (m, 10H)

ASAP Mass Spectrometry: Theoretical 1068.4, Found 1068.3

Measurement of $\Delta E_{st}$

The lowest excited singlet energy level $E_{S1}$ and the lowest excited triplet energy level $E_{T1}$ of the synthesized compounds were measured according to the following process. In addition, the energy difference $\Delta E_{st}$ between the lowest excited singlet state and the lowest excited triplet state at 77K was determined by calculating the difference between $E_{S1}$ and $E_{T1}$.

(1) Lowest Excited Singlet Energy Level $E_{S1}$

The compound to be analyzed was vapor-deposited on an Si substrate to prepare a sample, and the fluorescent spectrum of the sample was measured at room temperature (300 K). For the fluorescent spectrum, the emission intensity was on the vertical axis and the wavelength was on the horizontal axis. A tangent line was drawn to the rising of the emission spectrum on the short wavelength side, and the wavelength value λedge [nm] at the intersection between the tangent line and the horizontal axis was read. The wavelength value was converted into an energy value according to the following conversion expression to calculate $E_{S1}$.

$E_{S1}$ [eV]=1239.85/λedge    Conversion Expression:

For the measurement of the emission spectrum, a nitrogen laser (available from Lasertechnik Berlin, MNL200) was used as an excitation light source along with a streak camera (available from Hamamatsu Photonics K.K., C4334) as a detector.

(2) Lowest Excited Triplet Energy Level $E_{T1}$

The same sample as that for measurement of the singlet energy level $E_{S1}$ was cooled to 77 [K], and the sample for phosphorescence measurement was irradiated with excitation light (337 nm), and using a streak camera, the phosphorescence intensity thereof was measured. A tangent line was drawn to the rising of the phosphorescent spectrum on the short wavelength side, and the wavelength value λedge [nm] at the intersection between the tangent line and the horizontal axis was read. The wavelength value was converted into an energy value according to the following conversion expression to calculate $E_{T1}$.

$E_{T1}$ [eV]=1239.85/λedge    Conversion Expression:

The tangent line to the rising of the phosphorescent spectrum on the short wavelength side was drawn as follows. While moving on the spectral curve from the short wavelength side of the phosphorescent spectrum toward the maximum value on the shortest wavelength side among the maximum values of the spectrum, a tangent line at each point on the curve toward the long wavelength side was taken into consideration. With rising thereof (that is, with increase in the vertical axis), the inclination of the tangent line increases. The tangent line drawn at the point at which the inclination value has a maximum value was referred to as the tangent line to the rising on the short wavelength side of the phosphorescent spectrum.

The maximum point having a peak intensity of 10% or less of the maximum peak intensity of the spectrum was not included in the maximum value on the above-mentioned shortest wavelength side, and the tangent line drawn at the point which is closest to the maximum value on the shortest wavelength side and at which the inclination value has a maximum value was referred to as the tangent line to the rising on the short wavelength side of the phosphorescent spectrum.

Found data of $\Delta E_{st}$ of each compound are shown in the following Table.

TABLE 10

| Light-emitting material | $\Delta E_{st}$ (eV) |
| --- | --- |
| Compound 1 | 0.16 |
| Compound 2 | 0.17 |
| Compound 3 | 0.16 |
| Compound 4 | 0.15 |
| Compound 6 | 0.16 |
| Compound 11 | 0.11 |
| Compound 35 | 0.12 |
| Compound 38 | 0.13 |
| Compound 55 | 0.17 |
| Compound 150 | 0.15 |
| Compound 151 | 0.11 |
| Compound 152 | 0.09 |

Production and Evaluation of Organic Electroluminescent Device

Example 1

On a glass substrate having, as formed thereon, an anode of indium tin oxide (ITO) having a thickness of 110 nm, thin films were laminated according to a vacuum evaporation method under a vacuum degree of $5.0 \times 10^{-5}$ Pa or less. First, on ITO, HATCN was formed to have a thickness of 60 nm, then TrisPCz was formed thereon to have a thickness of 30 nm, and further thereon, mCBP was formed to have a thickness of 5 nm. Next, mCBP, the compound 1 and TBPb were co-deposited from different evaporation sources to form a layer having a thickness of 30 nm to be a light-emitting layer. At that time, the concentration of the compound 1 was 20% by weight, and the concentration of TBPb was 0.5% by weight. Next, SF3TRZ was formed to have a thickness of 10 nm, and SF3TRZ:Liq (weight ratio 7:3) was formed thereon to have a thickness of 30 nm. Further, Liq:Al (weight ratio 1:50) was vapor-deposited thereon to form a cathode, thereby producing an organic electroluminescent device, called device 1.

Other devices 2 to 8 were produced in the same manner as above, except that, as shown in the following Table, the concentration of the second organic compound in the light-emitting layer was changed, a compound A ($\Delta E_{st}$=0.17 eV) was used in place of the compound 1 in the light-emitting layer, and DPEPO was used in place of mCBP in the light-emitting layer.

These devices 1 to 8 all emitted delayed fluorescence, and the maximum emission wavelength and the external quantum efficiency at 0.01 mA/cm² thereof are as shown in the following Table. These all have a markedly improved external quantum efficiency as compared with a comparative device in which the second organic compound was not used in the light-emitting layer and, in place of using the second organic compound therein, the amount of the first organic compound in the layer was increased. In particular, the devices 1, 3, 5 and 7 using, as the second organic compound, the compound 1 in which all the five carbazol-9-yl groups bonding to benzonitrile were not the same had a further markedly increased external quantum efficiency as compared with the devices 2, 4, 6 and 8 using the compound A in which all the five carbazol-9-yl groups bonding to benzonitrile were the same.

Example 2

On a glass substrate having, as formed thereon, an anode of indium tin oxide (ITO) having a thickness of 110 nm, thin films were laminated according to a vacuum evaporation method under a vacuum degree of $5.0 \times 10^{-5}$ Pa or less. First, on ITO, HATCN was formed to have a thickness of 10 nm, then TrisPCz was formed thereon to have a thickness of 5 nm, and further thereon, mCBP was formed to have a thickness of 5 nm. Next, mCBP, the compound 3 and TTPA were co-deposited from different evaporation sources to form a layer having a thickness of 30 nm to be a light-emitting layer. At that time, the concentration of the compound 3 was 20% by weight, and the concentration of TTPA was 0.5% by weight. Next, SF3TRZ was formed to have a thickness of 10 nm, and SF3TRZ:Liq (weight ratio 7:3) was formed thereon to have a thickness of 40 nm. Further, Liq:Al (weight ratio 1:50) was vapor-deposited thereon to form a cathode, thereby producing an organic electroluminescent device, called device 9.

Other devices 10 to 12 were produced in the same manner as above, except that, as shown in the following Table, the compound A was used in place of the compound 3 in the light-emitting layer, and 2DPhAPA was used in place of TTPA in the light-emitting layer.

These devices 9 to 12 all emitted delayed fluorescence, and the maximum emission wavelength and the external quantum efficiency at 0.01 mA/cm² and 1000 cd/m² thereof are as shown in the following Table. These all have a markedly improved external quantum efficiency and a longer lifetime as compared with a comparative device in which the second organic compound was not used in the light-emitting layer and, in place of using the second organic compound therein, the amount of the first organic compound in the layer was increased. In particular, the device 9 using, as the second organic compound, the compound 3 in which all the five carbazol-9-yl groups bonding to benzonitrile were not the same had a further markedly increased external quantum efficiency and a longer lifetime as compared with the device 10 using the compound A in which all the five carbazol-9-yl groups bonding to benzonitrile were the same. The same tendency was recognized also in the device 12 using the compound A and the device 11 using the compound 3.

TABLE 11

| | Composition of light-emitting layer (% by weight) | | | External quantum efficiency, at 0.01 mA/cm² (%) | Maximum emission wavelength (nm) |
|---|---|---|---|---|---|
| | First organic compound | Second organic compound | Third organic compound | | |
| Device 1 | mCBP (79.5) | Compound 1 (20) | TBPe (0.5) | 18.4 | 500 |
| Device 2 | mCBP (79.5) | Compound A (20) | TBPe (0.5) | 14.5 | 496 |
| Device 3 | mCBP (89.5) | Compound 1 (10) | TBPe (0.5) | 18.5 | 496 |
| Device 4 | mCBP (89.5) | Compound A (10) | TBPe (0.5) | 15.3 | 495 |
| Device 5 | DPEPO (79.5) | Compound 1 (20) | TBPe (0.5) | 14.8 | 504 |
| Device 6 | DPEPO (79.5) | Compound A (20) | TBPe (0.5) | 12.7 | 495 |
| Device 7 | DPEPO (89.5) | Compound 1 (10) | TBPe (0.5) | 12.2 | 500 |
| Device 8 | DPEPO (89.5) | Compound A (10) | TBPe (0.5) | 11.7 | 493 |

| | Composition of light-emitting layer (% by weight) | | | External quantum efficiency (%) | | LT95 (hr) | Maximum |
|---|---|---|---|---|---|---|---|
| | First organic compound | Second organic compound | Third organic compound | at 0.01 mA/cm² | at 1000 cd/m² | at 1000 cd/m² | Emission Wavelength (nm) |
| Device 9 | mCBP (79.5) | Compound 3 (20) | TTPA (0.5) | 16.0 | 13.9 | 214 | 532 |
| Device 10 | mCBP (79.5) | Compound A (20) | TTPA (0.5) | 14.3 | 12.3 | 36 | 531 |
| Device 11 | mCBP (89.5) | Compound 3 (20) | 2DPhAPA (0.5) | 14.2 | 12.3 | 84 | 512 |
| Device 12 | mCBP (89.5) | Compound A (20) | 2DPhAPA (0.5) | 13.8 | 10.6 | 13 | 508 |

Organic electroluminescent devices produced using any of the compounds 2, 4 to 7, 11, 35, 38, 48, 55, 108, 149, 150, 151, 152, 313, the compound b, and the compound d in place of the compound 1 in the device 1 also have excellent external quantum efficiency and lifetime comparable to those of the device 1.

Compound 1

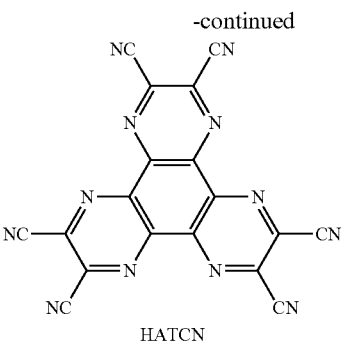

-continued

HATCN

Compound 3

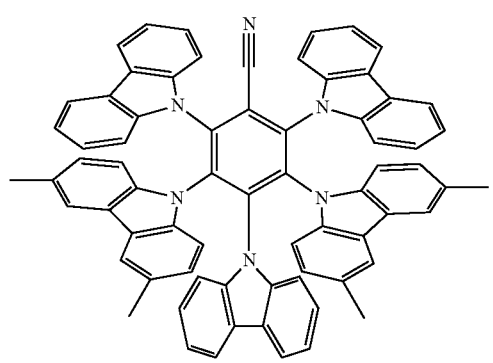

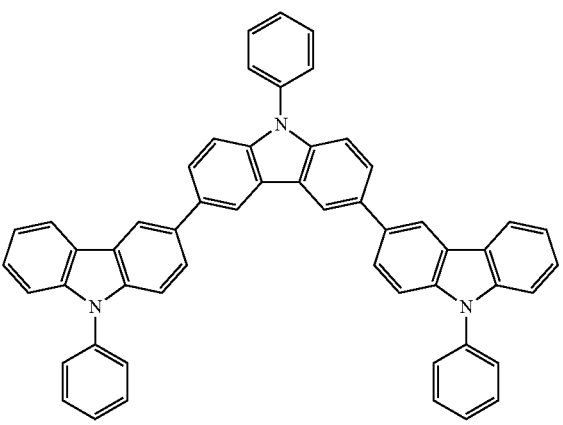

TrisPCz

Compound A

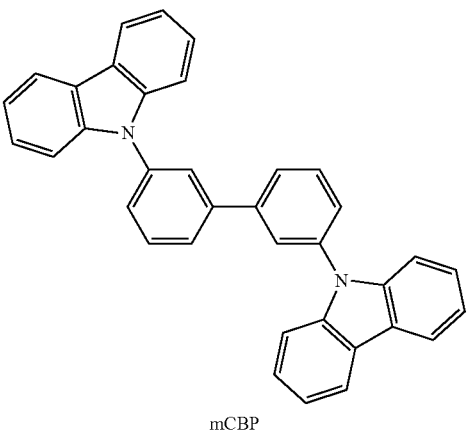

mCBP

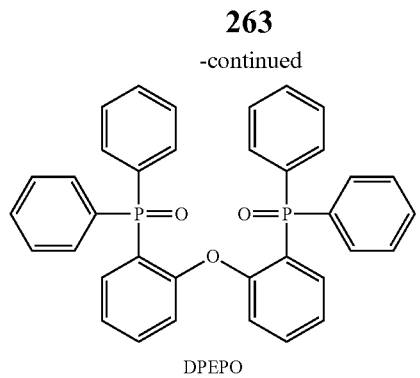

DPEPO

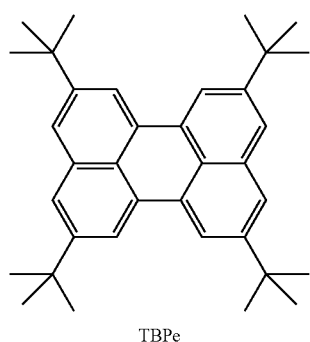

TBPe

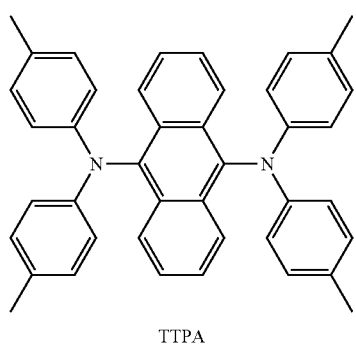

TTPA

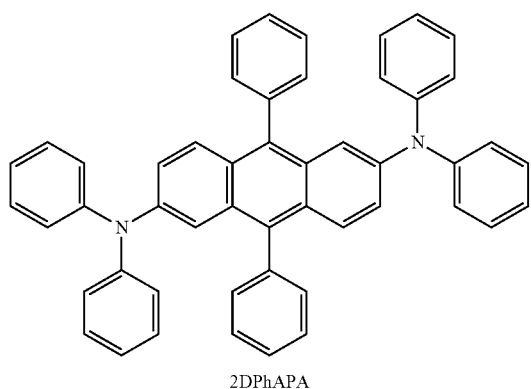

2DPhAPA

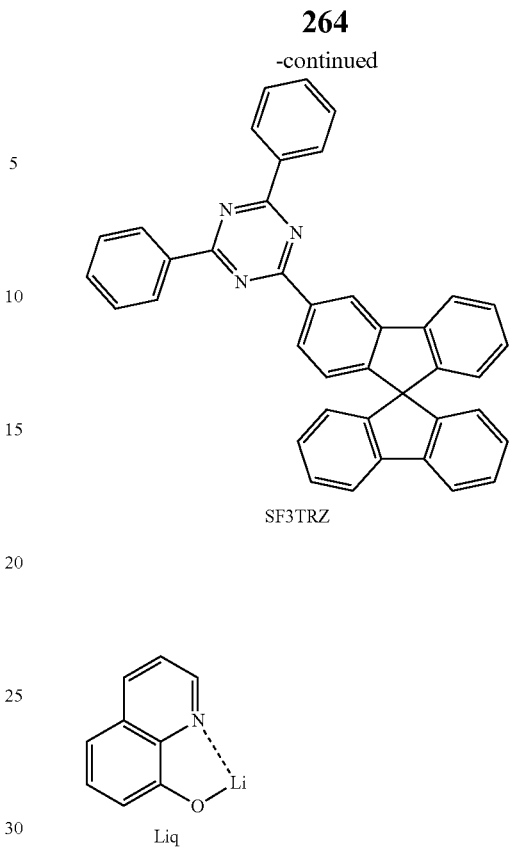

SF3TRZ

Liq

Example 3

Organic electroluminescent devices produced in the same manner as in the device 1, except that the combination of the second organic compound and the third organic compound in the light-emitting layer in the device 1 was changed to a combination of the second organic compound and the third organic compound of the combinations 1 to 16950 shown in Table 9, are referred to as devices 1a to 16950a.

Organic electroluminescent devices produced in the same manner as in the device 9, except that the combination of the second organic compound and the third organic compound in the light-emitting layer in the device 9 was changed to a combination of the second organic compound and the third organic compound of the combinations 1 to 16950 shown in Table 9, are referred to as devices 1b to 16950b.

Example 4

The device 1 has a markedly improved external quantum efficiency and a longer lifetime as compared with devices 1B to 1K produced using the following compounds B to K in place of the compound 1 in the device 1.

The device 9 has a markedly improved heat resistance and a longer lifetime as compared with devices 9B to 9K produced using the following compounds B to K in place of the compound 3 in the device 9.

-continued
Compound B
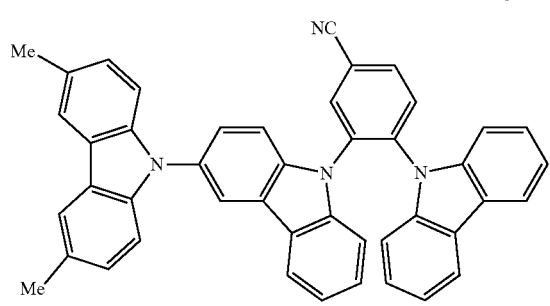
Compound C
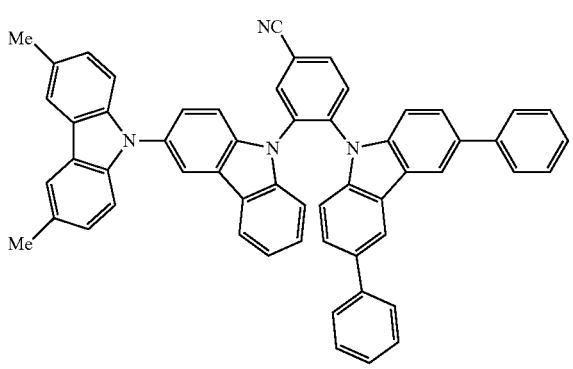
Compound D
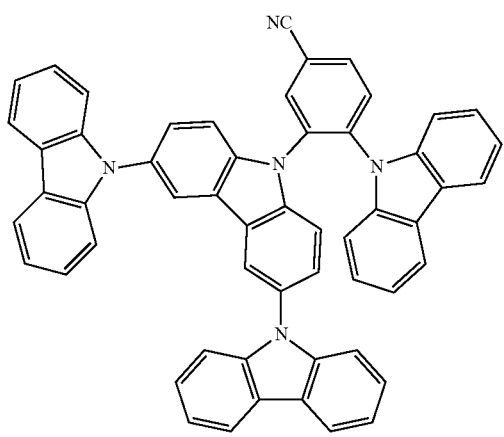
Compound E
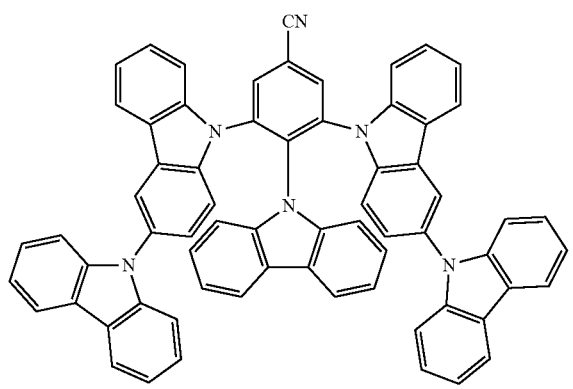
Compound F
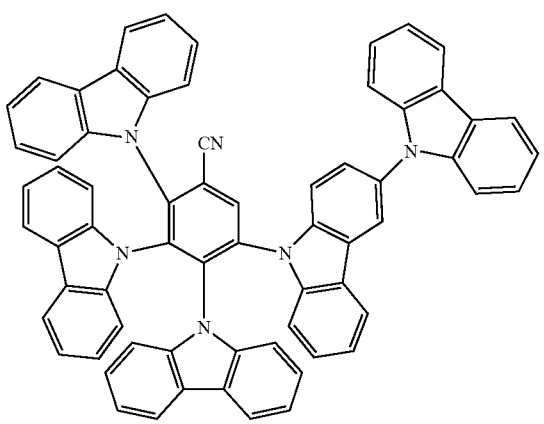
Compound G
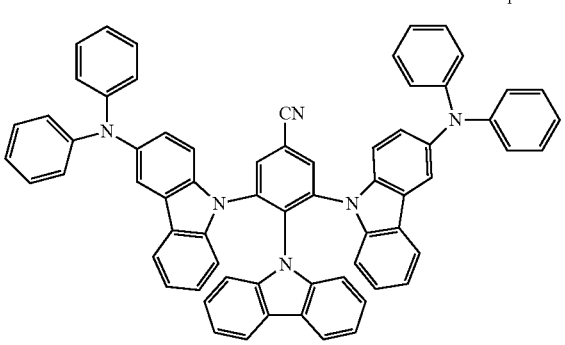
Compound I
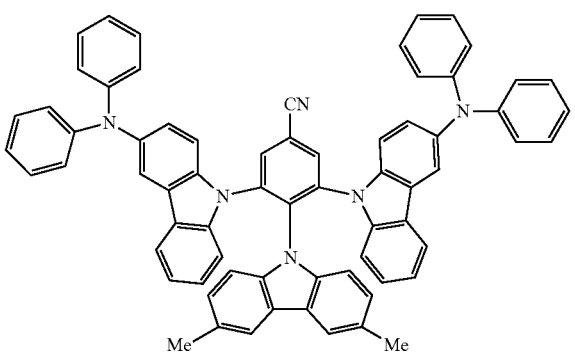
Compound J
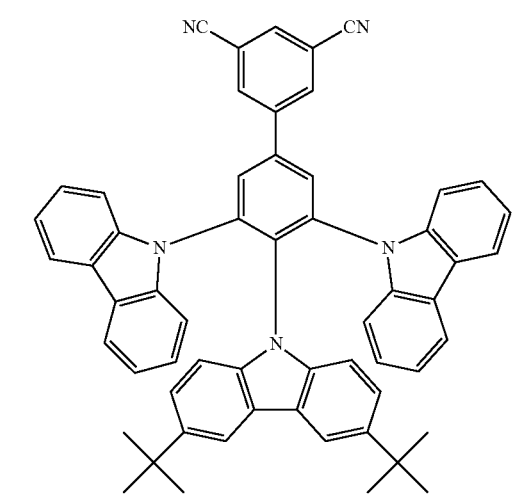

-continued

Compound K

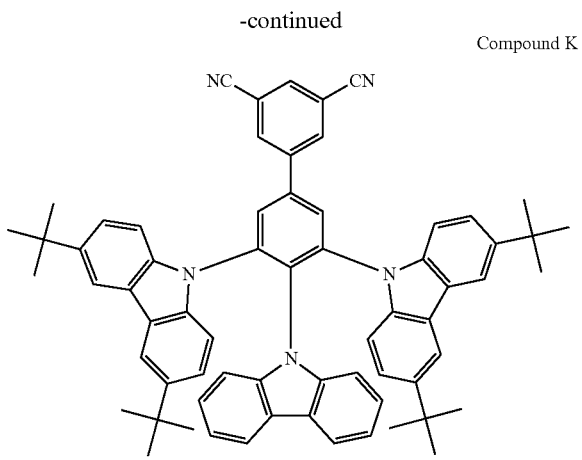

INDUSTRIAL APPLICABILITY

The organic electroluminescent device of the present invention has a high light emission efficiency, and is therefore applicable to various instruments as image display devices. Consequently, the industrial applicability of the present invention is great.

REFERENCE SIGNS LIST

1 Substrate
2 Anode
3 Hole Injection Layer
4 Hole Transport Layer
Light-Emitting Layer
6 Electron Transport Layer
7 Cathode

The invention claimed is:

1. An organic electroluminescent device having an anode, a cathode, and at least one organic layer that contains a light-emitting layer between the anode and the cathode, wherein:
the light-emitting layer contains at least a first organic compound, a second organic compound and a third organic compound satisfying the following formula (A), the second organic compound is a delayed fluorescent material represented by the following general formula (1), and the third organic compound is a light-emitting material:

$$E_{S1}(A) > E_{S1}(B) > E_{S1}(C) \qquad \text{Formula (A)}$$

wherein $E_{S1}(A)$ represents a lowest excited singlet energy level of the first organic compound, $E_{S1}(B)$ represents a lowest excited singlet energy level of the second organic compound, $E_{S1}(C)$ represents a lowest excited singlet energy level of the third organic compound;

$$(A)m\text{-}L\text{-}(D)n \qquad \text{General Formula (1)}$$

wherein L represents an (m+n)-valent aromatic linking group of a single ring; A represents a group having a positive Hammett's $\sigma_p$ value, or a phenyl group, provided that one or two of A's are a cyano group; D represents a group having a negative Hammett's $\sigma_p$ value except a phenyl group; m represents an integer of 1 or more; n represents an integer of 2 or more; when m is 2 or more, plural A's may be the same as or different from each other; two of plural D's are groups containing an aromatic ring common to them but having a different structure; and all the hydrogen atoms in the general formula (1) may be $^1$H, and all or a part of them may be $^2$H.

2. The organic electroluminescent device according to claim 1, wherein the second organic compound is such that the energy difference $\Delta E_t$ between the lowest excited singlet state and the lowest excited triplet state at 77 K thereof is 0.3 eV or less.

3. The organic electroluminescent device according to claim 1, wherein the second organic compound is such that the energy difference $\Delta E_{st}$ between the lowest excited singlet state and the lowest excited triplet state at 77 K thereof is 0.08 eV or less.

4. The organic electroluminescent device according to claim 1, wherein the first organic compound and the second organic compound satisfy the following formula (B):

$$E_{T1}(A) > E_{T1}(B) \qquad \text{Formula (B)}$$

wherein $E_{T1}(A)$ represents a lowest excited triplet energy level at 77 K of the first organic compound, $E_{T1}(B)$ represents a lowest excited triplet energy level at 77 K of the second organic compound.

5. The organic electroluminescent device according to claim 1, wherein the third organic compound emits fluorescence when returning back to the ground state energy level from the lowest excited singlet energy level.

6. The organic electroluminescent device according to claim 1, wherein the content of the second organic compound in the light-emitting layer is smaller than the content of the first organic compound therein.

7. The organic electroluminescent device according to claim 1, wherein the light-emitting layer contains two or more compounds as the third organic compound.

8. The organic electroluminescent device according to claim 1, wherein the light-emitting layer contains one or more organic compounds in addition to the first organic compound, the second organic compound and the third organic compound.

9. The organic electroluminescent device according to claim 1, wherein the second organic compound is a compound represented by the following general formula (12):

General Formula (12)

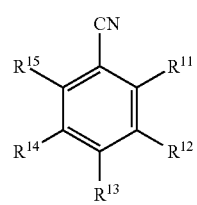

wherein at least three of $R^{11}$ to $R^{15}$ are selected from a substituted or unsubstituted diarylamino group provided that the two aryl groups constituting the diarylamino group may bond to each other and a halogen atom, and all the selected groups are not the same, and at least two are a substituted or unsubstituted diarylamino group provided that the two aryl groups constituting the diarylamino group may bond to each other, and two of the at least two substituted or unsubstituted diarylamino groups have a common aromatic ring that contains an atom bonding to the benzene ring of the general formula (12), but the two differ from each other in point of at least one condition of the number of the substituents on the aromatic ring, the substitution site of the aromatic ring substituted with the substituent, and the structure of the substituent on the aromatic ring, and the remaining 0 to 2 of $R^{11}$ to $R^{15}$ each represent a hydrogen atom, a substituted or unsubstituted aryl group, or a cyano group but at most one represents a cyano group; and all the hydrogen atoms in the general formula (1) may be $^1H$, and all or a part of them may be $^2H$.

10. The organic electroluminescent device according to claim 1, wherein the second organic compound is a compound represented by the following general formula (14):

General Formula (14)

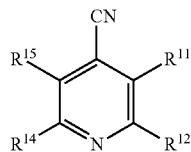

wherein at least three of $R^{11}$, $R^{12}$, $R^{14}$ and $R^{15}$ are selected from a substituted or unsubstituted diarylamino group provided that the two aryl groups constituting the diarylamino group may bond to each other and a halogen atom, and all the selected groups are not the same, and at least one is a substituted or unsubstituted diarylamino group provided that the two aryl groups constituting the diarylamino group may bond to each other, and two of the at least two substituted or unsubstituted diarylamino groups have a common aromatic ring that contains an atom bonding to the pyridine ring of the general formula (14), but the two differ from each other in point of at least one condition of the number of the substituents on the aromatic ring, the substitution site of the aromatic ring substituted with the substituent, and the structure of the substituent on the aromatic ring, and the remaining 0 to 1 of $R^{11}$, $R^{12}$, $R^{14}$ and $R^{15}$ represents a hydrogen atom, a substituted or unsubstituted aryl group, or a cyano group; and all the hydrogen atoms in the general formula (1) may be $^1H$, and all or a part of them may be $^2H$.

11. A compound represented by the following general formula (13):

General Formula (13)

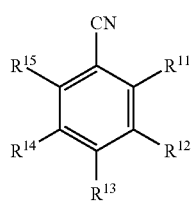

wherein at least three of $R^{11}$ to $R^{15}$ each represent a substituted or unsubstituted carbazol-9-yl group, and all these at least three substituted or unsubstituted carbazol-9-yl groups are not the same, and are not substituted with a substituted or unsubstituted diarylamino group provided that the two aryl groups constituting the diarylamino group may bond to each other, the remaining 0 to 2 of $R^{11}$ to $R^{15}$ each represent a hydrogen atom, a substituted or unsubstituted aryl group, a halogen atom, or a cyano group, and all the hydrogen atoms in the general formula (1) may be $^1H$, and all or a part of them may be $^2H$.

12. The organic electroluminescent device according to claim 1, wherein A is a cyano group.

13. The organic electroluminescent device according to claim 1, wherein D is a diarylamino group or a carbazolyl group.

14. The organic electroluminescent device according to claim 1, wherein the second organic compound is a compound represented by the following general formula (10):

General Formula (10)

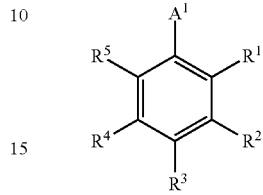

wherein $A^1$ represents a cyano group, $R^1$ to $R^5$ each represent a hydrogen atom, a group having a positive Hammett's $\sigma_p$ value, or a group having a negative Hammett's $\sigma_p$ value, and at least two of $R^1$ to $R^5$ each are a group having a negative Hammett's $\sigma_p$ value except a phenyl group; and two of the at least two groups having a negative Hammett's $\sigma_p$ value have a common aromatic ring bonding to the benzene ring of the general formula (10), but the two differ from each other in point of at least one condition of the number of the substituents on the aromatic ring, the substitution site of the aromatic ring substituted with the substituent, and the structure of the substituent on the aromatic ring; when one or more of $R^1$ to $R^5$ each are a group having a positive Hammett's $\sigma_p$ value, at most one of $R^1$ to $R^5$ is a cyano group; and all the hydrogen atoms in the general formula (1) may be $^1H$, and all or a part of them may be $^2H$.

15. The organic electroluminescent device according to claim 14, wherein $A^1$ is a cyano group, and at least four of $R^1$ to $R^5$ each are a group having a negative Hammett's $\sigma_p$ value (except a phenyl group).

16. The organic electroluminescent device according to claim 15, wherein $R^1$ and $R^5$ each are a group having a negative Hammett's $\sigma_p$ value (except a phenyl group).

17. The organic electroluminescent device according to claim 14, wherein $R^1$ and $R^5$ have same structure and are a group having a negative Hammett's $\sigma_p$ value (except a phenyl group).

18. The organic electroluminescent device according to claim 14, wherein $R^1$ and $R^4$ have same structure and are a group having a negative Hammett's $\sigma_p$ value (except a phenyl group).

19. The organic electroluminescent device according to claim 14, wherein $R^1$ and two of $R^2$ to $R^5$ each are a group having a negative Hammett's $\sigma_p$ value (except a phenyl group).

20. The organic electroluminescent device according to claim 14, wherein $R^1$, $R^5$ and two of $R^2$ to $R^4$ each are a group having a negative Hammett's $\sigma_p$ value (except a phenyl group).

21. The organic electroluminescent device according to claim 14, wherein at least four of $R^1$ to $R^5$ each are a group having a negative Hammett's $\sigma_p$ value (except a phenyl group), two of the at least four of $R^1$ to $R^5$ have a first common structure and the others have a common second structure that differs from the first common structure.

* * * * *